(12) United States Patent
Klaveness et al.

(10) Patent No.: US 6,264,917 B1
(45) Date of Patent: Jul. 24, 2001

(54) TARGETED ULTRASOUND CONTRAST AGENTS

(75) Inventors: Jo Klaveness; Pål Rongved; Dagfinn Løvhaug, all of Oslo (NO)

(73) Assignee: Nycomed Imaging AS, Oslo (NO)

( * ) Notice: Subject to any disclaimer, the term of this patent is extended or adjusted under 35 U.S.C. 154(b) by 0 days.

(21) Appl. No.: 08/958,993

(22) Filed: Oct. 28, 1997

Related U.S. Application Data

(60) Provisional application No. 60/049,264, filed on Jun. 7, 1997, provisional application No. 60/049,265, filed on Jun. 7, 1997, and provisional application No. 60/049,268, filed on Jun. 7, 1997.

(30) Foreign Application Priority Data

| Oct. 28, 1996 | (GB) | 9622366 |
|---|---|---|
| Oct. 28, 1996 | (GB) | 9622367 |
| Oct. 28, 1996 | (GB) | 9622368 |
| Jan. 15, 1997 | (GB) | 9700699 |
| Apr. 24, 1997 | (GB) | 9708265 |
| Jun. 6, 1997 | (GB) | 9711842 |
| Jun. 6, 1997 | (GB) | 9711846 |

(51) Int. Cl.⁷ .................. A61B 8/00; A61B 8/14
(52) U.S. Cl. .................. 424/9.52; 600/458
(58) Field of Search .................. 424/9.52, 9.51, 424/9.5, 450, 489; 530/300, 326, 327, 328, 329, 330; 600/441, 458

(56) References Cited

U.S. PATENT DOCUMENTS

| 4,927,916 | 5/1990 | Matsueda et al. ............ 530/387 |
|---|---|---|
| 5,013,556 | * 5/1991 | Woodle et al. ............ 424/450 |
| 5,154,924 | 10/1992 | Friden ............ 424/85.91 |
| 5,198,424 | 3/1993 | McEver ............ 514/13 |
| 5,356,633 | * 10/1994 | Woodle et al. ............ 424/450 |
| 5,498,421 | * 3/1996 | Grinstaff et al. ............ 424/450 |
| 5,505,932 | 4/1996 | Grinstaff et al. ............ 424/9.3 |
| 5,534,241 | 7/1996 | Torchilin et al. . |
| 5,612,057 | 3/1997 | Lanza et al. . |
| 5,632,986 | 5/1997 | Tait et al. . |
| 5,643,553 | 7/1997 | Schneider et al. . |
| 5,650,156 | 7/1997 | Grinstaff et al. . |
| 5,656,211 | 8/1997 | Unger et al. . |
| 5,665,383 | 9/1997 | Grinstaff et al. . |
| 5,690,907 | 11/1997 | Lanza et al. . |
| 5,716,594 | 2/1998 | Elmaleh et al. . |
| 5,733,572 | 3/1998 | Unger et al. . |
| 5,780,010 | 7/1998 | Lanza et al. . |
| 5,846,517 | 12/1998 | Unger ............ 424/9.52 |
| 5,849,727 | 12/1998 | Porter et al. ............ 514/156 |
| 5,910,300 | 6/1999 | Tournier et al. ............ 424/9.34 |

FOREIGN PATENT DOCUMENTS

| 2 145 505 | 4/1994 | (CA) . |
|---|---|---|
| 1 9 626 530 | 1/1998 | (DE) . |
| 0 727 225 | 8/1996 | (EP) . |
| WO91/15244 | 10/1991 | (WO) . |
| WO 93/20802 | 10/1993 | (WO) . |
| WO 94/07539 | 4/1994 | (WO) . |
| WO 94/28873 | 12/1994 | (WO) . |
| WO 94/28874 | 12/1994 | (WO) . |
| WO 95/03356 | 2/1995 | (WO) . |
| WO 95/03357 | 2/1995 | (WO) . |
| WO 95/07072 | 3/1995 | (WO) . |
| WO 95/15118 | 6/1995 | (WO) . |
| WO 96/39149 | 12/1996 | (WO) . |
| WO 96/40277 | 12/1996 | (WO) . |
| WO 96/40285 | 12/1996 | (WO) . |
| WO 96/41647 | 12/1996 | (WO) . |
| WO 97/23855 | 7/1997 | (WO) . |
| WO 97/33474 | 9/1997 | (WO) . |
| WO 97/41898 | 11/1997 | (WO) . |
| WO 98/00172 | 1/1998 | (WO) . |
| WO 98/04293 | 2/1998 | (WO) . |
| WO 98/19705 | 5/1998 | (WO) . |
| WO 98/20856 | 5/1998 | (WO) . |
| WO 98/42384 | 10/1998 | (WO) . |

OTHER PUBLICATIONS

U.S. application No. 08/640,464, Unger, filed May 1, 1996.
Medline database extract No. XP–002063692, 1997.
Biosis database extract No. XP–002063693, 1997.
Medline database extract No. KP–00206411, 1997.
Muzykantov et al., J. Nuclear Medicine, 35(8): 1358–1365 (1994).
Klibanov et al., Acta Radiologica, 38(Supp 412): 113–120 (1997).

* cited by examiner

Primary Examiner—Michael G. Hartley
(74) Attorney, Agent, or Firm—Bacon & Thomas

(57) ABSTRACT

Targetable diagnostic and/or therapeutically active agents, e.g. ultrasound contrast agents, having reporters comprising gas-filled microbubbles stabilised by monolayers of film-forming surfactants, the reporter being coupled or linked to at least one vector.

17 Claims, 2 Drawing Sheets

TARGETED ULTRASOUND CONTRAST AGENTS

This application claims benefit under 35 U.S.C. 119(e) of provisional applications Serial No. 60/049,264 and 60/049,265 both filed Jun. 7, 1997; and Ser. No. 60/049,268 filed Jun. 7, 1997.

This invention relates to diagnostic and/or therapeutically active agents, more particularly to diagnostic and/or therapeutically active agents incorporating moieties which interact with or have affinity for sites and/or structures within the body so that diagnostic imaging and/or therapy of particular locations within the body may be enhanced. Of particular interest are diagnostic agents for use in ultrasound imaging, which are hereinafter referred to as targeted ultrasound contrast agents.

It is well known that ultrasound imaging comprises a potentially valuable diagnostic tool, for example in studies of the vascular system, particularly in cardiography, and of tissue microvasculature. A variety of contrast agents has been proposed to enhance the acoustic images so obtained, including suspensions of solid particles, emulsified liquid droplets, gas bubbles and encapsulated gases or liquids. It is generally accepted that low density contrast agents which are easily compressible are particularly efficient in terms of the acoustic backscatter they generate, and considerable interest has therefore been shown in the preparation of gas-containing and gas-generating systems.

Gas-containing contrast media are also known to be effective in magnetic resonance (MR) imaging, e.g. as susceptibility contrast agents which will act to reduce MR signal intensity. Oxygen-containing contrast media also represent potentially useful paramagnetic MR contrast agents.

Furthermore, in the field of X-ray imaging it has been observed that gases such as carbon dioxide may be used as negative oral contrast agents or intravascular contrast agents.

The use of radioactive gases, e.g. radioactive isotopes of inert gases such as xenon, has also been proposed in scintigraphy, for example for blood pool imaging.

Targeted ultrasound contrast agents may be regarded as comprising (i) a reporter moiety capable of interacting with ultrasound irradiation to generate a detectable signal; (ii) one or more vectors having affinity for particular target sites and/or structures within the body, e.g. for specific cells or areas of pathology; and (iii) one or more linkers connecting said reporter and vector(s), in the event that these are not directly joined.

The molecules and/or structure to which the agent is intended to bind will hereinafter be referred to as the target. In order to obtain specific imaging of or a therapeutic effect at a selected region/structure in the body the target must be present and available in this region/structure. Ideally it will be expressed only in the region of interest, but usually will also be present at other locations in the body, creating possible background problems. The target may either be a defined molecular species (i.e. a target molecule) or an unknown molecule or more complex structure (i.e. a target structure) which is present in the area to be imaged and/or treated, and is able to bind specifically or selectively to a given vector molecule.

The vector is attached or linked to the reporter moiety in order to bind these moieties to the region/structure to be imaged and/or treated. The vector may bind specifically to a chosen target, or it may bind only selectively, having affinty also for a limited number of other molecules/structures, again creating possible background problems.

There is a limited body of prior art relating to targeted ultrasound contrast agents. Thus, for example, U.S. Pat. No. 5,531,980 is directed to systems in which the reporter comprises an aqueous suspension of air or gas microbubbles stabilised by one or more film-forming surfactants present at least partially in lamellar or laminar form, said surfactant(s) being bound to one or more vectors comprising "bioactive species designed for specific targeting purposes". It is stated that the microbubbles are not directly encapsulated by surfactant material but rather that this is incorporated in liquid-filled liposomes which stabilise the microbubbles. It will be appreciated that lamellar or laminar surfactant material such as phospholipids present in such liposomes will inevitably be present in the form of one or more lipid bilayers with the lipophilic tails "back-to-back" and the hydrophilic heads both inside and outside (see e.g. Schneider, M. on "Liposomes as drug carriers: 10 years of research" in *Drug targeting*, Nyon, Switzerland, Oct. 3–5, 1984, Buri, P. and Gumma, A. (Ed), Elsevier, Amsterdam 1984).

EP-A-0727225 describes targeted ultrasound contrast agents in which the reporter comprises a chemical having a sufficient vapour pressure such that a proportion of it is a gas at the body temperature of the subject. This chemical is associated with a surfactant or albumin carrier which includes a protein-, peptide- or carbohydrate-based cell adhesion molecule ligand as vector. The reporter moieties in such contrast agents correspond to the phase shift colloid systems described in WO-A-9416739; it is now recognised that administration of such phase shift colloids may lead to generation of microbubbles which grow uncontrollably, possibly to the extent where they cause potentially dangerous embolisation of, for example, the myocardial vasculature and brain (see e.g. Schwarz, *Advances in Echo-Contrast* [1994(3)], pp 48–49).

WO-A-9320802 proposes that tissue-specific ultrasonic image enhancement may be achieved using acoustically reflective oligolamellar liposomes conjugated to tissue-specific ligands such as antibodies, peptides, lectins etc. The liposomes are deliberately chosen to be devoid of gas and so will not have the advantageous echogenic properties of gas-based ultrasound contrast agents. Further references to this technology, e.g. in targeting to fibrin, thrombi and atherosclerotic areas are found in publications by Alkanonyuksel, H. et al. in *J. Pharm. Sci.* (1996) 85(5), 486–490; *J. Am. Coll. Cardiol.* (1996) 27(2) Suppl A, 298A; and *Circulation*, 68 Sci. Sessions, Anaheim Nov. 13–16, 1995.

There is also a number of publications concerning ultrasound contrast agents which refer in passing to possible use of monoclonal antibodies as vectors without giving significant practical detail and/or to reporters comprising materials which may be taken up by the reticuloendothelial system and thereby permit image enhancement of organs such as the liver—see, for example WO-A-9300933, WO-A-9401140, WO-A-9408627, WO-A-9428874, U.S. Pat. No. 5,088,499, U.S. Pat. No. 5,348,016 and U.S. Pat. No. 5,469,854.

The present invention is based on the finding that gas-filled microbubbles stabilised by monolayers of film-forming surfactant material are particularly useful reporters in targeted diagnostic and/or therapeutic agents. Thus, for example, the flexibility and deformability of such thin monolayer membranes substantially enhances the echogenicity of such reporters relative to liposome systems containing lipid bilayers or multiples of such bilayers. This may permit the use of very low doses of the reporter material to achieve high ultrasound contrast efficacy, with consequent safety benefits.

Thus according to one aspect of the present invention there is provided a targetable diagnostic and/or therapeutically active agent, e.g. an ultrasound contrast agent, comprising a suspension in an aqueous carrier liquid, e.g. an injectable carrier liquid, of a reporter comprising gas-filled microbubbles stabilised by monolayers of film-forming surfactant material, said agent further comprising at least one vector.

The term "monolayer" is used herein to denote that the amphiphilic surfactant moieties form monolayer films or membranes similar to so-called Langmuir-Blodgett films at the gas-liquid interfaces, with the lipophilic parts of the amphiphiles aligning towards the gas phase and the hydrophilic parts interacting with the water phase.

As indicated in WO-A-9729783, it is believed that electrostatic repulsion between charged phospholipid membranes encourages the formation of stable and stabilising monolayers at microbubble-carrier liquid interfaces. The flexibility and deformability of such thin membranes is believed to enhance the echogenicity of products according to the invention disclosed therein relative to gas-filled liposomes comprising one or more lipid bilayers. The amount of phospholipid used to stabilise such microbubble-containing aqueous suspensions may be as low as that necessary for formation of single monolayers of surfactant around each gas microbubble, the resulting film-like structure stabilising the microbubbles against collapse or coalescence. Microbubbles with a liposome-like surfactant bilayer are believed not to be obtained when such low phospholipid concentrations are used.

One advantageous embodiment of the invention is based on the additional finding that limited adhesion to targets is a highly useful property of diagnostic and/or therapeutically active agents, which property may be achieved using vectors giving temporary retention rather than fixed adhesion to a target. Thus such agents, rather than being fixedly retained at specific sites, may for example effectively exhibit a form of retarded flow along the vascular endothelium by virtue of their transient interactions with endothelial cells. Such agents may thus become concentrated on the walls of blood vessels, in the case of ultrasound contrast agents providing enhanced echogenicity thereof relative to the bulk of the bloodstream, which is devoid of anatomical features. They therefore may permit enhanced imaging of the capillary system, including the microvasculature, and so may facilitate distinction between normal and inadequately perfused tissue, e.g. in the heart, and may also be useful in visualising structures such as Kupffer cells, thrombi and atherosclerotic lesions or for visualising neo-vascularised and inflamed tissue areas. The present invention is particularly suited to imaging changes which occur in normal blood vessels situated in areas of tissue necrosis.

In a further embodiment of the present invention, one or more vectors may be attached to or included within the reporter in a manner such that the vectors are not readily exposed to the target or target receptors. Increased tissue specificity may therefore be achieved by applying an additional process to expose the vectors, for example by exposing the agent after administration to external ultrasound so as to modify the diffusibility of the moieties containing the vectors.

Figure 1:
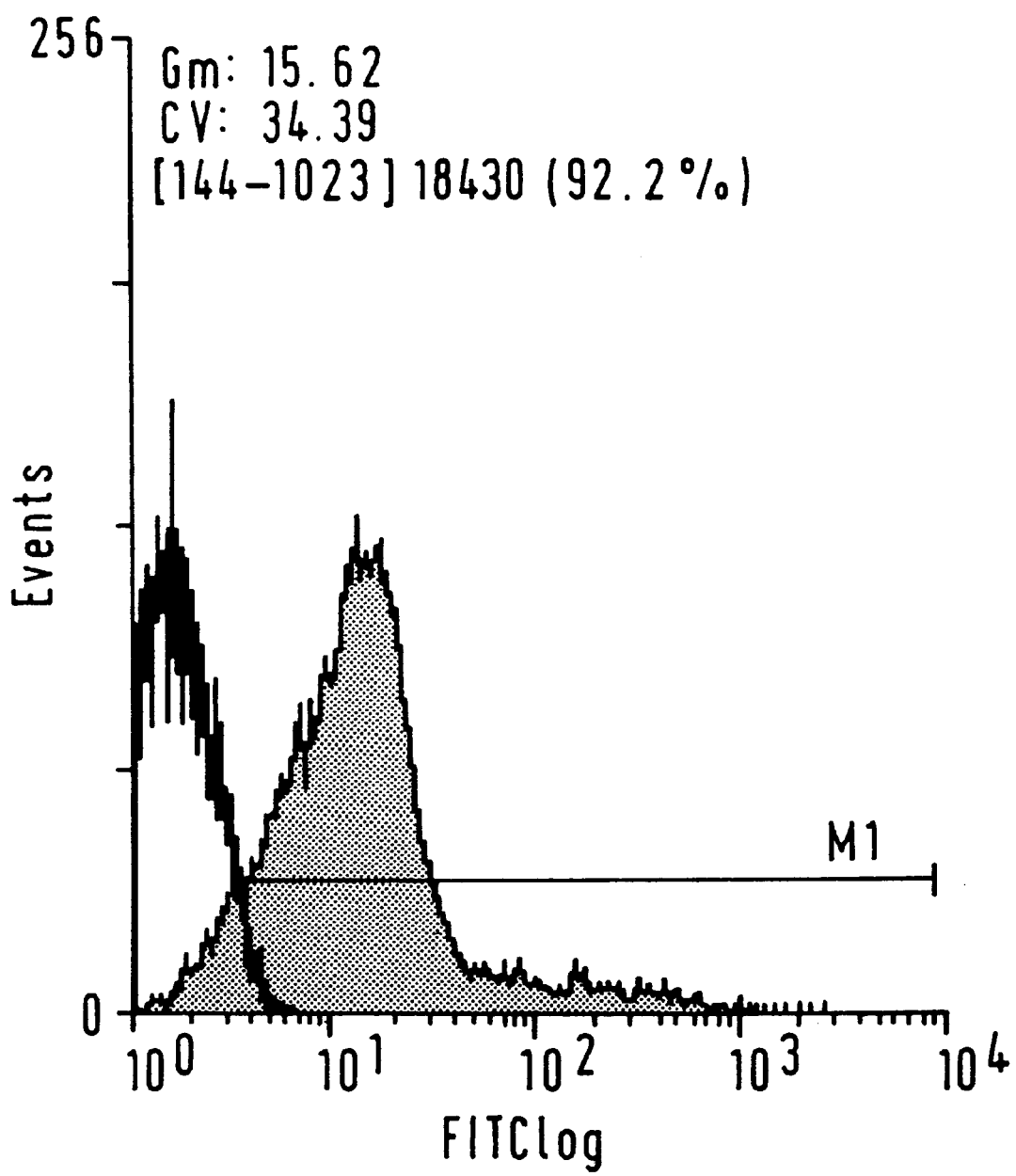
FIG. 1: Flow cytometric comparison of negative control microbubbles of DSPS (left curve) with bubbles conjugated with CD71 FITC-labelled anti-transferrin antibody (filled curve, right) showing that 92% of the population fluoresce.

Any biocompatible gas may be present in the reporter, the term "gas" as used herein including any substances (including mixtures) substantially or completely in gaseous (including vapour) form at the normal human body temperature of 37° C. The gas may thus, for example, comprise air; nitrogen; oxygen; carbon dioxide; hydrogen; an inert gas such as helium, argon, xenon or krypton; a sulphur fluoride such as sulphur hexafluoride, disulphur decafluoride or trifluoromethylsulphur pentafluoride; selenium hexafluoride; an optionally halogenated silane such as methylsilane or dimethylsilane; a low molecular weight hydrocarbon (e.g. containing up to 7 carbon atoms), for example an alkane such as methane, ethane, a propane, a butane or a pentane, a cycloalkane such as cyclopropane, cyclobutane or cyclopentane, an alkene such as ethylene, propene, propadiene or a butene, or an alkyne such as acetylene or propyne; an ether such as dimethyl ether; a ketone; an ester; a halogenated low molecular weight hydrocarbon (e.g. containing up to 7 carbon atoms); or a mixture of any of the foregoing. Advantageously at least some of the halogen atoms in halogenated gases are fluorine atoms; thus biocompatible halogenated hydrocarbon gases may, for example, be selected from bromochlorodifluoromethane, chlorodifluoromethane, dichlorodifluoromethane, bromotrifluoromethane, chlorotrifluoromethane, chloropentafluoroethane, dichlorotetrafluoroethane, chlorotrifluoroethylene, fluoroethylene, ethylfluoride, 1,1-difluoroethane and perfluorocarbons, e.g. perfluoroalkanes such as perfluoromethane, perfluoroethane, perfluoropropanes, perfluorobutanes (e.g. perfluoro-n-butane, optionally in admixture with other isomers such as perfluoro-iso-butane), perfluoropentanes, perfluorohexanes and perfluoroheptanes; perfluoroalkenes such as perfluoropropene, perfluorobutenes (e.g. perfluorobut-2-ene) and perfluorobutadiene; perfluoroalkynes such as perfluorobut-2-yne; and perfluorocycloalkanes such as perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane. Other halogenated gases include methyl chloride, fluorinated (e.g. perfluorinated) ketones such as perfluoroacetone and fluorinated (e.g. perfluorinated) ethers such as perfluorodiethyl ether. The use of perfluorinated gases, for example sulphur hexafluoride and perfluorocarbons such as perfluoropropane, perfluorobutanes and perfluoropentanes, may be particularly advantageous in view of the recognised high stability in the bloodstream of microbubbles containing such gases.

The gas may comprise a substance such as butane, cyclobutane, n-pentane, isopentane, neopentane, cyclopentane, perfluoropentane, perfluorocyclopentane, perfluorohexane or a mixture containing one or more such gases which is liquid at handling or processing temperatures but gaseous at body temperature, e.g. as described in the aforementioned WO-A-9416739, since the film-forming surfactant monolayers in reporter units according to the invention may stabilise the resulting microbubbles against uncontrollable growth.

In principle, any appropriate film-forming surfactant may be employed to form the gas-encapsulating monolayers, including non-polymeric and non-polymerisable wall-forming surfactant materials, e.g. as described in WO-A-9521631; polymer surfactant material, e.g. as described in WO-A-9506518; and phospholipids, e.g. as described in WO-A-9211873, WO-A-9217212, WO-A-9222247, WO-A-9428780, WO-A-9503835 or WO-A-9729783. Advantageously 75%, preferably substantially all, of the film-forming surfactant present in agents according to the invention is incorporated into monolayers at the gas-liquid interfaces.

Representative examples of useful phospholipids include lecithins (i.e. phosphatidylcholines), for example natural lecithins such as egg yolk lecithin or soya bean lecithin and synthetic or semisynthetic lecithins such as dimyristoylphosphatidylcholine, dipalmitoylphosphatidylcholine or distearoylphosphatidylcholine; phosphatidic acids; phosphatidylethanolamines; phosphatidylserines; phosphatidylglycerols; phosphatidylinositols; cardiolipins; sphingomyelins; fluorinated analogues of any of the foregoing; mixtures of any of the foregoing and mixtures with other lipids such as cholesterol.

It has been found that the use of phospholipids predominantly (e.g. at least 75%) comprising molecules individually bearing net overall charge may be particularly advantageous, especially when used as essentially the sole amphiphilic component of the reporter, and may convey valuable benefits in terms of parameters such as product stability and acoustic properties. Without wishing to be bound by theoretical considerations, it is believed that electrostatic repulsion between charged phospholipid membranes may encourage the formation of stable monolayers at the gas-liquid interfaces; as noted above, the flexibility and deformability of such thin membranes will enhance the echogenicity of reporters used in accordance with the invention relative to gas-filled liposomes comprising one or more lipid bilayers.

The use of charged phospholipids may also provide reporters with advantageous properties regarding, for example, stability, dispersibility and resistance to coalescence without recourse to additives such as further surfactants and/or viscosity enhancers, thereby ensuring that the number of components administered to the body of a subject upon injection of the contrast agents is kept to a minimum. Thus, for example, the charged surfaces of the microbubbles may minimise or prevent their aggregation as a result of electrostatic repulsion.

Desirably at least 75%, preferably substantially all of phospholipid material used in reporters in agents of the invention consists of molecules bearing a net overall charge under conditions of preparation and/or use, which charge may be positive or, more preferably, negative. Representative positively charged phospholipids include esters of phosphatidic acids such as dipalmitoylphosphatidic acid or distearoylphosphatidic acid with aminoalcohols such as hydroxyethylethylenediamine. Examples of negatively charged phospholipids include naturally occurring (e.g. soya bean or egg yolk derived), semisynthetic (e.g. partially or fully hydrogenated) and synthetic phosphatidylserines, phosphatidylglycerols, phosphatidylinositols, phosphatidic acids and cardiolipins. The fatty acyl groups of such phospholipids will typically each contain about 14–22 carbon atoms, for example as in palmitoyl and stearoyl groups. Lyso forms of such charged phospholipids are also useful in accordance with the invention, the term "lyso" denoting phospholipids containing only one fatty acyl group, this preferably being ester-linked to the 1-position carbon atom of the glyceryl moiety. Such lyso forms of charged phospholipids may advantageously be used in admixture with charged phospholipids containing two fatty acyl groups.

Phosphatidylserines represent particularly preferred phospholipids of use in agents according to the invention and preferably constitute a substantial part, e.g. at least 80% of the phospholipid content thereof, for example 85–92%. While we do not wish to be bound by theoretical considerations, it may be that ionic bridging between the carboxyl and amino groups of adjacent serine moieties contributes to the stability of such reporter systems. Preferred phosphatidylserines include saturated (e.g. hydrogenated or synthetic) natural phosphatidylserine and synthetic distearoylphosphatidylserine, dipalmitoylphosphatidylserine and diarachidoylphosphatidylserine.

Other potentially useful lipids include phosphatidylethanolamines optionally admixed with one or more lipids such as stearic acid, palmitic acid, stearylamine, palmitylamine, cholesterol, bisalkyl glycerols, sphingoglycolipids, synthetic lipids such as N,N-dimethyl-N-octadecyl-1-octadecanammonium chloride or bromide (DODAC, DODAB), and/or maleic acid bisalkylesters.

Additional exemplary lipids which may be used to prepare gas-containing contrast agents include fatty acids, stearic acid, palmitic acid, 2-n-hexadecylstearic acid, oleic acid and other acid-containing lipid structures. Such lipid structures may be coupled by amide bond formation to amino acids containing one or more amino groups; the resulting lipid-modified amino acids (e.g. dipalmitoyllysine or distearoyl-2,3-diaminopropionic acid) may be useful precursors for the attachment of functionalised spacer elements having coupling sites for conjugation of one or more vector molecules.

Further useful stabilisers include lipopeptides comprising a lipid attached to a peptide linker portion which is suitably functionalised for coupling to one or more vector molecules. A particular preference is the inclusion of a positively charged peptide linker element (e.g. comprising two or more lysine residues) capable of anchoring through electrostatic interaction with reporter microbubbles stabilised by negatively charged phospholipid or other surfactant membranes.

Another embodiment of the invention comprises functionalised microbubbles carrying one or more reactive groups for non-specific reaction with receptor molecules located on cell surfaces. Microbubbles comprising a thiol moiety, for example, may bind to cell surface receptors via disulphide exchange reactions. The reversible nature of such reactions means that microbubble flow may be controlled by altering the redox environment. Similarly, functionalised microbubbles with membranes comprising activated esters such as N-hydroxysuccinimide esters may be used to react with amino groups found on a multiplicity of cell surface molecules.

Previously proposed microbubble-containing contrast agents based on phospholipids, for example as described in WO-A-9409829, are typically prepared by contacting powdered surfactant, e.g. freeze-dried preformed liposomes or freeze-dried or spray-dried phospholipid solutions, with air or other gas and then with aqueous carrier, agitating to generate a microbubble suspension which must then be administered shortly after its preparation. Such processes, however, suffer the disadvantages that substantial agitational energy must be imparted to generate the required dispersion and that the size and size distribution of the microbubbles are dependent on the amount of energy applied and so cannot in practice be controlled.

The reporters or agents according to the present invention, on the other hand, may advantageously be prepared by generating a gas microbubble dispersion in an appropriate surfactant (e.g. phospholipid)-containing aqueous medium, which may if desired previously have been autoclaved or otherwise sterilised, and then, preferably after washing and/or size fractionation of the thus-formed microbubbles, subjecting the dispersion to lyophilisation, e.g. in the presence of one or more cryoprotectants/lyoprotectants, to yield a dried product which is readily reconstitutable in water/aqueous solutions to generate consistently reproducible microbubble dispersions. This process is described in greater detail in WO-A-9729783, the contents of which are incorporated herein by reference; the ability to remove bubbles of unwanted size and excess surfactant material render this process of substantial advantage over processes such as those described in the aforementioned WO-A-9409829 and in prior art such as WO-A-9608234 (where bubbles are generated on site prior to injection by shaking a suspension of different phospholipids and viscosity enhancers such as propylene glycol and glycerol).

The above-described process may be used to generate reporter microbubbles with a very narrow size distribution, e.g. such that over 90% (e.g. at least 95%, preferably at least 98%) of the microbubbles have volume mean diameter in the range 1–7 μm and less than 5% (e.g. not more than 3%, preferably not more than 2%) of the microbubbles have volume mean diameter above 7 μm. The washing step may be used to ensure that the reporter is substantially free of unwanted components such as excess lipids or viscosity enhancers. Agents containing reporters prepared in this way may exhibit the following advantages over prior art contrast agent materials:

Echogenicity per dose may be greatly enhanced since substantially all of the surfactant material participate in stabilisation of the microbubbles as monolayers. In vivo ultrasound tests in dogs have shown that ultrasound contrast agents prepared as above may produce an increase in backscattered signal intensity from the myocardium of 15 dB following intravenous injection of doses as low as 0.1 μl microbubbles/kg body weight.

Safety in vivo is improved for the same reasons, since such agents may, for example, be administered in doses such that the amount of phospholipid injected is as low as 0.1–10 μg/kg body weight, e.g. 1–5 μg/kg. The use of such low levels of surfactant may clearly be of substantial advantage in minimising possible toxic side effects.

The high efficacy/dose ratio is also particularly advantageous in targeting applications, since it is generally understood that rather low amounts of reporter will accumulate at sites of interest when using products comprising vectors having affinity for such sites. These preferred reporters according to the invention may therefore considerably improve contrast at sites of interest compared to known targetable ultrasound contrast agents. Their high efficacy may effectively make it possible to "see" single microbubbles using ultrasound, giving a sensitivity close to or potentially even higher than that of scintigraphy, which currently is probably the most useful technique in targeting, although the resolution in scintigraphic pictures is not impressive.

A particular advantage of phosphatidylserine-based agents is their biocompatibility; thus no acute toxic effects such as changes in blood pressure or heart rate have been observed in animal tests on dogs injected with intravenous boluses of phosphatidylserine-based contrast agents prepared as described above at doses of up to ten times a normal imaging dose.

The use of charged phospholipids may also be of advantage in that they will contain functional groups such as carboxyl or amino which permit ready linking of vectors, if desired by way of linking units. It should be noted that other functional groups may also be incorporated into such systems by mixing a lipid containing a desired functional group with the film-forming surfactant prior to microbubble generation.

It is generally unnecessary to incorporate additives such as emulsifying agents and/or viscosity enhancers such as are commonly employed in many existing contrast agent formulations into agents of the invention. As noted above, this is of advantage in keeping to a minimum the number of components administered to the body of a subject and ensuring that the viscosity of the agents is as low as possible. Since preparation of the agents typically involves a freeze drying step as discussed above, it may however be advantageous to include a cryoprotectant/lyoprotectant or bulking agent, for example an alcohol, e.g. an aliphatic alcohol such as t-butanol; a polyol such as glycerol; a carbohydrate, e.g. a sugar such as sucrose, mannitol, trehalose or a cyclodextrin, or a polysaccharide such as dextran; or a polyglycol such as polyethylene glycol. The use of physiologically well-tolerated sugars such as sucrose is preferred.

Lyophilised dried products prepared as described above are especially readily reconstitutable in water, requiring only minimal agitation such as may, for example, be provided by gentle hand-shaking for a few seconds. The size of the microbubbles so generated is consistently reproducible and is independent of the amount of agitational energy applied, in practice being determined by the size of the microbubbles formed in the initial microbubble dispersion; surprisingly this size parameter is substantially maintained in the lyophilised and reconstituted product. Thus, since the size of the microbubbles in the initial dispersion may readily be controlled by process parameters such as the method, speed and duration of agitation, the final microbubble size may readily be controlled.

The lyophilised dried products have also proved to be storage stable for at least several months under ambient conditions. The microbubble dispersions generated upon reconstitution in water are stable for at least 8 hours, permitting considerable flexibility as to when the dried product is reconstituted prior to injection.

The high efficacy of these preferred reporters may make it possible to use smaller bubbles than usual while still generating ultrasound contrast effects significantly above the minimum detection levels of current ultrasound imaging equipment. Such smaller bubbles have potential advantages such as reduced clogging of vessels, longer circulation times, greater ability to reach targets, and lower accumulation in lungs or other non-target organs, and their use and agents containing them constitute further features of the invention.

It may also be possible to use such smaller bubbles to exploit the enhanced ultrasound contrast effects of bubble clusters. It is known from theory that the ultrasound contrast effect of a specific number of bubbles with total volume V in a dilute dispersion increases when the bubbles aggregate to form a larger gas phase with the same total volume V. It may therefore be possible to use small bubbles which give substantially no ultrasound contrast until they are clustered (as may occur in target areas in preference to non-target sites having low densities of target molecules). Small bubbles may also be designed to fuse, e.g. through interbubble binding promoted by interaction with the target, so as to enhance contrast in target areas. Interbubble crosslinking and consequent clustering may also be effected if the reporter, in addition to carrying a vector leading to retention at specific sites, has unreacted linker moieties capable of reaction with functional groups on other bubbles.

Within the context of the present invention, the reporter unit will usually remain attached to the vectors. However, in one type of targeting procedure, sometimes called "pre-targeting", the vector (often a monoclonal antibody) is administered alone; subsequently the reporter is administered, coupled to a moiety which is capable of specifically binding the pre-targeting vector molecule (when the pre-targeting vector is an antibody, the reporter may be coupled to an immunoglobulin-binding molecule, such as protein A or an anti-immunoglobulin antibody). The advantage of this protocol is that time may be allowed for elimination of the vector molecules that do not bind their targets, substantially reducing the background problems that are connected with the presence of an excess of reporter-vector conjugate. Within the context of the present invention, pre-targeting with one specific vector might be envisaged, followed by reporter units that are coupled to another vector and a moiety which binds the first vector.

Again in the context of the present invention, for example in assessment of blood perfusion rates in targeted areas such as the myocardium, it is of interest to measure the rate at which contrast agents bound to the target are displaced or released therefrom. This may be achieved in a controlled manner by administration of an additional vector and/or other substance able to displace or release the contrast agent from its target.

Ultrasound imaging modalities which may be used in accordance with the invention include two- and three-dimensional imaging techniques such as B-mode imaging (for example using the time-varying amplitude of the signal envelope generated from the fundamental frequency of the emitted ultrasound pulse, from sub-harmonics or higher harmonics thereof or from sum or difference frequencies derived from the emitted pulse and such harmonics, images generated from the fundamental frequency or the second harmonic thereof being preferred), colour Doppler imaging and Doppler amplitude imaging, and combinations of the two latter with any of the above modalities. Surprisingly excellent second harmonic signals have been obtained from targeted monolayer-stabilised microspheres in accordance with the present invention. To reduce the effects of movement, successive images of tissues such as the heart or kidney may be collected with the aid of suitable synchronisation techniques (e.g. gating to the ECG or respiratory movement of the subject). Measurement of changes in resonance frequency or frequency absorption which accompany arrested or retarded microbubbles may also usefully be made to detect the contrast agent.

The present invention provides a tool for therapeutic drug delivery in combination with vector-mediated direction of the product to the desired site. By "therapeutic" or "drug" is meant an agent having a beneficial effect on a specific disease in a living human or non-human animal. Whilst combinations of drugs and ultrasound contrast agents have been proposed in, for example, WO-A-9428873 and WO-A-9507072, these products lack vectors having affinity for particular sites and thereby show comparitively poor specific retention at desired sites prior to or during drug release.

Therapeutic compounds used in accordance with the present invention may be encapsulated in the interior of the microbubbles or attached to or incorporated in the stabilising membranes. Thus, the therapeutic compound may be linked to a part of the membrane, for example through covalent or ionic bonds, or may be physically mixed into the stabilising material, particularly if the drug has similar polarity or solubility to the membrane material, so as to prevent it from leaking out of the product before it is intended to act in the body. The release of the drug may be initiated merely by wetting contact with blood following administration or as a consequence of other internal or external influences, e.g. dissolution processes catalyzed by enzymes or the use of of ultrasound. The destruction of gas-containing microparticles using external ultrasound is a well known phenomenon in respect of ultrasound contrast agents, e.g. as described in WO-A-9325241; the rate of drug release may be varied depending on the type of therapeutic application, using a specific amount of ultrasound energy from the transducer.

The therapeutic may be covalently linked to the encapsulating membrane surface using a suitable linking agent, e.g. as described herein. Thus, for example, one may initially prepare a phospholipid or lipopeptide derivative to which the drug is bonded through a biodegradable bond or linker, and then incorporate this derivative into the material used to prepare the reporter, as described above.

Representative therapeutics suitable for use in the present drug delivery compositions include any known therapeutic drugs or active analogues thereof containing thiol groups which may be coupled to thiol-containing microbubbles under oxidative conditions yielding disulphide groups. In combination with a vector or vectors such drug/vector-modified microbubbles may be allowed to accumulate in target tissue; administration of a reducing agent such as reduced glutathione may then liberate the drug molecule from the targeted microbubble in the vicinity of the target cell, increasing the local concentration of the drug and enhancing its therapeutic effect. Alternatively the composition may initially be prepared without the therapeutic, which may then be coupled to or coated on the microbubbles immediately prior to use; thus, for example, a therapeutic may be added to a suspension of microbubbles in aqueous media and shaken in order to attach or adhere the therapeutic to the microbubbles.

Other drug delivery systems include vector-modified phospholipid membranes doped with lipopeptide structures comprising a poly-L-lysine or poly-D-lysine chain in combination with a targeting vector. Applied to gene therapy/antisense technologies with particular emphasis on receptor-mediated drug delivery, the microbubble carrier is condensed with DNA or RNA via elecrostatic interaction with the cationic polylysine. This method has the advantage that the vector or vectors used for targeted delivery are not directly attached to the polylysine carrier moiety. The polylysine chain is also anchored more tightly in the microbubble membrane due to the presence of the lipid chains. The use of ultrasound to increase the effectiveness of delivery is also considered useful.

Alternatively free polylysine chains are firstly modified with drug or vector molecules then condensed onto the negative surface of targeted microbubbles.

Representative and non-limiting examples of drugs useful in accordance with the invention include antineoplastic agents such as vincristine, vinblastine, vindesine, busulfan, chlorambucil, spiroplatin, cisplatin, carboplatin, methotrexate, adriamycin, mitomycin, bleomycin, cytosine arabinoside, arabinosyl adenine, mercaptopurine, mitotane, procarbazine, dactinomycin (antinomycin D), daunorubicin, doxorubicin hydrochloride, taxol, plicamycin, aminoglutethimide, estramustine, flutamide, leuprolide, megestrol acetate, tamoxifen, testolactone, trilostane, amsacrine (m-AMSA), asparaginase (L-asparaginase), etoposide, interferon a-2a and 2b, blood products such as hematoporphyrins or derivatives of the foregoing; biological response modifiers such as muramylpeptides; antifungal agents such as ketoconazole, nystatin, griseofulvin, flucytosine, miconazole or amphotericin B; hormones or hormone analogues such as growth hormone, melanocyte stimulating hormone, estradiol, beclomethasone dipropionate, betamethasone, cortisone acetate, dexamethasone, flunisolide, hydrocortisone, methylprednisolone, paramethasone acetate, prednisolone, prednisone, triamcinolone or fludrocortisone acetate; vitamins such as cyanocobalamin or retinoids; enzymes such as alkaline phosphatase or manganese superoxide dismutase; antiallergic agents such as amelexanox; inhibitors of tissue factor such as monoclonal antibodies and Fab fragments thereof, synthetic peptides, non-peptides and compounds downregulating tissue factor expression; inhibitors of platelets such as GPIa, GPIb and GPIIb-IIIa, ADP receptors, thrombin receptors, von Willebrand factor, prostaglandins, aspirin, ticlopidin, clopigogrel and reopro; inhibitors of coagulation protein targets such as FIIa, FVa, FVIIa, FVIIIa, FIXa, FXa, tissue factor, heparins, hirudin, hirulog, argatroban, DEGR-rFVIIa and annexin V: inhibitors of fibrin formation and promoters of fibrinolysis such as t-PA, urokinase, Plasmin, Streptokinase, rt-Plasminogen Activator and rStaphylokinase; antiangiogenic factors such as medroxyprogesteron, pentosan polysulphate, suramin, taxol, thalidomide, angiostatin, interferon-alpha, metalloproteinase inhibitors, platelet factor 4, somatostatin, thromobospondin; circulatory drugs such as propranolol; metabolic potentiators such as glutathione; antituberculars such as p-aminosalicylic acid, isoniazid, capreomycin sulfate, cyclosexine, ethambutol, ethionamide, pyrazinamide, rifampin or streptomycin sulphate; antivirals such as acyclovir, amantadine, azidothymidine, ribavirin or vidarabine; blood vessel dilating agents such as diltiazem, nifedipine, verapamil, erythritol tetranitrate, isosorbide dinitrate, nitroglycerin or pentaerythritol tetranitrate; antibiotics such as dapsone, chloramphenicol, neomycin, cefaclor, cefadroxil, cephalexin, cephradine, erythromycin, clindamycin, lincomycin, amoxicillin, ampicillin, bacampicillin, carbenicillin, dicloxacillin, cyclacillin, picloxacillin, hetacillin, methicillin, nafcillin, penicillin, polymyxin or tetracycline; antiinflammatories such as diflunisal, ibuprofen, indomethacin, meclefenamate, mefenamic acid, naproxen, phenylbutazone, piroxicam, tolmetin, aspirin or salicylates; antiprotozoans such as chloroquine, metronidazole, quinine or meglumine antimonate; antirheumatics such as penicillamine; narcotics such as paregoric; opiates such as codeine, morphine or opium; cardiac glycosides such as deslaneside, digitoxin, digoxin, digitalin or digitalis; neuromuscular blockers such as atracurium mesylate, gallamine triethiodide, hexafluorenium bromide, metocurine iodide, pancuronium bromide, succinylcholine chloride, tubocurarine chloride or vecuronium bromide; sedatives such as amobarbital, amobarbital sodium, apropbarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, secobarbital sodium, talbutal, temazepam or triazolam; local anaesthetics such as bupivacaine, chloroprocaine, etidocaine, lidocaine, mepivacaine, procaine or tetracaine; general anaesthetics such as droperidol, etomidate, fentanyl citrate with droperidol, ketamine hydrochloride, methohexital sodium or thiopental and pharmaceutically acceptable salts (e.g. acid addition salts such as the hydrochloride or hydrobromide or base salts such as sodium, calcium or magnesium salts) or derivatives (e.g. acetates) thereof. Other examples of therapeutics include genetic material such as nucleic acids, RNA, and DNA of natural or synthetic origin, including recombinant RNA and DNA. DNA encoding certain proteins may be used in the treatment of many different types of diseases. For example, tumor necrosis factor or interleukin-2 genes may be provided to treat advanced cancers; thymidine kinase genes may be provided to treat ovarian cancer or brain tumors; interleukin-2 genes may be provided to treat neuroblastoma, malignant melanoma or kidney cancer; and interleukin-4 genes may be provided to treat cancer.

Lipophilic derivatives of drugs linked to the microbubble membrane through hydrophobic interactions may exhibit therapeutic effects as part of the microbubble or after release from the microbubble, e.g. by use of ultrasound. If the drug does not possess the desired physical properties, a lipophilic group may be introduced for anchoring the drug to the membrane. Preferably the lipophilic group should be introduced in a way that does not influence the in vivo potency of the molecule, or the lipophilic group may be cleaved releasing the active drug. Lipophilic groups may be introduced by various chemical means depending on functional groups available in the drug molecule. Covalent coupling may be effected using functional groups in the drug molecule capable of reacting with appropriately functionalised lipophilic compounds. Examples of lipophilic moieties include branched and unbranched alkyl chains, cyclic compounds, aromatic residues and fused aromatic and non-aromatic cyclic systems. In some instances the lipophilic moiety will consist of a suitably functionalised steroid, such as cholesterol or a related compound. Examples of functional groups particularly suitable for derivatisation include nucleophilic groups like amino, hydroxy and sulfhydryl groups. Suitable processes for lipophilic derivatisation of any drug containing a sulfhydryl group, such as captopril, may include direct alkylation, e.g. reaction with an alkyl halide under basic conditions and thiol ester formation by reaction with an activated carboxylic acid. Representative examples of derivatisation of any drug having carboxylic functions, for example atenolol or chlorambucil, include amide and ester formation by coupling respectively with amines and alcohols possessing appropriate physical properties. A preferred embodiment comprises attachment of cholesterol to a therapeutic compound by forming a degradable ester bond.

A preferred application of the present invention relates to angiogenesis, which is the formation of new blood vessels by branching from existing vessels. The primary stimulus for this process may be inadequate supply of nutrients and oxygen (hypoxia) to cells in a tissue. The cells may respond by secreting angiogenetic factors, of which there are many; one example is vascular endothelial growth factor. These factors initiate the secretion of proteolytic enzymes which break down the proteins of the basement membrane, as well as inhibitors which limit the action of these potentially harmful enzymes. The combined effect of loss of attachment and signals from the receptors for angiogenetic factors is to cause the endothelial cells to move, multiply, and rearrange themselves, and finally to synthesise a basement membrane around the new vessels.

Tumors must initiate angiogenesis when they reach millimeter size in order to keep up their rate of growth. As angiogenesis is accompanied by characteristic changes in the endothelial cells and their environment, this process is a promising target for therapeutic intervention. The transformations accompanying angiogenesis are also very promising for diagnosis, a preferred example being malignant disease, but the concept also shows great promise in inflammation and a variety of inflammation-related diseases. These factors are also involved in re-vascularisation of infarcted parts of the myocardium, which occurs if a stenosis is released within a short time.

A number of known receptors/targets associated with angiogenesis are given in subsequent tables. Using the targeting principles described in the present disclosure, angiogenesis mav be detected by the majority of the imaging modalities in use in medicine. Contrast-enhanced ultrasound may possess additional advantages, the contrast medium being microspheres which are restricted to the interior of blood vessels. Even if the target antigens are found on many cell types, the microspheres will attach exclusively to endothelial cells.

So-called prodrugs may also be used in agents according to the invention. Thus drugs may be derivatised to alter their physicochemical properties and to adapt them for inclusion into the reporter; such derivatised drugs may be regarded as prodrugs and are usually inactive until cleavage of the derivatising group regenerates the active form of the drug.

By targeting gas-filled microbubbles containing a prodrug-activating enzyme to areas of pathology, one may image targeting the enzyme, making it possible to visualise when the microbubbles are targeted properly to the area of pathology and at the same time have disappeared from non-target areas. In this way one can determine the optimal time for injection of prodrug into individual patients.

Another alternative is to incorporate the prodrug, prodrug-activating enzyme and vector in the same microbubbles in a system where the prodrug will only be activated after some external stimulus. Such a stimulus may, for example, be a tumour-specific protease as described above, or bursting of the microbubbles by external ultrasound after the desired targeting has been achieved.

Therapeutics may easily be delivered in accordance with the invention to diseased or necrotic areas, for example in the heart, general vasculature, and to the liver, spleen, kidneys and other regions such as the lymph system, body cavities or gastrointestinal system.

Products according to the present invention may be used for targeted therapeutic delivery either in vivo or in vitro. In the latter context the products may be useful in in vitro systems such as kits for diagnosis of different diseases or characterisation of different components in blood or tissue samples. Similar techniques to those used to attach certain blood components or cells to polymer particles (e.g. monodisperse magnetic particles) in vitro to separate them from a sample may be used in the present invention, using the low density of the reporter units in agents of the present invention to effect separation of the gas-containing material by flotation and repeated washing.

Coupling of a reporter unit to a desired vector (and/or therapeutic drug) may be achieved by covalent or non-covalent means, usually involving interaction with one or more functional groups located on the reporter and/or vector and/or any intervening linker group/spacer element. Examples of chemically reactive functional groups which may be employed for this purpose include amino, hydroxyl, sulfhydryl, carboxyl, and carbonyl groups, as well as carbohydrate groups, vicinal diols, thioethers, 2-aminoalcohols, 2-aminothiols, guanidinyl, imidazolyl and phenolic groups.

Covalent coupling of reporter and vector may therefore be effected using linking agents containing reactive moities capable of reaction with such functional groups. Examples of reactive moieties capable of reaction with sulfhydryl groups include α-haloacetyl compounds of the type X—CH$_2$CO— (where X=Br, Cl or I), which show particular reactivity for sulfhydryl groups but which can also be used to modify imidazolyl, thioether, phenol and amino groups as described by Gurd, F. R. N. in *Methods Enzymol.* (1967) 11, 532. N-Maleimide derivatives are also considered selective towards sulfhydryl groups, but may additionaly be useful in coupling to amino groups under certain conditions. N-maleimides may be incorporated into linking systems for reporter-vector conjugation as described by Kitagawa, T. et al. in *Chem. Pharm. Bull.* (1981) 29, 1130 or used as polymer crosslinkers for bubble stabilisation as described by Kovacic, P. et al. in *J. Am. Chem. Soc.* (1959) 81, 1887. Reagents such as 2-iminothiolane, e.g. as described by Traut, R. et al. in *Biochemistry* (1973) 12, 3266, which introduce a thiol group through conversion of an amino group, may be considered as sulfhydryl reagents if linking occurs through the formation of disulphide bridges. Thus reagents which introduce reactive disulphide bonds into either the reporter or the vector may be useful, since linking may be brought about by disulphide exchange between the vector and reporter; examples of such reagents include Ellman's reagent (DTNB), 4,4'-dithiodipyridine, methyl-3-nitro-2-pyridyl disulphide and methyl-2-pyridyl disulphide (described by Kimura, T. et al. in *Analyt. Biochem.* (1982) 122, 271).

Examples of reactive moieties capable of reaction with amino groups include alkylating and acylating agents. Representative alkylating agents include:

i) α-haloacetyl compounds, which show specificity towards amino groups in the absence of reactive thiol groups and are of the type X—CH$_2$CO— (where X=Cl, Br or I), e.g. as described by Wong, Y-H. H. in *Biochemistry* (1979) 24, 5337;

ii) N-maleimide derivatives, which may react with amino groups either through a Michael type reaction or through acylation by addition to the ring carbonyl group as described by Smyth, D. G. et al. in *J. Am. Chem. Soc.* (1960) 82, 4600 and *Biochem. J.* (1964) 91, 589;

iii) aryl halides such as reactive nitrohaloaromatic compounds;

iv) alkyl halides as described by McKenzie, J. A. et al. in *J. Protein Chem.* (1988) 7, 581;

v) aldehydes and ketones capable of Schiff's base formation with amino groups, the adducts formed usually being stabilised through reduction to give a stable amine;

vi) epoxide derivatives such as epichlorohydrin and bisoxiranes,which may react with amino, sulfhydryl or phenolic hydroxyl groups;

vii) chlorine-containing derivatives of s-triazines, which are very reactive towards nucleophiles such as amino, sufhydryl and hydroxy groups;

viii) aziridines based on s-triazine compounds detailed above, e.g. as described by Ross, W. C. J. in *Adv. Cancer Res.* (1954) 2, 1, which react with nucleophiles such as amino groups by ring opening;

ix) squaric acid diethyl esters as described by Tietze, L. F. in *Chem. Ber.* (1991) 124, 1215; and x) α-haloalkyl ethers, which are more reactive alkylating agents than normal alkyl halides because of the activation caused by the ether oxygen atom, e.g. as described by Benneche, T. et al. in *Eur. J. Med. Chem.* (1993) 28, 463.

Representative amino-reactive acylating agents include:

i) isocyanates and isothiocyanates, particularly aromatic derivatives, Which form stable urea and thiourea derivatives respectively and have been used for protein crosslinking as described by Schick, A. F. et al. in *J. Biol. Chem.* (1961) 236, 2477;

ii) sulfonyl chlorides, which have been described by Herzig, D. J. et al. in *Biopolymers* (1964) 2, 349 and which may be useful for the introduction of a fluorescent reporter group into the linker;

iii) Acid halides;

iv) Active esters such as nitrophenylesters or N-hydroxysuccinimidyl esters;

v) acid anhydrides such as mixed, symmetrical or N-carboxyanhydrides;

vi) other useful reagents for amide bond formation as described by Bodansky, M. et al. in *'Principles of Peptide Synthesis'* (1984) Springer-Verlag;

vii) acylazides, e.g. wherein the azide group is generated from a preformed hydrazide derivative using sodium nitrite, e.g. as described by Wetz, K. et al. in *Anal. Biochem.* (1974) 58, 347;

viii) azlactones attached to polymers such as bis-acrylamide, e.g. as described by Rasmussen, J. K. in *Reactive Polymers* (1991) 16, 199; and ix) Imidoesters, which form stable amidines on reaction with amino groups, e.g. as described by Hunter, M. J. and Ludwig, M. L. in *J. Am. Chem. Soc.* (1962) 84, 3491.

Carbonyl groups such as aldehyde functions may be reacted with weak protein bases at a pH such that nucleophilic protein side-chain functions are protonated. Weak bases include 1,2-aminothiols such as those found in N-terminal cysteine residues, which selectively form stable 5-membered thiazolidine rings with aldehyde groups, e.g. as described by Ratner, S. et al. in *J. Am. Chem. Soc.* (1937) 59, 200. Other weak bases such as phenyl hydrazones may be used, e.g. as described by Heitzman, H. et al. in *Proc. Natl. Acad. Sci. USA* (1974) 71, 3537.

Aldehydes and ketones may also be reacted with amines to form Schiff's bases, which may advantageously be stabilised through reductive amination. Alkoxylamino moieties readily react with ketones and aldehydes to produce stable alkoxamines, e.g. as described by Webb, R. et al. in *Bioconjugate Chem.* (1990) 1, 96.

Examples of reactive moieties capable of reaction with carboxyl groups include diazo compounds such as diazoacetate esters and diazoacetamides, which react with high specificity to generate ester groups, e.g. as described by Herriot R. M. in *Adv. Protein Chem.* (1947) 3, 169. Carboxylic acid modifying reagents such as carbodiimides, which react through O-acylurea formation followed by amide bond formation, may also usefully be employed; linking may be facilitated through addition of an amine or may result in direct vector-receptor coupling. Useful water soluble carbodiimides include 1-cyclohexyl-3-(2-morpholinyl-4-ethyl)carbodiimide (CMC) and 1-ethyl-3-(3-dimethylaminopropyl)carbodiimide (EDC), e.g. as described by Zot, H. G. and Puett, D. in *J. Biol. Chem.* (1989) 264, 15552. Other useful carboxylic acid modifying reagents include isoxazolium derivatives such as Woodwards reagent K; chloroformates such as p-nitrophenylchloroformate; carbonyldiimidazoles such as 1,1'-carbonyldiimidazole; and N-carbalkoxydihydroquinolines such as N-(ethoxycarbonyl)-2-ethoxy-1,2-dihydroquinoline.

Other potentially useful reactive moieties include vicinal diones such as p-phenylenediglyoxal, which may be used to react with guanidinyl groups, e.g. as described by Wagner et al. in *Nucleic acid Res.* (1978) 5, 4065; and diazonium salts, which may undergo electrophilic substitution reactions, e.g. as described by Ishizaka, K. and Ishizaka T. in *J. Immunol.* (1960) 85, 163. Bis-diazonium compounds are readily prepared by treatment of aryl diamines with sodium nitrite in acidic solutions. It will be appreciated that functional groups in the reporter and/or vector may if desired be converted to other functional groups prior to reaction, e.g. to confer additional reactivity or selectivity. Examples of methods useful for this purpose include conversion of amines to carboxylic acids using reagents such as dicarboxylic anhydrides; conversion of amines to thiols using reagents such as N-acetylhomocysteine thiolactone, S-acetylmercaptosuccinic anhydride, 2-iminothiolane or thiol-containing succinimidyl derivatives; conversion of thiols to carboxylic acids using reagents such as α-haloacetates; conversion of thiols to amines using reagents such as ethylenimine or 2-bromoethylamine; conversion of carboxylic acids to amines using reagents such as carbodiimides followed by diamines; and conversion of alcohols to thiols using reagents such as tosyl chloride followed by transesterification with thioacetate and hydrolysis to the thiol with sodium acetate.

Vector-reporter coupling may also be effected using enzymes as zero-length linking agents; thus, for example, transglutaminase, peroxidase and xanthine oxidase may be used to produce linked products. Reverse proteolysis may also be used for linking through amide bond formation.

Non-covalent vector-reporter coupling may, for example, be effected by electrostatic charge interactions e.g. between a polylysinyl-functionalised reporter and a polyglutamyl-functionalised vector, through chelation in the form of stable metal complexes or through high affinity binding interaction such as avidin/biotin binding. Polylysine, coated non-covalently to a negatively charged membrane surface may also increase non-specifically the affinity of a microbubble for a cell through charge interactions.

Alternatively, a vector may be coupled to a protein known to bind phospholipids. In many instances, a single molecule of phospholipid may attach to a protein such as a translocase, while other proteins may attach to surfaces consisting mainly of phospholipid head groups and so may be used to attach vectors to phospholipid microspheres; one example of such a protein is β2-glycoprotein I (Chonn, A., Semple, S. C. and Cullis, P. R., *Journal of Biological Chemistry* (1995) 270, 25845–25849). Phosphatidylserine-binding proteins have been described, e.g. by Igarashi, K. et al. in *Journal of Biological Chemistry* 270(49), 29075–29078; a conjugate of a vector with such a phosphatidylserine-binding protein may therefore be used to attach the vector to phosphatidylserine-encapsulated microbubbles. When the amino acid sequence of a binding protein is known, the phospholipid-binding portion may be synthesised or isolated and used for conjugation with a vector, thus avoiding the biological activity which may be located elsewhere in the molecule.

It is also possible to obtain molecules that bind specifically to the surface (or in the "membrane") of microspheres by direct screening of molecular libraries for microsphere-binding molecules. For example, phage libraries displaying small peptides may be used for such selection. The selection may be made by simply mixing the microspheres and the phage display library and eluting the phages binding to the floating microspheres. If desired, the selection may be done under "physiological conditions" (e.g. in blood) to eliminate peptides which cross-react with blood components. An advantage of this type of selection procedure is that only binding molecules that do not destabilise the microspheres should be selected, since only binding molecules attached to intact floating microspheres will rise to the top. It may also be possible to introduce some kind of "stress" during the selection procedure (e.g. pressure) to ensure that destabilising binding moieties are not selected. Furthermore the selection may be done under shear conditions, for example by first letting the phages react with the microspheres and then letting the microspheres pass through a surface coated with anti-phage antibodies under flow conditions. In this way it may be possible to select binders which may resist shear conditions present in vivo. Binding moieties identified in this way may be coupled (by chemical conjugation or via peptide synthesis, or at the DNA-level for recombinant vectors) to a vector molecule, constituting a general tool for attaching any vector molecule to the microspheres.

A vector which comprises or is coupled to a peptide, lipo-oligosaccharide or lipopeptide linker which contains a element capable of mediating membrane insertion may also be useful. One example is described by Leenhouts, J. M. et al. in *Febs Letters* (1995) 370(3), 189–192. Non-bioactive molecules consisting of known membrane insertion anchor/ signal groups may also be used as vectors for certain applications, an example being the H1 hydrophobic segment from the Na,K-ATPase $\alpha$-subunit described by Xie, Y. and Morimoto, T. in *J. Biol. Chem.* (1995) 270(20), 11985–11991. The anchor group may also be fatty acid(s) or cholesterol.

Coupling may also be effected using avidin or streptavidin, which have four high affinity binding sites for biotin. Avidin may therefore be used to conjugate vector to reporter if both vector and reporter are biotinylated. Examples are described by Bayer, E. A. and Wilchek, M. in *Methods Biochem. Anal.* (1980) 26, 1. This method may also be extended to include linking of reporter to reporter, a process which may encourage bubble association and consequent potentially increased echogenicity. Alternatively, avidin or streptavidin may be attached directly to the surface of reporter microparticles.

Non-covalent coupling may also utilise the bifunctional nature of bispecific immunoglobulins. These molecules can specifically bind two antigens, thus linking them. For example, either bispecific IgG or chemically engineered bispecific F(ab)'2 fragments may be used as linking agents. Heterobifunctional bispecific antibodies have also been reported for linking two different antigens, e.g. as described by Bode, C. et al. in *J. Biol. Chem.* (1989) 264, 944 and by Staerz, U. D. et al. in *Proc. Natl. Acad. Sci. USA* (1986) 83, 1453. Similarly, any reporter and/or vector containing two or more antigenic determinants (e.g. as described by Chen, Aa et al. in *Am. J. Pathol.* (1988) 130, 216) may be crosslinked by antibody molecules and lead to formation of multi-bubble cross-linked assemblies of potentially increased echogenicity.

Linking agents used in accordance with the invention will in general bring about linking of vector to reporter or reporter to reporter with some degree of specificity, and may also be used to attach one or more therapeutically active agents.

In some instances it is considered advantageous to include a PEG component as a stabiliser in conjunction with a vector or vectors or directly to the reporter in the same molecule where the PEG does not serve as a spacer.

So-called zero-length linking agents, which induce direct covalent joining of two reactive chemical groups without introducing additional linking material (e.g. as in amide bond formation induced using carbodiimides or enzymatically) may, if desired, be used in accordance with the invention, as may agents such as biotin/avidin systems which induce non-covalent reporter-vector linking and agents which induce hydrophobic or electrostatic interactions.

Most commonly, however, the linking agent will comprise two or more reactive moieties, e.g. as described above, connected by a spacer element. The presence of such a spacer permits bifunctional linkers to react with specific functional groups within a molecule or between two different molecules, resulting in a bond between these two components and introducing extrinsic linker-derived material into the reporter-vector conjugate. The reactive moieties in a linking agent may be the same (homobifunctional agents) or different (heterobifunctional agents or, where several dissimilar reactive moieties are present, heteromultifunctional agents), providing a diversity of potential reagents that may bring about covalent bonding between any chemical species, either intramolecularly or intermolecularly.

The nature of extrinsic material introduced by the linking agent may have a critical bearing on the targeting ability and general stability of the ultimate product. Thus it may be desirable to introduce labile linkages, e.g. containing spacer arms which are biodegradable or chemically sensitive or which incorporate enzymatic cleavage sites. Alternatively the spacer may include polymeric components, e.g. to act as surfactants and enhance bubble stability. The spacer may also contain reactive moieties, e.g. as described above to enhance surface crosslinking, or it may contain a tracer element such as a fluorescent probe, spin label or radioactive material.

Contrast agents according to the present invention are therefore useful in all imaging modalities since contrast elements such as X-ray contrast agents, light imaging probes, spin labels or radioactive units may readily be incorporated in or attached to the reporter units.

Spacer elements may typically consist of aliphatic chains which effectively separate the reactive moieties of the linker by distances of between 5 and 30 Å. They may also comprise macromolecular structures such as PEGs, which have been given much attention in biotechnical and biomedical applications (see e.g. Milton Harris, J. (ed) "*Poly(ethylene glycol) chemistry, biotechnical and biomedical applications*" Plenum Press, New York, 1992). PEGs are soluble in most solvents, including water, and are highly hydrated in aqueous environments, with two or three water molecules bound to each ethylene glycol segment; this has the effect of preventing adsorption either of other polymers or of proteins onto PEG-modified surfaces. PEGs are known to be non-toxic and not to harm active proteins or cells, whilst covalently linked PEGs are known to be non-immunogenic and non-antigenic. Furthermore, PEGs may readily be modified and bound to other molecules with only little effect on their chemistry. Their advantageous solubility and biological properties are apparent from the many possible uses of PEGs and copolymers thereof, including block copolymers such as PEG-polyurethanes and PEG-polypropylenes.

Appropriate molecular weights for PEG spacers used in accordance with the invention may, for example, be between 120 Daltons and 20 kDaltons.

The major mechanism for uptake of particles by the cells of the reticuloendothelial system (RES) is opsonisation by plasma proteins in blood; these mark foreign particles which are then taken up by the RES. The biological properties of PEG spacer elements used in accordance with the invention may serve to increase contrast agent circulation time in a similar manner to that observed for PEGylated liposomes (see e.g. Klibanov, A. L. et al. in *FEBS Letters* (1990) 268, 235–237 and Blume, G. and Cevc, G. in *Biochim. Biophys. Acta* (1990) 1029, 91–97). Increased coupling efficiency to areas of interest may also be achieved using antibodies bound to the terminii of PEG spacers (see e.g. Maruyama, K. et al. in *Biochim. Biophys. Acta* (1995) 1234, 74–80 and Hansen, C. B. et al. in *Biochim. Biophys. Acta* (1995) 1239, 133–144).

In some instances it is considered advantageous to include a PEG component as a stabiliser in conjunction with a vector or vectors or directly to the reporter in the same molecule where the PEG does not serve as a spacer.

Other representative spacer elements include structural-type polysaccharides such as polygalacturonic acid, glycosaminoglycans, heparinoids, cellulose and marine polysaccharides such as alginates, chitosans and carrageenans; storage-type polysaccharides such as starch, glycogen, dextran and aminodextrans; polyamino acids and methyl and ethyl esters thereof, as in homo- and co-polymers of lysine, glutamic acid and aspartic acid; and polypeptides, oligosaccharides and oligonucleotides, which may or may not contain enzyme cleavage sites.

In general, spacer elements may contain cleavable groups such as vicinal glycol, azo, sulfone, ester, thioester or disulphide groups. Spacers containing biodegradable methylene diester or diamide groups of formula

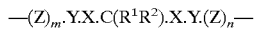

[where X and Z are selected from —O—, —S—, and —NR— (where R is hydrogen or an organic group); each Y is a carbonyl, thiocarbonyl, sulphonyl, phosphoryl or similar acid-forming group: m and n are each zero or 1; and $R^1$ and $R^2$ are each hydrogen, an organic group or a group —X.Y.$(Z)_m$—, or together form a divalent organic group] may also be useful; as discussed in, for example, WO-A-9217436 such groups are readily biodegraded in the presence of esterases, e.g. in vivo, but are stable in the absence of such enzymes. They may therefore advantageously be linked to therapeutic agents to permit slow release thereof.

Poly[N-(2-hydroxyethyl)methacrylamides] are potentially useful spacer materials by virtue of their low degree of interaction with cells and tissues (see e.g. Volfová, I., Říhová, B. and V. R. and Vetvicka, P. in *J. Bioact. Comp. Polymers* (1992) 7, 175–190). Work on a similar polymer consisting mainly of the closely related 2-hydroxypropyl derivative showed that it was endocytosed by the mononuclear phagocyte system only to a rather low extent (see Goddard, P., Williamson, I., Bron, J., Hutchinson, L. E., Nicholls, J. and Petrak, K. in *J. Bioct. Compat. Polym.* (1991) 6, 4–24.).

Other potentially useful polymeric spacer materials include:

i) copolymers of methyl methacrylate with methacrylic acid; these may be erodible (see Lee, P. I. in *Pharm. Res.* (1993) 10, 980) and the carboxylate substituents may cause a higher degree of swelling than with neutral polymers;

ii) block copolymers of polymethacrylates with biodegradable polyesters (see e.g. San Roman, J. and Guillen-Garcia, P. in *Biomaterials* (1991) 12, 236–241);

ii) cyanoacrylates, i.e. polymers of esters of 2-cyanoacrylic acid—these are biodegradable and have been used in the form of nanoparticles for selective drug delivery (see Forestier, F., Gerrier, P., Chaumard, C., Quero, A. M., Couvreur, P. and Labarre, C. in *J. Antimicrob. Chemoter.* (1992) 30, 173–179);

iv) polyvinyl alcohols, which are water-soluble and generally regarded as biocompatible (see e.g. Langer, R. in *J. Control. Release* (1991) 16, 53–60);

v) copolymers of vinyl methyl ether with maleic anhydride, which have been stated to be bioerodible (see Finne, U., Hannus, M. and Urtti, A. in *Int. J. Pharm.* (1992) 78. 237–241);

vi) polyvinylpyrrolidones, e.g. with molecular weight less than about 25,000, which are rapidly filtered by the kidneys (see Hespe, W., Meier, A. M. and Blankwater, Y. M. in *Arzeim.-Forsch./Drug Res.* (1977) 27, 1158–1162);

vii) polymers and copolymers of short-chain aliphatic hydroxyacids such as glycolic, lactic, butyric, valeric and caproic acids (see e.g. Carli, F. in *Chim. Ind.* (Milan) (1993) 75, 494–9), including copolymers which incorporate aromatic hydroxyacids in order to increase their degradation rate (see Imasaki, K., Yoshida, M., Fukuzaki, H., Asano, M., Kumakura, M., Mashimo, T., Yamanaka, H. and Nagai. T. in *Int. J. Pharm.* (1992) 81, 31–38);

viii) polyesters consisting of alternating units of ethylene glycol and terephthalic acid, e.g. Dacron®, which are non-degradable but highly biocompatible;

ix) block copolymers comprising biodegradable segments of aliphatic hydroxyacid polymers (see e.g. Younes, H., Nataf, P. R., Cohn, D., Appelbaum, Y. J., Pizov, G. and Uretzky, G. in *Biomater. Artif. Cells Artif. Organs* (1988) 16, 705–719), for instance in conjunction with polyurethanes (see Kobayashi, H., Hyon, S. H. and Ikada, Y. in "Water-curable and biodegradable prepolymers"—*J. Biomed. Mater. Res.* (1991) 25, 1481–1494);

x) polyurethanes, which are known to be well-tolerated in implants, and which may be combined with flexible "soft" segments, e.g. comprising poly(tetra methylene glycol), poly(propylene glycol) or poly(ethylene glycol) and aromatic "hard" segments, e.g. comprising 4,4'-methylenebis(phenylene isocyanate) (see e.g. Ratner, B. D., Johnston, A. B. and Lenk, T. J. in *J. Biomed. Mater. Res: Applied Biomaterials* (1987) 21, 59–90; Sa Da Costa, V. et al. in *J. Coll. Interface Sci.* (1981) 80, 445–452 and Affrossman, S. et al. in *Clinical Materials* (1991) 8, 25–31);

xi) poly(1,4-dioxan-2-ones), which may be regarded as biodegradable esters in view of their hydrolysable ester linkages (see e.g. Song, C. X., Cui, X. M. and Schindler, A. in *Med. Biol. Eng. Comput.* (1993) 31, S147–150), and which may include glycolide units to improve their absorbability (see Bezwada, R. S., Shalaby, S. W. and Newman, H. D. J. in *Agricultural and synthetic polymers: Biodegradability and utilization* (1990) (ed Glass, J. E. and Swift, G.), 167–174—ACS symposium Series, #433, Washington D.C., U.S.A.—American Chemical Society);

xii) polyanhydrides such as copolymers of sebacic acid (octanedioic acid) with bis(4-carboxy-phenoxy) propane, which have been shown in rabbit studies (see Brem, H., Kader, A., Epstein, J. I., Tamargo, R. J., Domb, A., Langer, R. and Leong, K. W. in *Sel. Cancer Ther.* (1989) 5, 55–65) and rat studies (see Tamargo, R. J., Epstein, J. I., Reinhard, C. S., Chasin, M. and Brem, H. in *J. Biomed. Mater. Res.* (1989) 23, 253–266) to be useful for controlled release of drugs in the brain without evident toxic effects;

xiii) biodegradable polymers containing ortho-ester groups, which have been employed for controlled release in vivo (see Maa, Y. F. and Heller, J. in *J. Control. Release* (1990) 14, 21–28); and xiv) polyphosphazenes, which are inorganic polymers consisting of alternate phosphorus and nitrogen atoms (see Crommen, J. H., Vandorpe, J. and Schacht, E. H. in *J. Control. Release* (1993) 24, 167–180).

The following tables list linking agents and agents for protein modification which may be useful in preparing targetable agents in accordance with the invention.

Heterobifunctional Linking Agents

| Linking agent | Reactivity 1 | Reactivity 2 | Comments |
|---|---|---|---|
| ABH | carbohydrate | photoreactive | |
| ANB-NOS | $-NH_2$ | photoreactive | |
| APDP(1) | -SH | photoreactive | iodinable disulphide linker |
| APG | $-NH_2$ | photoreactive | reacts selectively with Arg at pH 7–8 |
| ASIB(1) | -SH | photoreactive | iodinable |
| ASBA(1) | -COOH | photoreactive | iodinable |
| EDC | $-NH_2$ | -COOH | zero-length linker |
| GMBS | $-NH_2$ | -SH | |
| sulfo-GMBS | $-NH_2$ | -SH | water-soluble |
| HSAB | $-NH_2$ | photoreactive | |
| sulfo-HSAB | $-NH_2$ | photoreactive | water-soluble |
| MBS | $-NH_2$ | -SH | |
| sulfo-MBS | $-NH_2$ | -SH | water-soluble |
| $M_2C_2H$ | carbohydrate | -SH | |
| MPBH | carbohydrate | -SH | |
| NHS-ASA(1) | $-NH_2$ | photoreactive | iodinable |
| sulfo-NHS-ASA(1) | $-NH_2$ | photoreactive | water-soluble, iodinable |
| sulfo-NHS-LC-ASA(1) | $-NH_2$ | photoreactive | water-soluble, iodinable |
| PDPH | carbohydrate | -SH | disulphide linker |
| PNP-DTP | $-NH_2$ | photoreactive | |
| SADP | $-NH_2$ | photoreactive | disulphide linker |
| sulfo-SADP | $-NH_2$ | photoreactive | water-soluble disulphide linker |
| SAED | $-NH_2$ | photoreactive | disulphide linker |
| SAND | $-NH_2$ | photoreactive | water-soluble disulphide linker |
| SANPAH | $-NH_2$ | photoreactive | |
| sulfo-SANPAH | $-NH_2$ | photoreactive | water-soluble |
| SASD(1) | $-NH_2$ | photoreactive | water-soluble iodinable disulphide linker |
| SIAB | $-NH_2$ | -SH | |
| sulfo-SIAB | $-NH_2$ | -SH | water-soluble |
| SMCC | $-NH_2$ | -SH | |
| sulfo-SMCC | $-NH_2$ | -SH | water-soluble |
| SMPB | $-NH_2$ | -SH | |
| sulfo-SMPB | $-NH_2$ | -SH | water-soluble |
| SMPT | $-NH_2$ | -SH | |
| sulfo-LC-SMPT | $-NH_2$ | -SH | water-soluble |
| SPDP | $-NH_2$ | -SH | |
| sulfo-SPDP | $-NH_2$ | -SH | water-soluble |
| sulfo-LC-SPDP | $-NH_2$ | -SH | water-soluble |
| sulfo-SAMCA(2) | $-NH_2$ | photoreactive | |
| sulfo-SAPB | $-NH_2$ | photoreactive | water-soluble |

Notes: (1) = iodinable; (2) = fluorescent

Homobifunctional Linking Agents

| Linking agent | Reactivity | Comments |
|---|---|---|
| BS | $-NH_2$ | |
| BMH | -SH | |
| BASED(1) | photoreactive | iodinable disulphide linker |
| BSCOES | $-NH_2$ | |
| sulfo-BSCOES | $-NH_2$ | water-soluble |
| DFDNB | $-NH_2$ | |
| DMA | $-NH_2$ | |
| DMP | $-NH_2$ | |
| DMS | $-NH_2$ | |
| DPDPB | -SH | disulphide linker |
| DSG | $-NH_2$ | |
| DSP | $-NH_2$ | disulphide linker |
| DSS | $-NH_2$ | |
| DST | $-NH_2$ | |
| sulfo-DST | $-NH_2$ | water-soluble |
| DTBP | $-NH_2$ | disulphide linker |
| DTSSP | $-NH_2$ | disulphide linker |
| EGS | $-NH_2$ | |
| sulfo-EGS | $-NH_2$ | water-soluble |
| SPBP | $-NH_2$ | |

Biotinylation Agents

| Agent | Reactivity | Comments |
|---|---|---|
| biotin-BMCC | -SH | |
| bitoin-DPPE* | | preparation of biotinylated liposomes |
| biotin-LC-DPPE* | | preparation of biotinylated liposomes |
| biotin-HPDP | -SH | disulphide linker |
| biotin-hydrazide | carbohydrate | |
| biotin-LC-hydrazide | carbohydrate | |
| iodoacetyl-LC-biotin | $-NH_2$ | |
| NHS-iminobiotin | $-NH_2$ | reduced affinity for avidin |
| NHS-SS-biotin | $-NH_2$ | disulphide linker |
| photoactivatable biotin | nucleic acids | |
| sulfo-NHS-biotin | $-NH_2$ | water-soluble |
| sulfo-NHS-LC-biotin | $-NH_2$ | |

Notes: DPPE = dipalmitoylphosphatidylethanolamine; LC = long chain

Agents for Protein Modification

| Agent | Reactivity | Function |
|---|---|---|
| Ellman's reagent | -SH | quantifies/detects/protects |
| DTT | -S.S- | reduction |
| 2-mercaptoethanol | -S.S- | reduction |
| 2-mercaptylamine | -S.S- | reduction |
| Traut's reagent | $-NH_2$ | introduces -SH |
| SATA | $-NH_2$ | introduces protected -SH |
| AMCA-NHS | $-NH_2$ | fluorescent labelling |
| AMCA-hydrazide | carbohydrate | fluorescent labelling |
| AMCA-HPDP | -S.S- | fluorescent labelling |
| SBF-chloride | -S.S- | fluorescent detection of -SH |
| N-ethylmaleimide | -S.S- | blocks -SH |
| NHS-acetate | $-NH_2$ | blocks and acetylates $-NH_2$ |

-continued

| Agent | Reactivity | Function |
|---|---|---|
| citraconic anhydride | -NH$_2$ | reversibly blocks and introduces negative charges |
| DTPA | -NH$_2$ | introduces chelator |
| BNPS-skatole | tryptophan | cleaves tryptophan residue |
| Bolton-Hunter | -NH$_2$ | introduces iodinable group |

Other potentially useful protein modifications include partial or complete deglycosidation by neuraminidase, endoglycosydases or periodate, since deglycosidation often results in less uptake by liver, spleen, macrophages etc., whereas neo-glycosylation of proteins often results in increased uptake by the liver and macrophages); preparation of truncated forms by proteolytic cleavage, leading to reduced size and shorter half life in circulation; and cationisation, e.g. as described by Kumagi et al. in *J. Biol. Chem.* (1987) 262, 15214–15219; Triguero et al. in *Proc. Natl. Acad. Sci. USA* (1989) 86, 4761–4765; Pardridge et al. in *J. Pharmacol. Exp. Therap.* (1989) 251, 821–826 and Pardridge and Boado, *Febs Lett.* (1991) 288, 30–32.

Vectors which may be usefully employed in targetable agents according to the invention include the following:

i) Antibodies, which can be used as vectors for a very wide range of targets, and which have advantageous properties such as very high specificity, high affinity (if desired), the possiblity of modifying affinity according to need etc. Whether or not antibodies will be bioactive will depend on the specific vector/target combination. Both conventional and genetically engineered antibodies may be employed, the latter permitting engineering of antibodies to particular needs, e.g. as regards affinity and specificity. The use of human antibodies may be preferred to avoid possible immune reactions against the vector molecule. A further useful class of antibodies comprises so-called bi- and multi-specific antibodies, i.e. antibodies having specificity for two or more different antigens in one antibody molecule. Such antibodies may, for example, be useful in promoting formation of bubble clusters and may also be used for various therapeutic purposes, e.g. for carrying toxic moieties to the target. Various aspects of bispecific antibodies are described by McGuinness, B. T. et al. in *Nat. Biotechnol.* (1996) 14, 1149–1154; by George, A. J. et al. in *J. Immunol.* (1994) 152, 1802–1811; by Bonardi et al. in *Cancer Res.* (1993) 53, 3015–3021; and by French, R. R. et al. in *Cancer Res.* (1991) 51, 2353–2361.

ii) Cell adhesion molecules, their receptors, cytokines, growth factors, peptide hormones and pieces thereof. Such vectors rely on normal biological protein-protein interactions with target molecule receptors, and so in many cases will generate a biological response on binding with the targets and thus be bioactive; this may be a relatively insignificant concern with vectors which target proteoglycans.

iii) Non-peptide agonists/antagonists or non-bioactive binders of receptors for cell adhesion molecules, cytokines, growth factors and peptide hormones. This category may include non-bioactive vectors which will be neither agonists nor antagonist but which may nonetheless exhibit valuable targeting ability.

iv) oligonucleotides and modified oligonucleotides which bind DNA or RNA through Watson-Crick or other types of base-pairing. DNA is usually only present in extrecelluar space as a consequence of cell damage, so that such oligonucleotides, which will usually be non-bioactive, may be useful in, for example, targeting of necrotic regions, which are associated with many different pathological conditions. Oligonucleotides may also be designed to bind to specific DNA- or RNA-binding proteins, for example transcription factors which are very often highly overexpressed or activated in tumour cells or in activated immune or endothelial cells. Combinatorial libraries may be used to select oligonucleotides which bind specifically to any possible target molecules and which therefore may be employed as vectors for targeting.

v) DNA-binding drugs may behave similarly to oligonuclotides, but may exhibit biological acitvity and/or toxic effects if taken up by cells.

vi) Protease substrates/inhibitors. Proteases are involved in many pathological conditions. Many substrates/inhibitors are non-peptidic but, at least in the case of inhibitors, are often bioactive.

vii) Vector molecules may be generated from combinatorial libraries without necessarily knowing the exact molecular target, by functionally selecting (in vitro, ex vivo or in vivo) for molecules binding to the region/structure to be imaged.

viii) Various small molecules, including bioactive compounds known to bind to biological receptors of various kinds. Such vectors or their targets may be used for generate non-bioactive compounds binding to the same targets.

ix) Proteins or peptides which bind to glucosamioglycan side chains e.g. heparan sulphate, including glucosoaminoglycan-binding portions of larger molecules, as binding to glucosoaminoglycans does not result in a biological response. Proteoglycans are not found on red blood cells, which eliminates undesirable adsorption to these cells.

Other peptide vectors and lipopeptides thereof of particular interest for targeted ultrasound imaging are listed below: Atherosclerotic plaque binding peptides such as YRALVDTLK (SEQ ID NO:26), YAKFRETLEDTRDRMY (SEQ ID NO:27) and RALVDTEFKVKQEAGAK (SEQ ID NO:28); Thrombus binding peptides such as NDGDFEEIPEEYLQ (SEQ ID NO:29) and GPRG (SEQ ID NO:30), Platelet binding peptides such as PLYKKIIKKLLES (SEQ ID NO:31); and cholecystokinin, α-melanocyte-stimulating hormone, heat stable enterotoxin 1, vasoactive intestinal peptide, synthetic alpha-M2 peptide from the third heavy chain complementarity-determininig region and analogues thereof for tumour targeting.

The following tables identify various vectors which may be targeted to particular types of targets and indicated areas of use for targetable diagnostic and/or therapeutic agents according to the invention which contain such vectors.

Protein and Peptide Vectors—Antibodies

| Vector type | Target | Comments/areas of use | Ref |
|---|---|---|---|
| antibodies (general) | CD34 | vascular diseases in general, normal vessel wall (e.g myocardium), activated endothelium, immune cells | 1 |
| antibodies (general) | ICAM-1 | vascular diseases in general normal vessel wall (e.g myocardium), activated endothelium, immune cells | 1 |
| antibodies (general) | ICAM-2 | vascular diseases in general normal vessel wall (e.g myocardium), activated endothelium, immune cells | 1 |
| antibodies (general) | ICAM-3 | vascular diseases in general normal vessel wall (e.g | 1 |

-continued

| Vector type | Target | Comments/areas of use | Ref |
|---|---|---|---|
| antibodies (general) | E-selectin | myocardium), activated endothelium, immune cells vascular diseases in general normal vessel wall (e.g myocardium), activated endothelium, immune cells | 1 |
| antibodies (general) | P-selectin | vascular diseases in general normal vessel wall (e.g myocardium), activated endothelium, immune cells | 1 |
| antibodies (general) | PECAM | vascular diseases in general normal vessel wall (e.g myocardium), activated endothelium, immune cells | 1 |
| antibodies (general) | Integrins, e.g. VLA-1, VLA-2, VLA-3, VLA-4, VLA-5, VLA-6, $\beta_1\alpha_7$, $\beta_1\alpha_8$, $\beta_1\alpha_v$, LFA-1, Mac-1, CD41a, etc. | vascular diseases in general normal vessel wall (e.g myocardium), activated endothelium, immune cells | 2 |
| antibodies (general) | GlyCAM | Vessel wall in lymph nodes (quite specific for lymph nodes) | 3 |
| antibodies (general) | MadCam 1 | Vessel wall in lymph nodes (quite specific for lymph nodes) | 3 |
| antibodies (general) | fibrin | Thrombi | 4 |
| antibodies (general) | Tissue Factor | Activated endothelium, tumours | 5 |
| antibodies (general) | Myosin | Necrosis, myocardial infaction | 6 |
| antibodies (general) | CEA (carcino-embryonal antigen) | Tumours | 7 |
| antibodies (general) | Mucins | Tumours | 8 |
| antibodies (general) | Multiple drug resistance protein | Tumours | 9 |
| antibodies (general) | Prostate specific antigen | Prostate cancer | |
| antibodies (general) | Cathepsin B | Tumours (proteases of various kinds are often more or less specifically overexpressed in a variety of tumours - Cathepsin B is such a protease) | 10 |
| antibodies (general) | Transferrin receptor | Tumours, vessel wall | 11 |
| MoAb 9.2.27 | | Tumours | 12 |
| | VAP-1 | Antigen unregulated on cell growth Adhesion molecule | 13 |
| | Band 3 protein | Upregulated during phagocytic activity | |
| antibodies | CD34 (sialomucin) | endothelial cells | |
| antibodies | CD 31 (PECAM-1) | endothelial cells | |
| antibodies | intermediate filaments necrotic cells/tissue CD44 | tumour cells | a |
| antibodies | $\beta$2-microglobulin | general | b |
| antibodies | MHC class 1 | general | b |
| antibodies | integrin | tumours; angiogenesis | c |
| antibodies | $\alpha v \beta 3$ | | |

REFERENCES a) Heider, K. H., M. Sproll, S. Susani, E. Patzelt, P. Beaumier, E. Ostermann, H. Ahorn, and G. R. Adolf. 1996. "Characterization of a high-affinity monoclonal antibody specific for CD44v6 as candidate for immunotherapy of squamous cell carcinomas". *Cancer Immunology Immunotherapy* 43: 245–253.

b) I. Roitt, J. Brostoff, and D. Male. 1985. *Immunology*, London: Gower Medical Publishing, p. 4.7 c) Stromblad, S., and D. A. Cheresh. 1996. "Integrins, angiogenesis and vascular cell survival". *Chemistry & Biology* 3: 881–885.

Protein and Peptide Vectors—Cell Adhesion Molecules etc.

| Vector type | Target | Comments/areas of use | Ref |
|---|---|---|---|
| L-selectin | CD34 MadCAM1 GlyCam 1 | vascular diseases in general, normal vessel wall (e.g myocardium), activated endothelium, Lymph nodes | 3 |
| Other selectins | carbohydrate ligands (sialyl Lewis x) heparan sulfate | vascular diseases in general, normal vessel wall (e.g myocardium), activated endothelium | 14 |
| RGD-peptides | integrins | vascular diseases in general, normal vessel wall (e.g myocardium), activated endothelium | 2 |
| PECAM | PECAM, and other | Endothelium, Cells in immune system | 15 |
| Integrins, e.g. VLA-1, VLA-2, VLA-3, VLA-4, VLA-5, VLA-6, $\beta_1\alpha_7$, $\beta_1\alpha_8$, $\beta_1\alpha_v$, LFA-1, Mac-1, CD41a, etc. | Laminin, collagen, fibronectin, VCAM-1, thrombospondin, vitronectin etc. | Endothelium, Vessel wall etc. | 16 |
| Integrin receptors, e.g. Laminin, collagen, fibronectin, VCAM-1, thrombospondin, vitronectin etc. | Integrins, e.g. VLA-1, VLA-2, VLA-3, VLA-4, VLA-5, VLA-6, $\beta_1\alpha_7$, $\beta_1\alpha_8$, $\beta_1\alpha_v$, LFA-1, Mac-1, CD41a, etc. | Cells in immune system vessel wall etc. | 17 18 |
| Nerve cell adhesion molecule (N-CAM) | proteoglycans N-CAM (homophilic) | | 19 |
| integrin $\alpha v \beta 3$ | CD31 (PECAM-1) | endothelial cells | |
| RGD-peptides | integrins | angiogenesis | c |

Vectors Comprising Cytokines/growth Factors/peptide Hormones and Fragments Thereof

| Vector type | Target | Comments/areas of use | Ref |
|---|---|---|---|
| Epidermal growth factor | EGF-receptor or related receptors | Tumours | 20 |
| Nerve growth factor | NGF-receptor | Tumours | 21 |
| Somatostatin | ST-receptor | Tumours | 22 |
| Endothelin | Endothelin-receptor | Vessel wall | |
| Interleukin-1 | IL-1-receptor | Inflammation, activated cells of different kinds | 23 |
| Interleukin-2 | IL-2-receptor | Inflammation, activated | 24 |

-continued

| Vector type | Target | Comments/areas of use | Ref |
|---|---|---|---|
| Chemokines (ca. 20 different cytokines partly sharing receptors) | Chemokine receptors, proteoglycans | cells of different kinds Inflammation | 25 |
| Tumour necrosis factor | TNF-receptors | Inflammation | |
| Parathyroid hormone | PTH-receptors | Bone diseases Kidney diseases | |
| Bone Morphogenetic Protein | BMP-receptors | Bone Diseases | |
| Calcitonin | CT-receptors | Bone diseases | |
| Colony stimulating factors (G-CSF, GM-CSF, M-CSF, IL-3) | Corresponding specific receptors, proteoglycans | Endothelium | 26 |
| Insulin like growth factor I | IGF-I receptor | Tumours, other growing tissues | |
| Atrial Natriuretic Factor | ANF-receptors | Kidney, vessel wall | |
| Vasopressin | Vasopressin receptor | Kidney, vessel wall | |
| VEGF | VEGF-receptor | Endothelium, regions of angiogenesis | |
| Fibroblast growth factors | FGF-receptors, Proteoglycans | Endothelium Angiogenesis | 27 |
| Schwann cell growth factor | proteoglycans specific receptors | | 28 |

Miscellaneous Protein and Peptide Vectors

| Vector type | Target | Comments/areas of use | Ref |
|---|---|---|---|
| Streptavidin | Kidney | Kidney diseases | 29 |
| Bacterial fibronectin-binding proteins | Fibronectin | Vessel wall | 30 |
| Fc-part of antibodies | Fc-receptors | Monocytes macrophages liver | 31 |
| Transferrin | transferrin-receptor | Tumours vessel walls | 11 |
| Streptokinase/tissue plasminogen activator | thrombi | thrombi | |
| Plasminogen, plasmin | Fibrin | Thrombi, tumours | 32 |
| Mast cell proteinases | proteoglycans | | 33 |
| Elastase | proteoglycans | | 34 |
| Lipoprotein lipase | proteoglycans | | 35 |
| Coagulation enzymes | proteoglycans | | 36 |
| Extracellular superoxide dismutase | proteoglycans | | 37 |
| Heparin cofactor II | proteoglycans | | 38 |
| Retinal survival factor | proteoglycans specific receptors | | 39 |
| Heparin-binding brain mitogen | proteoglycans specific receptors | | 40 |
| Apolipoprotein, e.g. | proteoglycans specific | | 41 |

-continued

| Vector type | Target | Comments/areas of use | Ref |
|---|---|---|---|
| apolipoprotein B | receptors (e.g., LDL receptor) | | |
| Apolipoprotein E | LDL receptor proteoglycans | | 42 |
| Adhesion-promoting proteins, e.g. Purpurin | proteoglycans | | 43 |
| Viral coat proteins, e.g. HIV, Herpes | proteoglycans | | 44 |
| Microbial adhesins, e.g. "Antigen 85" complex of mycobacteria | fibronectin, collagen, fibrinogen, vitronectin, heparan sulfate | | 45 |
| β-amyloid precursor | proteoglycans | β-amyloid accumulates in Alzheimer's disease | 46 |
| Tenascin, e.g. tenascin C | heparan sulfate, integrins | | 47 |

Vectors Comprising Non-peptide Agonists/antagonists or Non-bioactive Binders of Receptors for Cytokines/growth Factors/peptide Hormones/cell Adhesion Molecules

| Vector type | Target | Comments/areas of use | Ref |
|---|---|---|---|
| | | Several agonists/ antagonists are known for such factors acting through G-protein coupled receptors | 48 49 |
| Endothelin antagonist | Endothelin receptor | Vessel wall | |
| Desmopressin (vasopressin analogue) | Vasopressin receptor | Kidney Vessel wall | |
| Demoxytocin (oxytocin analogue) | Oxytocin Receptor | Reproductive organs, Mammary glands, Brain | |
| Angiotensin II receptor antagonists CV-11974, TCV-116 | Angiotensin II receptors | Vessel wall brain adrenal gland | |
| non-peptide RGD-analogues | integrins | Cells in immune system vessel wall etc. | 50 |

Vectors Comprising Anti-angiogenic Factors

| Vector type | Target | Comments/areas of use | Ref |
|---|---|---|---|
| Angiostatin | EC of tumors | plasminogen fragment | K |
| cartilage-derived inhibitor | EC of tumors | | J |
| β-Cyclodextrin tetradecasulfate | tumors, inflammation | | C |
| fumagillin and analogs | tumors, inflammation | | E |
| Interferon-α | EC of tumors | | K |
| Interferon-γ | EC of tumors | | E |
| interleukin-12 | EC of tumors | | E |
| linomide | tumors, inflammation | | A |
| medroxyprogesterone | EC of tumors | | K |
| metalloproteinase | EC of tumors | | K |

-continued

| Vector type | Target | Comments/areas of use | Ref |
|---|---|---|---|
| inhibitors | | | |
| pentosan polysulfate | EC of tumors | | K |
| platelet factor 4 | EC of tumors | | M |
| Somatostatin | EC of tumors | | K |
| Suramin | EC of tumors | K | |
| Taxol | EC of tumors | | K |
| thalidomide | EC of tumors | | K |
| Thrombospondin | EC of tumors | | K |

Vectors Comprising Angiogenic Factors

| Vector type | Target | Comments/areas of use | Ref |
|---|---|---|---|
| acidic fibroblast growth factor | EC of tumors | | K |
| adenosine | EC of tumors | | K |
| Angiogenin | EC of tumors | | K |
| Angiotensin II | EC of tumors | | K |
| basement membrane components | tumors | e.g., tenascin, collagen IV | M |
| basic fibroblast growth factor | EC of tumors | | K |
| Bradykinin | EC of tumors | | K |
| Calcitonin gene-related peptide | EC of tumors | | K |
| epidermal growth factor | EC of tumors | | K |
| Fibrin | tumors | | K |
| Fibrinogen | tumors | | K |
| Heparin | EC of tumors | | K |
| histamine | EC of tumors | | K |
| hyaluronic acid or fragments thereof | EC of tumors | | K |
| Interleukin-1α | EC of tumors | | K |
| laminin, laminin fragments | EC of tumors | | K |
| nicotinamide | EC of tumors | | K |
| platelet activating factor | EC of tumors | | K |
| Platelet-derived endothelial growth factor | EC of tumors | | K |
| prostaglandins E1, E2 | EC of tumors | | K |
| spermine | EC of tumors | | K |
| spermine | EC of tumors | | K |
| Substance P | EC of tumors | | |
| transforming growth factor-α | EC of tumors | | K |
| transforming growth factor-β | EC of tumors | | K |
| Tumor necrosis factor-α | EC of tumors | | K |
| vascular endothelial growth factor/vascular permeability factor | EC of tumors | | K |
| vitronectin | | | A |

Vector Molecules Other Than Recognized Angiogenetic Factors with Known Affinity for Receptors Associated with Angiogenesis

| Vector type | Target | Comments/areas of use | Ref |
|---|---|---|---|
| angiopoietin | tumors, inflammation | | B |
| α₂-antiplasmin | tumors, inflammation | | |
| combinatorial libraries, compounds from | tumors, inflammation | for instance: compounds that bind to basement membrane after degradation | |
| endoglin | tumors, inflammation | | D |
| endosialin | tumors, inflammation | | D |
| endostatin [collagen fragment] | tumors, inflammation | | M |
| Factor VII related antigen | tumors, inflammation | | D |
| fibrinopeptides | tumors, inflammation | | ZC |
| fibroblast growth factor, basic | tumors, inflammation | | E |
| hepatocyte growth factor | tumors, inflammation | | I |
| insulin-like growth factor | tumors, inflammation | | R |
| interleukins | tumors, inflammation | e.g.,: IL-8 | I |
| leukemia inhibitory factor | tumors, inflammation | | A |
| metalloproteinase inhibitors | tumors, inflammation | e.g., batimastat | E |
| Monoclonal antibodies | tumors, inflammation | for instance: to angiogenetic factors or their receptors, or to components of the fibrinolytic system | |
| peptides, for instance cyclic RGD_DFV | tumors, inflammation | | B, Q |
| placental growth factor | tumors, inflammation | | J |
| placental proliferin-related protein | tumors, inflammation | | E |
| plasminogen | tumors, inflammation | | M |
| plasminogen activators | tumors, inflammation | | D |
| plasminogen activator inhibitors | tumors, inflammation | | U, V |
| platelet activating factor antagonists | tumors, inflammation | inhibitors of angiogenesis | A |
| platelet-derived growth factor | tumors, inflammation | | E |
| pleiotropin | tumors, inflammation | | ZA |
| proliferin | tumors, inflammation | | E |
| proliferin related protein | tumors, inflammation | | E |
| selectins | tumors, inflammation | e.g., E-selectin | D |
| SPARC | tumors, inflammation | | M |
| snake venoms (RGD-containing) | tumors, inflammation | | Q |
| Tissue inhibitor of metalloproteinases | tumors, inflammation | e.g., TIMP-2 | U |
| thrombin | tumors, inflammation | | H |
| thrombin-receptor-activating tetradecapeptide | tumors, inflammation | | H |
| thymidine phosphorylase | tumors, inflammation | | D |
| tumor growth factor | tumors, inflammation | | ZA |

Receptors/targets Associated with Angiogenesis

| Vector type | Target | Comments/areas of use | Ref |
|---|---|---|---|
| biglycan | tumors, inflammation | dermatan sulfate proteoglycan | X |

-continued

| Vector type | Target | Comments/areas of use | Ref |
|---|---|---|---|
| CD34 | tumors, inflammation | | L |
| CD44 | tumors, inflammation | | F |
| collagen type I, IV, VI, VIII | tumors, inflammation | | A |
| decorin | tumors, inflammation | dermatan sulfate proteoglycan | Y |
| dermatan sulfate proteoglycans | tumors, inflammation | | X |
| endothelin | tumors, inflammation | | G |
| endothelin receptors | tumors, inflammation | | G |
| fibronectin | tumors | | P |
| Flk-1/KDR, Flt-4 | tumors, inflammation | VEGF receptor | D |
| FLT-1 (fms-like tyrosine kinase) | tumors, inflammation | VEGF-A receptor | O |
| heparan sulfate | tumors, inflammation | | P |
| hepatocyte growth factor receptor (c-met) | tumors, inflammation | | I |
| insulin-like growth factor/mannose-6-phosphate receptor | tumors, inflammation | | R |
| integrins β$_3$ and β$_5$, integrin α$_v$β$_3$, integrin α$_6$β$_1$, , integrins α$_6$, integrins β$_1$, integrin α$_v$β$_1$, integrin α$_v$β$_3$, integrin α$_5$ | Tumors, inflammation | laminin receptor subunit of the fibronectin receptor | D, P |
| integrin α$_v$β$_5$, fibrin receptors. | | | |
| Intercellular adhesion molecule −1 and −2 | tumors, inflammation | | P |
| Jagged gene product | tumors, inflammation | | T |
| Ly-6 | tumors, inflammation | a lymphocyte activation protein | N |
| matrix metalloproteinases | tumors, inflammation | | D |
| MHC class II | tumors, inflammation | | |
| Notch gene product | tumors, inflammation | | T |
| Osteopontin | tumors | | Z |
| PECAM | tumors, inflammation | alias CD31 | P |
| plasminogen activator receptor | tumors, inflammation | | ZC |
| platelet-derived growth factor receptors | tumors, inflammation | | E |
| Selectins: E−, P− | tumors, inflammation | | D |
| Sialyl Lewis-X | tumors, inflammation | blood group antigen | M |
| stress proteins: glucose regulated, heat shock families and others | tumors, inflammation | molecular chaperones | |
| syndecan | tumors, inflammation | | T |
| thrombospondin | tumors, inflammation | | M |
| TIE receptors | tumors, inflammation | tyrosine kinases with Ig- and EGF-like domains | E |
| tissue factor | tumors, inflammation | | Z |
| tissue inhibitor of metalloproteinases | tumors, inflammation | e.g., TIMP-2 | U |
| transforming growth factor receptor | tumors, inflammation | | E |

-continued

| Vector type | Target | Comments/areas of use | Ref |
|---|---|---|---|
| urokinase-type plasminogen activator receptor | tumors, inflammation | | D |
| Vascular cellular adhesion molecule (VCAM) | tumors, inflammation | | D |
| Vascular endothelial growth factor related protein | tumors, inflammation | | |
| Vascular endothelial growth factor-A receptor | tumors, inflammation | | K |
| von Willebrand factor-related antigen | tumors, inflammation | | L |

Oligonucleotide Vectors

| Vector type | Target | Comments/areas of use | Ref |
|---|---|---|---|
| Oligonucleotides complementary to repeated sequences, e.g. genes for ribosomal RNA, Alu-sequences | DNA made available by necrosis | Tumours Myocardial infarction All other diseases that involves necrosis | 51 |
| Oligonucleotides complementary to disease-specific mutations (e.g. mutated oncogenes) | DNA made available by necrosis in a region of the relevant disease | Tumours | 51 |
| Oligonucleotides complementary to DNA of infecting agent. | DNA of infective agent | Viral or bacterial infections | 51 |
| Triple or quadruple-helix forming oligonucleotides | As in above examples | As in above examples | 51 |
| Oligonucleotides with recognition sequence for DNA- or RNA-binding proteins | DNA-binding protein, e.g. transcription factors (often overexpressed/ activated in tumours or activated endothelium/ immune cells | Tumours Activated endothelium Activated immune cells | |

Modified Oligonucleotide Vectors

| Vector type | Target | Comments/areas of use | Ref |
|---|---|---|---|
| Phosphoro-thioate oligos | As for unmodified oligos | As for unmodified oligos | 51 |
| 2'-O-methyl substituted oligos | " | " | 51 |
| circular oligos | " | " | 51 |
| oligos containing hairpin structure to decrease degradation | " | " | 51 |
| oligos with | " | " | 51 |

-continued

| Vector type | Target | Comments/areas of use | Ref |
|---|---|---|---|
| terminal phosphorothioate 2'-fluoro oligos | " | " | 51 |
| 2'-amino oligos | " | " | 51 |
| DNA-binding drugs conjugated to oligos (for examples, see below) | " | Increased binding affinity as compared to pure oligos | 52 |
| Peptide Nucleic Acids (PNAs, oligo-nucleotidss with a peptide backbone) | " | Increased binding affinity and stability compared to standard oligos. | 53 |

Nucleoside and Nucleotide Vectors

| Vector type | Target | Comments/areas of use | Ref |
|---|---|---|---|
| Adenosine or analogues | Adenosine receptors | Vessel wall Heart | 54 |
| ADP, UDP, UTP and others | Various nucleotide receptors | Many tissues, e.g. brain, spinal cord, kidney, spleen | 55 |

Receptors Comprising DNA-binding Drugs

| Vector type | Target | Comments/areas of use | Ref |
|---|---|---|---|
| acridine derivatives distamycin netropsin actinomycin D echinomycin bleomycin etc. | DNA made available by necrosis | Tumours, Myocardial infarction and all other diseases involving necrosis or other processes liberating DNA from cells | |

Receptors Comprising Protease Substrates

| Vector type | Target | Comments/areas of use | Ref |
|---|---|---|---|
| Peptidic or non-peptidic substrates | Cathepsin B | Tumours, a variety of which may more or less specifically overexpress proteases of various kinds, e.g. Cathepsin B | 10 |

Receptors Comprising Protease Inhibitors

| Vector type | Target | Comments/areas of use | Ref |
|---|---|---|---|
| Peptidic or non-peptidic inhibitors e.g. N-acetyl-Leu-Leu-norleucinal | Cathepsin B | Tumours, a variety of which may more or less specifically overexpress proteases of various kinds, e.g. Cathepsin B | 10 |
| bestatin ([(2S,3R)-3-Amino-2-hydroxy-4-phenyl-butanoyl]-L-leucine hydrochloride) | Aminopeptidases | Tumours, e.g. on cell surfaces | |
| Pefabloc (4-(2-aminoethyl)-benzenesulfonyl fluoride hydrochloride) | Serine proteases | Tumours, vessel wall etc. | |
| Commercially available inhibitors e.g. kaptopril enalapril ricionopril | Angiotensin converting enzyme | Endothelial cells | |
| Low specificity non-peptidic compounds | Coagulation factors | Vessel wall injury, tumours, etc. | |
| Protease nexins (extracellular protease inhibitors) | proteoglycans | | 56 |
| Antithrombin | proteoglycans, Coagulation factors | | 57 |

Vectors from Combinatorial Libraries

| Vector type | Target | Comments/areas of use | Ref |
|---|---|---|---|
| Antibodies with structure determined during generation process | Any of above targets - or may be unknown when make functional selection of vector binding to chosen diseased structure | Any diseased or normal structure of interest, e.g. thrombi, tumours or walls of myocardial vessels | 58, 59, 60 |
| Peptides with sequence determined during generation process | Any of above targets - or may be unknown when make functional selection of vector binding to chosen diseased structure | Any diseased or normal structure of interest, e.g. thrombi, tumours or walls of myocardial vessels | 58, 59, 60 |
| Oligonucleotides with sequence determined during generation process | Any of above targets - or may be unknown when make functional selection of vector binding to chosen diseased structure | Any diseased or normal structure of interest, e.g. thrombi, tumours or walls of myocardial vessels | 58, 59, 60 |
| Modifications of oligos obtained as above | Any of above targets - or may be unknown when make | Any diseased or normal structure of interest, e.g. thrombi, tumours or walls of myocardial vessels | 58, 59, 60 |

-continued

| Vector type | Target | Comments/areas of use | Ref |
|---|---|---|---|
| | functional selection of vector binding to chosen diseased structure | | |
| Other chemicals with structure determined during generation process | Any of above targets - or may be unknown when make functional selection of vector binding to chosen diseased structure | Any diseased or normal structure of interest, e.g. thrombi, tumours or walls of myocardial vessels | 58, 59, 60 |

Carbohydrate Vectors

| Vector type | Target | Comments/areas of use | Ref |
|---|---|---|---|
| neo-glycoproteins | macrophages | general activation/inflammation | |
| oligosaccharides with terminal galactose | Asialo-glycoprotein receptor | liver | 61 |
| Hyaluronan | aggrecan (a proteoglycan) "link proteins" cell-surface receptors: CD44 | | 62 |
| Mannose | | Blood brain barrier, Brain tumours and other diseases causing changes in BBB | 63 |
| Bacterial glycopeptides | | Blood brain barrier, Brain tumours and other diseases causing changes in BBB | 64 |

(Glyco)Lipid Vectors

| Vector type | Target | Comments/areas of use | Ref |
|---|---|---|---|
| GM1 gangliosides | cholera bacteria in the gastrointestinal tract | diagnosis/treatment of cholera | |
| platelet activating factor (PAF) antagonists | PAF receptors | diagnosis of inflammation | |
| Prostoglandin antagonists of inflammation | Prostoglandin receptors | diagnosis of inflammation | |
| Thromboxane antagonists of inflammation | Leukotriene receptors | diagnosis of inflammation | |

Small Molecule Vectors

| Vector type | Target | Comments/areas of use | Ref |
|---|---|---|---|
| Adrenalin | Corresponding receptors | | |
| Betablockers | Adrenergic beta-receptors | Myocardium for beta-1 blockers | |
| Alpha-blockers | Adrenergic alpha-receptors | Vessel wall | |
| benzodiazepines serotonin-analogues | Serotonin-receptors | | |
| anti-histamines | Histamine-receptors | Vessel wall | |
| Acetyl-choline receptor antagonists | ACh-receptors | | |
| verapamil | $Ca^{2+}$-channel blocker | Heart muscle | |
| nifedipin | $Ca^{2+}$-channel blocker | Heart muscle | |

Representative examples of drugs useful in accordance with the invention include: abamectin, abundiazole, acaprazine, acabrose, acebrochol, aceburic acid, acebutolol, acecainide, acecarbromal, aceclidine, aceclofenac, acedapsone, acediasulfone, acedoben, acefluranol, acefurtiamine, acefylline clofibrol, acefylline piperazine, aceglatone, aceglutamide, aceglutamide aluminium, acemetacin, acenocoumarol, aceperone, acepromazine, aceprometazine, acequinoline, acesulfame, acetaminophen, acetaminosalol, acetanilide, acetarsone, acetazolamide, acetergamine, acetiamine, acetiromate, acetohexamide, acetohydroxamic acid, acetomeroctol, acetophenazine, acetorphine, acetosulfone, acetriozate, acetryptine, acetylcholine chloride, acetylcolchinol, acetylcysteine, acetyldigitoxin, acetylleucine, acetylsalicyclic acid, acevaltrate, acexamic acid, acifran, acipimox, acitemate, acitretin, acivicin, aclantate, aclarubicin, aclatonium napadisilate, acodazole, aconiazide, aconitine, acoxatrine, acridorex, acrihellin, acrisorcin, acrivastine, acrocinide, acronine, actinoquinol, actodigin, acyclovir, adafenoxate, adamexine, ademetionine, adenosine phosphate, adibendan, adicillin, adimolol, adinazolam, adiphenine, aditeren, aditoprim, adrafinil, adrenalone, afloqualone, afurolol, aganodine, ajmaline, aklomide, alacepril, alafosfalin, alanine mustard, alanosine, alaproclate, alazanine triclofenate, albendazole, albendazole oxide, albuterol, albutoin, alclofenac, alcometasone dipropionate, alcloxa, alcuronium chloride, aldioxa, aldosterone, alepride, aletamine, alexidine, alfacalcidol, alfadex, alfadolone, alfaprostol, alfaxalone, alfentanil, alfuzosin, algestone acetonide, algestone acetophenide, alibendol, aliconazole, alifedrine, aliflurane, alimadol, alinidine, alipamide, alitame, alizapride, allantoin, alletorphine, allobarbital, alloclamide, allocupreide, allomethadione, allopurinol, allylestrenol, allyl isothicyanate, allylprodine, allylthiourea, almadrate sulfate, almasilate, almecillin, almestrone, alminoprofen, almitrine, almoxatone, alonacic, alonimid, aloxistatin, alozafone, alpertine, alphacetylmethadol, alphameprodine, alphamethadol, alphaprodine, alpha-vinylaziridinoethyl acetate, alpidem, alpiropride, alprazolam, alprenolol, alprostadil, alrestatin, altanserin, altapizone, alteconazole, althiazide, altrenogest, altretamine, aluminium acetate, aluminium clofibrate, aluminium subacetate, alverine, amadinone acetate, amafolone, amanozine, amantadine, amantanium bromide, amantocillin, ambasilide, ambazone, ambenonium chloride, ambenoxan, ambroxol, ambruticin, ambucaine, ambucetamide, ambuphylline, ambuside, ambutonium bromide, amcinafal, amcinafide, amcinonide, amdinocillin, amdinocillin pivoxil, amebucort, amedalin, ametantrone, amezepine, amezinium metilsulfate, amfenac, amfepentorex, amfetaminil, amflutizole, amfonelic acid, amicarbalide, amicibone, amicloral, amicycline, amidantel, amidapsone, amidephrine, amiflamine, amifloverine, amifloxacin, amifostine, amikacin, amikhelline, amiloride, aminacrine, amindocate, amineptine, aminobenzoic acid, aminocaproic acid, aminoethyl nitrate, aminoglutethimide, aminohippuric acid, aminometradine, aminopentamide, aminophylline, aminopromazine, aminopterin, aminopyrine, aminoquinol, aminoquinuride, aminorex, aminosalicyclic acid, aminothiadiazole, aminothiazole, amiodarone, amiperone, amipheazole, amipizone, amiprilose, amiquinsin, amisometradine, amisulpride, amiterol, amithiozone, amitraz, amitriptyline, amitriptylinoxide, amixetrine, amlexanox, amlodipine, amobarbital, amodiaquine, amogastrin, amolanone, amonofide, amoproxan, amopyroquin, amorolfine, amocanate, amosulalol, amotriphene, amoxapine, amoxecaine, amoxicillin, amoxydramine camsilate, amperozide, ampheclora, amphenidone, amphetamine, amphotalide, amphotericin B, ampicillin, ampiroxicam, amprolium, ampyrimine, ampyzine, amquinate, amrinone, amsacrine, amygdalin, amylene, amylmetacresol, amyl nitrite, anagestone acetate, anagrelide, anaxirone, anazocine, anazolene, ancarolol, ancitabine, androstanediol, androstanol propionate, androstenetrione, androstenonol propionate, anethole, anguidine, anidoxime, anilamate, anileridine, aniline, anilopam, anipamil, aniracetam, anirolac, anisacril, anisindione, anisopirol, anisoylbromacrylic acid, anitrazafen, anpirtoline, ansoxetine, antafenite, antazoline, antazonite, anthelmycin, anthiolimine, anthralin, anthramycin, antienite, antimony potassium tartrate, antimony thioglycollate, antipyrine, antrafenine, apalcillin, apazone, apicycline, apomorphine, apovincamine, apraclonidine, apramycin, aprindine, aprobarbital, aprofene, aptazapine, aptocaine, arabinosylmercaptopurine, aranotin, arbaprostil, arbekacin, arclofenin, arfendazam, arginine, arginine glutamat, arildone, arnolol, aronixil, arotinolol, arpinocid, arpromidine, arsanilic acid, arsthinol, artemisinin, articaine, asaley, ascorbic acid, ascorbyl palmitate, asocainol, aspartame, aspartic acid, asperlin, aspoxicillin, astemizole, atamestane, atenolol, atipamezole, atiprosin, atolide, atracurium besilate, atromepine, atropine, atropine oxide, auranofin, aurothioglucose, aurothioglycanide, avilamycin-A, avridine, axamozide, azabon, azabuperone, azacitodine, azaclorzine, azaconazole, azacosterol, azacyclonol, azaftozine, azaguanidine, azaloxan, azamethonium bromide, azamulin, azanator, azanidazole, azaperone, azapicyl, azaprocin, azaquinzole, azaribine, azarole, azaserine, azaspirium chloride, azastene, azastrptonigrin, azatodine, azathioprine, azauridine, azelastine, azepexole, azepindole, azetepa, azidamfenicol, azidocillin, azimexon, azintamide, azipramine, azithromycin, azlocillin, azolimine, azosemide, azotomycin, aztreonam, azumolene, bacampicillin, baclofen, bacmecillinam, balsalazide, bamaluzole, bambuterol, bamethan, bamifylline, bamipine, bamnidazole, baquiloprim, barbexaclone, barbital, barucainide, batilol, bazinaprine, becanthone, beclamide, beclobrate, beclomethasone dipropionate, beclotiamine, befiperide, befunolol, befuraline, bekanamycin, belarizine, beloxamide, bemarinone, bemegride, bemetizide, bemitradine, benactyzine, benafentrine, benanserin, benapryzine, benaxibine, benazepril, bencianol, bencisteine, benclonidine, bencyclane, bendamustine, bendazac, bendazol, benderizine, bendroflumethiazide, benethamide penicillin, benexate, benflorex, benfosformin, benfotiamine, benfurodil hemisuccinate, benhepazone, benidipine, benmoxin, benolizime, benorilate, benorterone, benoxafos, benoxaprofen, benoxinate, benperidol, benproperine, benrixate, bensalan, benserazide, bensuldazic acid, bentazepam, bentemazole, bentiamine, bentipimine, bentiromide, benurestat, benzaldehyde, benzalkonium chloride, benzaprinoxide, benzarone, benzbromarone, benzestrol, benzethidine, benzethonium chloride, benzetimide, benzilonium bromide, benzindopyrine, benziodarone, benzmalecene, benznidazole, benzobarbital, benzocaine, benzoclidine, benzoctamide, benzodepa, benzododecinium chloride, benzoic acid, benzoin, benzonatate, benzopyrronium bromide, benzoquinium chloride, benzotript, benzoxiquine, benzoxonium chloride, benzoyl peroxide, benzoylpas, benzphetamine, benzpiperylon, benzpyrinium bromide, benzquercin, benzquinamide, benzthiazide, benztropine, benzydamine, benzylpenicillin, benzylsulfamide, beperidium iodide, bephenium naphtoate, bepiastine, bepridil, beraprost, berberine sulfate, bermastine, bermoprofen, berythromycin, besulpamide, beslunide, beta carotene, betacetylmethadol, betahistine, betaine, betameprodine, betamethadol, betamethasone, betamethasone acetate, betamethasone acibutate, betamethasone benzoate, betamethasone dipropionate, betamethasone phosphate, betamethasone valerate, betamicin, betaprodine, betaxolol, betazole, bethanechol chloride, bethanidine, betiatide, betoxycaine, bevantolol, bevonium metilsulfate, bezafibrate, bezitramide, bialamicol, bibenzonium bromide, bibrocathol, bicifadine, biclodil, biclofibrate, biclotymol, bicozamycin, bidimazium iodine, bietamiverine, bietaserpine, bifemelane, bifepramide, bifluranol, bifonazole, binedaline, binfloxacin, binifibrate, bioallethrin, bioresmethrin, biotin, bipenamol, biperiden, biphenamine, biriperone, bisacodyl, bisantrene, bis(aziridinyl) butanediol, bisbendazole, bisbentiamine, bisfenazone, bisfentidine, bismuth betanaphthol, bismuth-triglycollamate, bismuth subgallate, bismuth subsalicylate, bisorbin, bisoprolol, bisorcic, bioxatin acetate, bispyrithione magsulfex, bithionol, bithionoloxide, bitipazone, bitoterol, bitoscantate, bleomycin, bluensomycin, bofumustine, bolandiol dipropionate, bolasterone, bolazine, boldenone undecylenate, bolenol, bolmantalate, bometolol, bopindolol, bornaprine, bornaprolol, bornelone, botiacrine, boxidine, brallobarbital, brazergoline, brefonalol, bremazocine, brequinar, bretylium tosylate, brindoxime, brivundine, brobactam, broclepride, brocresine, brocrinat, brodimoprim, brofaromine, brofezil, brofoxine, brolaconazole, brolamfetamine, bromacrylide, bromadoline, bromamid, bromazepam, bromchlorenone, bromebric acid, bromerguride, brometenamine, bromfenac, bromhexine, bromindione, bromisovalum, bromociclen, bromocriptine, bromodiphenhydramine, bromofenofos, bromopride, bromoxandide, bromperidol, bromperidol decanoate, brompheniramine, bronopol, broparestrol, broperamole, bropirimine, broquinaldol, brosotamide, brosuximide, brotianide, brotizolam, brovanexine, brovincamine, broxaldine, broxaterol, broxitalamic acid, broxuridine, broxyquinoline, bruceantin, brucine, bucainide, bucetin, buciclovir, bucillamine, bucindolol, bucladesine, buclizine, buclosamide, bucloxic acid, bucolome, bucricaine, bucromarone, bucrylate, bucumolol, budesonide, budipine, budotitane, budralazine, bufenadrine, bufeniode, bufetolol, bufexamac, bufezolac, buflomedil, bufogenin, buformin, bufrolin, bufuralol, bumadizone, bumecaine, bumepidil, bumetanide, bumetrizole, bunaftine, bunamidine, bunamiodyl, bunaprolast, bunazosin, bunitrolol, bunolol, buparvaquone, bupicomide, bupivacaine, bupranolol, buprenorphine, bupropion, buquineran, buquinolate, buquiterine, buramate, burodiline, buspirone, busulfan, butabarbital, butacaine, butacetin, butaclamol, butadiazamide, butafosfan, butalamine, butalbital, butamben, butamirate, butamisole, butamoxane, butanediol cyclic sulfite, butanilicaine, butanixin, butanserin, butantrone, butaperazine, butaprost, butaverine, butedronate, buterizine, butetamate, butethamine, buthiazide, butibufen, butidrine, butikacin, butilfenin, butinazocine, butinoline, butirosin, butixirate, butobendine, butoconazole, butocrolol, butoctamide, butofilolol, butonate, butopamine, butopiprine, butoprozine, butopyrammonium iodide, butorphanol, butoxamine, butoxylate, butriptyline, butropium bromide, butylated hydroxyanisole, butylated hydroxytoluene, butylparaben, butynamine, buzepide metiodide, cabastine, cabergoline, cadralazine, cafaminol, cafedrine, caffeine, calcifediol, calcitrol, calcium citrate, calcium dobesilate, calcium glubionate, calcium gluceptate, calcium gluconate, calcium glycerophosphate, calcium hypophosphite, calcium lactate, calcium lactobionate, calcium levulinate, calcium mandelate, calcium pantothenate, calcium phosphate dibasic, calcium phophate tribasic, calcium saccharate, calcium stearate, calusterone, camazepam, cambendazole, camiverine, camostast, camphotamide, camptothecin, camylofin, canbisol, cannabinol, canrenoic acid, canrenone, cantharidine, capobenic acid, capreomycin, caproxamine, capsaicine, captamine, captodiame, captopril, capuride, caracemide, caramiphen, carazolol, carbachol, carbadox, carbaldrate, carbamazepine, carbamide peroxide, carbantel lauryl sulfate, carbaril, carbarsone, carbaspirin calcium, carbazeran, carbazochrome, carbazachrome salicylate, carbazachrome sulfonate, carbazocine, carbeniciltin, carbenicillin indanyl, carbencillin phenyl, carbenoxolone, carbenzide, carbestrol, carbetapentane, carbidopa, carbimazole, carbinoxamine, carbiphene, carbocloral, carbocysteine, carbofenotion, carbol-fuschin, carbomycin, carboplatin, carboprost, carboprost methyl, carboquone, carbromal, carbubarb, carburazepam, carbutamide, carbuterol, carcainium chloride, carebastine, carfentanil, carfimate, carisoprodol, carmantadine, carmetizide, carmofur, carmustine, carnidazole, carnitine, carocainide, caroverine, caroxazone, carperidine, caperone, carphenazine, carpindolol, carpiramine, carprofen, carpronium chloride, carsalam, cartazolate, carteolol, carubicin, carumonam, carvedilol, carzenide, carzolamide, cathine, cathinone, cefaclor, cefadroxil, cefalonium, cefaloram, cefamandole, cefamandole naftate, cefaparole, cefatrizine, cefazaflur, cefazedone, cefazolin, cefbuperazone, cefcanel, cefcanel daloxate, cefedrolor, cefempidone, cefepime, cefetamet, cefetrizole, cefvitril, cefixime, cefmenoxime, cefmepidium chloride, cefmetazole, cefminox, cefodizime, cefonizid, cefoperazone, ceforanide, cefotaxime, cefotetan, cefotiam, cefoxazole, cefoxitin, cefpimizole, cefpiramide, cefpirome, cefpodoxime, cefpodoxime proxetil, cefquinome, cefrotil, cefroxadine, cefsulodin, cefsumide, ceftazidime, cefteram, ceftezole, ceftiofur, ceftiolene, ceftioxide, ceftizoxime, ceftriaxone, cefuracetime, cefuroxime, cefuraxime axetil, cefurzonam, celiprolol, cephacetrile, cephalexin, cephaloglycin, cephaloridine, cephalothin, cephapirin, cephradine, cetaben, cetamolol, cethexonium chloride, cetiedil, cetirizine, cetocycline, cetohexazine, cetophenicol, cetotiamine, cetoxime, cetraxate, chaulmosulfone, chendiol, chiniofon, chlophedianol, chloracyzine, chloral betaine, chloral hydrate, chloralose, chlorambucil, chloramine, chloramphenicol, chloramphenicol palmitate, chloramphenicol succinate, chlorazanil, chlorbenzoxamine, chlorbetamide, chlorcyclizine, chlordantoin, chlordiazepoxide, chlordimorine, chlorhexadol, chlorhexidine, chlorhexidine phosphanilate, chlorindanol, chlorisondamine chloride, chlormadinone acetate, chlormerodrin, chlormezanone, chlormidazole, chloronaphazine, chloroazodin, chlorobutanol, chlorocresol, chlorodihydroxyandrostenone, chloroethyl mesylate, 5-chloro-3'-fluoro-2'3-dideoxyuridine, chloroguanide, chlorophenothane, chloroprednisone acetate, chloroprocaine, chloropyramine, chloroquine, chloroserpidine, chlorothen, chlorothiazide, chlorotriansene, chloroxine, chloroxylenol, chlorozotocin, chlorphenesin, chlorphenesin carbamate, chlorpheniramine, chlorphenoctium amsonate, chlorphenoxamine, chlorphentermine, chlorproethazine, chlorproguanil, chlorpromazine, chlorpropamide, chlorprothixene, chlorquinaldol, chlortetracycline, chlorthalidone, chlorthenoxazine, chlorzoaxazone, chloecalciferol, cholic acid, choline chloride, choline glycerophosphate, chromocarb, chromonar, ciadox, ciamexon, cianergoline, cianidol, cianopramine, ciapilome, cicaprost, cicarperone, ciclactate, ciclafrine, ciclazindol, cicletanine, ciclomenol, ciclonicate, ciclonium bromide, ciclopirox, ciclopramine, cicloprofen, cicloprolol, ciclosidomine, ciclotizolam, ciclotropium bromide, cicloxilic acid, cicloxolone, cicortonide, cicrotic acid, cidoxepin, cifenline, cifostodine, ciglitazone, ciheptolane, ciladopa, cilastatine, cilazapril, cilazaprilat, cilobamine, cilofungin, cilostamide, cilostazol, ciltoprazine, cimaterol, cimemoxin, cimepanol, cimetidine, cimetropium bromide, cimoxatone, cinchonine, cinchophen, cinecromen, cinepaxadil, cinepazet, cinepazic acid, cinepazide, cinfenine, cinfenoac, cinflumide, cingestol, cinitapride, cinmetacin, cinnamaverine, cinnamedrine, cinnarizine, cinnarizine clofibrate, cinnofuradione, cincotramide, cinodine, cinolazepam, cinoquidox, cinoaxin, cinoxate, cinoxolone, cinooxopazide, cinperene, cinprazole, cinpropazide, cinromide, cintazone, cintriamide, cinperone, ciprafamide, ciprafazone, ciprefadol, ciprocinonide, ciprofibrate, ciprofloxacin, cipropride, ciproquazone, ciprostene, ciramadol, cirazoline, cisapride, cisconazole, cismadinone, cisplatin, cistinexine, citalopram, citatepine, citenamide, citenazone, citicoline, citiolone, clamidoxic acid, clamoxyquin, clanfenur, clanobutin, clantifen, clarithromycin, clavulanic acid, clazolam, clazolimine, clazuril, clebopride, clefamide, clemastine, clemeprol, clemizole, clenbuterol, clenpirin, cletoquine, clibucaine, clidafidine, clidanac, clidinum bromide, climazolam, climbazole, climiqualine, clindamycin, clindamycin palmitate, clindamycin phosphate, clinofibrate, clinolamide, cliquinol, clioxanide, clipoxamine, cliprofen, clobazam, clobenoside, clobenzepam, clobenzorex, clobenztropine, clobetasol propionate, clobetasone butyrate, clobutinol, clobuzarit, clocanfamide, clocapramine, clociguanil, clocinizine, clocortolone acetate, clocortolone pivalate, clocoumarol, clodacaine, clodanolene, clodazon, clodoxopone, clodronic acid, clofazimine, clofenamic acid, clofenamide, clofenciclan, clofenetamine, clofenoxyde, clofenvinfos, clofeverine, clofexamide, clofezone, clofibrate, clofibric acid, clofibride, clofilium phosphate, cloflucarban, clofoctol, cloforex, clofurac, clogestone acetate, cloguanamil, clomacran, clomegestone acetate, clometacin, clometherone, clomethiazole, clometocillin, clomifenoxide, clominorex, clomiphene, clomipramine, clomocycline, clomoxir, clonazepam, clonazoline, clonidine, clonitazene, clonitrate, clonixeril, clonixin, clopamide, clopenthixol, cloperastine, cloperidone, clopidogrel, clopidol, clopimozide, clopipazan, clopirac, cloponone, cloprednol, cloprostenol, cloprothiazole, cloquinate, cloquinozine, cloracetadol, cloranolol, clorazepate, clorethate, clorexolone, clorgiline, cloricromen, cloridarol, clorindanic acid, clorindione, clormecaine, cloroperone, clorophene, cloroqualone, clorotepine, clorprenaline, clorsulon, clortermine, closantel, closiramine, clostebol, clothiapine, clothixamide, clotiazepam, cloticasone propionate, clotioxone, clotrimazole, clovoxamine, cloxacepride, cloxacillin, cloxacillin benzathine, cloxazolam, cloxestradiol, cloximate, cloxotestosterone, cloxypendyl, cloxyquin, clozapine, cobamide, cocaine, cocarboxylase, codeine, codoxime, cofisatin, cogazocine, colchicine, colestolone, colfenamate, colforsin, colterol, conessine, conorphone, copper gluconate, cormethasone acetate, corticosterone, cortisone acetate, cortisuzol, cortivazol, cortodoxone, cotarnine chloride, cotinine, cotriptyline, coumaphos, coumazoline, coumermycin, coumetarol, creatinolfosfate, crisnatol, croconazole, cromakalim, cromitrile, cromolyn, cropropamide, crospovidone, crotamiton, crotetamide, crotoniazide, crufomate, cuprimyxin, cuproxoline, cyacetacide, cyamemazine, cyanocobalamine, cyclacillin, cyclandelate, cyclarbamate, cyclazocine, cyclazodone, cyclexanone, cyclindole, cycliramine, cyclizine, cyclobarbital, cyclobendazole, cyclobenzaprine, cyclobutoic acid, cyclobutyrol, cyclofenil, cycloguanil, cloheximide, cycloleucine, cyclomenol, cyclomethicone, cyclomethycaine, cyclopentamine, cyclopenthiazide, cyclopentolate, cyclopenazine, cyclophosphamide, cyclopregnol, cyclopyrronium bromide, cycloserine, cyciosporine, cyclothiazide, cyclovalone, cycotiamine, cycrimine, cyheptamide, cyheptropine, cynarine, cypenamine, cypothrin, cyprazepam, cyprenophine, cyprodenate, cyproheptadine, cyprolidol, cyproquinate, cyproterone acetate, cyproximide, cystine, cytarabine, dacarbazine, dacemazine, dacisteine, dacinomycin, dacuronium bromide, dagapamil, dalbraminol, daledalin, daltroban, dametralast, damotepine, danazol, danitracen, danosteine, danthron, dantrolene, dapiprazole, dapsone, daptomycin, darenzepine, darodipine, datelliptium chloride, dunorubicin, dazadrol, dazepinil, dazidamine, dazmegrel, dazolicine, dazopride, dazoquinast, dacoxiben, deanol aceglumate, deanol acetaminobenzoate, deazauridine, deboxamet, debrisoquin, decamethonium bromide, decimemide, decitropine, declaben, declenperone, decloxizine, decominol, decoquinate, deditonium bromide, deferoxamine, deflazacort, defosfamide, dehydroacetic acid, dehydroemetine, dehydro-7-methyltestosterone, delanterone, delapril, delergotrile, delfantrine, delmadinone acetate, delmetacin, delmopinol, delorazepam, deloxone, delprostenate, dembrexine, demecarium bromide, demeclacycline, demecolcine, demecycline, demegestone, demelverine, demexiptiline, democonazole, demoxepam, denaverine, denbutylline, denipride, denopamine, denpidazone, denzimol, deoxyspergualin, depramine, deprodone, deprostil, deptropine, derpanicate, desacetylcolchicine tartrate, desaspidin, desiclovir, descinolone acetonide, deserpidine, desipramine, deslanoside, desmethylcolchicine, desmethylmisonidazole, desmethylmoramide, desocriptine, desogestrel, desomorphine, desonide, desoximetasone, desoxycorticosterone acetate, desoxycorticosterone pivalate, desoxypyridoxine, detajmium bitartrate, detanosal, deterenol, detomidine, detorubicin, detrothronine, devapamil, dexamethasone, dexamethasone acefurate, dexamethasone acetate, dexamethasone dipropionate, dexamethasone phosphate, dexamisole, dexbrompheniramine, dexchlorpheniramine, dexclamol, dexetimide, dexetozoline, dexfenfluramine, deximafen, dexindoprofen, dexivacaine, dexlofexidine, dexmedetomidine, dexoxadrol, dexpanthenol, dexpropranolol, dexproxibutene, dexecoverine, dextilidine, dextroamphetamine, dextrofemine, dextromethorphan, dextromoramide, dextrorphan, dextrothyroxine, dezaguanine, dezocine, diacerein, diacetamate, diacetolol, diacetylmorphine, diamfenetide, diaminomethylphenazinium chloride, diamocaine, diampromide, diamthazole, dianhydrogalactitol, diapamide, diarbarone, diathymosulfone, diatrizoic acid, diaveridine, diazepam, diaziquone, diazoacetylglycine hydrazide, diazouracil, diazoxide, dibekacin, dibemethine, dibenamine, dibenzepin, dibrompropamidine, dibromsalan, dibrospidium chloride, dibucaine, dibuprol, dibupyrone, dibusadol, dicarbine, dicarfen, dichlorallyl lawsone, dichlorisone acetate, dichlormezanone, dichlorofluormethane, dichloromethotrexate, dichlorophen, dichlorophenarsine, dichlorotetrafluoroethane, dichloroxylenol, dichlorphenamide, dichlorvos, diciferron, dicirenone, diclazuril, diclofenac, diclofensine, diclofurime, diclometide, diclonixin, dicloxacillin, dicobalt edetate, dicolinium iodide, dicresulene, dicumarol, dicyclomine, didemnin, dideoxycytidine, didrovaltrate, dieldrin, dienestrol, dienogest, diethadione, diethazine, diethylpropion, diethylstilbestrol, diethylstilbestrol diphosphate, diethylstilbestrol dipropionate, diethylthiambutene, diethyltoluamide, dietifen, difebarbamate, difemerine, difemetorex, difenamizole, difencloxazine, difenoximide, difenoxin, difetarsone, difeterol, diflorasone diacetate, difloxacin, difluanine, diflucortolone, diflurcortolone pivalate, diflumidone, diflunisal, difluprednate, diftalone, digalloyl trioleate, digitoxin, digoxin, dihexyverine, dihydralazine, dihydroazacytidine, dihydroergotamine, dihydrolenperone, dihydrostreptomycin, dihydrotachysterol, dihydroxyfluoroprogestrone, diisopromine, diisopropanolamine, dilazep, dilevalol, dilmefone, diloxanide, diltiazem, dimabefylline, dimecamine, dimecolonium iodide, dimecrotic acid, dimefadane, dimefline, dimelazine, dimemorfan, dimenhydrinate, dimenoxadol, dimeheptanol, dimepranol, dimepregnen, dimeprozan, dimercaprol, dimesna, dimesone, dimetacrine, dimetamfetamine, dimethadione, dimethaminostyrylquinoline, dimethazan, dimethindene, dimethiodal, dimethisoquin, dimethisterone, dimetholizine, dimethoxanate, dimethylhydroxytestosterone, dimethylnorandrostadienone, dimethylnortestosterone, dimethylstilbestrol, dimethyl, dimethylthiambutene, dimethyltubocurarinium chloride, dimetipirium bromide, dimetofrine, dimetridazole, diminazene, dimoxamine, dimoxaprost, dimoxyline, dimpylate, dinaline, dinazafone, diniprofylline, dinitolmide, dinoprost, dinoprostone, dinsed, diosmin, dioxadilol, dioxadrol, dioxamate, dioxaphetyl butyrate, dioxethedrin, dioxifedrine, dioxybenzone, dipenine bromide, diperodon, diphemanil methylsulfate, diphenadione, diphenan, diphenhydramine, diphendiol, diphenoxylate, diphenylpraline, diphoxazide, dipipanone, dipipoverine, dipiverin, diprafenone, diprenorphine, diprobutine, diprofene, diprogulic acid, diproleandromycin, diproqualone, diproteverine, diprotriozate, diproxadol, dipyridamole, dipyrithione, dipyrocetyl, dipyrone, dirithromycin, disobutamide, disofenin, disogluside, disopyramide, disoxaril, distigmine bromide, disulergine, disulfamide, disulfiram, disuprazole, ditazole, ditercalinium chloride, dithiazanine iodide, ditiocarb, ditiomustine, ditolamide, ditophal, divabuterol, dixanthogen, dizatrifone, dizocilpine, dobupride, dobutamine, docarpamine, doconazole, docusate, doliracetam, domazoline, domiodol, domiphen bromide, domipizone, domoprednate, domoxin, domperidone, don, donetidine, dopamantine, dopamine, dopexamine, dopropidil, doqualast, dorastine, doreptide, dosergoside, dotarizine, dotefonium bromide, dothiepin, doxacurium chloride, doxaminol, doxapram, doxaprost, doxazosin, doxefazepam, doxenitoin, doxepin, doxibetasol, doxifluridine, doxofylline, doxorubicin, doxpicomine, doxycycline, doxylamine, dramedilol, draquinolol, deazidox, dribendazole, drindene, drobuline, drocinonide, droclidinium bromide, drocode, drofenine, droloxifene, drometrizole, dromostanolone, dromostanolone propionate, dronabinol, dropempine, droperidol, droprenilamine, dropropizine, drotaverine, drotebanol, droxacin, droxicainide, droxicam, droxidopa, droxypropine, dulofibrate, dulozafone, duometacin, duoperone, dupracetam, durapatite, dyclonine, dydrogesterone, dymanthine, dyphylline, ebastine, ebrotidine, ebselen, ecastolol, echinomycin, echothiophate iodide, ecipramidil, eclanamine, eclazolast, econazole, ectylurea, edelfosine, edetic acid, edetol, edifolone, edogestrone, edoxudine, edrophonicum chloride, efaroxan, efetozole, eflornithine, efloxate, efrotomycin, elantrine, elanzepine, elderfield's pyrimidine mustard, elfazepam, ellagic acid, elliptinium acetate, elmustine, elnadipine, eltenac, eltoprazine, elucaine, elziverine, embramine, embutramide, emepronium bromide, emetine, emiglitate, emilium tosylate, emopanil, emorfazone, emylcamate, enalapril, enalaprilat, enbucrilate, encainide, enciprazine, enclomiphene, encyprate, endomide, endralazine, endrysone, enefexine, enestebol, enfenamic acid, enflurane, eniclobrate, enilconazole, enilospirone, enisoprost, enocitabine, enolicam, enoxacin, enoxamast, enoximone, enoxolone, eniprazole, eniproline, enprazepine, enprofylline, enpromate, enprostil, enrofloxacin, entsufon sodium, enviomycin, enviradene, epalretat, epanolol, eperisone, ephedrine, epicainide, epicillin, epicriptine, epiestriol, epimestrol, epinastine, epinephrine, epinephryl borate, epipropidine, epirizole, epiroprim, epirubicin, epithiazide, epitiostanol, epoprostenol, epostane, eprazinone, eprovafen, eproxindine, eprozinol, epsiprantel, eptaloprost, eptazocine, equilin, erdosteine, ergocalciferol, ergoloid mesylates, ergonovine, ergosterol, ergotamine, ericolol, erizepine, erocainide, erythrityl tetranitrate, erythromycin, erythromycin acistrate, erythromycin ethylsuccinate, erythromycin propionate, erythrosine, esaprazole, esculamine, eseridine, esflurbiprofen, esmolol, esorubicin, esproquin, estazolam, estradiol, estradiol benzoate, estradiol cypionate, estradiol dipropionate, estradiol enanthate, estradiol undecylate, estradiol valerate, estramustine, estramustine phosphate, estrapronicate, estrazinol, estriol, estrofurate, estrone, estrone hydrogen sulfate, estropipate, esuprone, etabenzarone, etacepride, etafedrine, etafenone, etamestrol, etamiline, etamiphyllin, etamocycline, etanidazole, etanterol, etaqualone, etasuline, etazepine, etazolate, etebenecid, eterobarb, etersalate, ethacridine, ethacrynic acid, ethambutol, ethamivan, ethamsylate, ethanolamine oleate, ethaverine, ethchlorvynol, ethenzamide, ethazide, ethidium chloride, ethinamate, ethinyl estradiol, ethiofos, ethionamide, ethsterone, ethoheptazine, ethomoxane, ethonam, ethopropazine, ethosuximide, ethotoin, ethoxazene, ethoxazorutoside, ethoxzolamide, ethyybenztropine, ethyl biscoumacetate, ethyl carfluzepate, ethyl cartrizoate, ethyl dibunate, ethyl dirazepate, ethylenediamine, ethylestrenol, ethylhydrocupreine, ethyl loflazepate, ethylmethylthiambutene, ethylmorphine, 9-ethyl-6-mercaptopurine, ethyl nitrite, ethylnorepinephrine, ethylparaben, ethylphenacemide, ethylstibamine, ethynerone, ethynodiol diacetate, ethypicone, etibendazole, eticlopride, eticyclidine, etidocaine, etidronic acid, etifelmine, etifenin, etifoxine, etilamfetamine, etilefrine, etilefrine pivalate, etintidine, etiochlanolone, etipirium iodide, etiproston, etiracetam, etiroxate, etisazole, etisomicin, etisulergine, etizolam, etocarlide, etocrylene, etodolac, etodroxzine, etofamide, etofenamate, etofenprox, etofibrate, etoformin, etofuradine, etofylline, etoglucid, etolorex, etolotifen, etoloxamine, etomidate, etomidoline, etomoxir, etonitazene, etoperidone, etoposide, etoprindole, etoprine, etorphine, etosalamide, etoxadrol, etoxeridine, etozolin, etrabamine, etretinate, etryptamine, etymemazine, eucalyptol, eucatropine, eugenol, euprocin, evandamine, Evans blue, exalamide, exametazine, exaprolol, exepanol, exifone, exiproben, falintolol, falipamil, famiraprinium chloride, famotidine, famotine, famiprofazone, fanetizole, fantridone, fazadinium bromide, fazaribine, febantel, febarbamate, februpol, febuverine, feclemine, feclobuzone, fedrilate, felbamate, felbinac, felipyrine, felodipine, femoxetine, fenabutene, fenacetinol, fenaclon, fenadiazole, fenaptic acid, fenalamide, fenalcomine, fenamifuril, penamole, fenaperone, fenbendazole, fenbencillin, fenbufen, fenbutrazate, fencamfamine, fencibutirol, fenclexonium metilsulfate, fenclofenac, fenclonine, fenclorac, fenlozic acid, fendiline, fendosal, feneritrol, fenestrel, fenethazine, fenethylline, fenetradil, fenflumizole, fenfluramine, fenfluthrin, fengabine, fenharmane, fenimide, feniodium chloride, fenipentol, fenirofibrate, fenisorex, fenmetozole, fenmetramide, fenobam, fenocinol, fenoctimine, fenofibrate, fenoldopam, fenoprofen, fenoterol, fenoverine, fenoxazoline, fenoxedil, fenozolone, fenpentadiol, fenperate, fenipalone, fenipramide, fenprane, fenpiverinium bromide, fenprinast, fenproporex, fenprostalene, fenquizone, fenretinide, fenspiride, fentanyl, fentiazac, fenticlor, fenticonazole, fentonium bromide, fenyripol, fepentolic acid, fepitrizol, fepradinol, feprazone, fepromide, feprosidnine,ferriclate calcium, ferrotrenine, ferrous fumarate, ferrous gluconate, fetoxylate, fexicaine, fexinidazole, fezatione, fezolamine, fiacitabine, fibracillin, filenadol, filipin, fifexide, flamenol, flavamine, flavodic acid, flavodil, flavoneactic acid, flavoxate, flazalone, flecainide, flerobuterol, fleroxacin, flesinoxan, flestolol, fletazepam, floctafenine, flomoxef, flopropione, florantyrone, flordipine, floredil, florfenicol, florifenine, flosequinan, flotrenizine, floverine, floxacillin, floxacrine, floxuridine, fluacizine, flualamide, fluanisone, fluazacort, flubanilate, flubendazole, flubepride, flucabril, flucetorex, flucindole, fluciprazine, flucloronide, fluconazole, flucrylate, flucytosine, fludalanine, fludarabine phosphate, fludazonium chloride, fludiazepam, fludorex, fludoxopone, fludrocortisone acetate, flufenamic acid, flufenisal, flufosal, flufylline, fluindarol, fluindione, flumazenil, flumecinol, flumedroxone-17-acetate, flumequine, flumeridone, flumethasone, flumethasone pivalate,flumethiazide, flumetramide, flumexadol, flumezapine, fluminorex, flumizole, flumoxonide, flunamine, flunarizine, flunidazole, flunisolide, flunisolide acetate, flunitrazepan, flunixin, flunoprost, flunoxaprofen, fluocinolone acetonide, fluocinonide, flourcortin butyrate, fluocortolone, fluocortolone caproate, fluorescein, fluoresone, fluoroadenosine, 3-fluoroandrostanol, fluorodopane, fluorohydroxyandrosterone, fluorometholone, fluorometholone acetate, fluorosalan, 6-fluorotestosterone propionate, fluorouracil, 9-fluoroxotestenololactone, 9-fluoroxotestololacetone, fluotracen, fluoxetine, fluoxymesterone, fluparoxan, flupentixol, fluperamide, fluperlapine, fluperolone acetate, fluphenazine, fluphenazine enanthate, flupimazine, flupirtine, flupranone, fluprazine, fluprednidene, fluprednisolone, fluprednisolone valerate, fluprofen, fluprofylline, fluproquazone, fluprostenol, fluquazone, fluradoline, flurandrenoline, flurantel, flurazepam, flurbiprofen, fluretofen, flurithromycin, flurocitabine, flurofamide, flurogestone acetate, flurothyl, fluroxene, flusoxolol, fluspiperone, fluspirilene, flutamide, flutazolam, flutemazepam, flutiazin, fluticasone propionate, flutizenol, flutonidine, flutoprazepam, flutroline, flutropium bromide, fluvoxamine, fluzinamide, fluzoperine, folescutol, folic acid, fomidacillin, fominoben, fomocaine, fonazine, fopirtoline, forfenimex, formebolone, formetorex, formintrazole, formocortal, formoterol, fosarilate, fosazepam, foscarnet, foscolic acid, fosenazide, fosfocreatine, fosfomycin, fosfonet, fosfosal, fosinapril, fosmenic acid, fosmidomycin, forpirate, fostedil, fostriecin, fotemustine, fotreamine, frabuprofen, frentizole, fronepidil, froxiprost, ftaxilide, ftivazide, ftorafur, ftormetazine, ftorpropazine, fubrogonium iodide, fuchsin, fumagillin, fumoxcillin, fuprazole, furacrinic acid, furafylline, furalazine, furaltadone, furaprofen, furazabol, furazolidone, furazolium chloride, furbucillin, furcloprofen, furegrelate, furethidine, furfenorex, furidarone, furmethoxadone, furobufen, furodazole, furofenac, furomazine, furosemide, furostilbestrol, fursalan, fursultiamine, furterene, furtrethonium iodide, fusidic acid, fuzlocillin, gabapentin, gabexate, gaboxadol, galantamine, gallamine triethodide, gallopamil, galosemide, galtifenin, gampexine, gamolenic acid, ganciclovir, ganglefene, gapicomine, gapromidine, gefarnate, gemazocine, gemcadiol, gemeprost, gemfibrozil, gentamicin, gentian violet, gepefrine, gepirone, geroquinol, gestaclone, gestadienol, gestodene, gestonorone caproate, gestrinone, giparmen, gitaloxin, gitoformate, glafenine, glaziovine, gliamilide, glibornuride, glibutimine, glicaramide, glicetanile, geroquinol, gestaclone, gestadienol, gestodene, gestonorone caproate, gestrinone, giparmen, gitaloxin, gitoformate, glafenine, glaziovine, gliamilide, glibornuride, glibutimine, glicaramide, glicetanile, gliclazide, glicondamide, glidazamide, gliflumide, glimepiride, glipentide, glipizide, gliquidone, glisamuride, glisindamide, glisolamide, glisoxepide, gloxazone, gloximonam, glucametacin, glucosamine, glucosulfamide, glucosulfone, glucurolactone, glucuronamide, glunicate, glutamic acid, glutaral, glutarimide, glutaurine, glutethimide, glyburide, glybuthiazol, glybuzole, glyceryl monostearate, glycidyl methacrylate, glycine, glyclopyramide, glybiarsol, glycopyrrolate, glycyclamide, glyhexamide, glymidine, glyoctamide, glypinamide, glyprothiazol, glysobuzole, gold thiomalate, gold sodium thiosulfate, granisetron, griseofulvin, guabenxan, guacetisal, guafecainol, guaiactamine, guaiapate, guaietolin, guaifenesin, guaimesal, guaisteine, guaithylline, guamecycline, guanabenz, guanacline, guanadrel, guanazodine, guanazole, guanclofine, guancydine, guanethidine, guanfacine, guanisoquin, guanoclor, guanoctine, guanoxabenz, guanoxan, guanoxyfen, hadacidin, halazepam, halazone, halcinonide, halethazole, halocortolone, halofantrine, halofenate, halofuginone, halometasone, halonamine, halopemide, halopenium chloride, haloperidol, haloperidol decanoate, haloperidone acetate, haloprogesterone, haloprogin, halothane, haloxazolam, haloxon, halquinols, hedaquinium chloride, hepronicate, heptabarbital, heptaminol, heptaverine, heptolamide, hepzidine, hetacillin, hetaflur, heteronium bromide, hexachlorophene, hexacyclonate, hexacyprone, hexadiline, hexadimethrine bromide, hexafluorenium bromide, hexamethonium bromide, hexamidine, hexapradol, hexaprofen, hexapropymate, hexasonium iodide, hexacarbacholine bromide, hexedine, hexestrol, hexetidine, hexobarbital, hexobendine, hexocyclium methylsulfate, hexoprenaline, hexopyrronium bromide, hexylcaine, hexylene glycol, hexylresorcinol, histamine, histapyrrodine, homarylamine, homatropine, homatropine methylbromide, homidium bromide, homochlorcyclizine, homofenazine, homoharringtonine, homopipramol, homosalate, homotestosterone propionate, homprenorphine, hopantenic acid, hoquizil, hycanthone, hydracarbazine, hydralazine, hydrargaphen, hydrobentizide, hydrochlorthiazide, hydrocodone, hydrocortamate, hydrocortisone, hydrocortisone aceponate, hydrocortisone acetate, hydrocortisone butyrate, hydrocortisone cypionate, hydrocortisone-phosphate, hydrocortisone succinate, hydrocortisone valerate, hydroflumethiazide, hydromadinone, hydromorphinol, hydromorphone, hydroquinone, hydroxindasate, hydroxindasol, hydroxyoxocobalamin, hydroxy amphetamine, hydroxychloroquine, hydroxydimethandrostadienone, hydroxydione succinate, hydroxymethylandrostanone, 10-hydroxynorehisterone, hydroxypethidine, hydroxyphenamate, hydroxyprocaine, hydroxyprogeserone, hydroxyprogesterone caproate, hydroxypyridine tartrate, hydroxystilbamidine, 7-hydroxytestololacetone, hydroxytestosterone propionate, hydroxytetracaine, hydroxytoluic acid, hydroxyurea, hydroxyzine, hymecromone, hyoscyamine, hypericin, ibacitabine, ibafloxacin, ibazocine, ibopamine, ibrotamide, ibudilast, ibufenac, ibuprofen, ibuprofen piconol, ibuproxam, ibuterol, ibuverine, icazepam, icosipiramide, icotidine, idarubicin, idaverine, idazoxan, idebenone, idenast, idoxuridine, idralfidine, idrocilamide, idropranolol, ifenprodil, ifosfamide, ifoxetine, ilmofosine, iloprost, imafen, imanixil, imazodan, imcarbofos, imexon, imiclopazine, imidazole salicylate, imidazopyrazole, imidecyl iodine, imidocarb, imidoline, imidurea, imiloxan, iminophendimide, imipenem, imipramine, imipraminoxide, imirestat, imolamine, imoxiterol, impacarzine, impromidine, improsulfan, imuracetam, inaperisone, indacrinone, indalpine, indanazoline, indanidine, indanorex, indapamide, indatraline, indacainide, indeloxazine, indenolol, indicine-N-oxide, indigotindisulfonic acid, indobufen, indocate, indocyanine green, indolapril, indolidan, indomethacin, indopanolol, indopine, indoprofen, indoramin, indorenate, indoxole, indriline, inicarone, inocoterone, inosine, inosine dialdehyde, inositol niacinate, inproquone, intrazole, intriptyline, iobenzamic acid, iobutic acid, iocarmic acid, iocetamic acid, iodamide, iodecimol, iodetryl, iodipamide, iodixanol, iodoalphionic acid, iodol, iodophthalein, iodoquinol, iodothiouracil, iodoxamic acid, ioglicic acid, ioglucol, ioglucomide, ioglunide, ioglycamic acid, iogulamide, iohexol, iodlidonic acid, iolixanic acid, iomeglamic acid, iomeprol, iomorinic acid, iopamidol, iopanoic acid, iopentol, iophendylate, iophenoxic acid, ioprocemic acid, iopromide, iopronic acid, iopydol, iopydone, iosarcol, iosefamic acid, ioseric acid, iosimide, iosulamide, iosumetic acid, iotasul, iotetric acid, iothalamic acid, iotranic acid, iotrizoic acid, iotrolan, iotroxic acid, ioversol, ioxabrolic acid, ioxaglic acid, ioxitalamic acid, ioxotrizoic acid, iozomic acid, ipexidine, ipodic acid, ipragratine, ipramidil, ipratropium bromide, iprazochrome, ipriflavone, iprindole, iprocinodine, iproclozide, iprocrolol, iprofenin, iproheptine, iproniazid, iproidazole, iproplatin, iprotiazem, iproxamine, iprozilamine, ipsalazide, ipsapirone, iquindamine, irindalone, irloxacin, irolapride, irsogladine, isamfazone, isamoltan, isamoxole, isaxonine, isbogrel, isepamicin, isoaminile, isobromindione, isobucaine, isobutamben, isocarboxazid, isoconazole, isocromil, isoetharine, isofezolac, isoflupredone acetate, isoflurane, isoflurophate, isoleucine, isomazole, isomerol, isometamidium, isomethadone, isometheptene, isomylamine, isoniazid, isonixin, isoprazone, isoprednidene, isoprofen, isoprofamide iodide, isopropicillin, isopropyl myristate, isopropyl palmitate, isoproterenol, isosorbide, isosorbide dinitrate, isosorbide mononitrate, isospalglumic acid, isosulfan blue, isosulpride, isothipendyl, isotic, isotiquimide, isotretinoin, isoxaprolol, isoxepac, isoxicam, isoxsuprine, isradipine, itanoxone, itazigrel, itraconazole, itrocainide, ivermectin bib, ivoqualine, josamycin, kainic acid, kalafungin, kanamycin, kebuzone, keracyanin, ketamine, ketanserin, ketazocine, ketazolam, kethoxal, ketipramine, ketobemidone, ketocaine, ketocainol, ketoconazole, ketoprofen, ketorfanol, ketorolac, ketotifen, ketotrexate, khellin, khelloside, kitasamycin, labetalol, lacidipine, lactalfate, lactose, lactulose, lamotrigine, lamtidine, lanatoside, lapachol, lapinone, lapyrium chloride, lasalocid, laudexium methyl sulfate, lauralkonium chloride, laureth, laurixamine, laurocapram, lauroguadine, laurolinium acetate, lauryl isoquinolinium, lefetamine, leflunomide, leiopyrrole, lemidosul, lenampicillin, leniquinsin, lenperone, leptacline, lergotrile, letimide, letosteine, leucine, leucinocaine, leucocianidol, leucovorin, levacecarnine, levallorphan, levamfetamine, levamisole, levdropropizine, levisoprenaline, levlofexidine, levobunolol, levocabastine, levocarnitine, levodopa, levofacetoperane, levofenfluramine, levofuraltadone, levoglutamide, levomenol, levomethadone, levomethadyl acetate, levomethorphan, levometiomeprazine, levomopranol, levomoramide,levonantradol, levonordeprin, levonorgestrel, levophenacyl morphan, levopropoxyphene, levopropylcillin, levopropylhexedrine, levoprotiline, levorin, levorphanol, levothyroxine, levoxadrol, lexofenac, libecillide, libenzapril, lidamidine, lidocaine, lidofenin, lidoflazine, lifibrate, lilopristone, limaprost, lincomycin, lindane, linsidomine, liothyronine, liroldine, lisinopril, lisuride, lithium carbonate, lithium citrate, litracen, lividomycin, lixazinone, lobeline, lobendazole, lobenzarit, lobuprofen, locicortone, lodaxaprine, lodacezarlodinixil, lodiperone, lodoxamide, lodoxamide ethyl, lofemizole, lofendazam, lofentanil, lofepramine, lofexidine, loflucarban, lombazole, lomefloxacin, lometraline, lomevactone, lomifylline, lomofungin, lomustine, lonapalene,lonaprofen, lonazolac, lonidamine, loperamide, loperamide oxide, lopirazepam, loprazolam, loprodiol, lorajmine, loapride, loratadine, lorazepam, lorbamate, lorcainide, lorcinadol, lorglumide, lormetazepam, lortalamine, lorzafone, losindole, losulazine, lotifazole, lotrifen, lotucaine, lovastatin, loxanast, loxapine, loxiglumide, loxoprofen, loxtidine, lozilurea, lucanthone, lucartamide, lucimycin, lufuradom, lupitidine, luprostiol, luxabendazole, lyapolate sodium, lycetamine, lydimycin, lymecycline, lynestrenol, lysergide, lysine, mabuterol, maduramicin, mafenide, mafoprazine, mafosfamide, magnesium citrate, magnesium gluconate, magnesium salicylate, malathion, malethamer, malic acid, malotilate, manidipine, manganese gluconate, mannitol, mannitol hexanitrate, mannomustine, mannosulfan, manozodil, maprotiline, maridomycin, mariptiline, maroxepin, maytansine, mazaticol, mazindol, mazipredone, mebanazine, mebendazole, mebenoside, mebeverine, mebezonium iodide, mebhydrolin, mebiquine, mebolazine, mebrofenin, mebutamate, mebutizide, mecamylamine, mecarbinate, mecetronium ethylsulfate, mechlorethamine, meciadanol, mecinarone, meclizine, meclocycline, meclocycline sulfosalicylate, meclofenamic acid, meclofenoxate, meclonazepam, mecloqualone, mecloralurea, meclorisone dibutyrate, mecloxamine, mecobalamin, mecrylate, mecysteine, medazepam, medazomide, medetomidine, medibazine, medifoxamine, medorinone, medorubicin, medrogestone, medronic acid, medroxalol, medroxyprogestrone, medroxyprogestrone acetate, medrylamine, medrysone, mefeclorazine, mefenamic acid, mefenidil, mefenidramium metilsulfate, mefenorex, mefeserpine, mefexamide, mefloquine, mefruside, megalomicin, megestrol acetate, meglitinide, megucycline, meglumine, meglutol, meladrazine, melarsonyl, melarsoprol, melengestrol acetate, meletimide, melinamide, melitracen, melizame, meloxicam, melperone, melphalan, memantine, memotine, menabitan, menadiol, menadiol diphosphate, menadiol disulfate, menadione, menadione sodium bisulfite, menatetrenone, menbutone, menfegol, menglytate, menitrazepam, menoctone, menogaril, menthol, meobentine, meparfynol, mepazine, mepenzolate bromide, meperidine, mephenesin, mephenoxalone, mephentermine, mephenyton, mephobarbital, mepindolol, mepiprazole, mepiroxol, mepitiostane, mepivacaine, mepixanox, mepramidil, meprednisone, meprobamate, meproscillarin, meproxitol, meprylcaine, meptazinol, mequidox, mequinol, mequitazine, meralein, meralluride, merbarone, merbromin, mercaptamine, mercaptomerin, mercaptopurine, mercuderamide, mercufenol chloride, mercumatilin, mercurobutol, mergocriptine, merophan, mersalyl, mesabolone, mesalamine, meseclazone, mesna, mesocarb, meso-hexestrol, mesoridazine, mesipirenone,mestanolone, mesterolone, mestranol,mesudipine, mesulergine, mesulfamide, mesulfen, mesuprine, metabromsalan, metacetamol, metaclazepam, metaglycodol, metahexamide, metamelfalan, metamfazone, metamfepramone, metampicillin, metanixin, metapramine, metaproterenol, metaraminol, metaterol, metaxalone, metazamide, metazide, metazocine, metbufen, meteneprost, metergoline, metergotamine, metescufylline, metesculetol, metethoheptazine, metformin, methacholine chloride, methacycline, methadone, methadyl acetate, methallenestril, methallibure, methalthiazide, methamphetamine, methandriol, methandrostenolone, methaniazide, methantheline bromide, methaphenilene, methapyrilene, methaqualone, metharbital, methastyridone, methazolamide, methdilazine, methenamine, methenolone acetate, methenolone enanthate, metheptazine, methestrol, methetoin, methicillin, methimazole, methiodal sodium, methioguanine, methiomeprazine, methionine, methisazone, methitural, methixene, methocarbamol, methohexital, methopholine, methoserpidine, methotrexate, methotrimeprazine, methoxamine, methoxsalen, methoxyflurane, methoxyphedrine, methoxyphenamine, methoxypromazine, methscopolamine bromide, methsuximide, methylclothiazide, N-methyladrealone hcl, methyl alcohol, methylatropine nitrate, methylbenactyzium bromide, methylbenzethonium, methylchromone, methyldesorphine, methyldihydromorphine, methyldopa, methyldopate, methylene blue, methylphedrine, methylergonovine, methylformamide, methyl nicotinate, 2-methyl-19-nortestosterone, 2-methyl-11-oxoprogestrone, methyl palmoxirate, methylparaben, methylphendiate, methylprednisolone, methylprednisolone aceponate, methylprednisolone acetate, methylprednisolone hemisuccinate, methylprednisolone phosphate, methylprednisolone suleptanate, methyl salicylate, methylstreptonigrin, 4-methyltestosterone, 7-methyltestosterone, 17-methyltestosterone, 7-methyltesosterone propionate, methylthionosine, 16-methylthioprogestone, methylthiouracil, methynodiol diacetate, methyprylon, methysergide, metiamide, metiapine, metiazinic acid, metibride, meticrane, metildigoxin, metindizate, metioprim, metioxate, metipirox, metipranolol, metiprenaline, metitepine, metizoline, metkephamid, metochalcone, metocinium iodide, metoclopramide, metocurine iodide, metofenazate, metogest, metolazone, metomidate, metopimazine, metopon, metoprine, metoprolol, metoquizine, metoserpate, metostilenol, metoxepin, metrafazoline, metralindole, metrazifone, metrenperone, metribolone, metrifonate, metrifudil, metrizamide, metrizoic acid, metronidazole, meturedepa, metyrapone, metyridine, metyrosine, mevastatin, mexafylline, mexazolam, mexenone, mexiletine, mexiprostil, mexoprofen, mexrenoate, mezacopride, mezepine, mezilamine, mezlocillin, mianserin, mibolerone, micinicate, miconazole, micronomicin, midaflur, midaglizole, midalcipran, midamaline, midazogrel, midazolam, midecamycin, midodrine, mifentidine, mifepristone, mifobate, miglitol, mikamycin, milacemide, milenperone, milipertine, miloxacin, milrinone, milverine, mimbane, minaprine, minaxolone, mindolilol, mindoperone, minepentate, minocromil, minocycline, minoxidil, mioflazine, mipimazole, mirincamycin, miristalkonium chloride, miroprofen, mirosamicin, misonidazole, misoprostol, mitindomide, mitobronitol, mitoclomine, mitoguazone, mitolactol, mitomycin, mitonafide, mitopodozide, mitoquidone, mitotane, mitotenamine, mitoxantrone, mitozolomide, mivacurium chloride, mixidine, misoprostol, mitindomide, mitobronitol, mitoclomine, mitoguazone, mitolactol, mitomycin, mitonafide, mitopodozide, mitoquidone, mitotane, mitotenamine, mitoxantrone, mitozolomide, mivacurium chloride, mixidine, mizoribine, mobecarb, mobenzoxamine, mocimycin, mociprazine, moclobemide, moctamide, modafinil, modaline, mofebutazone, mofloverine, mofoxime, molfarnate, molinazone, molindone, molracetam, molsidomine, mometasone furoate, monalazone disodium, monensin, monobenzone, monoethanolamine, monometacrine, monophosphothiamine, monothioglycerol, monoxerutin, montirelin, moperone, mopidamol, mopidralazine, moprolol, moquizone, morantel, morazone, morclofone, morforex, moricizine, morinamide, morniflumate, morocromen, moroxydine, morpheridine, morphine, morsuximide, motapizone, motrazepam, motretinide, moveltipril, moxadolen, moxalactam, moxaprindine, moxastine, moxaverine, moxazocine, moxestrol, moxicoumone, moxipraquine, moxisylyte, moxnidazole, moxonidine, mupirocin, murabutide, murocainide, muzolimine, mycophenolic acid, myfadol, myralact, myrophine, myrtecaine, nabazenil, nabilone, nabitan, naboctate, nabumetone, nadide, nadolol, nadoxolol, naepaine, nafamostat, nafazatrom, nafcaproic acid, nafcillin, nafenodone, nafenopin, nafetolol, nafimidone, nafiverine, naflocort, nafomine, nafoxadol, nafoxidine, nafronyl, naftalofos, naftazone, naftifine, naftopidil, naftoxate, naftypramide, nalbuphine, nalidixic acid, nalmefene, nalmexone, nalorphine, naltrexone, naminterol, namoxyrate, nanaprocin, nandrolone cyclotate, nandrolone decanoate, nandrolone phenpropionate, nanofin, nantradol, napactadine, napamezole, naphazoline, naphthonone, naprodoxime, naproxen, naproxol, naranol, narasin, natamycin, naxagolide, naxaprostene, nealbarbital, nebidrazine, nebivolol, nebracetam, nedocromil, nefazodone, neflumozide, nefopam, nelezaprine, neoarsphenamine, neocinchophen, neomycin, neostigmine bromide, nequinate, neraminol, nerbacadol, nesapidil, nesosteine, netilmicin, netobimin, neutramycin, nexeridine, niacin, niacinamide, nialamide, niaprazine, nibroxane, nicafenine, nicainoprol, nicametate, nicarbazin, nicarpidine, nicergoline, niceritrol, niceverine, niclofolan, niclosamide, nicoboxil, nicoclonate, nicocodine, nicocortonide, nicodicodine, nicofibrate, nicofuranose, nicofurate, nicogrelate, nicomol, nicomorphine, nicopholine, nicorandil, nicothiazone, nicotinyl alcohol, nicoxamat, nictiazem, nictindole, nodroxyzone, nifedipine, nifenalol, nifenazone, niflumic acid, nifluridide, nifuradene, nifuraldezone, nifuralide, nifuratel, nifuratrone, nifurdazil, nifurethazone, nifurfoline, nifurimide, nifurizone, nifurmazole, nifurmerone, nifuroquine, nifuroxazide, nifuroxime, nifurpipone, nifurpirinol, nifurprazine, nifurquinazole, nifursemizone, nifursol, nifurthiazole, nifurtimox, nifurtoinol, nifurvidine, nifurzide, niguldipine, nihydrazone, nikethamide, nileprost, nilprazole, niludipine, nilutamide, nilvadipine, nimazone, nimesulide, nimetazepam, nimidane, nimodipine, nimorazole, nimustine, niometacin, niperotidine, nipradilol, niprofazone, niridazole, nisbuterol, nisobamate, nisoldipine, nisoxetine, nisterime acetate, nitarsone, nitazoxanide, nithiamide, nitracrine, nitrafudam, nitralamine, nitramisole, nitraquazone, nitrazepam, nitrefazole, nitrendipine, nitricholine, nitrochlofene, nitrocycline, nitrodan, nitrofurantoin, nitrofurazone, nitroglycerin, nitromersol, nitromide, nitromifene, nitroscanate, nitrosulfathiazole, nitroxinil, nitroxoline, nivazol, nivimeldone, nixylic acid, nizatidine, nizofenone, noberastine, nocloprost, nocodazole, nofecainide, nogalamycin, nolinium bromide, nomegestrol, nomelidine, nomifensine, nonabine, nonaperone, nonapyrimine, nonoxynol-4, nonoxynol-9, noracymethadol, norbolethone, norbudrine, norclostebol, norcodeine, nordazepam, nordefrin, nordinone, norepinephrine, norethandrolone, norethindrone, norethindrone acetate, norethynodrel, noreximide, norfenefrine, norfloxacin, norfloxacin succinil, norflurane, norgesterone, norgestimate, norgestomet, norgestrel, norgestrienone, norletimol, norlevorphanol, normethadone, normethandrone, normorphine, norpipanone, nortestosterone propionate, nortetrazepam, nortriptyline, norvinisterone, nosantine, noscapine, nosiheptide, novobiocin, noxiptiline, noxytiolin, nuclomedone, nuclotixine, nufenoxole, nuvenzepine, nylestriol, nylidrin, nystatin, obidoxime, ociltide, ocrylate, octabenzone, octacaine, octafonium chloride, octamoxin, octamylamine, octanoic acid, octapinol, octastine, octaverine, octazamide, octenidine, octenidine saccharin, octicizer, octimibate, octorylene, octodrine, octopamine, octotiamine, octoxynol-9, octriptyline, octrizole, ofloxacin, ofornine, oftasceine, olaflur, olaquindox, oleanomycin, oletimol, oleyl alcohol, olivomycin a, olmidine, olpimedone, olsalazine, oltipraz, olvanil, omeprazole, omidoline, omoconazole, omonasteine, onapristone, ondansetron, ontianil, opiniazide, opipramol, orazamide, orbutopril, orconazole, orestrate, ormetoprim, ornidazole, ornipressin, ornithine, ornoprostil, orotic acid, orotirelin, orpanoxin, orphenadrine, ortetamine, osalmid, osmadizone, otilonium bromide, otimerate sodium, ouabain, oxabolone cipionate, oxabrexine, oxaceprol, oxacillin, oxadimedine, oxaflozane, oxaflumazine, oxagrelate, oxalinast, oxaliplatin, oxamarin, oxametacin, oxamisole, oxamniquine, oxanamide, oxandrolone, oxantel, oxapadol, oxapium iodide, oxapropanium iodide, oxaprotiline, oxaprozin, oxarbazole, oxatomide, oxazafone, oxazepam, oxazidione, oxazolam, oxazorone, oxcarbazepine, oxdralazine, oxeladin, oxendolone, oxepinac, oxetacillin, oxethazaine, oxetorone, oxfendazole, oxfenicine, oxibendazole, oxibetaine, oxiconazole, oxidopamine, oxidronic acid, oxifentorex, oxifungin, oxilorphan, oximonam, oxindanac, oxiniacic acid, oxiperomide, oxiracetam, oxiramide, oxisopred, oxisuran, oxitefonium bromide, oxitriptan, oxitriptyline, oxitropium bromide, oxmetidine, oxodipine, oxogestone phenpropionate, oxolamine, oxolinic acid, oxomemazine, oxonazine, oxophenarsine, oxoprostol, oxpheneridine, oxprenoate potassium, oxprenolol, oxtriphylline, oxybenzone, oxybutynin, oxychlorosene, oxycinchophen, oxyclozanide, oxycodone, oxydipentonium chloride, oxyfedrine, oxymesterone, oxymetazoline, oxymetholone, oxymorphone, oxypendyl, oxypertine, oxyphenbutazone, oxyphenonium bromide, oxypurinol, oxypyrronium bromide, oxyquinoline, oxyridazine, oxysonium iodide, oxytetracycline, oxytiocin, ozagrel, ozolinone, pacrinolol, pactamycin, padimate, pafenolol, palatrigine, paldimycin, palmidrol, palmoxiric acid, pamabrom, pamaquine, pamatolol, pamidronic acid, pancuronium bromide, panidazole, panomifene, patenicate, panthenol, pantothenic acid, panuramine, papaverine, papaveroline, parachlorophenol, paraflutizide, paraldehyde, paramethadione, paramethasone acetate, paranyline, parapenzolate bromide, parapropamol, pararosaniline, pararosaniline embonate, paraxazone, parbendazole, parconazole, pareptide, parethoxycaine, pargeverine, pargolol, pargyline, paridocaine, parodilol, paromomycin, paroxetine, paroxypropione, parsalmide, partricin, parvaquone, pasiniazid, paulomycin, paxamate, pazelliptine, pazoxide, pcnu, pecilocin, pecocycline, pefloxacin, pelanserin, pelretin, pelrinone, pemedolac, pemerid, pemoline, pempidine, penamecillin, penbutolol, pendecamaine, penfluridol, penflutizide, pengitoxin, penicillamine, penicillin procaine, penicillin, penimepicycline, penimocycline, penirolol, penmesterol, penoctonium bromide, penprostene, pentabamate, pentacynium chloride, pentaerythritol tetranitrate, pentafluranol, pentagastrin, pentagestrone, pentalamide, pentamethonium bromide, pentamethylmelamine, pentamidine, pentamoxane, pentamustine, pentapiperide, pentapiperium methylsulfate, pentaquine, pentazocine, pentetate calcium trisodium, pentetic acid, penthienate bromide, penthrichloral, pentiapine maleate, pentifylline, pentigetide, pentisomicin, pentisomide, pentizidone, pentobarbital, pentolinium tartrate, pentomone, pentopril, pentorex, pentosan polysulfate sodium, pentostatin, pentoxifylline, pentrinitrol, pentylenetrazole, peplomycin, pepstatin, peraclopone, peradoxime, perafensine, peralopride, peraquinsin, perastine, peratizole, perbufylline, perfluamine, perflunafene, pergolide, perhexilene, periciazine, perimetazine, perindopril, perindoprilat, perisoxal, perlapine, permethrin, perphenazine, persilic acid, petrichloral, pexantel, phanquone, phenacaine, phenacemide, phenacetin, phenacttropinium chloride, phenadoxone, phenaglycodol, phenamazoline, phenampromide, phenarsone sulfoxylate, phenazocine, phenazopyridine, phencarbamide, phencyclidine, phendimetrazine, phenelzine, pheneridine, phenesterin, penethicillin, phenformin, phenglutarimide, phenicarbazide, phenindamine, phenindione, pheniprazine, pheniramine, phenisonone, phenmetrazine, phenobarbital, phenobutiodil, phenolphtalein, phenolsulfonphthalein, phenomorphan, phenoperidine, phenothiazine, phenothrin, phenoxybenzamine, phenoxypropazine, phenprobamate, phenprocoumon, phenpromethamine, phensuximide, phentermine, phentolamine, phenylalanine, phenyl aminosalicylate, phenylbutazone, phenylrphrine, phenylethyl alcohol, phenylmercuric acetate, phenylmercuric borate, phenylmercuric chloride, phenylmercuric nitrate, phenylmethylbarbituric acid, phenylpropanolamine, phenylthilone, phenyltoloxamine, phenyramidol, phenytoin, phetharbital, pholcodine, pholedrine, phosphoramide mustard, phoxim, phthalofyne, phthalysulfacetamide, phthalylsulfamethizole, phthalylsulfathiazole, physostigmine, phytic acid, phytonadiol diphosphate, phytonadione, pibecarb, pibenzimol, pibecarb, pibenzimol, piberaline, picafibrate, picartamide, picenadol, picilorex, piclonidine, piclopastine, picloxydine, picobenzide, picodralazine, picolamine, piconol, picoperine, picoprazole, picotamide, picotrin diolamine, picumast, pidolic acid, pifarnine, pifenate, pifexole, piflutixole, pifoxime, piketoprofen, pildralazine, pilocarpine, pimoclone, pimefylline, pimelautde, pimetacin, pimethixene, pimetine, pimetremide, piminodine, pimobendan, pimondiazole, pimozide, pinacidil, pinadoline, pinafide, pinaverium bromide, pinazepam, pincainide, pindolol, pinolcaine, pinoxepin, pioglitazone, pipacycline, pipamazine, pipaperone, pipazethate, pipebuzone, pipecuronium bromide, pipemidic acid, pipenzolate bromide, pipequaline, piperacetazine, piperacillin, piperamide, piperazine, piperazinedione, piperidolate, piperilate, piperocaine, piperoxan, piperylone, pipobroman, pipoctanone, pipofezine, piposulfan, pipotiazine palmiate, pipoxizine, pipoxolan, pipradimadol, pipradol, pipramadol, pipratecol, piprinhydrinate, piprocurarium iodide, piprofurol, piprozolin, piquindone, piquizil, piracetam, pirandamine, pirarubicin, piraxelate, pirazmonam, pirazolac, pirbenicillin, pirbuterol, pirdonium bromide, pirenoxine, pirenperone, pirenzepine, pirepolol, piretanide, pirfenidone, piribedil, piridicillin, piridocaine, piridoxilate, piridronic acid, pirifibrate, pirindazole, pirinixic acid, pirinixil, piriprost, piriqualone, pirisudanol, piritramide, piritrexim, pirlimycin, pirlindole, pirmagrel, pirmenol, pirnabine, piroctone, pirogliride, piroheptine, pirolate, pirolazamide, piromidic acid, piroxantrone hcl, piroxicam, piroxicam cinnamate, piroxicillin, piroximone, pirozadil, pirprofen, pirquinozol, pirralkonium bromide, pirtenidine, pitenodil, pitofenone, pituxate, pivampicillin, pivenfrine, pivopril, pivoxazepam, pizotyline, plafibride, plaunotol, pleuromulin, plicamycin, podilfen, podophylloxoxin, poldine methylsulfate, polidocanol, ploymyxin, polythiazide, ponalrestat, ponfibrate, porfiromycin, poskine, potassium guaiacolsulfonate, potassium nitrazepate, potassium sodium tartrate, potassium sorbate, potassium thiocyanate, practolol, prajmalium, pralidoxime chloride, pramipexole, pramiracetam, pramiverine, pramoxime, prampine, pranolium chloride, pranoprofen, pranosal, prasterone, pravastatin, praxadine, prazepam, prazepine, praziquantel, prazitone, prazocillin, prazosin, preclamol, prednazate, prednazoline, prednicarbate, prednimustine, prednisolamate, prednisolone, prednisolone acetate, prednisolone hemisuccinate, prednisolone phosphate, prednisolone steaglate, prednisolone tebutate, prednisone, prednival, prednylidene, prefenamate, pregnenolone, pregnenolone succinate, premazepam, prenalterol, prenisteine, prenoverine, prenoxdiazine, prenylamine, pretamazium iodide, pretiadil, pribecarb, pridefine, prideperone, pridinol, prifelone, prifinium bromide, prifuroline, prilocaine, primaperone, primaquine, primidolol, primidone, primycin, prinomide, pristinamycin, prizidilol, proadifen, probarbital, probenecid, probicromil, probucol, procainamide, procaine, procarbazine, procaterol, prochlorperazine, procinolol, procinonide, proclonol, procodazole, procyclidine, procymate, prodeconium bromide, prodilidine, prodipine, prodolic acid, profadol, profexalone, proflavine, proflazepam, progabide, progesterone, proglumetacin, proglumide, proheptazine, proligestone, proline, prolintane, prolonium iodide, promazine, promegestone, promestriene, promethazine, promolate, promoxolane, pronetalol, propacetamol, propafenone, propamidine, propanidid, propanocaine, propantheline bromide, proparacaine, propatyl nitrate, propazolamide, propendiazole, propentofylline, propenzolate, properidine, propetamide, propetandrol, propicillin, propikacin, propinetidine, propiolactone, propiomazine, propipocaine, propiram, propisergide, propiverine, propizepine, propofol, propoxate, propoxycaine, propoxyphene, propranolol, propyl docetrizoate, propylene glycol, propylene glycol monostearate, propyl gallate, propylhexedrine, propyliodone, propylparaben, propylthiouracil, propyperone, propyphenazone, propyromazine bromide, proquazone, proquinolate, prorenoate potassium, proroxan, proscillaridin, prospidium chloride, prostalene, prosulpride, prosultiamine, proterguride, protheobromine, prothipendyl, prothixene, protiofate, protionamide, protirelin, protizinic acid, protokylol, protoveratine, protriptyline, proxazole, proxibarbal, proxibutene, proxicromil, proxifezone, proxorphan, proxyphylline, prozapine, pseudoephedrine, psilocybine, pumiteba, puromycin, pyrabrom, pyran copolymer, pyrantel, pyrathiazine, pyrazinamide, pyrazofurin, pyricarbate, pyridarone, pyridofylline, pyridostigmine bromide, pyridoxine, pyrilamine, pyrimethamine, pyrimitate, pyrinoline, pyrithione zinc, pyrithyldione, pyritidium bromide, pyritinol, pyronine, pyrophenindane, pyrovalerone, pyroxamine, pyrrobutamine, pyrrocaine, pyrroliphene, pyrrolnitrin, pyrvinium chloride, pytamine, quadazocine, quadrosilan, quatacaine, quazepam, quazinone, quazodine, quazolast, quifenadine, quillifoline, quinacainol, quinacillin, quinacrine, quinaldine blue, quinapril, quinaprilat, quinazosin, quinbolone, quincarbate, quindecamine, quindonium bromide, quindoxin, quinestradol, quinestrol, quinethazone, quinetolate, quinezamide, quinfamide, quingestanol acetate, quingestrone, quindine, quinine, quinocide, quinpirole, quinterenol, quintiofos, quinuclium bromide, quinupramine, quipazine, quisultazine, racefemine, racemethionine, racemethorphan, racemetirosine, raclopride, ractopamine, rafoxanide, ralitoline, raloxifene, ramciclane, ramefenazone, ramipril, ramiprilat, ramixotidine, ramnodignin, ranimustine, ranimycin, ranitidine, ranolazine, rathyronine, razinodil, razobazam, razoxane, reboxetine, recainam, reclazepam, relomycin, remoxipride, renanolone, rentiapril, repirinast, repromicin, reproterol, recimetol, rescinnamine, reserpine, resorantel, resorcinol, resorcinol monoacetate, retelliptine, retinol, revenast, ribavirin, riboflavin, riboflavin 5'-phosphate, riboprine, ribostamycin, ridazolol, ridiflone, rifabutin, rifamide, rifampin, rifamycin, rifapentine, rifaximin, rilapine, rilmazafone, rilmenidine, rilopirox, rilozarone, rimantadine, rimazolium metilsulfate, rimcazole, rimexolone, rimiterol, rimoprogin, riodipine, rioprostil, ripazepam, risocaine, risperidone, ristianol, ristocetin, ritanserin, ritiometan, ritodrine, ritopirronium bromide, ritrosulfan, robenidine, rocastine, rociverine, rodocaine, rodorubicin, rofelodine, roflurante, rokitamycin, roletamide, rolgamidine, rolicyclidine, rolicyprine, rolipram, rolitetracycline, rolodine, rolziracetam, romifenone, romifidine, ronactolol, ronidazole, ronifibrate, ronipamil, ronnel, ropitoin, ropivacaine, ropizine, roquinimex, rosaprostol, rosaramicin, rosaramicin butyrate, rosaramicin propionate, rosoxacin, rosterolone, rotamicillin, rotoxamine, rotraxate, roxarsone, roxatidine acetate, roxibolone, roxindole, roxithromycin, roxolonium metilsulfate, roxoperone, rufloxacin, rutamycin, rutin, ruvazone, sabeluzole, saccharin, salacetamide, salafibrate, salantel, salazodine, salazossulfadimedine, salazosulfamide, salazosulfathiazole, salethamide, salfluverine, salicin, salicyl alcohol, salicylamide, salicylanilide, salicylic acid, salinazid, salinomycin, salmefanol, salmeterol, salmisteine, salprotoside, salsalate, salverine, sancycline, sangivamycin, saperconazole, sarcolysin, sarmazenil, sarmoxicillin, sarpicillin, saterinone, satranidazole, savoxepin, scarlet red, scopafungin, scopolamine, seclazone, secnidazole, secobarbital, secoverine, securinine, sedecamycin, seganserin, seglitide, selegiline, selenium sulfide, selprazine, sematilide, semustine, sepazonium chloride, seperidol, sequifenadine, serfibrate, sergolexole, serine, sermetacin, serotonin, sertaconazole, sertraline, setastine, setazindol, setiptiline, setoperone, sevitropium mesilate, sevoflurane, sevopramide, siagoside, sibutramine, siccanin, silandrone, silibinin, silicristin, silidianin, silver sulfadiazine, simetride, simfibrate, simtrazene, simvastatin, sinefungin, sintropium bromide, sisomicin, sitalidone, sitofibrate, sitogluside, sodium benzoate, sodium dibunate, sodium ethasulfate, sodium formaldehyde sulfoxylate, sodium gentisate, sodium gualenate, sodium nitrite, sodium nitroprusside, sodium oxybate, sodium phenylacetate, sodium picofosfate, sodium picosulfate, sodium propionate, sodium stibocaptate, sodium stibogluconate, sodium tetradecyl sulfate, sodium thiosulfate, sofalcone, solasulfone, solpecainol, solypertine, somantadine, sopitazine, sopromidine, soquinolol, sorbic acid, sorbinicate, sorbinil, sorbitan monolaurate, sorbitan monooleate, sorbitan monopalmitate, sorbitan monostearate, sorbitan trioleate, sorbitan tristearate, sorbitol, sorndipine, sotalol, soterenol, spaglumic acid, sparfosic acid, sparsomycin, sparteine, spectinomycin, spiclamine, spiclomazine, spiperone, spiradoline, spiramide, spiramycin, spirapril, spiraprilat, spirendolol, spirgetine, spirilene, spirofylline, spirogermanium, spiromustine, spironolactone, spiroplatin, spirorenone, spirotriazine, spiroxasone, spiroxatrine, spiroxepin, spizofurone, stallimycin, stanolone, stanzolol, stearic acid, stearyl alcohol, stearylsulfamide, steffimycin, stenbolone acetate, stepronin, stercuronium iodide, stevaladil, stibamine glucoside, stibophen, stilbamidine, stilbazium iodide, stilonium iodide, stirimazole, stiripentol, stirocainide, stirifos, streptomycin, streptonicozid, streptonigrin, streptovarycin, streptozocin, strinoline, strychnine, styramate, subathizone, subendazole, succimer, succinylcholine chloride, succinylsulfathiazole, succisulfone, suclofenide, sucralfate, sucrose octaacetate, sudexanox, sudoxicam, sufentanil, sufosfamide, sufotidine, sulazepam, sulbactam, sulbactam pivoxil, sulbenicillin, sulbenox, sulbentine, sulbutiamine, sulclamide, sulconazole, sulfabenz, sulfabenzamide, sulfacarbamide, sulfacecole, sulfacetamide, sulfachlorpyridazine, sulfachrysoidine, sulfaclomide, sulfaclorazole, sulfaclozine, sulfacytine, sulfadiazine, sulfadicramide, sulfadimethoxine, sulfadoxine, sulfaethidole, sulfaguandide, sulfaguanole, sulfalene, sulfaloxic acid, sulfamazone, sulfamerazine, sulfameter, sulfamethazine, sulfamethizole, sulfamethoxazole, sulfamethoxypyridazine, sulfamethoxypyridazine acetyl, sulfametomidine, sulfametrole, sulfamonomethoxine, sulfamoxole, sulfanil amide, sulfanitran, sulfaperin, sulfaphenazole, sulfaproxyline, sulfapyridine, sulfaquinoxaline, sulfarsphenamine, sulfasalazine, sulfasomizole, sulfasuccinamide, sulfasymazine, sulfathiazole, sulfathiourea, sulfatolamide, sulfatroxazole, sulfatrozole, sulfazamet, sulfinalol, sulfinpyrazone, sulfiram, sulfisomidine, sulfisoxazole, sulfisoxazole, sulfobromophthalein, sulfonethylmethane, sulfonmethane, sulfonterol, sulforidazine, sulfoxone sodium, sulicrinat, sulindac, sulisatin, sulisobenzone, sulmarin, sulmazole, sulmepride, sulinidazole, sulocarbilate, suloctidil, sulosemide, sulotroban, suloxifen, sulpiride, sulprosal, sulprostone, sultamicillin, sulthiame, sultopride, sultosilic acid, sultroponium, sulverapride, sumacetamol, sumatriptan, sumetizide, sunagrel, suncillin, supidimide, suproclone, suprofen, suramin, suricainide, suriclone, suxemerid, suxethonium chloride, suxibuzone, symclosene, symetine, synephrine, syrisingopine, taclamine, tacrine, taglutimide, talampicillin, talastine, talbutal, taleranol, talinolol, talipexole, talisomycin, talmetacin, talmetoprim, talniflumate, talopram, talosalate, taloximine, talsupram, taltrimide, tameridone, tameticillin, tametraline, tamitinol, tamoxipen, tampramine, tandamine, taprostene, tartaric acid, tasuldine, taurocholic acid, taurolidine, tauromustine, tauroselcholic acid, taurultam, taxol, tazadolene, tazanolast, tazaburate, tazepfrofen, tazifylline, taziprinone, tazolol, tebatizole, tebuquine, teclothiazide, teclozan, tedisamil, tefazoline, tefenperate, tefludazine, teflurane, teflutixol, tegafur, telenzepine, temafloxacin, temarotene, temazepam, temefos, temelastine, temocillin, temodox, temozolomide, temurtide, tenamfetamine, tenilapine, teniloxazine, tenilsetam, teniposide, tenocyclidine, tenonitrozole, tenoxicam, tenylidone, teopranitol, teoprolol, tepirindole, tepoxalin, terazosin, terbinafine, terbucromil, terbufibrol, terbuficin, terbuprol, terbutaline, terciprazine, terconazole, terfenadine, terfluranol, terguride, terizidone, ternidazole, terodiline, terofenamate, teroxalene, teroxirone, terpin hydrate, tertatolol, tesicam, tesimide, testolactone, testosterone, testosterone cypionate, testosterone enanthate, testosterone ketolaurate, testosterone phenylacetate, testosterone propionate, tetrabarbital, tetrabenazine, tetracaine, tetrachloroethylene, tetracycline, tetradonium bromide, tetraethylammonium chloride, tetrahydrozoline, tetramethrin, tetramisole, tetrandrine, tetrantoin, tetrazepam, tetriprofen, tetronasin 5930, tetroquinone, tetroxoprim, tetrydamine, texacromil, thalicarpine, thalidomide, thebacon, thebaine, thenalidine, thenium closylate, thenyldiamine, theobromine, theodrenaline, theofibrate, theophylline, thiabendazole, thiacetarsamide, thialbarbital, thiambutosine, thiamine, thiamiprine, thiamphenicol, thiamylal, thiazesim, thiazinamium chloride, thiazolsulfone, thiethyperazine, thihexinol methylbromide, thimerfonate, thimerosal, thiocarbanidin, thiocarzolamide, thiocolchioside, thiofuradene, thioguanine, thioguanine alpha-deoxyriboside, thioguanine beta-deoxyriboside, thioguanosine, thiohexamide, thioinosine, thiopental, thiopropazate, thioproperazine, thioridazine, thiosalan, thiotepa, thiotetrabarbital, thiothixene, thiouracil, thiphenamil, thiphencillin, thiram, thonzonium bromide, thonzylamine, thozalinone, threonine, thymidine, thymol, thymol iodide, thymopentin, thyromedan, thyropropic acid, tiacrilast, tiadenol, tiafibrate, tiamenidine, tiametonium iodide, tiamulin, tianafac, tianeptine, tiapamil, tiapirinol, tiapride, tiaprofenic acid, tiaprost, tiaramide, tiazofurin, tiazuril, tibalosin, tibenalast sodium, tibenzate, tibezonium iodide, tibolone, tibric acid, tibrofan, tic-mustard, ticabesone propionate, ticarbodine, ticarcillin, ticarcillin cresyl, ticlatone, ticlopidine, ticrynafen, tidiacic, tiemoium iodide, tienocarbine, tienopramine, tienoxoloi, tifemoxone, tiflamizole, tiflorex, tifluadom, tiflucarbine, tiformin, tifurac, tigemonam, tigestol, tigloidine, tilbroquinol, tiletamine, tilidine, tiliquinol, tilisolol, tilmicosin, tilomisole, tilorone, tilozepine, tilsuprost, timefurone, timegadine, timelotem, timepidium bromide, timiperone, timobesone acetate, timofibrate, timolol, timonacic, timoprazole, tinabinol, tinazoline, tinidazole, tinisulpride, tinofedrine, tinoridine, tiocarlide, tioclomarol, tioconazole, tioctilate, tiodazosin, tiodonium chloride, tiomergine, tiomesterone, tioperidone, tiopinac, tiopronin, tiopropamine, tiospirone, tiotidine, tioxacin, tioxamast, tioxaprofen, tioxidazole, tioxolone, tipentosin, tipepidine, tipetropium bromide, tipindole, tipredane, tiprenolol, tiprinast, tipropidil, tiprostanide, tiprotimod, tiquinamide, tiquizium bromide, tiratricol, tiropramide, tisocromide, tisopurine, tisoquone, tivandizole, tixadil, tixanox, tixocortol pivalate, tizabrin, tianidine, tizolemide, tizoprolic acid, tobramycin, tobuterol, tocainide, tocamphyl, tocofenoxate, tocofibrate, tocophersolan, todralazine, tofenacin, tofetridine, tofisoline, tofisopam, tolamolol, tolazamide, tolazoline, tolboxane, tolbutamide, tolciclate, toldimfos, tolfamide, tolfenamic acid, tolgabide, tolimidone, tolindate, toliodium chloride, toliprolol, tolmesoxide, tolmetin, tolnaftate, tolnapersine, tolnidamine, toloconium metilsulfate, tolonidine, tolonium chloride, toloxatone, toloxychlorinol, tolpadol, tolpentamide, tolperisone, toliprazole, tolpronine, tolpropamine, tolpyrramide, tolquinzole, tolrestat, toltrazuril, tolufazepam, tolycaine, tomelukast, tomoglumide, tomoxetine, tomoxiprole, tonazocine, topiramate, toprilidine, tonazocine, topiramate, toprilidine, topterone, toquizine, torasemide, toebafylline, toremifene, tosifen, tosufloxacin, tosulur, toyocamycin, toyomycin, traboxepine, tracazolate, tralonide, tramadol, tramazoline, trandolapril, tranexamic acid, tranilast, transcainide, trantelinium bromide, tranylcypromine, trapencaine, trapidil, traxanox, trazilitine, trazium esilate, trazodone, trazolopride, trebenzomine, trecadrine, treloxinate, trenbolone acetate, trengestone, trenizine, trosulfan, trepibutone, trepipam, trepirium iodide, treptilamine, trequensin, trestolone acetate, trethinium tosilate, trethocanoic acid, tretinoin, tretoquinol, triacetin, triafungin, triamcinolone, triamcinolone acetonide, triamcinolone acetonide-phosphate, triamcinolone benetonide, triamcinolone diacetate, triamcinolone furetonide, triamcinolone hexacetonide, triampyzine, triamterene, triazinate, triaziquone, triazolam, tribendilol, tribenoside, tribromoethanol, tribromsalan, tribuzone, triacetamide, trichlormethiazide, trichlormethine, trichloroacetic acid, trichloroethylene, tricribine phosphate, triclabendazole, triclacetamol, triclazate, triclobisonicum chloride, triclocarban, triclodazol, triclofenol, piperazine, triclofos, triclofylline, triclonide, triclosan, tricyclamol chloride, tridihexethyl chloride, trientine, triethylenemelamine, triethylenephosphoramide, trifenagrel, trifezolac, triflocin, triflubazam, triflumidate, trifluomeprazine, trifluoperazine, trifluperidol, triflupromazine, trifluridine, triflusal, trigevolol, trihexyphenidyl, triletide, trilostane, trimazosin, trimebutine, trimecaine, trimedoxime bromide, trimeperidine, trimeprazine, trimetazidine, trimethadione, trimethamide, trimethaphan camsylate, trimethidinium methosulfate, trimethobenzamide, trimethoprim, trimetozine, trimetrexate, trimexiline, trimipramine, trimoprostil, trimoxamine, trioxifene, trioxsalen, tripamide, triparanol, tripelennamine, tripotassium dicitratobismuthate, triprolidine, tritiozine, tritoqualine, trityl cysteine, trixolane, trizoxime, trocimine, troclosene potassium, trofosfamide, troleandomycin, trolnitrate, tromantadine, tromethamine, tropabazate, tropanserin, tropapride, tropatepine, tropenziline bromide, tropicamide, tropigline, tropiprine, tropodifene, trospectomycin, trospium chloride, troxerutin, troxipide, troxolamide, troxonium tosilate, troxypyrrolium tosilate, troxypyrrolium tosilate, truxicurium iodide, truxipicurium iodide, tryparsamide, tryptophan, tryptophane mustard, tuaminoheptane, tubercidine, tubocurarine chloride, tubulozole, tuclazepam, tulobutrol, tuvatidine, tybamate, tylocrebin, tylosin, tyramine, tyropanic acid, tyrosine, ubenimex, ubidecarenone, ubisindine, ufenamate, ufiprazole, uldazepam, ulobetasol, undecoylium chloride, undecyclenic acid, uracil mustard, urapidil, urea, uredepa, uredofos, urefibrate, urethane, uridine, ursodeoxycholic acid, ursucholic acid, vadocaine, valconazole, valdetamide, valdipromide, valine, valnoctamide, valofane, valperinol, valproate pivoxil, valproic acid, valpromide, valtrate, vancomycin hcl, vaneprim, vanillin, vanitolide, vanyldisulfamide, vapiprost, vecuronium bromide, velnacrine maleate, venlafaxine, veradoline, veralipride, verapamil, verazide, verilopam, verofylline, vesnarinone, vetrabutine, vidarabine, vidarabine phophate, vigabatrin, viloxazine, viminol, vinbarbital, vinblastine, vinburnine, vincamine, vincanol, vincantril, vincofos, vinconate, vincristine, vindrburnol, vindesine, vindepidine, vinformide, vinglycinate, vinorelbine, vinpocetine, vinpoline, vinrosidine, vintiamol, vintriptol, vinylbital, vinylether, vinzolidine, viomycin, viprostol, viqualine, viquidil, virginiamycin factors, viroxime, visnadine, visnafylline, vitamin e, volazocine, warfarin, xamoterol, xanoxic acid, xanthinol niacinate, xanthiol, xantifibrate, xantocillin, xenalipin, xenazoic acid, xenbucin, xenipentone, xenthiorate, xenygloxal, xenyhexenic acid, xenytropium bromide, xibenolol, xibornol, xilobam, ximoprofen, xinidamine, xinomiline, xipamide, xipranolol, xorphanol, xylamidine, xylazine, xylocoumarol, xylometazoline, xyloxemine, yohimbic acid, zabicipril, zacopride, zafuleptine, zaltidine, zapizolam, zaprinast, zardaverine, zenazocine mesylate, zepastine, zeranol, zetidoline, zidapamide, zidometacin, zidovudine, zilantel, zimeldine, zimidoben, zinc acetate, zinc phenolsulfonate, zinc undecylenate, zindotrine, zindoxifene, zinoconazole, zinterol, zinviroxime, zipeprol, zocainone, zofenopril, zoficonazole, zolamine, zolazepam, zolenzepine, zolertine, zolimidine, zoliprofen, zoloperone, zolpidem, zomebazam, zomepirac, zometapine, zonisamide, zopiclone, zorubicin, zotepine, zoxazolamine, zuclomiphene, zuclophenthixol, zylofuramine.

The following non-limitative examples serve to illustrate the invention. Confirmation of the microparticulate nature of products is performed using microscopy as described in WO-A-9607434. Ultrasonic transmission measurements may be made using a broadband transducer to indicate microbubble suspensions giving an increased sound beam attenuation compared to a standard. Flow cytometric analysis of products can be used to confirm attachment of macromolecules thereto. The ability of targeted microbubbles to bind specifically to cells expressing a target may be studied in vitro by microscopy and/or using a flow chamber containing immobilised cells, for example employing a population of cells expressing the target structure and a further population of cells not expressing the target. Radioactive, fluorescent or enzyme-labelled streptavidin/avidin may be used to analyse biotin attachment.

EXAMPLE 1

Adhesion of poly-L-lysine-coated phosphatidylserine-encapsulated Microbubbles to Endothelial Cells Poly-L-lysine (8 mg) having a molecular weight of 115 kDa was dissolved in water (400 μl). Freshly redispersed microbubbles of phosphatidylserine-encapsulated perfluorobutane (40 μl) were incubated in either water (400 μl) or the poly-L-lysine solution for 15 minutes at room temperature. Zeta potential measurements confirmed that the poly-L-lysine-coated microbubbles were positively charged while the uncoated bubbles were negatively charged. A cell adhesion study using human endothelial cells grown in culture dishes was performed with the above-described microbubbles, the uncoated microbubbles being used as a control. Microscopy of the endothelial cells after incubation showed a much increased number of poly-L-lysine-coated microbubbles adhering to endothelial cells in comparison to the uncoated microbubbles.

EXAMPLE 2

Gas-filled Microbubbles Comprising Phosphatidylserine and RGDC-Mal-PEG$_{3400}$-DSPE (SEQ ID NO:1)

a) Synthesis of Boc-NH-PEG$_{3400}$-DSPE (t-butyl carbamate poly(ethylene glycol)distearoylphosphatidylethanolamine)

DSPE (distearoylphosphatidylethanolamine) (31 mg, Sygena Inc.) was added to a solution of Boc-NH-PEG$_{3400}$-SC (t-butyl carbamate poly(ethylene glycol)-succinimidyl carbonate) (150 mg) in chloroform (2 ml), followed by triethylamine (33 μl). The mixture formed a clear solution after stirring at 41° C. for 10 minutes. The solvent was rotary evaporated and the residue taken up in acetonitrile (5 ml). The thus-obtained dispersion was cooled to 4° C. and centrifuged, whereafter the solution was separated from the undissolved material and evaporated to dryness. The structure of the resulting product was confirmed by NMR.

b) Synthesis of H$_2$N-PEG$_{3400}$-DSPE (amino-poly(ethylene glycol)-distearoylphosphatidylethanolamine)

Boc-NH-PEG$_{3400}$-DSPE (167 mg) was stirred in 4 M hydrochloric acid in dioxane (5 ml) for 2.5 hours at ambient temperature. The solvent was removed by rotary evaporation and the residue was taken up in chloroform (1.5 ml) and washed with water (2×1.5 ml). The organic phase was removed by rotary evaporation. TLC (chloroform/methanol/water 13:5:0.8) gave the title product with Rf=0.6; the structure of the product, which was ninhydrin positive, was confirmed by NMR.

c) Synthesis of Mal-PEG$_{3400}$-DSPE (3-maleimidopropionate poly(ethylene glycol) distearoylphosphatidylethanolamine)

A solution of N-succinimidyl-3-maleimidopropionate (5.6 mg, 0.018 mmol) in tetrahydrofuran (0.2 ml) is added to H$_2$N-PEG$_{3400}$-DSPE (65 mg, 0.012 mmol) dissolved in tetrahydrofuran (1 ml) and 0.1 M sodium phosphate buffer pH 7.5 (2 ml). The reaction mixture is heated to 30° C. and the reaction is followed to completion by TLC, whereafter the solvent is evaporated.

d) Synthesis of RGDC-Mal-PEG$_{3400}$-DSPE (SEQ ID NO:1)

Mal-PEG$_{3400}$-DSPE (0.010 mmol) in 0.1 M sodium phosphate buffer having a pH of 7.5 is added to the peptide RGDC (SEQ ID NO:1) (0.010 mmol). The reaction mixture is heated to 37° C. if necessary and the reaction is followed by TLC to completion, whereafter the solvent is removed.

e) Preparation of Gas-filled Microbubbles Encapsulated by phosphatidylserine and RGDC-Mal-PEG$_{3400}$-DSPE (SEQ ID NO:1)

To a mixture (5 mg) of phosphatidylserine (90–99.9 mol %) and Mal-PEG$_{3400}$-DSPE (10–0.1 mol %) is added 5 propylene glycol-glycerol in water (1 ml). The dispersion is heated to not more than 80° C. for 5 minutes and then cooled to ambient temperature. The dispersion (0.8 ml) is then transferred to a vial (1 ml) and the head space is flushed with perfluorobutane. The vial is shaken in a cap-mixer for 45 seconds, whereafter the sample is put on a roller table. After centrifugation the infranatant is exchanged with 0.1 M sodium phosphate buffer having a pH of 7.5. The peptide RGDC (SEQ ID NO:1), dissolved in 0.1 M sodium phosphate buffer having a pH of 7.5, is added to the washed microbubbles, which are placed on the roller table. The washing procedure is then repeated.

f) Alternative Preparation of Gas-filled Microbubbles Encapsulated by Phosphatidylserine and RGDC-Mal-PEG$_{3400}$-DSPE (SEQ ID NO:1)

To phosphatidylserine (5 mg) is added 5% propylene glycol-glycerol in water (1 ml). The dispersion is heated to not more than 80° C. for 5 minutes and then cooled to ambient temperature. The dispersion (0.8 ml) is transferred to a vial (1 ml) and the head space is flushed with perfluorobutane. The vial is shaken in a cap-mixer for 45 seconds, whereafter the sample is put on a roller table. After centrifugation the infranatant is exchanged with 0.1 M sodium phosphate buffer having a pH of 7.5. RGDC-Mal-PEG$_{3400}$-DSPE (SEQ ID NO:1) dissolved in 0.1 M sodium phosphate buffer having a pH of 7.5 is added to the washed microbubbles, which are then placed on the roller table. The washing procedure is repeated following incorporation of the RGDC-Mal-PEG$_{3400}$-DSPE (SEQ ID NO:1) into the microbubble membranes.

EXAMPLE 3

Gas-filled Microbubbles Encapsulated with Phosphatidylserine, Phosphatidylcholine and biotinamidocaproate-PEG$_{3400}$-Ala-cholesterol a) Synthesis of Z-Ala-cholesterol (3-O-(carbobenzyloxy-L-alanyl)cholesterol)

Cholesterol (4 mmol), Z-alanine (5 mmol) and dimethylaminopyridine (4 mmol) were dissolved in dimethylformamide/tetrahydrofuran (20 ml +5 ml) and dicyclohexylcarbodiimide was added. The reaction mixture was stirred at ambient temperature overnight. Dicyclohexylurea was filtered off and the solvent was rotary evaporated. The residue was taken up in chloroform, undissolved dicyclohexylurea was filtered off and the solvent was removed by rotary evaporation. The residue was placed on a column of silica gel, and Z-Ala-cholesterol was eluted with toluene/petroleum ether (20:2) followed by toluene/diethyl ether (20:2). The fractions containing the title compound were combined and the solvent was removed by rotary evaporation. The structure of the product was confirmed by NMR.

b) Synthesis of Ala-cholesterol (3-O-(L-alanyl)-cholesterol)

Z-Ala-cholesterol (0.48 mmol) is placed in tetrahydrofuran (20 ml) and glacial acetic acid (3 ml) and hydrogenated in the presence of 5% palladium on charcoal for 2 hours. The reaction mixture is filtered and concentrated in vacuo.

c) Synthesis of Boc-NH-PEG$_{3400}$-Ala-cholesterol

Ala-cholesterol is added to a solution of Boc-NH-PEG$_{3400}$-SC (t-butyl carbamate poly(ethylene glycol)-succinimidyl carbonate) in chloroform, followed by triethylamine. The suspension is stirred at 41° C. for 10 minutes. The crude product is purified by chromatography.

d) Synthesis of H$_2$N-PEG$_{3400}$-Ala-cholesterol

Boc-NH-PEG$_{3400}$-Ala-cholesterol is stirred in 4 M hydrochloric acid in dioxane for 2.5 hours at ambient temperature. The solvent is removed by rotary evaporation and the residue is taken up in chloroform and washed with water. The organic phase is rotary evaporated to dryness. The crude product may be purified by chromatography.

e) Synthesis of biotinamidocaproate-PEG$_{3400}$-Ala-cholesterol

A solution of biotinamidocaproate N-hydroxysuccinimide ester in tetrahydrofuran is added to H$_2$N-PEG$_3$400-Ala-cholesterol dissolved in tetrahydrofuran and 0.1 M sodium phosphate buffer having a pH of 7.5 (2 ml). The reaction mixture is heated to 30° C. and the reaction is followed to completion by TLC, whereafter the solvent is evaporated.

f) Preparation of Gas-filled Microbubbles Encapsulated with Phosphatidylserine, Phosphatidylcholine and biotinamidocaproate-PEG$_{3400}$-Ala-cholesterol To a mixture (5 mg) of phosphatidylserine and phosphatidylcholine (in total 90–99.9 mol %) and biotinamidocaproate-PEG$_{3400}$-Ala-cholesterol (10–0.1 mol %) is added 5% propylene glycol-glycerol in water (1 ml). The dispersion is heated to not more than 80° C. for 5 minutes and then cooled to ambient temperature. The dispersion (0.8 ml) is then transferred to a vial (1 ml) and the head space is flushed with perfluorobutane. The vial is shaken in a cap-mixer for 45 seconds, whereafter the sample is put on a roller table. After centrifugation the infranatant is exchanged with water and the washing is repeated.

g) Alternative Preparation of Gas-filled Microbubbles Encapsulated with Phosphatidylserine, Phosphatidylcholine and biotinamidocaproate-PEG$_{3400}$-Ala-cholesterol To a mixture (5 mg) of phosphatidylserine and phosphatidylcholine is added 5% propylene glycol-glycerol in water (1 ml). The dispersion is heated to not more than 80° C. for 5 minutes and then cooled to ambient temperature. The dispersion (0.8 ml) is then transferred to a vial (1 ml) and the head space is flushed with perfluorobutane. The vial is shaken in a cap-mixer for 45 seconds, whereafter the sample is put on a roller table. After centrifugation the infranatant is exchanged with water. Biotinamidocaproate-PEG$_{3400}$-Ala-cholesterol dissolved in water is added to the washed microbubbles, which are placed on a roller table for several hours. The washing procedure is repeated following incorporation of the biotinamidocaproate-PEG$_{3400}$-Ala-cholesterol into the microbubble membranes.

EXAMPLE 4

Gas-filled Microbubbles Comprising Phosphatidylserine, Phosphatidylcholine, biotinamidocaproate-PEG$_{3400}$-Ala-Cholesterol and Drug-cholesterol a) Synthesis of Drug-cholesterol Cholesterol (4 mmol), a drug having an acid group and dimethylaminopyridine (4 mmol) are dissolved in dimethylformamide/tetrahydrofuran (20 ml+5 ml) and dicyclohexylcarbodiimide is added. The reaction mixture is stirred at ambient temperature overnight. Dicyclohexylurea is filtered off and the solvent is rotary evaporated. The title compound is purified by chromatography.

b) Preparation of Gas-filled Microbubbles Encapsulated with Phosphatidylserine, Phosphatidylcholine, biotinamidocaproate-PEG$_{3400}$-Ala-cholesterol and Drug-cholesterol To a mixture (5 mg) of phosphatidylserine and phosphatidylcholine (in total 90–99.9 mol %) and biotinamidocaproate-PEG$_{3400}$-Ala-cholesterol (prepared as in Example 3) and drug-cholesterol (in total 10–0.1 mol %) is added 5% propylene glycol-glycerol in water (1 ml). The dispersion is heated to not more than 80° C. for 5 minutes and then cooled to ambient temperature. The dispersion (0.8 ml) is transferred to a vial (1 ml) and the head space is flushed with perfluorobutane. The vial is shaken in a cap-mixer for 45 seconds whereafter the sample is put on a roller table. After centrifugation the infranatant is exchanged with water and the washing is repeated.

EXAMPLE 5

Gas-filled Microbubbles Encapsulated with Phosphatidylserine and thiolated-anti-CD34-Mal-PEG$_{3400}$-DSPE a) Preparation of Thiolated anti-CD34 Antibodies Thiolation of anti-CD34 antibodies may be effected as described by Hansen, C. B. et al.(1995) *Biochim. Biophys. Acta* 1239, 133–144.

b) Preparation of Gas-filled Microbubbles Encapsulated with Phosphatidylserine and thiolated-anti-CD34-Mal-PEG$_{3400}$-DSPE To a mixture (5 mg) of phosphatidylserine (90–99.9 mol %) and Mal-PEG$_{3400}$-DSPE (10–0.1 mol %, prepared as in Example 2) is added 5% propylene glycol-glycerol in water (1 ml). The dispersion is heated to not more than 80° C. for 5 minutes and then cooled to ambient temperature. The dispersion (0.8 ml) is transferred to a vial (1 ml) and the head space is flushed with perfluorobutane. The vial is shaken in a cap-mixer for 45 seconds, whereafter the sample is put on a roller table. After centrifugation the infranatant is exchanged with an appropriate buffer and coupling of the thiolated antibody to the microbubbles is performed, e.g. as described by Goundalkar, A., Ghose, T. and Mezei, M. in *J. Pharm. Pharmacol.* (1984) 36 465–66 or Hansen, C. B. et al.(1995) *Biochim. Biophys. Acta* 1239 133–144. The microbubbles are then placed on a roller table for several hours and are washed. Flow cytometric analysis of the resulting microbubbles (employing a fluorescently labeled secondary antibody) is used to confirm attachment of the anti-CD34 antibody to the bubbles. The ability of the bubbles to bind specifically to CD34-expressing cells is studied by microscopy employing one population of cells expressing CD34 and one population that do not express CD34.

EXAMPLE 6

Biotin Attached to Gas-filled Microbubbles

Biotin may be attached to microbubbles in many different ways, e.g. in a similar way to that described by Corley, P. and Loughrey, H. C. in (1994) *Biochim. Biophys. Acta* 1195, 149–156. The resulting bubbles are analysed by flow cytometry, e.g. by employing fluorescent streptavidin to detect attachment of biotin to the bubbles. Alternatively radioactive or enzyme-labelled streptavidin/avidin is used to analyse biotin attachment.

EXAMPLE 7

Gas-filled Microbubbles Encapsulated with Distearoylphosphatidylserine and biotin-DPPE To distearoylphosphatidylserine (DSPS) (22.6 mg) was added 4% propylene glycol-glycerol in water (4 ml). The dispersion was heated to not more than 80° C. for five minutes and then cooled to ambient temperature. An aqueous dispersion of biotin-DPPE (1.5 mg) in 4% propylene glycol-glycerol (1 ml) was added and the sample was put on a roller table for 1–2 hours. The suspension was filled into vials and the head spaces were flushed with perfluorobutane. The vials were shaken for 45 seconds, whereafter they were put on a roller table. After centrifugation for 7 minutes the infranatant was exchanged with water and the washing was repeated twice. Normal phase HPLC with an Evaporative Light Scattering Detector confirmed that the membranes of the microbubbles contained 4 mol % biotin-DPPE. The mean particle diameter of the microbubbles was 4 µm measured by Coulter Counter. Ultrasound transmission measurements using a 3.5 MHz broadband transducer showed that a particle dispersion of <2 mg/ml gave a sound beam attenuation higher than 5 dB/cm.

EXAMPLE 8

Gas-filled Microbubbles Encapsulated with Phosphatidylserine and Biotinylated Antibody Non-covalently Bound to streptavidin-Succ-PEG-DSPE a) Synthesis of Succ-PEG$_{3400}$-DSPE NH$_2$-PEG$_{3400}$-DSPE (prepared as in Example 2) is carboxylated using succinic anhydride, e.g. by a similar method to that described by Nayar, R. and Schroit, A. J. in *Biochemistry* (1985) 24, 5967–71.

b) Preparation of Gas-filled Microbubbles Encapsulated with Phosphatidylserine and Succ-PEG$_{3400}$-DSPE To a mixture (5 mg) of phosphatidylserine (90–99.9 mol %) and Succ-PEG$_{3400}$-DSPE (10–0.1 mol %) is added 5% propylene glycol-glycerol in water (1 ml). The dispersion is heated to not more than 80° C. for 5 minutes and then coooled to ambient temperature. The dispersion (0.8 ml) is transferred to a vial (1 ml) and the head space is flushed with perfluorobutane. The vial is shaken in a cap-mixer for 45 seconds, whereafter the sample is put on a roller table. After centrifugation the infranatant is exchanged with water and the washing is repeated. Alternatively the microbubbles may be prepared as described in Example 2(f).

c) Coupling of Streptavidin to Gas-filled Microbubbles Encapsulated with Phosphatidylserine and Succ-PEG$_{3400}$-DSPE Streptavidin is covalently bound to Succ-PEG$_{3400}$-DSPE in the microbubble membranes by standard coupling methods using a water-soluble carbodiimide. The sample is placed on a roller table during the reaction. After centrifugation the infranatant is exchanged with water and the washing is repeated. The functionality of the attached streptavidin is analysed by binding, e.g. to fluorescently labeled biotin, biotinylated antibodies (detected with a fluorescently labeled secondary antibody) or biotinylated and fluorescence- or radioactively-labeled oligonucleotides. Analysis is performed by fluorescence microscopy or scintillation counting.

d) Preparation of Gas-filled Microbubbles Encapsulated with Phosphatidylserine and Biotin Non-covalently Bound to streptavidin-Succ-PEG$_{3400}$-DSPE Microbubbles from Example 8(c) are incubated in a solution containing biotinylated vectors, e.g. biotinylated antibodies. The vector-coated microbubbles are washed as described above.

EXAMPLE 9

Gas-filled Microbubbles Encapsulated with Phosphatidylserine and Biotinylated Oligonucleotide Non-covalently Bound to streptavidin-Succ-PEG-DSPE a) Synthesis of Succ-PEG$_{3400}$-DSPE NH$_2$-PEG$_{3400}$-DSPE (prepared as in Example 2) is carboxylated using succinic anhydride, e.g. by a similar method to that described by Nayar, R. and Schroit, A. J. in *Biochemistry* (1985) 24, 5967–71.

b) Preparation of Gas-filled Microbubbles Encapsulated with Phosphatidylserine and Succ-PEG$_{3400}$-DSPE To a mixture (5 mg) of phosphatidylserine (90–99.9 mol %) and Succ-PEG$_{3400}$-DSPE (10–0.1 mol %) is added 5% propylene glycol-glycerol in water (1 ml). The dispersion is heated to not more than 80° C. for 5 minutes and then cooled to ambient temperature. The dispersion (0.8 ml) is transferred to a vial (1 ml) and the head space is flushed with perfluorobutane. The vial is shaken in a cap-mixer for 45 seconds, whereafter the sample is put on a roller table. After centrifugation the infranatant is exchanged with water and the washing is repeated. Alternatively the microbubbles may be prepared as described in Example 2(f).

c) Coupling of Streptavidin to Gas-filled Microbubbles Encapsulated with Phosphatidylserine and Succ-PEG$_{3400}$-DSPE Streptavidin is covalently bound to Succ-PEG$_{3400}$-DSPE in the microbubble membraness by standard coupling methods using a water-soluble carbodiimide. The sample is placed on a roller table during the reaction. After centrifugation the infranatant is exchanged with water and the washing is repeated. The functionality of the attached streptavidin is analyzed by binding, e.g. to fluorescently labeled biotin, biotinylated antibodies (detected with a fluorescently labeled secondary antibody) or biotinylated and fluorescence- or radioactively-labeled oligonucleotides. Analysis is performed by fluorescence microscopy or scintillation counting.

d) Preparation of Gas-filled Microbubbles Encapsulated with Phosphatidylserine and a Biotinylated Oligonucleotide Non-covalently Bound to streptavidin-Succ-PEG$_{3400}$-DSPE Microbubbles from Example 9(c) are incubated in a solution containing a biotinylated oligonucleotide. The oligonucleotide-coated bubbles are washed as described above. Binding of the oligonucleotide to the bubbles is detected e.g. by using fluorescent-labeled oligonucleotides for attachment to the bubbles, or by hybridising the attached oligonucleotide to a labeled (fluorescence or radioactivity) complementary oligonucleotide. The functionality of the oligonucleotide-carrying microbubbles is analysed, e.g. by hybridising the bubbles with immobilized DNA-containing sequences complementary to the attached oligonucleotide. As examples, an oligonucleotide complementary to ribosomal DNA (of which there are many copies per haploid genome) and an oligonucleotide complementary to an oncogene (e.g. ras of which there is one copy per haploid genome) may be used.

EXAMPLE 10

Gas-filled Microbubbles Encapsulated with Phosphatidylserine and Folate-PEG-Succ-DSPE a) Preparation of Folate-PEG-Succ-DSPE Folate-PEG-Succ-DSPE is synthesised as described by Lee, R. J. and Low, P. S. in (1995) *Biochimica. Biophysica. Acta* 1233, 134–144.

b) Preparation of Gas-filled Microbubbles Encapsulated with Phosphatidylserine and Folate-PEG-Succ-DSPE To a mixture (5 mg) of phosphatidylserine (90–99.9 mol %) and folate-PEG-DSPE (10–0.1 mol %) is added 5% propylene glycol-glycerol in water (1 ml). The dispersion is heated to not more than 80° C. for 5 minutes and is then cooled to ambient temperature. The dispersion (0.8 ml) is transferred to a vial (1 ml) and the head space is flushed with perfluorobutane. The vial is shaken in a cap-mixer for 45 seconds, whereafter the sample is put on a roller table. After centrifugation the infranatant is exchanged with water and the washing is repeated. Alternatively the microbubbles are prepared as described in Example 2(e) or 2(f). Analysis of folate attachment may for example be done by microscopic study of the binding of the folate-containing microbubbles to cells expressing different levels of folate receptors.

EXAMPLE 11

Gas-filled Microbubbles Encapsulated with Phosphatidylserine and thiolated-anti-CD34-Mal-PEG$_{3400}$-DSPE, thiolated-anti-ICAM-1-Mal-PEG$_{3400}$-DSPE and thiolated-anti-E-Selectin-Mal-PEG$_{3400}$-DSPE a) Preparation of thiolated-anti-CD34 Antibodies Thiolation of anti-CD34 antibodies may be effected as described by Hansen, C. B. et al. in (1995) *Biochim. Biophys. Acta* 1239, 133–144.

b) Preparation of thiolated-anti-ICAM-1 Antibodies

Thiolation of anti-ICAM-1 antibodies may be effected as described by Hansen, C. B. et al. in (1995) *Biochim. Biophys. Acta* 1239, 133–144.

c) Preparation of thiolated-anti-E-selectin Antibodies

Thiolation of anti-E-selectin antibodies may be effected as described by Hansen, C. B. et al. in (1995) *Biochim. Biophys. Acta* 1239, 133–144.

d) Preparation of Gas-filled Microbubbles Encapsulated with Phosphatidylserine and thiolated-anti-CD34-Mal-PEG$_{3400}$-DSPE, thiolated-anti-ICAM-1-Mal-PEG$_{3400}$-DSPE thiolated-anti-E-selectin-Mal-PEG$_{3400}$-DSPE To a mixture (5 mg) of phosphatidylserine (90–99.9 mol %) and Mal-PEG$_{3400}$-DSPE (10–0.1 mol %, prepared as in Example 2) is added 5 propylene glycol-glycerol in water (1 ml). The dispersion is heated to not more than 80° C. for 5 minutes and is then cooled to ambient temperature. The dispersion (0.8 ml) is transferred to a vial (1 ml) and the head space is flushed with perfluorobutane. The vial is shaken in a cap-mixer for 45 seconds, whereafter the sample is put on a roller table. After centrifugation the infranatant is exchanged with an appropriate buffer, and coupling of the antibodies from Example 11(a), 11(b) and 11(c) to the microbubbles is performed, e.g. as described by Goundalkar, A., Ghose, T. and Mezei, M. in *J. Pharm. Pharmacol.* (1984) 36, 465–466 or by Hansen, C. B. et al. in (1995) *Biochim. Biophys. Acta* 1239, 133–144. The microbubbles are placed on a roller table for several hours and are then washed.

EXAMPLE 12

The peptide FNFRLKAGQKIRFGAAAWEPPRARI (SEQ ID NO:2) Attached to Gas-filled Microbubbles Encapsulated with Phosphatidylserine The peptide FNFRLKAGQKIRFGAAAWEPPRARI (SEQ ID NO:2), comprising Phosphatidylserine-binding and heparin-binding sections, is synthesised. The peptide is added to preformed Phosphatidylserine-encapsulated perfluorobutane microbubbles and thoroughly mixed.

EXAMPLE 13

Fibronectin Covalently Bound to Gas-filled Microbubbles Encapsulated with Phosphatidylserine and Phosphatidylethanolamine a) Microbubbles Preparation DSPS (25 mg) and DSPE (5.0 mg) were weighed into a clean vial and 5 ml of a solution of 1.4% propylene glycol/2.4% glycerol was added. The mixture was warmed to 80° C. for 5 minutes. The sample was cooled to room temperature and the head space was flushed with perfluorobutane gas. The vials were shaken in a cap mixer for 45 seconds and the microbubbles were twice washed with distilled water then resuspended in 0.1 M sodium borate buffer, pH 9.

b) Modification of Fibronectin

Fibronectin (1.0 mg) in 5 ml 0.01 M Hepes buffer, pH 8, was added to 0.1 mmol of the crosslinker SDBP. The mixture was incubated on ice for 2 hours.

c) Microbubble Modification.

To the protein solution from (b) was added the microbubble suspension from (a) and incubation was allowed to proceed for 2 hours at room temperature on a roller table. Unreacted material was removed by allowing the microbubbles to float and then replacing the buffer with 0.1 M sodium borate buffer, pH 9. This process was repeated three times.

d) In vitro Analysis.

The microbubbles were tested in the in vitro assay detailed in Example 21. A gradual accumulation of microbubbles binding to the cells was observed.

EXAMPLE 14

Gas-filled Microbubbles Encapsulated with Phosphatidylserine, and 3β-[N-(N,N'-dimethylaminoethane)carbamoyl]cholesterol a) Synthesis of 3β-[N-(N',N'-dimethylaminoethane) carbamoyl]cholesterol (DC-chol) (Farhood H., Gao, X, Barsoum, J. and Huang, L., *Anal. Biochem.* 225, 89–93 (1995))

To a stirred solution of 2-dimethylaminoethylamine (19.40 mg, 24:1, 0.22 mmol) and triethylamine (310 µl, 2.23 mmol) in dichloromethane (3 ml) at room temperature was slowly added a solution of cholesteryl chloroformate (100 mg, 0.22 mmol) in 1,4-dioxane. When the reaction was completed, the mixture was evaporated to dryness and the residue was purified by flash chromatography (CHCl$_3$/MeOH, 4:1). A white solid was obtained, yield 105 mg (95%). The structure was verified by NMR and MALDI.

b) Preparation of Microbubble Dispersion

Monolayer-encapsulated Microbubbles containing perfluorobutane are made from a mixture of 90% phosphatidylserine and 10% (DC-chol) by weighing DSPS (4.5 mg) and (DC-chol) (0.5 mg) into a 2 ml vial. 0.8 ml propylene glycol/glycerol (4%) in water was added. The solution was heated at 80° C. for 5 minutes and shaken. The solution was then cooled to ambient temperature and the headspace was flushed with perfluorobutane. The vial was shaken on a cap-mixer at 4450 oscillations/minute for 45 seconds and put on a roller table. The sample was washed by centrifuging at 2000 rpm for 5 minutes. The infranatant was removed by a syringe and distilled water was added to the same volume. The headspace was again flushed with perfluorobutane and the sample was kept on a roller table until a homogeneous appearance was obtained. The washing procedure was repeated again.

EXAMPLE 15

Gas-filled Microbubbles Encapsulated with Phosphatidylserine and WEPPRARI-PE (SEQ ID NO:3)

Phosphatidylethanolamine (PE) is reacted with an equimolar amount of the crosslinker N-hydroxysuccinimidyl-2,3-dibromopropionate in a 1:1 mixture of dioxane and 0.02 M HEPES buffer, pH 8.0. Following incubation for 2 hours on ice, an equimolar amount of the heparin-binding peptide WEPPRARI (SEQ ID NO:3) is added, the pH is brought to 9 by the addition of 0.2 M disodium tetraborate, and the incubation is continued for 2 hours at room temperature. The reaction product is purified by chromatography. Monolayer-encapsulated microbubbles containing perfluorobutane are made from a mixture of 80–95% phosphatidylserine (PS) and 5–20% of peptide-substituted PE.

EXAMPLE 16

Gas-filled Microbubbles Encapsulated with Phosphatidylserine and Inactivated Human thrombin-Succ-PEG$_{3400}$-DSPE a) Inactivation of Human Thrombin Human thrombin was inactivated by incubation with a 20% molar excess of D-Phe-L-Pro-L-Arg-chloromethyl ketone in 0.05 M HEPES buffer, pH 8.0, at 37° C. for 30 minutes.

b) Preparation of Gas-filled Microbubbles Encapsulated with Phosphatidylserine and Succ-PEG$_{3400}$-DSPE To a mixture (5 mg) of phosphatidylserine (90–99.9 mol %) and Succ-PEG$_{3400}$-DSPE (10–0.1 mol %, prepared as in Example 9(a)) was added 5% propylene glycol-glycerol in water (1 ml). The dispersion was heated to not more than 80° C. for 5 minutes and was then cooled to ambient temperature. The dispersion (0.8 ml) was transferred to a vial (1 ml) and the head space was flushed with perfluorobutane. The vial was shaken in a cap-mixer for 45 seconds, whereafter the sample was put on a roller table. After centrifugation the infranatant was exchanged with water and the washing was repeated. Alternatively the microbubbles may be prepared as described in Example 2(f).

c) Preparation of Gas-filled Microbubbles Encapsulated with Phosphatidylserine and Inactivated Human thrombin-Succ-PEG$_{3400}$-DSPE Inactivated human thrombin was covalently bound to Succ-PEG$_{3400}$-DSPE in the microbubbles from Example 16(b) by standard coupling methods using a water-soluble carbodiimide. The sample was placed on a roller table during the reaction. After centrifugation the infranatant was exchanged with water and the washing was repeated.

EXAMPLE 17

Gas-filled Microbubbles Having Methotrexate and Prodrug-activating Enzyme Attached a) Methotrexate Attached via a Peptide Linker to Gas-filled Micrububbles Methods for attaching aminoacids to the anticancer drug methotrexate (MTX) are well described in the literature (see e.g. Huennekens, F. M. (1994), TIBTECH 12, 234–239 and references therein). Instead of a single amino acid a peptide may be attached to MTX using the same technology. Such a peptide may constitute a linker for the attachment of MTX to the surface of microbubbles. One class of such linkers comprises peptides of the general structure (MTX)-F-K/R-X-R-Z-C where X is any amino acid and Z is a hydrophobic amino acid. A specific example of such a linker is (MTX)-F-K-L-R-L-C (SEQ ID NO:4). The SH-group in the Cys-residue is employed for attachment of the MTX-peptide to the microbubbles (e.g. composed of phosphatidylserine and Mal-PEG-DSPE) using standard technology, e.g. as in Example 2. A linker of this kind is expected to be cleaved by the enzyme cathepsin B which often is selectively overexpressed outside and on the surface of tumour cells (Panchal, R. G. et al. (1996), Nat. Biotechnol. 14, 852–856). Thus, the potential prodrug (MTX)-F-K/R-X-R would be liberated selectively in tumours. This prodrug can further be activated to the active drug MTX by the action of carboxypeptidases, either present endogeneously in the tumour or targeted to the tumour e.g. by tumour-associated antibodies (see below).

b) Prodrug-activating Enzyme Covalently Attached to the Surface of Gas-filled Microbubbles An example of a prodrug-activating enzyme is carboxypeptidase A (CPA), which may be conjugated to the surface of microbubbles encapsulated by, for example, a mixture of phosphatidylserine and phosphatidylethanolamine, e.g. by using a 3400 Da poly(ethylene glycol) chain bearing an N-hydroxysuccinimide group at both ends (Perron, M. J. and Page, M., *Br. J. Cancer* 73, 281–287); the microbubbles may be prepared by standard methods. Microbubbles containing CPA may be targeted to areas of pathology by incorporating a suitable targeting vector in the CPA-containing bubbles. Alternatively CPA may be attached directly to a vector (e.g. an antibody), for example by the method as described above. In this latter case the CPA-vector conjugate will be attached to the surface of the microbubbles as described in Hansen, C. B. et al. (1995) *Biochim. Biophys. Acta* 1239 133–144. Examples of the many possible prodrug-enzyme pairs are described in e.g. Huennekens, F. M. (1994) TIBTECH 12, 234–239.

EXAMPLE 18

Gas-filled Microbubbles Encapsulated with Phosphatidylserine, thiolated-anti-CEA-Mal-PEG$_{3400}$-DSPE and the Anticancer Prodrug 3',5'-O-dipamitoyl-5-fluoro-2'-deoxyuridine a) Preparation of Thiolated anti-CEA Antibodies Thiolation of anti-CEA antibodies may be effected as described by Hansen, C. B. et al. in (1995) *Biochim. Biophys. Acta* 1239, 133–144.

b) Preparation of Gas-filled Microbubbles Encapsulated with Phosphatidylserine, thiolated-anti-CEA-Mal-PEG$_{3400}$-DSPE and the Anticancer Prodrug 3',5'-O-dipamitoyl-5-fluoro-2'-deoxyuridine To a mixture (5 mg) of phosphatidylserine (90–99.9 mol %), Mal-PEG$_{3400}$-DSPE (10–0.1 mol %, prepared as in Example 2) and the anticancer prodrug 3',5'-O-dipamitoyl-5-fluoro-2'-deoxyuridine (Mori, A. et al. (1995) *Cancer Chemother. Pharmacol.* 35, 447–456) is added 5% propylene glycol-glycerol in water (1 ml). The dispersion is heated to not more than 80° C. for 5 minutes and is then cooled to ambient temperature. The dispersion (0.8 ml) is transferred to a vial (1 ml) and the head space is flushed with perfluorobutane. The vial is shaken in a cap-mixer for 45 seconds, whereafter the sample is put on a roller table. After centrifugation the infranatant is exchanged with an approperiate buffer, and coupling of the antibody to the microbubble is performed, e.g. as described by Goundalkar, A., Ghose, T. and Mezei, M. in *J. Pharm. Pharmacol.* (1984) 36 465–466 or by Hansen, C. B. et al. in (1995) *Biochim. Biophys. Acta* 1239 133–144. The microbubbles are placed on a roller table for several hours and are then washed.

EXAMPLE 19

Gas-filled Microbubbles Encapsulated with Phosphatidylserine, thiolated-anti-CEA-Mal-PEG$_{3400}$-DSPE and the Anticancer Prodrug N-trifluoroacetyl-adriamycin-14-valerate a) Preparation of Thiolated anti-CEA Antibodies Thiolation of anti-CEA antibodies may be effected as described by Hansen, C. B. et al. in (1995) *Biochim. Biophys. Acta* 1239 133–144.

b) Preparation of Gas-filled Microbubbles Encapsulated with Phosphatidylserine, thiolated-anti-CEA-Mal-PEG$_{3400}$-DSPE and the Anticancer Prodrug N-trifluoroacetyl-adriamycin-14-valerate To a mixture (5 mg) of phosphatidylserine (90–99.9 mol %), Mal-PEG$_{3400}$-DSPE (10–0.1 mol %, prepared as in Example 2) and the anticancer prodrug N-trifluoroacetyl-adriamycin-14-valerate (Mori, A. et al. (1993) *Pharm. Res.* 10, 507–514), is added 5% propylene glycol-glycerol in water (1 ml). The dispersion is heated to not more than 80° C. for 5 minutes and is then cooled to ambient temperature. The dispersion (0.8 ml) is transferred to a vial (1 ml) and the head space is flushed with perfluorobutane. The vial is shaken in a cap-mixer for 45 seconds, whereafter the sample is put on a roller table. After centrifugation the infranatant is exchanged with an appropriate buffer, and coupling of the antibody to the microbubble is performed, e.g. as described by Goundalkar, A., Ghose, T. and Mezei, M. in *J. Pharm. Pharmacol.* (1984) 36 465–66 or by Hansen, C. B. et al. in (1995) *Biochim. Biophys. Acta* 1239 133–144. The microbubbles are placed on a roller table for several hours and are then washed.

EXAMPLE 20

Method of Use

An agent comprising phosphatidylserine-encapsulated microbubbles having inactivated human thrombin-Succ-PEG$_{3400}$-DSPE incorporated into the encapsulating membrane is lyophilised from 0.01 M phosphate buffer, pH 7.4. The product is redispersed in sterile water and injected intravenously into a patient with suspected venous thrombosis in a leg vein. The leg is examined by standard ultrasound techniques. The thrombus is located by increased contrast as compared with surrounding tissue.

EXAMPLE 21

Preparation and Biological Evaluation of Gas-containing Microbubbles of DSPS 'doped' with a Lipopeptide Comprising a Heparin Sulphate Binding Peptide (KRKR) (SEQ ID NO:5) and a Fibronectin Peptide (WOPPRARI) (SEQ ID NO:6)

This example is directed at the preparation of targeted microbubbles comprising multiple peptidic vectors arranged in a linear sequence.

a) Synthesis of a Lipopeptide Consisting of a Heparin Sulphate Binding Peptide (KRKR) (SEQ ID NO:5) and Fibronectin Peptide (WOPPRARI) (SEQ ID NO:6)

(SEQ ID NO: 7)
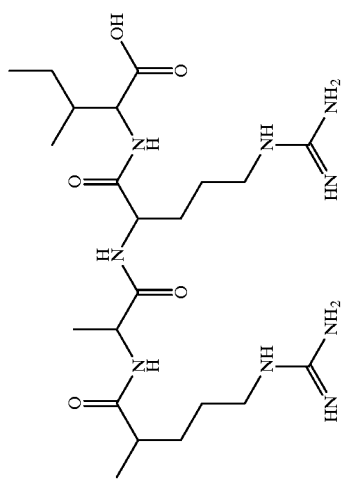
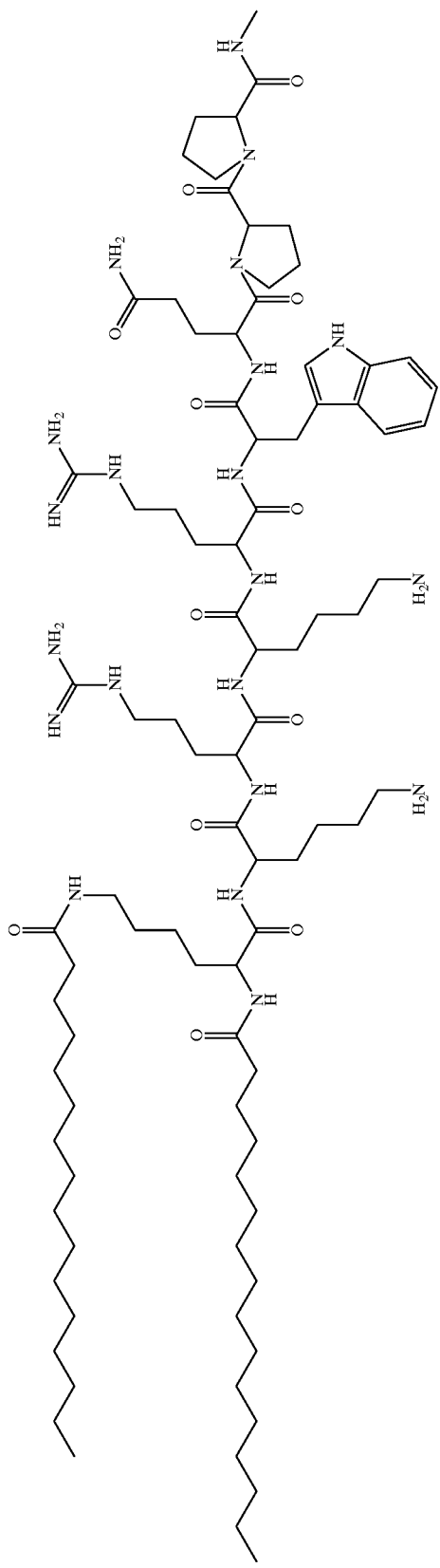

The lipopeptide was synthesised on an ABI 433A automatic peptide synthesiser starting with Fmoc-Ile-Wang resin on a 0.1 mmol scale using 1 mmol amino acid cartridges. All amino acids and palmitic acid were preactivated using HBTU before coupling. The simultaneous removal of peptide from the resin and side-chain protecting groups was carried out in TFA containing 5% phenol, 5% EDT, 5% anisole and 5% $H_2O$ for 2 hours, giving a crude product yield of 150 mg. Purification by preparative HPLC of a 40 mg aliquot of crude material was carried out using a gradient of 70 to 100% B over 40 minutes (A=0.1% TFA/water and B=MeOH) at a flow rate of 9 ml/min. After lyophilisation, 16 mg of pure material were obtained (analytical HPLC, gradient 70–100% B where B=MeOH, A=0.01% TFA/water: detection—UV 260 and fluorescence, $Ex_{280}$, $Em_{350}$— product retention time=19.44 minutes). Further product characterisation was carried out using MALDI mass spectrometry: expected M+H at 2198, found at 2199.

b) Preparation of Gas-filled Microbubbles of DSPS 'doped' with a Multiple-specific Lipopeptide Consisting of a Heparin Sulphate Binding Peptide (KRKR) (SEQ ID NO:5) and Fibronectin Peptide (WOPPRARI) (SEQ ID NO:6)

DSPS (4.5 mg) and lipopeptide from (a) (0.5 mg) were weighed into each of two vials and 0.8 ml of a solution of 1.4% propylene glycol/2.4% glycerol was added to each vial. The mixtures were warmed to 80° C. for 5 minutes (vials shaken during warming). The samples were cooled to room temperature and the head spaces flushed with perfluorobutane gas. The vials were shaken in a cap mixer for 45 seconds and rolled overnight. The resulting microbubbles were washed several times with deionised water and analysed by Coulter counter [size: 1–3 micron (87%), 3–5 micron (11.5%)] and acoustic attenuation (frequency at maximum attenuation: 3.5 MHz).

The microbubbles were stable at 120 mm Hg. MALDI mass spectral analysis was used to confirm incorporation of lipopeptide into DSPS microbubbles as follows: ca. 0.05–0.1 ml of microbubble suspension was transferred to a clean vial and 0.05–0.1 ml methanol was added. The suspension was sonicated for 30 seconds and the solution was analysed by MALDI MS. Positive mode gave M+H at 2200 (expected for lipopeptide, 2198).

c) In vitro Study of Gas-filled Microbubbles of DSPS 'doped' with a Multiple-specific Lipopeptide Consisting of a Heparin Sulphate-binding Peptide (KRKR) (SEQ ID NO:5) and Fibronectin Peptide (WOPPRARI) (SEQ ID NO:6): Binding to Endothelial Cells Under Flow Conditions The human endothelial cell line ECV 304, derived from a normal umbilical cord (ATCC CRL-1998) was cultured in 260 mL Nunc culture flasks (chutney 153732) in RPMI 1640 medium to which L-glutamine (200 mM), penicillin/streptomycin (10,000 U/ml and 10,000 µg/ml) and 10% fetal bovine serum were added. The cells were subcultured with a split ratio of 1:5 to 1:7 when reaching confluence. Coverglasses, 22 mm in diameter, were sterilised and placed on the bottom of 12 well culture plates, whereafter cells in 0.5 ml complete medium with serum were added above the plates. When the cells reached confluence the coverslips were placed in a custom-made flow chamber consisting of a groove carved into a glass plate upon which the cover slip with cells was placed, with the cells facing the groove, so as to form a flow channel. Microbubbles prepared as in (b) were passed from a reservoir held at 37° C. through the flow chamber and back to the reservoir using a peristaltic pump. The flow rate was adjusted to simulate physiologically relevant shear rates. The flow chamber was placed under a microscope and the interaction between the microbubbles and cells was viewed directly. A camera mounted on the microscope was connected to a colour video printer and a monitor. A gradual accumulation of microbubbles on the cells took place at a rate dependent on the flow rate. On further increasing the flow rate, cells started to become detached from the coverslip, but the microbubbles remained bound to the cells. Control bubbles not carrying the vector did not adhere to the endothelial cells and disappeared from the chamber under minimal flow conditions.

d) In vivo Experiment in Dog

Case 1)

A 22 kg mongrel dog was anaesthetised with pentobarbital and mechanically ventilated. The chest was opened by a midline sternotomy, the anterior pericardium was removed, and a 30 mm gelled silicone rubber spacer was inserted between the heart and a P5-3 transducer of an ATL HDI-3000 ultrasound scanner. The scanner was set for intermittent short axis imaging once in each end-systole by delayed EGC triggering. A net volume of 2 ml of microbubbles from (b) was injected as a rapid intravenous bolus; 3 seconds later, the imaged right ventricle was seen to contain contrast material, and another 3 seconds later the left ventricle was also filled and a transient attenuation shadow which obscured the view of the posterior parts of the left ventricle was observed. Substantial increases in brightness were seen in the myocardium and, when the attenuation shadow subsided, in the portions of the heart distal to the left ventricle. After passage of the inital bolus, the ultrasound scanner was set to continuous, high frame rate, high output power imaging, a procedure known to cause destruction of ultrasound contrast agent microbubbles in the imaged tissue regions. After a few seconds, the scanner was adjusted back to its initial setting. The myocardium was then darker, and closer to the baseline value. Moving the imaged slice to a new position resulted in re-appearance of contrast effects; moving the slice back to the initial position again resulted in a tissue brightness close to baseline.

Case 2) [comparative]

A net volume of 2 ml microbubbles prepared in an identical manner to (b) above with the exception that no lipopeptide was included in the preparation was injected, using the same imaging procedure as above. The myocardial echo enhancement was far less intense and of shorter duration than that observed in Case 1. At the completion of the left ventricular attenuation phase, there was also almost complete loss of myocardial contrast effects, and the myocardial echo increases in the posterior part of the left ventricle noted in Case 1 were not observed.

EXAMPLE 22

Preparation of Gas-filled Microbubbles Encapsuled with DSPS Comprising Thiolated anti-CD34-MAL-$PEG_{2000}$-PE a) Preparation of Gas-filled Microbubbles Encapsuled with DSPS and PE-$PEG_{2000}$-Mal DSPS (4.5 mg, 3.9 mmol) and PE-$PEG_{2000}$-Mal from Example 50 (0.5 mg) were weighed into a clean vial and 1 ml of a solution of 1.4% propylene glycol/2.4% glycerol was added. The mixture was warmed to 80° C. for 5 minutes then filtered through a 4.5 micron filter. The sample was cooled to room temperature and the head space was flushed with perfluorbutane gas. The vials were shaken in a cap mixer for 45 seconds and the resulting microbubbles were washed three times with distilled water.

b) Thiolation of anti-CD34 Antibodies

To 0.3 mg of anti-CD34 antibody dissolved in 0.5 ml phosphate buffered saline (PBS), pH7, was added 0.3 mg Traut's reagent and the solution was stirred at room temperature for 1 hour. Excess reagent was separated from the modified protein on a NAP-5 column.

c) Conjugation of Thiolated anti-CD34 Antibody to Gas-filled Microbubbles Encapsuled with DSPS and Comprising DSPE-PEG$_{2000}$-MAL 0.5 ml of the thiolated antibody praparation from (b) was added to an aliquot of microbubbles from (a) and the conjugation reaction was allowed to proceed for 30 minutes on a roller table. Following centifugation at 2000 rpm for 5 minutes the infranatant was removed. The microbubbles were washed a further three times with water.

d) Detection of the Antibody Encapsulated in the Microbubbles Using a FITC-conjugated Secondary Antibody To the microbubble suspension from (c) was added 0.025 mL FITC-conjugated goat-anti-mouse antibody. The mixture was incubated in the dark at room temperature for 30 minutes on a roller table and was then centrifuged at 2000 rpm for 5 minutes. The infranatant was then removed and the microbubbles were washed a further three times with water. Flow cytometric analysis of the microbubble suspension showed that 98% of the population was fluorescent.

EXAMPLE 23

Preparation of Gas-filled Microbubbles Encapsuled with DSPS Comprising Thiolated anti-CD62-MAL-PEG$_{2000}$-PE An identical procedure to that described in Example 22 was used to prepare microbubbles comprising anti-CD62 antibodies.

EXAMPLE 24

Preparation of Gas-filled Microbubbles Encapsuled with DSPS Comprising Thiolated anti-ICAM-1-MAL-PEG$_{2000}$-PE An identical procedure to that described in Example 22 was used to prepare microbubbles comprising anti-ICAM-1 antibodies.

EXAMPLE 25

Preparation of Gas-filled Microbubbles Encapsulated with DSPS and Thiolated anti-CD62-Mal-PEG$_{2000}$-PE and thiolated-anti-ICAM-1-Mal-PEG$_{2000}$-PE This example is directed to the preparation of microbubbles comprising multiple antibody vectors for targeted ultrasound imaging.

a) Preparation of Gas-filled Microbubbles Encapsulated with DSPS and PE-PEG$_{2000}$-Mal DSPS (4.5 mg) and PE-PEG$_{2000}$-Mal from Example 2(a) (0.5 mg) were weighed into a clean vial and 1 ml of a solution of 1.4% propylene glycol/2.4% glycerol was added. The mixture was warmed to 80° C. for 5 minutes and then filtered through a 4.5 micron filter. The sample was cooled to room temperature and the head space was flushed with perfluorobutane gas. The vials were shaken in a cap mixer for 45 seconds and the microbubbles were washed three times with distilled water.

b) Thiolation of anti-CD62 and anti-ICAM-1 Antibodies

To 0.3 mg each of anti-CD62 and anti-ICAM-1 antibodies dissolved in PBS buffer (pH 7, 0.5 ml) was added Traut's reagent and the solutions were stirred at room temperature for 1 hour. Excess reagent was separated from the modified protein on a NAP-5 column.

c) Conjugation of Thiolated anti-CD62 and anti-ICAM-1 Antibodies to Gas-filled Microbubbles Encapsulated with DSPS and DSPE-PEG$_{2000}$-Mal 0.5 ml of the mixed thiolated antibody preparation from (b) was added to an aliquot of Microbubbles from (a) and the conjugation reaction was allowed to proceed for 30 minutes on a roller table. Following centrifugation at 2000 rpm for 5 minutes, the infranatant was removed. The microbubbles were washed a further three times with water.

The PEG spacer length may be varied to include longer (e.g. PEG$_{3400}$ and PEG$_{5000}$) or shorter (e.g. PEG$_{600}$ or PEG$_{800}$) chains. Addition of a third antibody such as thiolated-anti-CD34 is also possible.

EXAMPLE 26

Targeted Gas-filled Microbubbles Comprising DSPS Coated Non-covalently with Polylysine and a Fusion Peptide Comprising a PS-binding Component and a Fibronectin Peptide Sequence FNFRLKAGOKIRFGGGGWOPPRAI (SEQ ID NO:8)

a) Synthesis of PS-binding/fibronectin Fragment Fusion Peptide FNFRLKAGOKIRFGGGGWOPPRAI (SEQ ID NO:8)

The peptide was synthesised on an ABI 433A automatic peptide synthesiser starting with Fmoc-Ile-Wang resin on a 0.1 mmol scale using 1 mmol amino acid cartridges. All amino acids were preactivated using HBTU before coupling. The simultaneous removal of peptide from the resin and side-chain protecting groups was carried out in TFA containing 5% phenol, 5% EDT and 5% H$_2$O for 2 hours, giving a crude product yield of 302 mg. Purification by preparative HPLC of a 25 mg aliquot of crude material was carried out using a gradient of 20 to 40% B over 40 minutes (A=0.1% TFA/water and B=0.1% TFA/acetonitrile) at a flow rate of 9 ml/min. After lyophilisation 10 mg of pure material was obtained (analytical HPLC, gradient 20 to 50% B where B=0.1% TFA/acetonitrile, A=0.01% TFA/water: detection—UV 214 and 260 nm—product retention time=12.4 minutes). Further product characterization was carried out using MALDI mass spectrometry: expected M+H at 2856, found at 2866.

b) Preparation of Gas-filled Microbubbles Comprising DSPS Coated Non-covalently with Polylysine and the PS-binding/fibronectin Fragment Fusion Peptide FNFRLK-AGOKIRFGGGGWOPPRAI (SEQ ID NO:8)

DSPS (5 mg) was weighed into a clean vial along with poly-L-lysine (0.2 mg) and peptide from (a) above (0.2 mg). To the vial was added 1.0 ml of a solution of 1.4% propylene glycol/2.4% glycerol. The mixture was warmed to 80° C. for 5 minutes. The sample was cooled to room temperature and the head space was flushed with perfluorobutane gas. The vials were shaken in a cap mixer for 45 seconds and the resulting microbubbles were centrifuged at 1000 rpm for 3 minutes. Following extensive washing with water, PBS and water, the final solution was examined for polylysine and peptide content using MALDI MS. No polypeptide material was observed in the final wash solution. Acetonitrile (0.5 ml) was then added and the microbubbles were destroyed by sonication. Analysis of the resulting solution for polylysine and PS-binding/fibronectin fusion peptide was then carried out using MALDI MS. The results were as follows:

|                     | MALDI expected         | MALDI found         |
|---------------------|------------------------|---------------------|
| Poly-L-lysine       | 786, 914, 1042, 1170   | 790, 919, 1048, 1177 |
| DSPS-binding peptide | 2856                   | 2866                |

The spacer element contained within the PS-binding/fibronectin fusion peptide (-GGG-) may also be replaced with other spacers such as PEG$_{2000}$ or poly alanine (-AAA-). A form of pre-targeting may also be employed, whereby the DSPS-binding/fibronectin fragment fusion peptide is firstly allowed to associate with cells via fibronectin peptide binding, followed by administration of PS microbubbles which then bind to the PS-binding peptide.

EXAMPLE 27

Gas-filled Microbubbles Encapsulated with Phosphatidylserine and biotin-PEG-alanyl-cholesterol and Functionalised with streptavidin/biotinyl-endothelin-1 Peptide (biotin-D-Trp-Leu-Asp-Ile-Ile-Trp.OH) (SEQ ID NO:9) and biotinyl-fibrin-anti-polymerant Peptide (biotin-GPRPPERHOS.$NH_2$) (SEQ ID NO:10)

This example is directed at the preparation of targeted ultrasound microbubbles whereby streptavidin is used as a lihker between biotinylated reporter(s) and vector(s).

a) Synthesis of biotin-$PEG_{3400}$-b-Alanine Cholesterol

To a solution of cholesteryl-b-alanine hydrochloride (as described in Example 59) (15 mg, 0.03 mmol) in 3 ml chloroform/wet methanol (2.6:1) was added triethylamine (42 ml, 0.30 mmol). The mixture was stired for 10 minutes at room temperature and a solution of biotin-$PEG_{3400}$-NHS (100 mg, 0.03 mmol) in 1,4-dioxane (1 ml) was added dropwise. After stirring at room temperature for 3 hours, the mixture was evaporated to dryness and the residue purified by flash chromatography to give white crystals, yield 102 mg (89%). The structure was verified by MALDI-MS and NMR.

b) Synthesis of biotinylated Endothelin-1 Peptide (biotin-D-Trp-Leu-Asp-Ile-Ile-Trp.OH) (SEQ ID NO:9)

The peptide was synthesised on a ABI 433A automatic peptide synthesiser starting with Fmoc-Trp(Boc)-Wang resin on a 0.1 mmol scale using 1 mmol amino acid cartridges. All amino acids were preactivated using HBTU before coupling. The simultaneous removal of peptide from the resin and side-chain protecting groups was carried out in TFA containing 5% anisole and 5% $H_2O$ for 2 hours giving a crude product yield of 75 mg. Purification by preparative HPLC of a 20 mg aliquot of crude material was carried out using a gradient of 30 to 80% B over 40 minutes (A=0.1% TFA/water and B=0.1% TFA/acetonitrile) and a flow rate of 9 ml/min. After lyophilisation of the pure fractions 2 mg of pure material was obtained (analytical HPLC, gradient 30–80% B where B=0.1% TFA/acetonitrile, A=0.01% TFA/water: detection UV 214 nm—product retention time=12.6 minutes). Further product characterization was carried out using MALDI mass spectrometry: expected M+H at 1077, found at 1077.

c) Synthesis of biotinyl-fibrin-anti-polymerant Peptide (biotin-GPRPPERHOS.$NH_2$)(SEQ ID NO:10)

This peptide was synthesised and purified using similar protocols to those described in (b) above. The pure product was characterised by HPLC and MALDI MS.

d) Preparation of Multiple-specific Gas-filled Microbubbles Encapsulated with Phosphatidylserine and biotin-$PEG_{3400}$-b-Alanine Cholesterol DSPS (4.5 mg) and biotin-$PEG_{3400}$-b-alanine cholesterol from (a) (0.5 mg) were weighed into a vial and 0.8 ml of a solution of 1.4% propylene glycol/2.4% glycerol was added. The mixture was warmed to 80° C. for 5 minutes (vials shaken during warming). The sample was cooled to room temperature and the head space was flushed with perfluorobutane gas. The vial was shaken in a cap-mixer for 45 seconds and the vial was rolled overnight. The microbubble suspension was washed several times with deionised water and analysed by Coulter counter and acoustic attenuation.

e) Conjugation with Fluorescein-labelled Streptavidin and Biotinylated Peptides from (b) and (c)

To the microbubble preparation from (d) was added fluorescein-conjugated streptavidin (0.2 mg) dissolved in PBS (1 ml). The bubbles were placed on a roller table for 3 hours at room temperature. Following extensive washing with water and analysis by fluorescence microscopy, the microbubbles were incubated in 1 ml of PBS containing biotinyl-endothelin-1 peptide (0.5 mg) and biotinyl-fibrin-anti-polymerant peptide (0.5 mg) from (b) and (c) respectively for 2 hours. Extensive washing of the microbubbles was performed to remove unconjugated peptide.

EXAMPLE 28

Gas-filled Microbubbles Encapsulated with Phosphatidylserine and biotin-DPPE used to Prepare a Streptavidin 'Sandwich' with a Mixture of biotinyl-endothelin-1 Peptide (biotin-D-Trp-Leu-Asp-Ile-Ile-Trp.OH) (SEQ ID NO:9) and biotinyl-fibrin-anti-polymerant Peptide (biotin-GPRPPERHOS.$NH_2$) (SEQ ID NO:10)

a) Preparation of Biotin-containing Microbubbles

To a mixture of phosphatidylserine (5 mg) and biotin-DPPE (0.6 mg) in a clean vial was added 5% propylene glycol-glycerol in water (1 ml). The dispersion was heated to 80° C. for 5 minutes and then cooled to ambient temperature. The head space was then flushed with perfluorobutane and the vial was shaken in a cap-mixer for 45 seconds. After centrifugation the infranatant was removed and the microbubbles were washed extensively with water.

b) Conlugation of Gas-filled Microbubbles Encapsulated with Phosphatidylserine and biotin-DPPE with Streptavidin and a Mixture of biotinyl-endothelin-1 (biotin-D-Trp-Leu-Asp-Ile-Ile-Trp.OH) (SEQ ID NO:9) and biotinyl-fibrin-anti-polymerant Peptide (biotin-GPRPPERHOS.$NH_2$) (SEQ ID NO:10)

The procedure detailed in Example 27 was followed.

EXAMPLE 29

PFB Gas-containing Microbubbles of DSPS Functionalised with Heparin Sulphate Binding Peptide/Fibronectin peptide/RGD Peptide and Fluorescein a) Synthesis of a Lipopeptide Containing the RGD Sequence and a Fluorescein Reporter Group: Dipalmitoyl-Lys-Lys-Lys-Lys[acetyl-Arg-Gly-Asp-Lys(fluorescein)]Gly.OH (SEQ ID NO:11)

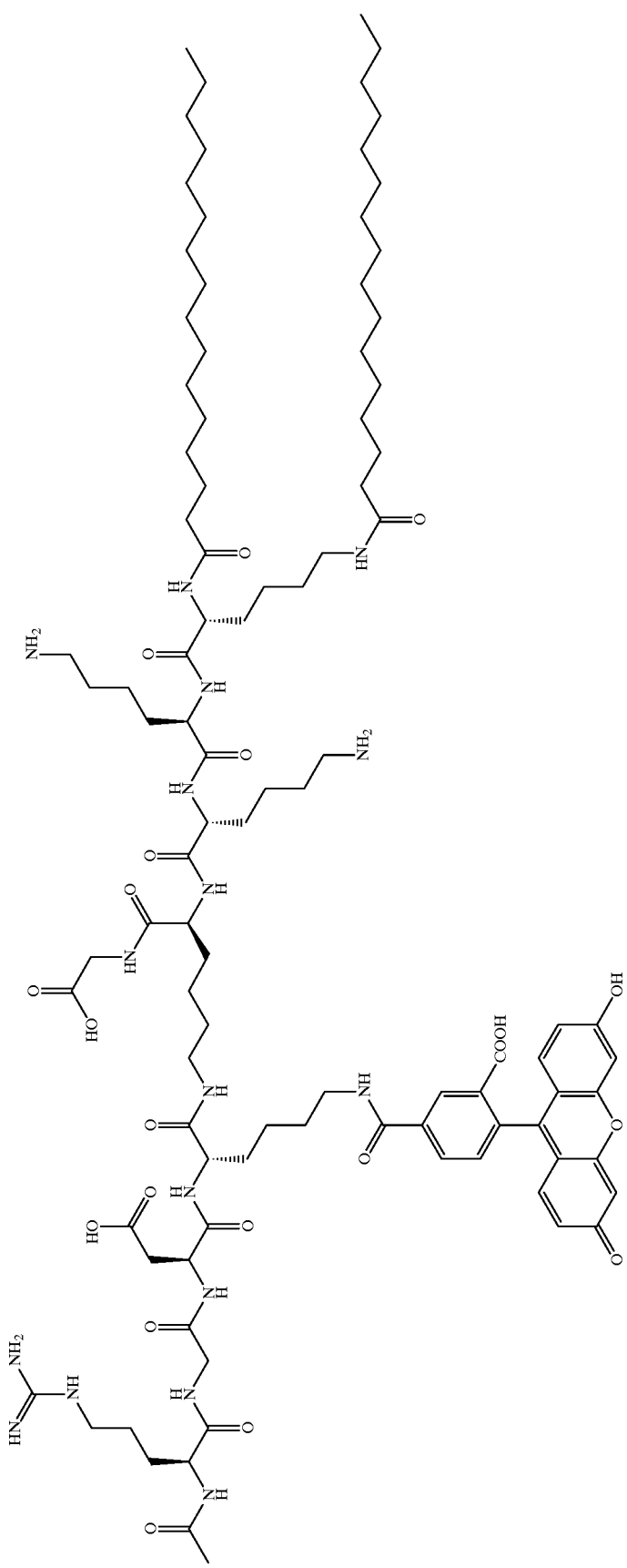

The lipopeptide was synthesised as described in Example 21(a) using commercially available amino acids and polymers. The lipopeptide was cleaved from the resin in TFA containing 5% water, 5% phenol and 5% EDT for 2 hours. Following evaporation in vacuo the crude product was precipitated and triturated with diethyl ether. Purification by preparative HPLC of a 40 mg aliquot of crude material was carried out using a gradient of 60 to 100% B over 40 minutes (A=0.1% TFA/water and B=0.1% TFA/acetonitrile) at a flow rate of 9 ml/min. After lyophilisation 10 mg of pure material (analytical HPLC, gradient 60–100% B where B=0.1% TFA/acetonitrile, A=0.01% TFA/water: detection—UV 260- product retention time=20–22 minutes). Further product characterisation was carried out using MALDI mass spectrometry: expected M+H at 1922, found at 1920.

b) Synthesis of a Lipopeptide Containing a Heparin Sulphate-binding Sequence and a Fibronectin Peptide Synthesis and purification were carried out as described in Example 21(a).

c) Preparation of Multiple-specific Gas-filled Microbubbles of DSPS Functionalised with a Heparin Sulphate-binding Peptide, a Fibronectin Peptide, Acetyl-RGD Peptide and Fluorescein DSPS (4 mg, 3.9 mmol), lipopeptide from (a) (0.5 mg, 0.2 mmol) and lipopeptide from (b) (0.5 mg) were weighed into each of two vials and 0.8 ml of a solution of 1.4% propylene glycol/2.4% glycerol was added to each vial. The mixtures were warmed to 80° C. for 5 minutes (vials shaken during warming). The samples were cooled to room temperature and the head spaces were flushed with perfluorobutane gas. The vials were shaken in a cap mixer for 45 seconds and then rolled overnight. The microbubbles so obtained were washed several times with deionised water and analysed by MALDI mass spectrometry as described in Example 21(b). The microbubbles were investigated by microscopy and were seen to have a range of sizes between 1 and 5 microns. Furthermore the microbubbles were fluorescent.

EXAMPLE 30

Gas-filled Microbubbles Comprising DSPS Covalently Modified with CD71 FITC-labelled anti-transferrin Receptor Antibody and 'doped' with a Lipopeptide with Affinity for Endothelial Cells This example is directed at the preparation of multiple vector targeted ultrasound agents.

a) Synthesis of an Endothelial Cell Binding Lipopeptide: 2-n-hexadecylstearyl-Lys-Leu-Ala-Leu-Lys-Leu-Ala-Leu-Lys—Ala-Leu-Lys-Ala-Ala-Leu-Lys-Leu-Ala-$NH_2$ (SEQ ID NO:12)

The lipopeptide shown below was synthesised on a ABI 433A automatic peptide synthesiser starting with a Rink amide resin on a 0.1 mmol scale using 1 mmol amino acid cartridges.

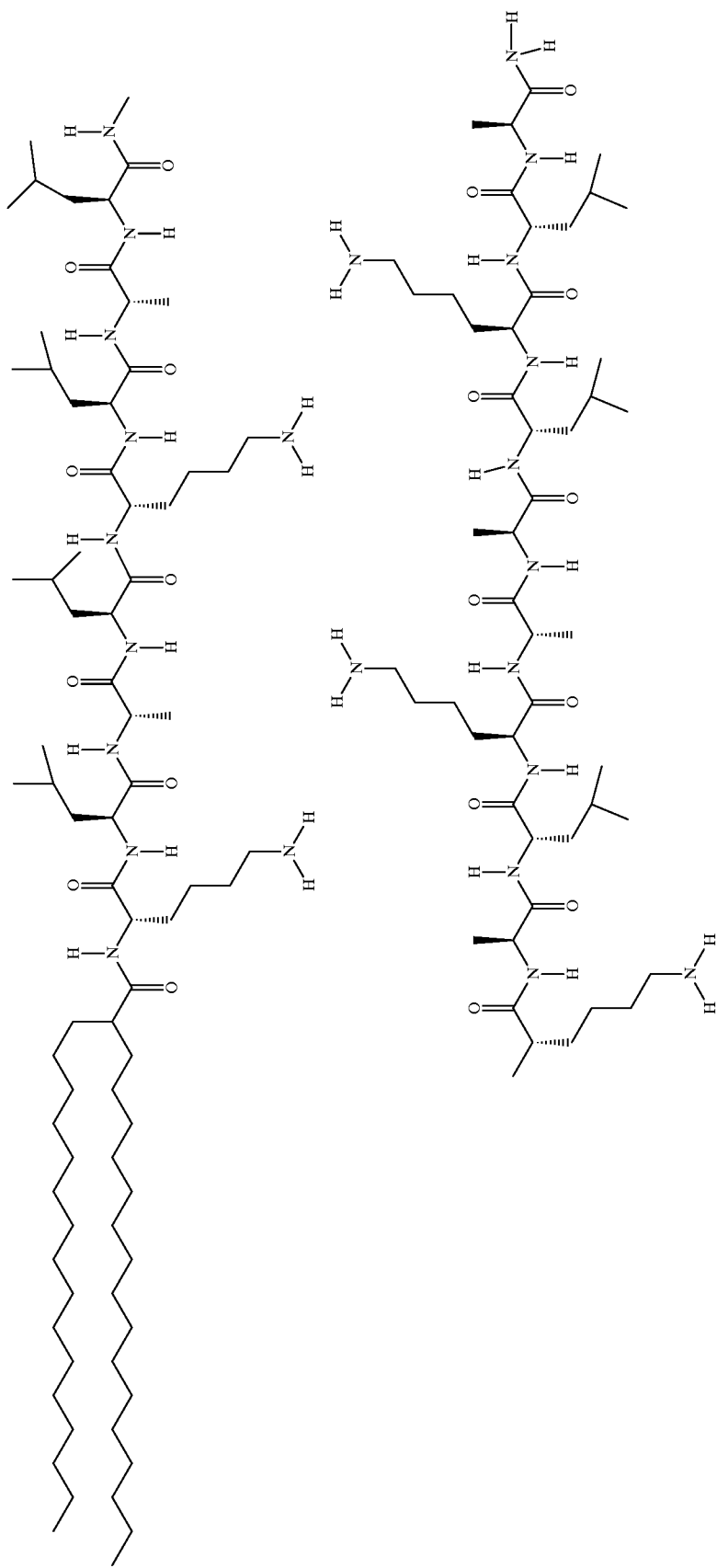

All amino acids and 2-n-hexadecylstearic acid were pre-activated using HBTU before coupling. The simultaneous removal of peptide from the resin and side-chain protecting groups was carried out in TFA containing 5% EDT and 5% $H_2O$ for 2 hours, giving a crude product yield of 150 mg. Purification by preparative HPLC of a 40 mg aliquot of crude material was carried out using a gradient of 90 to 100% B over 50 minutes (A=0.1% TFA/water and B=MeOH) at a flow rate of 9 ml/min. After lyophilisation, 10 mg of pure material was obtained (analytical HPLC, gradient 90–100% B where B=MeOH, A=0.01% TFA/water: detection—UV 214 nm—product retention time=23 minutes). Further product characterisation was carried out using MALDI mass spectrometry: expected M+H at 2369, found at 2373.

b) Preparation of Gas-filled Microbubbles Comprising DSPS 'doped' with a Endothelial Cell-binding Lipopeptide and PE-PEG$_{2000}$-Mal DSPS (4.5 mg) and lipopeptide from (a) (0.5 mg) along with PE-PEG$_{2000}$-Mal from Example 50 (0.5 mg) were weighed into a clean vial and 1 ml of a solution of 1.4% propylene glycol/2.4% glycerol was added. The mixture was warmed to 80° C. for 5 minutes and then filtered through a 4.5 micron filter. The sample was cooled to room temperature and the head space was flushed with perfluorobutane gas. The vial was shaken in a cap mixer for 45 seconds and the resulting microbubbles were washed three times with distilled water.

c) Thiolation of FITC-labelled Anti-transferrin Receptor Antibody

FITC-labelled CD71 anti-transferrin receptor Ab (100 mg/ml in PBS, 0.7 ml) was reacted with Traut's reagent (0.9 mg) at room temperature for 1 hour. Excess reagent was separated from modified protein on a NAP-S column.

d) Conjugation of Thiolated FITC-labelled Anti-transferrin Receptor Antibody to Gas-filled Microbubbles Comprising DSPS 'doped' with an Endothelial Cell-binding Lipopeptide and DSPE-PEG$_{2000}$-Mal A 0.5 ml aliquot of the protein fraction (2 ml in total) from (c) above was added to the microbubbles from (b) and the conjugation reaction was allowed to proceed for 10 minutes on a roller table. Following centrifugation at 1000 rpm for 3 minutes the protein solution was removed and the conjugation repeated twice more with 1 ml and 0.5 ml aliquots of protein solution respectively. The bubbles were then washed four times in distilled water and a sample analysed for the presence of antibody by flow cytometry and microscopy. A fluorescent population of >92% was observed (see FIG. 1).

Incorporation of lipopeptide into the microbubbles was confirmed by MALDI mass spectrometry as described in Example 21(b).

EXAMPLE 31

Gas-filled Microbubbles Comprising DSPS, a Lipopeptide for Endothelial Cell Targeting and a Captopril-containing Molecule This example is directed to the preparation of ultrasound agents for combined targeting and therapeutic applications.

a) Synthesis of a Lipopeptide Functionalised with Captopril (SEQ ID NO:13)
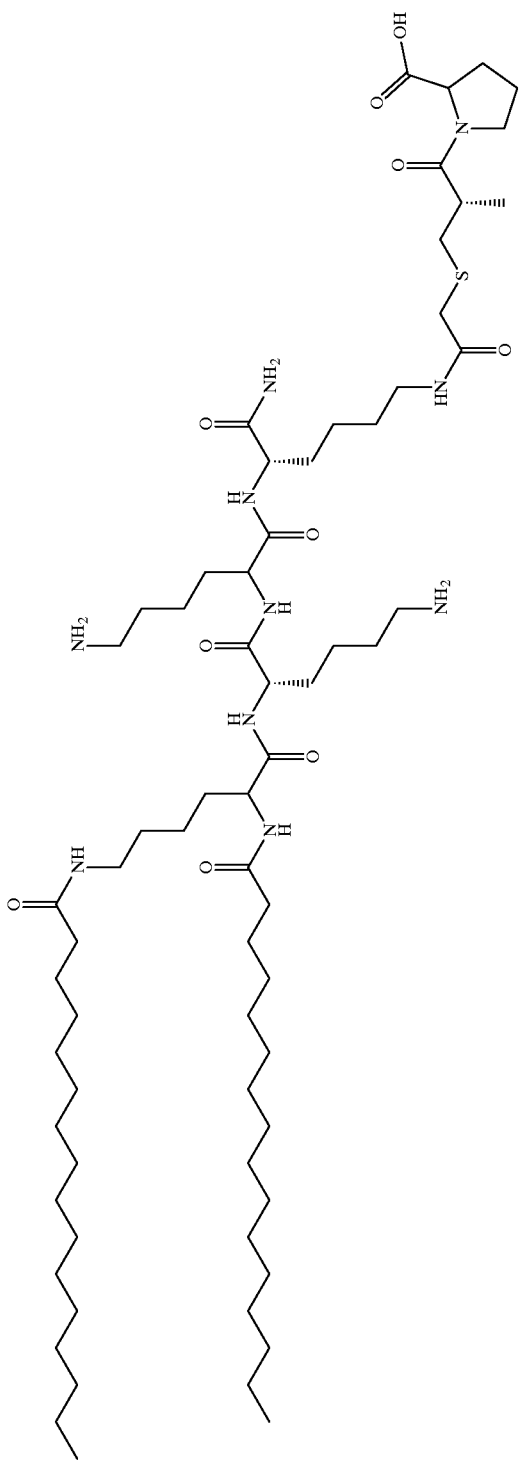

The structure shown above was synthesised using a manual nitrogen bubbler apparatus starting with Fmoc-protected Rink Amide MBHA resin on a 0.125 mmol scale. Coupling was carried out using standard TBTU/HOBt/DIEA protocols. Bromoacetic acid was coupled through the side-chain of Lys as a symmetrical anhydride using DIC preactivation. Captopril dissolved in DMF was introduced on the solid-phase using DBU as base. Simultaneous removal of the peptide from the resin and deprotection of side-chain protecting groups was carried out in TFA containing 5% EDT, 5% water and 5% ethyl methyl sulphide for 2 hours. An aliquot of 10 mg of the crude material was purified by preparative liquid chromatography using a gradient of 70 to 100% B over 60 minutes (A=0.1% TFA/water and B=0.1% TFA/acetonitrile) at a flow rate of 10 ml/min. After lyophilisation a yield of 2 mg of pure material was obtained (analytical HPLC, gradient 70–100% B over 20 minutes, A=0.1% TFA/water and B=0.1% TFA/acetonitrile, flow rate 1 ml/min., detection UV 214 nm, retention time 26 minutes). Further characterisation was carried out using MALDI mass spectrometry, giving M+H at 1265 as expected.

b) Synthesis of a lipopeptide with affinity for endothelial cells: Dipalmitoyl-Lys-Lys-Lys-Aca-Ile-Arg-Arg-Val-Ala-Arg-Pro-Pro-Leu-NH$_2$ (SEQ ID NO:14)

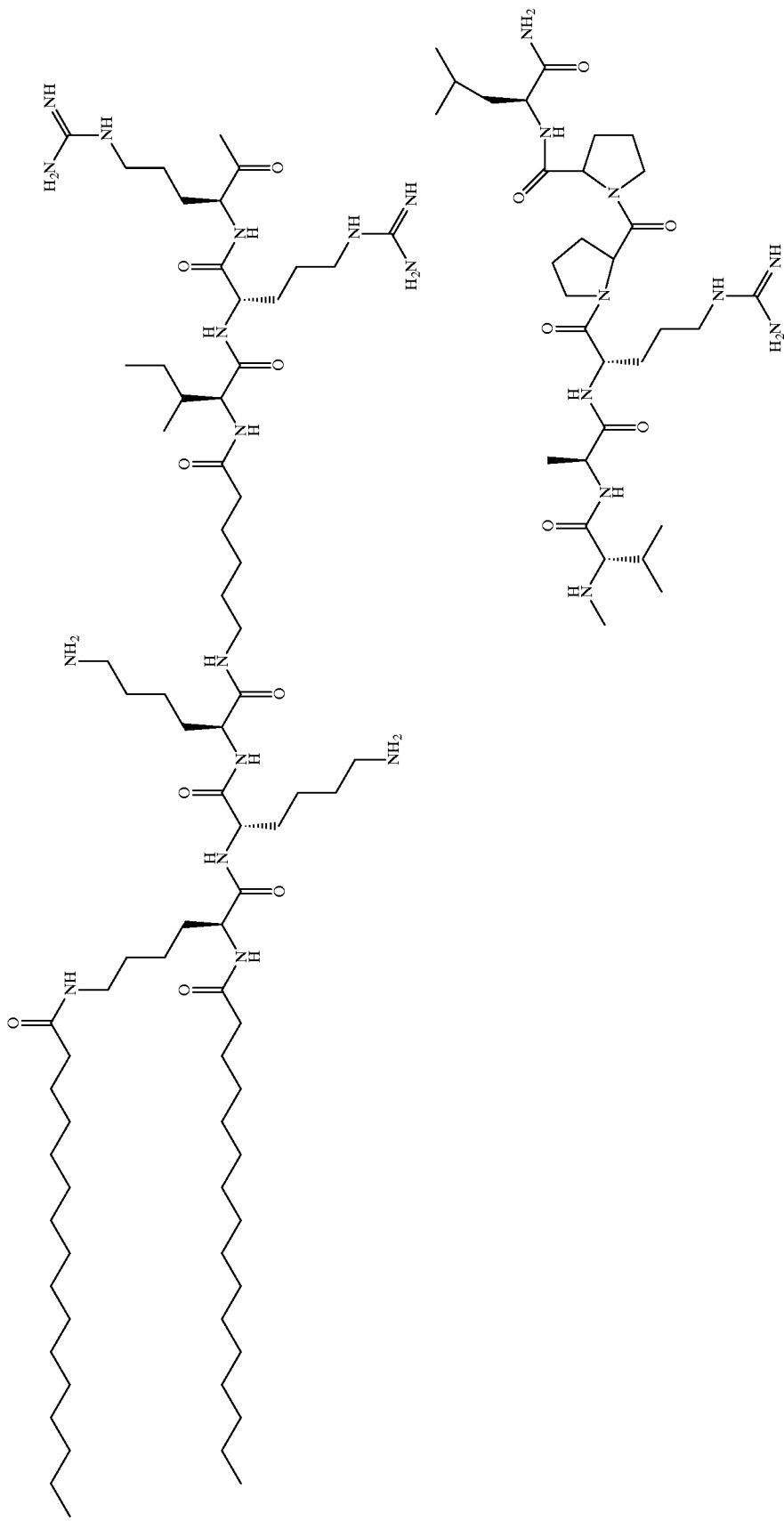

The lipopeptide was synthesised on a ABI 433A automatic peptide synthesiser starting with Rink amide resin on a 0.1 mmol scale using 1 mmol amino acid cartridges. All amino acids and palmitic acid were preactivated using HBTU before coupling. The simultaneous removal of peptide from the resin and side-chain protecting groups was carried out in TFA containing 5% phenol, 5% EDT and 5% $H_2O$ for 2 hours, giving a crude product yield of 160 mg. Purification by preparative HPLC of a 35 mg aliquot of crude material was carried out using a gradient of 70 to 100% B over 40 minutes (A=0.1% TFA/water and B=MeOH) at a flow rate of 9 ml/min. After lyophilisation, 20 mg of pure material was obtained (analytical HPLC, gradient 70–100% B where B=MeOH, A=0.01% TFA/water: detection—UV 214 and 260 nm—product retention time=16 minutes). Further product characterisation was carried out using MALDI mass spectrometry: expected M+H at 2050, found at 2055.

c) Preparation of Gas-filled Microbubbles Comprising DSPS, a Lipopeptide for Endothelial Cell Targeting and a Captopril-containing Molecule for Drug Delivery DSPS (4.5 mg), product from (a) (0.5 mg) and product from (b) (0.5 mg) were weighed into a vial and 1.0 ml of a solution of 1.4% propylene glycol/2.4% glycerol was added. The mixture was warmed to 80° C. for 5 minutes (vial shaken during warming). The sample was cooled to room temperature and the head space was flushed with perfluorobutane gas. The vial was firstly shaken in a cap-mixer for 45 seconds then rolled for 1 hour, whereafter the contents were extensively washed with deionised water. No detectable level of starting material was found in the final wash solution as evidenced by MALDI MS. MALDI mass spectral analysis was used to confirm incorporation of the products from (a) and (b) into the microbubbles as described in Example 21(b)

d) In vitro Study of Gas-filled Microbubbles Comprising DSPS, a Lipopeitde for Endothelial Cell Targeting and a Captopril-containing Molecule for Therapeutic Applications The in vitro assay decribed in Example 21(c) was used to examine cell binding under flow conditions. A gradual accumulation of microbubbles on the cells took place, depending on the flow rate. On further increasing the flow rate cells started to become detached from the coverslip, but the microbubbles remained bound to the cells. Control microbubbles not carrying the vector did not adhere to the endothelial cells and disappeared from the chamber under minimal flow conditions.

EXAMPLE 32

Preparation of Gas-filled Microbubbles Comprising DSPS Loaded with a Lipopeptide Comprising a Helical Peptide with Affinity for Cell Membranes and the Peptide Antibiotic Polymixin B Sulphate This example is directed to the preparation of targeted microbubbles comprising multiple peptidic vectors having a combined targeting and therapeutic application.

a) Synthesis of a Lipopeptide Comprising a Helical Peptide with Affinity for Cell Membranes: Hexadecylstearyl-Lys-Leu-Ala-Leu-Lys-Leu-Ala-Leu-Lys-Ala-Leu-Lys-Ala-Ala-Leu-Lys-Leu-Ala-$NH_2$ (SEQ ID NO:12)

This is prepared as described in Example 30(a).

b) Preparation of Multiple-specific Gas-filled Microbubbles

DSPS (5.0 mg), lipopeptide from (a) (0.3 mg) and polymixin B sulphate (0.5 mg) were weighed into a clean vial and 1.0 ml of a solution of 1.4% propylene glycol/2.4% glycerol was added. The mixture was sonicated for 3–5 minutes, warmed to 80° C. for 5 minutes and then filtered through a 4.5 micron filter. The mixture was cooled to room temperature and the head space was flushed with perfluorobutane gas. The vial was shaken in a cap-mixer for 45 seconds and the resulting microbubbles were centrifuged at 1000 rpm for 3 minutes. The microbubbles were washed with water until no polymixin B sulphate or lipopeptide could be detected in the infranatant by MALDI-MS. Microscopy showed that the size distribution of the bubble population was in the desired range of 1–8 micron. To the washed bubbles (ca. 0.2 ml) was added methanol (0.5 ml), and the mixture was placed in a sonicator bath for 2 minutes. The resulting clear solution, on analysis by MALDI-MS, was found to contain both lipopeptide and polymixin B sulphate (expected 1203, found 1207).

EXAMPLE 33

Preparation of Gas-filled Microbubbles Comprising DSPS 'doped' with a Lipopeptide Comprising a IL-1 Receptor-binding Sequence and Modified with a Branched Structure Containing the Drug Methotrexate This example is directed to the preparation of targeted microbubbles comprising multiple vectors for targeted/therapeutic applications.

a) Synthesis of a lipopeptide comprising an interleukin-1 receptor-binding peptide: Dipalmitoyl-Lys-Gly-Asp-Trp-Asp--Gln--Phe-Gly-Leu-Trp-Arg-Gly-Ala-Ala.OH (SEQ ID NO:15)

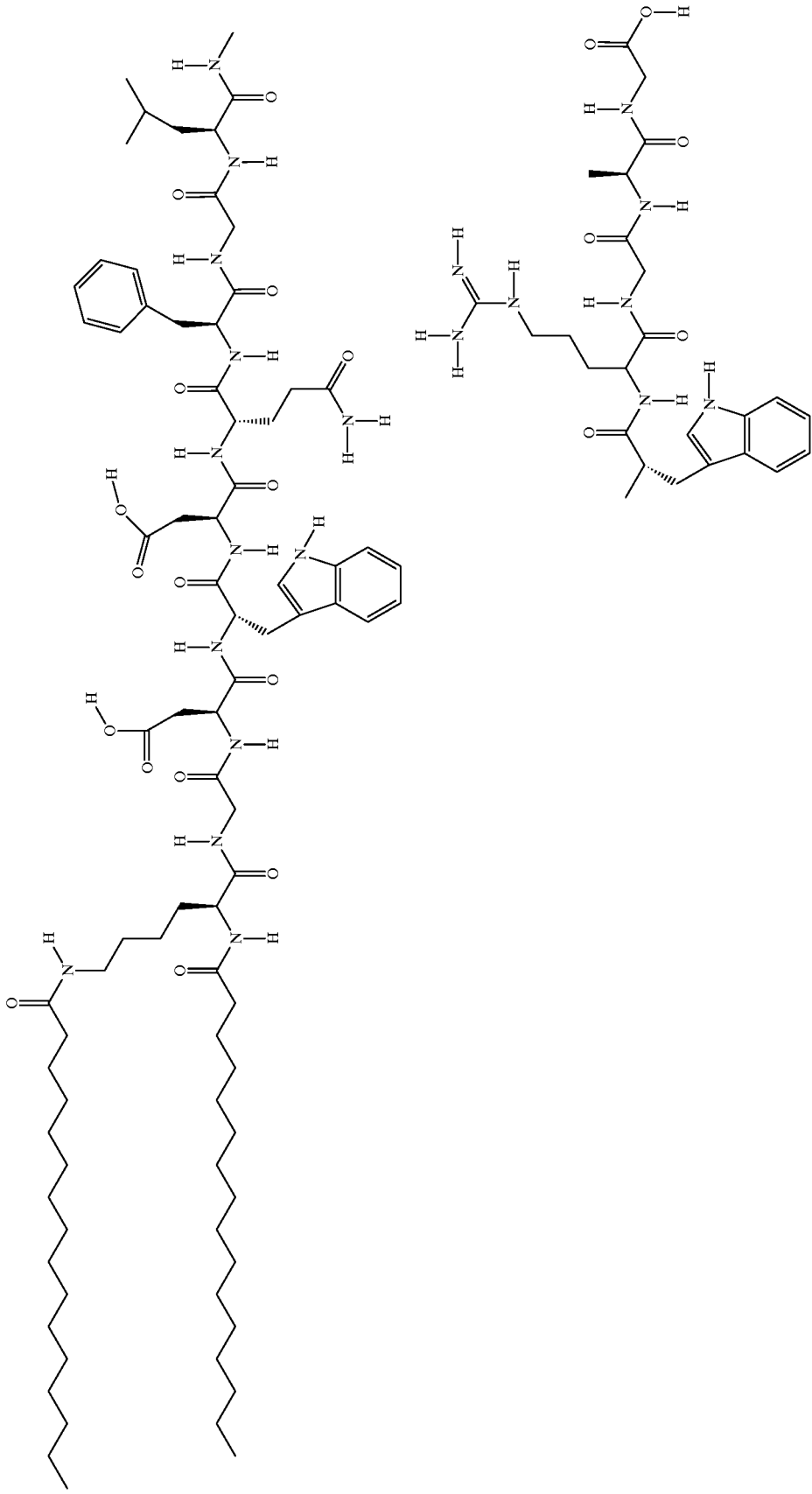

The lipopeptide was synthesised on a ABI 433A automatic peptide synthesiser starting with Fmoc-Ala-Wang resin on a 0.1 mmol scale using 1 mmol amino acid cartridges.

All amino acids and palmitic acid were preactivated using HBTU before coupling. The simultaneous removal of lipopeptide from the resin and side-chain protecting groups was carried out in TFA containing 5% $H_2O$, 5% anisole, 5% phenol and 5% EDT for 2 hours, giving a crude product yield of 150 mg. Purification by preparative HPLC of a 30 mg aliquot of crude material was carried out using a gradient of 90 to 100% B over 40 minutes (A=0.1% TFA/water and B=MeOH) at a flow rate of 9 mlmin. After lyophilisation, 4 mg of pure material was obtained (analytical HPLC, gradient 90–100% B over 20 minutes where B=MeOH, A=0.01% TFA/water: detection—UV 214 nm—product retention time=23 minutes). Further product characterisation was carried out using MALDI mass spectrometry: expected M+H at 2083, found at 2088.

b) Synthesis of a Branched Methotrexate Core Structure Containing a Thiol Moiety 5 minutes and then filtered through a 4.5 micron filter. The mixture was cooled to room temperature and the head space was flushed with perfluorobutane gas. The vial was shaken in a cap mixer for 45 seconds and the resulting microbubbles were centrifuged at 1000 rpm for 3 minutes, whereafter the infranatant was discarded.

d) Conjugation of Methotrexate Branched Structure to Thiolated Microbubbles

The methotrexate structure from (b) above (0.5 mg) was dissolved in PBS, pH 8.0. The solution was then added to the thiol-containing microbubbles from (c) and disulphide bond formation was allowed to proceed for 16 hours. Following extensive washing with PBS and water the bubbles were analysed by microscopy and MALDI MS.

The disulphide bond linking the methotrexate structure to the microbubbles may be reduced in vivo to liberate the free drug molecule, so that such microbubbles in combination with a tumour specific vector comprise a drug delivery system. A physiologically acceptable reducing agent such as glutathione may be used to bring about drug release.

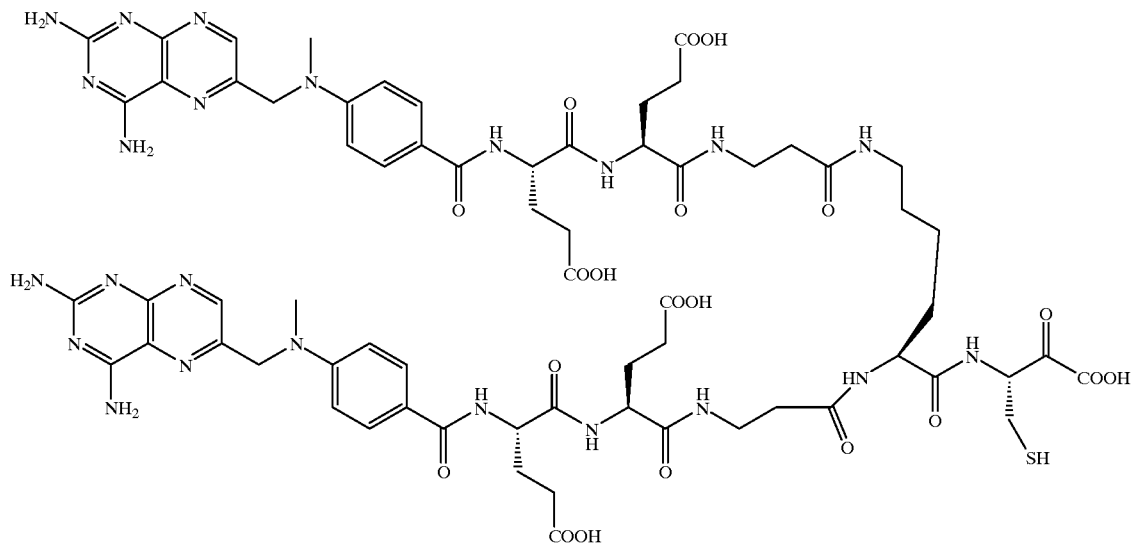

The methotrexate structure was synthesised on an ABI 433A automatic peptide synthesiser starting with Fmoc-Cys (Trt) Tentagel resin on a 0.1 mmol scale. The simultaneous removal of product from the resin and deprotection of protecting groups was carried out in TFA containing 5% EDT and 5% $H_2O$ for 2 hours, giving a crude product yield of 160 mg. Purification by preparative HPLC of a 30 mg aliquot of crude material was carried out using a gradient of 10 to 30% B over 40 minutes (A=0.1% TFA/water and B=0.1% TFA/acetonitrile) and a flow rate of 9 ml/min. After lyophilisation of the pure fractions, 9 mg of pure material was obtained (analytical HPLC, gradient 5–50% B where B=0.1% TFA/acetonitrile, A=0.01% TFA/water: detection—UV 214 nm—product retention time=9.5 minutes). Further product characterisation was carried out using MALDI mass spectrometry: expected M+H at 1523, found at 1523.

c) Preparation of Multiple-specific Gas-filled Microbubbles

DSPS (4.5 mg), thiol-containing lipopeptide from Example 64(a) (0.5 mg) and lipopeptide from (a) (0.2 mg) were weighed into a clean vial and 1.0 ml of a solution of 1.4% propylene glycol/2.4% glycerol was added. The mixture was sonicated for 3–5 minsutes, warmed to 80° C. for

EXAMPLE 34

Preparation of Gas-filled Microbubbles Coated with poly-L-lysine Complexed to Fluorescein-labeled DNA Fragments from Plasmid pBR322

This example is directed to the preparation of microbubbles for gene therapy/anti-sense applications. Specific targeting may be achieved by further doping of microbubble membranes with vector-modified lipid structures as described in Example 21.

a) Preparation of DSPS-encapsulated Gas-filled Microbubbles

DSPS (4.5 mg) was weighed into a clean vial. 1.0 ml of a solution of 1.4% propylene glycol/2.4% glycerol was added and the mixture was sonicated for 2 minutes and then warmed to 80° C. for 5 minutes. Immediately following warming the solution was filtered through a 4 micron filter. The sample was cooled to room temperature and the head space was flushed with perfluorobutane gas. The vial was shaken in a cap mixer for 45 seconds. The resulting microbubbles were then washed once with deionised water and the infranatant was discarded. The microbubbles were then resuspended in 0.5 ml water.

b) Preparation of poly-L-lysine/DNA Complex and Loading of DSPS-encapsulated Microbubbles To 1 mg of poly-L-lysine (70–150 kD) in a clean vial was added 0.1 ml of a fluorescein-labeled digest of plasmid pBR322 dissolved in TE buffer (10 mM tris-HCl, pH 8). The solution was made up to a total of 0.6 ml by addition of water and the pH was adjusted to 8. Complexing was allowed to proceed for 1 hour, after which 0.05 mL of the polylysine-DNA solution was added to the microbubble suspension from (a) above. After 1 hour microscopy was used to show that the bubbles were fluorescent, confirming the presence of DNA.

EXAMPLE 35

Preparation of Gas-filled Microbubbles Containing a Branched Core Peptide Comprising a Dabsylated-atherosclerotic Plaque-binding Sequence and RGDS This example is directed to the preparation of microbubbles having a thiol group on the surface for modification with thiol-containing vectors for targeting/drug delivery and drug release.

a) synthesis of the branched peptide Dabsyl-Tyr-Arg-Ala-Leu-Val-Asp-Thr-leu-Lys-Lys (NH$_2$ -Arg-Gly-Asp-Ser)-Gly- Cys.OH (SEQ ID NO:16)

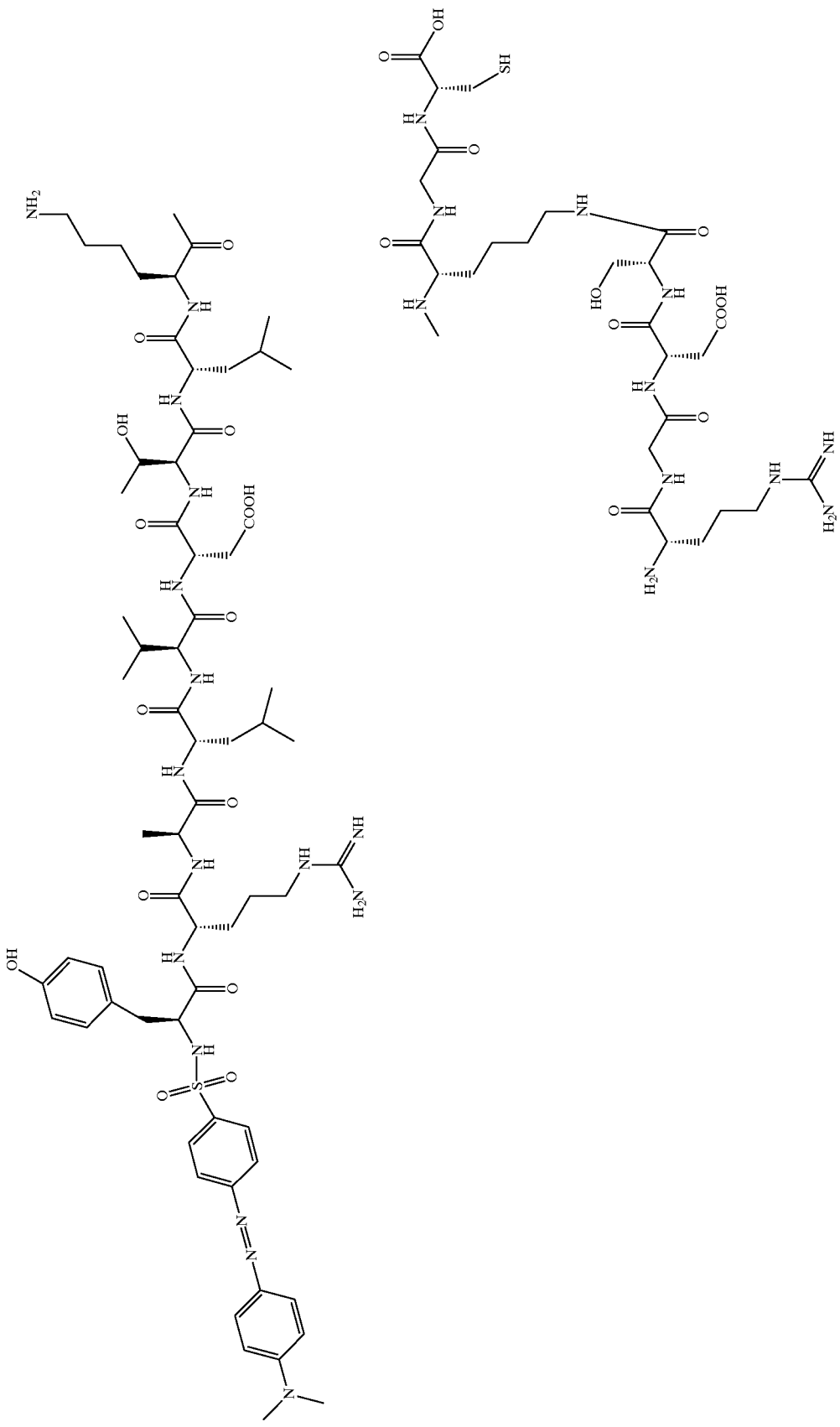

The peptide was synthesised on an ABI 433A automatic peptide synthesiser starting with Fmoc-Cys(Trt)-Tentagel resin on a 0.1 mmol scale using 1 mmol amino acid cartridges. All amino acids were preactivated using HBTU before coupling. The simultaneous removal of peptide from the resin and side-chain protecting groups was carried out in TFA containing 5% phenol, 5% EDT and 5% $H_2O$ for 2 hours, giving a crude product yield of 160 mg. Purification by preparative HPLC of a 30 mg aliquot of crude material was carried out using a gradient of 10 to 60% B over 40 minutes (where A=0.1% TFA/water and B=acetonitrile) at a flow rate of 9 ml/min. After lyophilisation, 2.5 mg of pure material was obtained (analytical HPLC, gradient 10–50% B over 20 minutes where B=0.1% TFA/acetonitrile and A=0.01% TFA/water: detection—UV 214 and 435 nm—product retention time 21 minutes). Further product characterisation was carried out using MALDI mass spectrometry: expected M+H at 2070, found at 2073.

b) Preparation of Thiol-containing Gas-filled Microbubbles

These were prepared as described in Example 64(a).

c) Oxidative Coupling of Thiolated Microbubbles with Multiple-specific Peptide via Disulphide Bond Formation The infranatant from the microbubbles from (b) above was discarded and replaced with a solution of dabsyl-peptide from (a) (1 mg) in 0.7 ml dilute ammonia solution (pH 8). To this was added 0.2 ml of a stock solution containing 6 mg of potassium ferricyanate dissolved in 2 ml of water. The vial was placed on a roller table and thiol oxidation allowed to proceed for 2 hours. The bubbles were then washed extensively with water until the infranatant was free of the dabsyl-peptide as evidenced by HPLC and MALDI MS. Detection of microbubble-bound peptide was carried out by reduction of the disulphide bond using the water souble reducing agent tris-(2-carboxyethyl)-phosphine. Following reduction, the infranatant was found to contain free dabsyl-peptide as evidenced by HPLC and MALDI MS. Other physiologically acceptable reducing agents such as reduced glutathione may also be useful for initiating release.

EXAMPLE 36

Preparation of Gas-filled Microbubbles Encapsulated with DSPS and biotin-$PEG_{3400}$-acyl-phosphatidylethanolamine and Functionalised with Streptavidin, Oligonucleotide biotin-GAAAGGTAGTGGGGTCGTGTGCCGG (SEQ ID NO:17) and Biotinylated Fibrin-anti-polymerant Peptide (Biotin-GPRPPERHOS.$NH_2$)(SEQ ID NO:10)

a) Synthesis of biotin-$PEG_{3400}$-acyl-phosphatidyl Ethanolamine

A mixture of dipalmitoyl phosphatidyl ethanolamine, (21.00 mg, 0.03 mmol), biotin-PEG-$CO_2$-NHS, (100 mg, 0.03 mmol) and triethylamine (42 µl, 0.30 mmol) in a solution of chloroform/methanol (3:1) was stirred at room temperature for 2 hours. After evaporation of the solvents under reduced pressure, the residue was flash chromatographed (methylene chloride/methanol/water, 40:8:1). The product was obtained as a yellow gum (112 mg, 94%), and structure was verified by NMR and MALDI-MS.

b) Binding of Fluorescein-conjugated Streptavidin to Gas-filled Microbubbles

Gas-filled microbubbles were prepared by mixing DSPS and biotin-$PEG_{3400}$-acyl-phosphatidylethanolamine as described in previous examples. The microbubble suspension was divided into 0.2 ml aliquots and fluorescein-conjugated streptavidin was added as shown in the table below. The samples were incubated on a roller table for 15 or 30 minutes at ambient temperature before removal of excess protein by washing in PBS. The samples were analysed by flow cytometry and Coulter Counter. The results are summarized in the table below.

Results:

| Aliquot no. | Added Streptavidin (mg/200:1 sample) | Incubation time (amb. temp.) | % Fluorescent particles | Particle median diameter (microns) |
|---|---|---|---|---|
| 1 | 0 | | 2.0 | — |
| 2 | 0 | | — | 12 (foam) |
| 3 | 0.2 ($3 \times 10^{-9}$ mmol) | 30 min | 7.8 | 3.9 |
| 4 | 2 ($3 \times 10^{-8}$ mmol) | 30 min | 26.2 | 4.2 |
| 5 | 10 ($1.5 \times 10^{-7}$ mmol) | 15 min | 30.5 | na |
| 6 | 20 ($3 \times 10^{-7}$ mmol) | 30 min | 97.9 | 5.2 |
| 7 | 40 ($6 \times 10^{-7}$ mmol) | 15 min | 96.7 | 5.1 |
| 8 DSPS control | 20 ($3 \times 10^{-7}$ mmol) | 15 min | 0.6 | 3.7 | c) Conjugation of Streptavin-coated Microbubbles with the Oligonucleotide biotin-GAAAGGTAGTGGGGTCGTGTGCCGG (SEQ ID NO:17) and Biotinylated Fibrin-anti-polymerant Peptide biotin-GPRPPERHOS (SEQ ID NO:10)

The particles from aliquot no. 6 above were centrifuged and the supernatant was replaced with 1 ml PBS buffer, pH 7.5, containing 0.2 mg of biotin-GAAAGGTAGTGGGGTCGTGTGCCGG (SEQ ID NO:17) and 0.2 mg of biotin-GPRPPERHQS (SEQ ID NO:10) (prepared as in Example 27(b) and (c)). After incubation for 24 hours the particles were washed extensively with PBS and water.

Other biotinylated vectors or therapeutic agents may be conjugated to streptavidin- or avidin-coated microbubbles using this procedure.

EXAMPLE 37

Preparation of Gas-filled Microbubbles Encapsulated with DSPS and Functionalised with a Thrombi-targeting Lipopeptide and the Thrombolytic Enzyme Tissue Plasminogen Activator This example is directed at the preparation of thrombus targeted ultrasound contrast agents comprising a therapeutic thromolytic agent.

a) synthesis of a lipopeptide with affinity for thrombi (Dipalmitoyl- Lys-Asn-Asp-Gly-Asp-Phe-Glu-Glu-Ile-Pro-Glu-Glu-Tyr-Leu-Gln.$NH_2$) (SEQ ID NO:18)

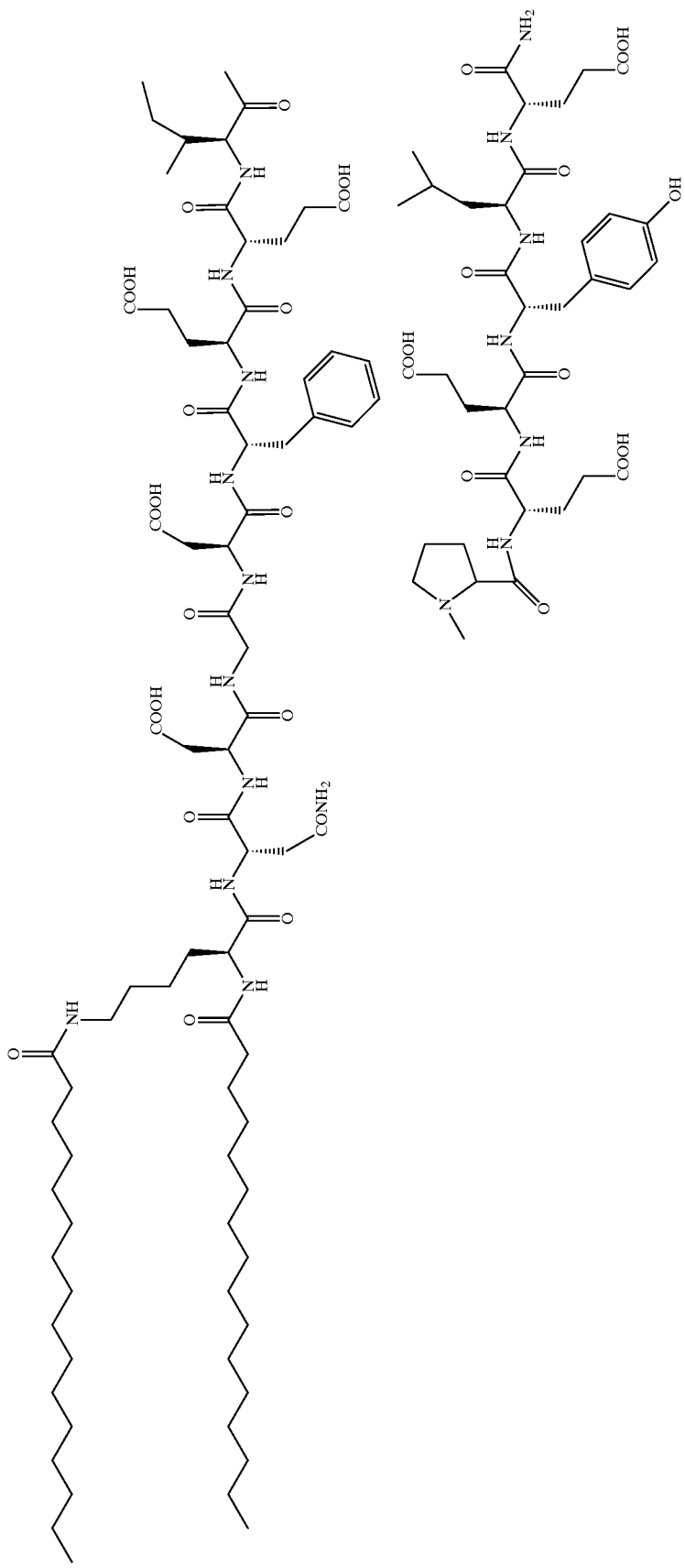

The lipopeptide was synthesised on an ABI 433 A automatic peptide synthesiser starting with Rink amide resin on a 0.1 mmol scale using 1 mmol amino acid cartridges. All amino acids and palmitic acid were preactivated using HBTU before coupling. The simultaneous removal of peptide from the resin and side-chain protecting groups was carried out in TFA containing 5% phenol, 5% EDT, 5% anisole and 5% $H_2O$ for 2 hours, giving a crude product yield of 80 mg. Purification by preparative HPLC of a 20 mg aliquot of the crude material was carried out. After lyophilisation, 6 mg of pure material was obtained. The product was characterised by MALDI mass spectrometry and analytical HPLC.

b) Modification of Tissue Plasminogen Activator with Sulpho-SMPB

A solution of 0.1 ml of ammonim carbonate buffer containing 0.1 mg of t-PA was made up to 0.2 ml by the addition of water. To this solution was added 0.4 mg of Sulpho-SMPB (dissolved in 0.05 ml DMSO. The protein solution was left standing at room temperature for 45 minutes, whereafter purification was carried out on a Superdex 200 column. The product was eluted in PBS and the modified protein fraction was collected.

c) Preparation of Gas-filled Microbubbles Encapsulated with DSPS/thrombi-binding Lipopeptide and Thiol-containing Lipopeptide and Conjugation of Modified Tissue Plasminogen Activator DSPS (5.0 mg) was weighed into a clean vial along with 0.5 mg of the lipopeptide from (a) and 0.5 mg of the thiol-containing lipopeptide from Example 64(a). To this was added 1.0 ml of a solution of 1.4% propylene glycol/ 2.4% glycerol and the mixture was sonicated for 2 minutes and then warmed to 80° C. for 5 minutes. Immediately following warming, the solution was filtered through a 4 micron filter. The sample was cooled to room temperature and the head space flushed with perfluorobutane gas. The vial was shaken in a cap mixer for 45 seconds and the resulting microbubbles were washed twice with deionised water. The infranatant was discarded and replaced with a 1 ml aliquot of the protein solution from (b) above. The conjugation reaction was allowed to proceed for 1 hour. The microbubbles were centrifuged and the infranatant was exchanged with a further 1 ml of protein solution. The incubation step was repeated until all protein solution was used up. The microbubbles were then washed extensively with water and analysed by Coulter counter. The microbubbles were tested in the flow chamber assay described in Example 21(c). Microbubbles modified with protein were found to bind in higher numbers than those comprising either lipopeptide/DSPS or DSPS alone.

The targeting/therapeutic/ultrasound activities of these microbubbles be evaluated in models of both in vitro and in vivo thrombogenisis.

EXAMPLE 38

Preparation of Gas-filled Microbubbles Comprising DSPS Loaded with a Lipopeptide Comprising a Helical Peptide with Affinity for Cell Membranes This example is directed to the preparation of targeted microbubbles comprising a peptidic vector for targeting of cell membrane structures.

a) Synthesis of a lipopeptide comprising a helical peptide with affinity for cell membranes (SEQ ID NO:12)

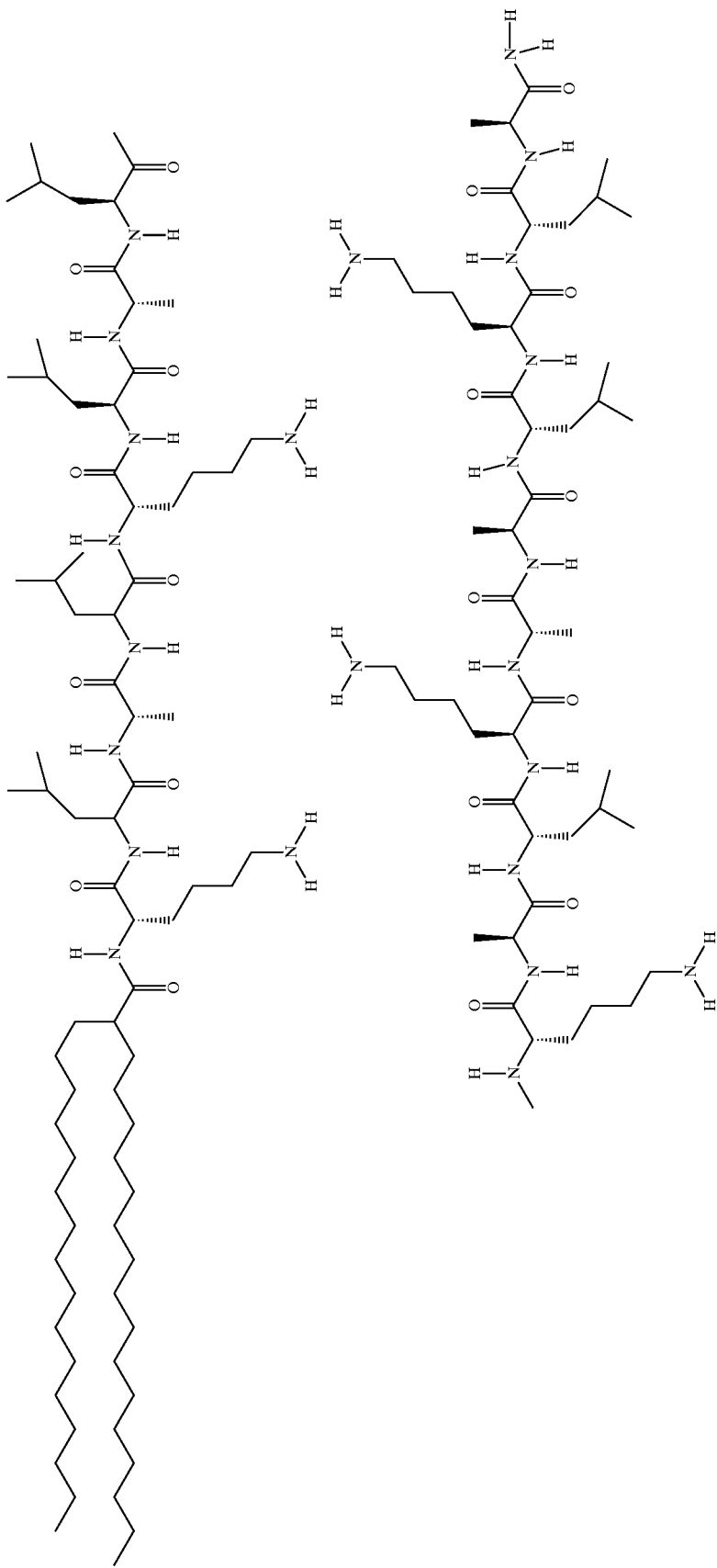

The lipopeptide was synthesised on an ABI 433A automatic peptide synthesiser starting with Rink amide resin on a 0.2 mmol scale using 1 mmol amino acid cartridges. All amino acids and 2-n-hexadecylstearic acid were preactivated using HBTU before coupling. The simultaneous removal of lipopeptide from the resin and side-chain protecting groups was carried out in TFA containing 5% $H_2O$ for 2 hours, giving a crude product yield of 520 mg. Purification by preparative HPLC of a 30 mg aliqout of crude material was carried out using a gradient of 90 to 100% B over 40 minutes (A=0.1% TFA/water and B=MeOH) at a flow rate of 9 ml/min. After lyophilisation, 10 mg of pure material was obtained (analytical HPLC, gradient 90–100% B over 20 minutes where B=MeOH, A=0.01% TFA/water: detection—UV 214 nm—product retention time=23 minutes). Further product characterisation was carried out using MALDI mass spectrometry: expected M+H at 2369, found at 2375.

b) Preparation of Gas-filled Microbubbles

DSPS (4.5 mg) and lipopeptide from (a) (0.5 mg) were weighed into a clean vial and 1.0 ml of a solution of 1.4% propylene glycol/2.4% glycerol was added. The mixture was sonicated for 3–5 minutes, warmed to 80° C. for 5 minutes and then filtered through a 4.5 mm filter. The mixture was cooled to room temperature and the head space was flushed with perfluorobutane gas. The vial was shaken in a cap mixer for 45 seconds and the resulting microbubbles were centrifuged at 1000 rpm for 3 minutes. The fnicrobubbles were then washed with water until no lipopeptide could be detected by MALDI-MS. Coulter counter, acoustic attenuation and pressure stability studies were performed. To an aliquot of the washed bubbles (ca. 0.2 ml) was added methanol (0.5 ml), and the mixture was placed in a sonicator bath for 2 minutes. The resulting clear solution, on analysis by MALDI-MS, was found to contain the lipopeptide.

c) In vitro and in vivo Tests

The microbubbles had similar characteristics in vitro and in vivo as was found for the microbubbles made in Example 21.

EXAMPLE 39

Gas-filled Microbubbles Encapsulated with Phosphatidylserine and a Biotinylated Lipopeptide a) Synthesis of Lipopeptide dipalmitoyl-lysinyl-tryptophanyl-lysinyl-lysinyl-lysinyl(biotinyl)-glycine (SEQ ID NO:19)

The lipopeptide was synthesised on an ABI 433A automatic peptide synthesiser starting with Fmoc-Gly-Wang resin on a 0.1 mmol scale using immol amino acid cartridges. All amino acids and palmitic acid were preactivated using HBTU before coupling. The simultaneous removal of peptide from the resin and side-chain protecting groups was carried out in TFA containing 5% phenol, 5% EDT, 5% anisole and 5% $H_2O$ for 2 hours, giving a crude product yield of 150 mg. Purification by preparative HPLC of a 40 mg aliqout of crude material was carred out using a gradient of 70 to 100% B over 40 minutes (A=0.1% TFA/water and B=MeOH) at a flow rate of 9 ml/min. After lyophilisation. 14 mg of pure material (analytical HPLC, gradient 70–100% B where B=MeOH, A=0.01% TFA/water: detection—UV 260 and fluorescence, Ex280, Em350—product retention time=22 minutes). Further product characterisation was carried out using MALDI mass spectrometry: expected M+H at 1478, found at 1471.

b) Preparation of Gas-filled Microbubbles Comprising DSPS 'doped' with the Biotinylated Lipopeptide Sequence from (a)

DSPS (4.5 mg) and lipopeptide from (a) (0.5 mg, 0.2 mmol) were weighed into each of two vials, and 0.8 ml of a solution of 1.4% propylene glycol/2.4% glycerol was added to each vial. The mixtures were warmed to 80° C. for 5 minutes (vials shaken during warming). The samples were cooled to room temperature and the head spaces were flushed with perfluorobutane gas. The vials were shaken in a cap mixer for 45 seconds and then rolled overnight. The resulting microbubbles were washed several times with deionised water and analysed by Coulter counter and acoustic attenuation. MALDI mass spectral analysis was used to confirm incorporation of lipopeptide into DSPS microbubbles as follows: ca. 50–100 ml of microbubbles were transferred to a clean vial and 50–100 ml water were added. The mixture was sonicated for 30 seconds and spotted onto a clean target disc (1 ml+0.5 ml ACH matrix). Positive mode gave M+H at 1474, expected for lipopeptide at 1478.

EXAMPLE 40

Preparation of Multiple-specific Gas-filled Microbubbles Comprising DSPS Loaded with a Lipopeptide Comprising a Non-bioactive Interleukin-1 Receptor-binding Peptide This example is directed to the preparation of targeted microbubbles comprising a non-bioactive peptidic vector for targeting at the IL-1 recptor which does not induce signal tranduction or prevent IL-1 binding.

a) Synthesis of lipopeptide comprising a non-bioactive interleukin-1 receptor-binding peptide SEQ ID NO:15)

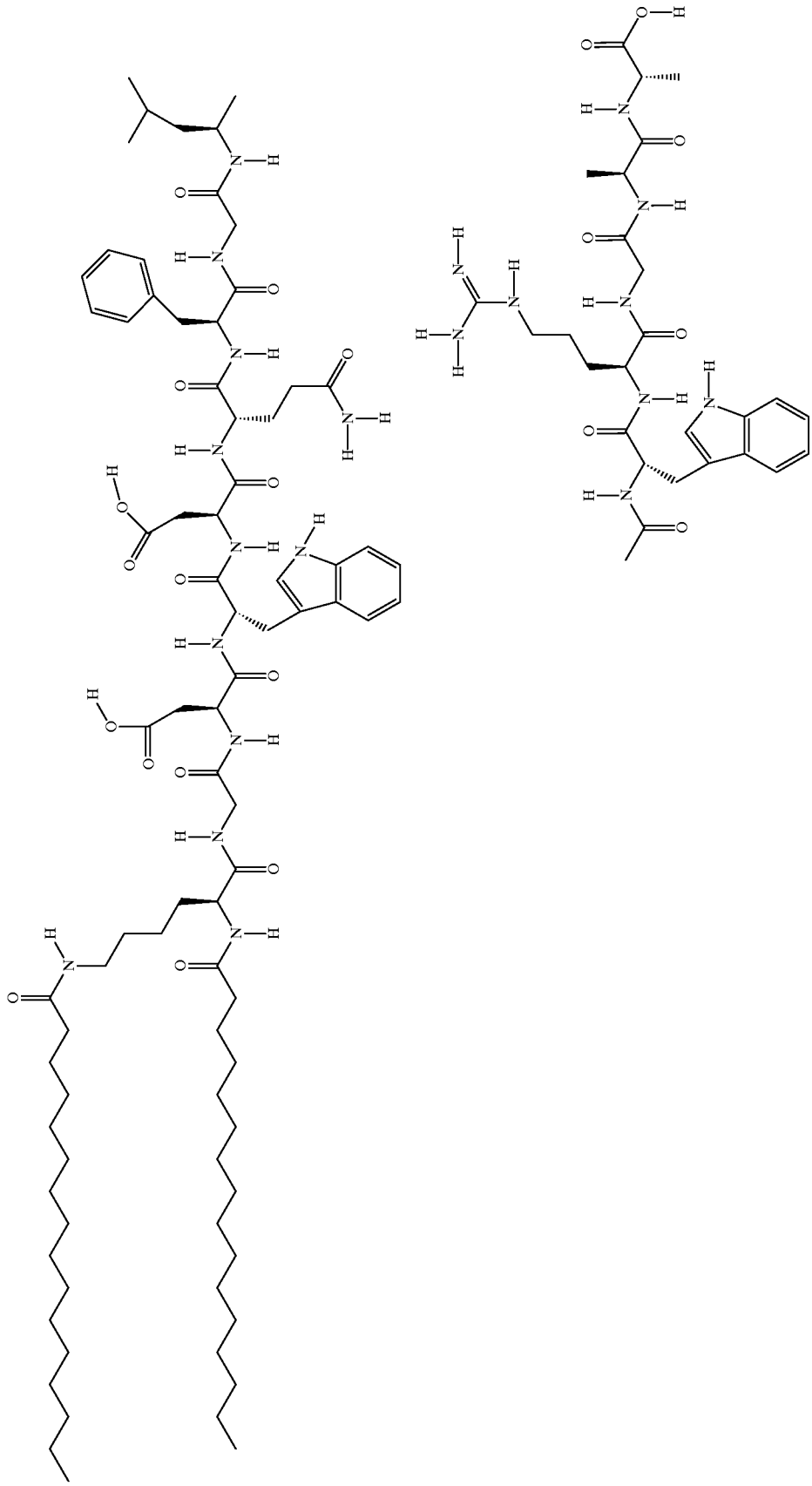

The lipopeptide was synthesised on an ABI 433A automatic peptide synthesiser starting with Fmoc-Ala-Wang resin on a 0.1 mmol scale using 1 mmol amino acid cartridges. All amino acids and palmitic acid were preactivated using HBTU before coupling. The simultaneous removal of lipopeptide from the resin and side-chain protecting groups was carried out in TFA containing 5% $H_2O$, 5% anisole, 5% phenol and 5% EDT for 2 hours, giving a crude product yield of 150 mg. Purification by preparative HPLC of a 30 mg aliquot of crude material was carried out using a gradient of 90 to 100% B over 40 minutes (A=0.1% TFA/water and B=MeOH) at a flow rate of 9 ml/min. After lyophilisation, 4 mg of pure material was obtained (analytical HPLC, gradient 90–100% B over 20 minutes where B=MeOH, A=0.01% TFA/water: detection—UV 214 nm—product retention time=23 minutes). Further product characterisation was carried out using MALDI mass spectrometry: expected M+H at 2083, found at 2088.

b) Preparation of Gas-filled Microbubbles

DSPS (4.5 mg) and lipopeptide from (a) (0.5 mg) were weighed into a clean vial and 1.0 ml of a solution of 1.4% propylene glycol/2.4% glycerol was added. The mixture was sonicated for 3–5 mins, warmed to 80° C. for 5 minutes and then filtered through a 4.5 micron filter. The mixture was cooled to room temperature and the head space was flushed with perfluorobutane gas. The vials were shaken in a cap mixer for 45 seconds and the resulting microbubbles were centrifuged at 1000 rpm for 3 minutes. The microbubbles were then washed with water until no lipopeptide could be detected by MALDI-MS. To the washed microbubbles (ca. 0.2 ml) was added methanol (0.5 ml), and the mixture was placed in a sonicator bath for 2 minutes. The resulting clear solution, on analysis by MALDI-MS, was found to contain lipopeptide (expected 2083, found 2088).

EXAMPLE 41

Preparation of Perfluoropropane-filled Microbubbles Comprising DSPC, DSPS and Endothelial Cell-binding Lipopeptide for Targeted Ultrasound Imaging To 0.8 ml of a solution containing DSPC:DSPS (3:1) (5 mg/ml) in propylene glycol/glycerol (4% in water) was added 0.5 mg of the lipopeptide from Example 31(b). The mixture was heated to 80° C. for 5 minutes and shaken. The solution was then cooled to ambient temperature and the headspace was flushed with perfluoropropane. The vial was shaken on a cap-mixer for 45 seconds and placed on a roller table for 5 minutes. The sample was centrifuged at 2000 rpm for 5 minutes and the infranatant was removed and replaced with distilled water. The headspace was again flushed with perfluoropropane and the sample was kept on a roller table until a homogeneous appearance was obtained. The washing procedure was repeated. The resulting ultrasound contrast agent was characterised by Coulter counter analysis, acoustic attenuation measurements and resistance to external pressure. The microbubbles were tested in the in vitro assay as detailed in Example 21. A gradual accumulation of microbubbles binding to the cells was observed.

EXAMPLE 42

Preparation of Sulphur Hexafluoride-containing Microbubbles Comprising DSPC, DSPS and Endothelial Cell-binding Lipopeptide for Targeted Ultrasound Imaging To 0.8 ml of a solution containing DSPC:DSPS (3:1) (5 mg/ml) in propylene glycol/glycerol (4% in water) was added 0.5 mg of the lipopeptide from Example 31(b). The mixture was heated to 80° C. for 5 minutes and shaken. The solution was then cooled to ambient temperature and the headspace was flushed with sulphur hexafluoride gas. The vial was shaken on a cap-mixer for 45 seconds and placed on a roller table for 5 minutes. The sample was centrifuged at 2000 rpm for 5 minutes and the infranatant was removed and replaced with distilled water. The headspace was again flushed with sulphur hexafluoride and the sample was kept on a roller table until a homogenous appearance was obtained. The washing procedure was repeated. The resulting ultrasound contrast agent was confirmed by Coulter counter, acoustic attenuation measurements and resistance to external pressure.

EXAMPLE 43

Preparation of Gas-filled Microbubbles Comprising DSPG and Endothelial Cell-binding Lipopeptide for Targeted Ultrasound Imaging To 0.8 ml of a solution containing DSPG (5 mg/ml) in propylene glycol/glycerol (4% in water) was added 0.5 mg of the lipopeptide from Example 31(b). The mixture was heated to 80° C. for 5 minutes and shaken. The solution was then cooled to ambient temperature and the headspace was flushed with perfluorobutane. The vial was shaken on a cap-mixer for 45 seconds and placed on a roller table for 5 minutes. The sample was centrifuged at 2000 rpm for 5 minutes and the infranatant was removed and replaced with distilled water. The headspace was again flushed with perfluorobutane and the sample was kept on a roller table until a homogenous appearance was obtained. The washing procedure was repeated. The resulting ultrasound contrast agent was characterised by Coulter counter analysis, acoustic attenuation measurements and resistance to external pressure. The microbubbles were tested in the in vitro assay as detailed in Example 21: a gradual accumulation of microbubbles binding to the cells was observed.

EXAMPLE 44

Preparation of Perfluoropropane-filled Microbubbles Comprising DSPG and Endothelial Cell Binding Lipopeptide for Targeted Ultrasound Imaging To 0.8 ml of a solution containing DSPG (5 mg/ml) in propylene glycol/glycerol (4% in water) was added 0.5 mg of the lipopeptide from Example 31(b). The mixture was heated to 80° C. for 5 minutes and then shaken. The solution was then cooled to ambient temperature and the headspace was flushed with perfluoropropane. The vial was shaken on a cap-mixer for 45 seconds and placed on a roller table for 5 minutes. The sample was centrifuged at 2000 rpm for 5 minutes and the infranatant was removed and replaced with distilled water. The headspace was again flushed with perfluorobutane and the sample was kept on a roller table until a homogeneous appearance was obtained. The washing procedure was repeated. The resulting ultrasound contrast agent was characterised by Coulter counter analysis, acoustic attenuation measurements and resistance to external pressure. The microbubbles were tested in the in vitro assay as detailed in Example 21: a gradual accumulation of microbubbles binding to the cells was observed.

EXAMPLE 45

Preparation of Sulphur Hexafluoride-containing Microbubbles Comprising DSPG and Endothelial Cell-binding Lipopeptide for Targeted Ultrasound Imaging To 0.8 ml of a solution containing DSPG (5 mg/ml) in propylene glycol/glycerol (4% in water) was added 0.5 mg of the lipopeptide from Example 31(b). The mixture was heated to 80° C. for 5 minutes and shaken. The solution was then cooled to ambient temperature and the headspace was flushed with sulphur hexafluoride gas. The vial was shaken on a cap-mixer for 45 seconds and placed on a roller table for 5 minutes. The sample was centrifuged at 2000 rpm for 5 minutes and the infranatant was removed and replaced with distilled water. The headspace was again flushed with sulphur hexafluoride and the sample was kept on a roller table until a homogeneous appearance was obtained. The washing procedure was repeated. The resulting ultrasound contrast agent was characterised by Coulter counter analysis, acoustic attenuation measurements and resistance to external pressure.

EXAMPLE 46

Targeted Gas-filled Microbubbles Comprising DSPS Coated Non-covalently with Polylysine DSPS (5 mg) was weighed into a clean vial along with poly-L-lysine (0.2 mg). To the vial was added 1.0 ml of a solution of 1.4% propylene glycol/2.4% glycerol. The mixture was warmed to 80° C. for 5 minutes. The sample was cooled to room temperature and the head space flushed with perfluorobutane gas. The vial was shaken in a cap mixer for 45 seconds and the resulting microbubbles were centrifuged at 1000 rpm for 3 minutes. Following extensive washing with water, PBS and water, the final solution was examined for polylysine content using MALDI MS. No polypeptide material was observed in the final wash solution. Acetonitrile (0.5 ml) was then added and the microbubbles were sonicated until all bubbles had burst. Analysis of the resulting solution for polylysine was again carried out using MALDI MS. The results were as follows:

|  | MALDI expected | MALDI found |
|---|---|---|
| Poly-L-lysine | 786, 914, 1042, 1170 | 790, 919, 1048, 1177 |

EXAMPLE 47

Preparation of Functionalised Gas-filled Microbubbles for Targeted Ultrasound Imaging (SEQ ID NO:20)

This example is directed to the preparation of microbubbles having a reactive group on the surface for non-specific targeting, principally utilising disulphide exchange reactions to effect binding to a multiplicity of cellular targets.

a) Synthesis of a thiol-functionalised lipid molecule (SEQ ID NO:20)

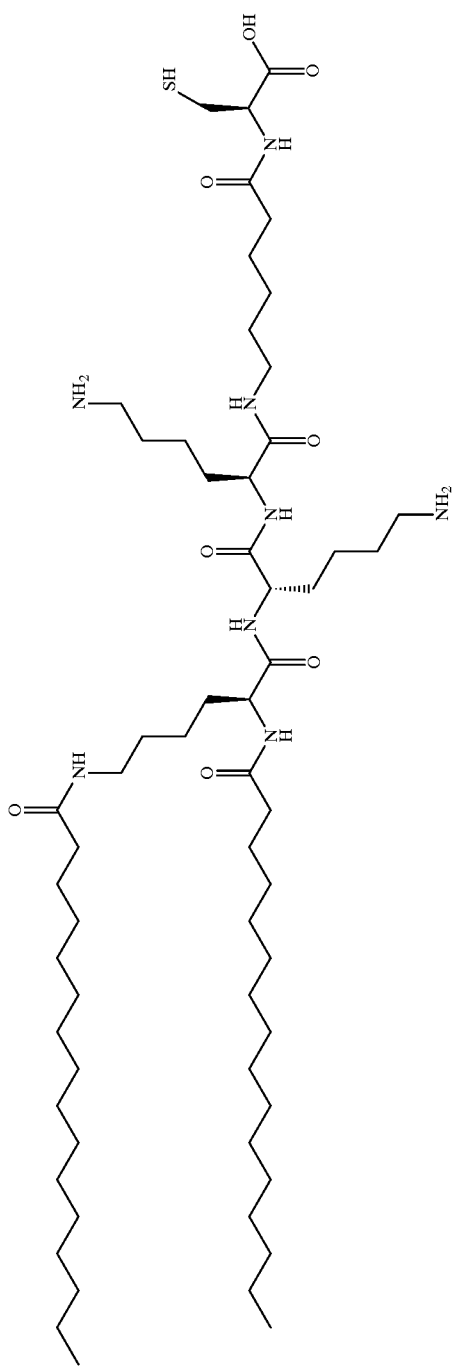

The lipid structure shown above was synthesised on an ABI 433A automatic peptide synthesiser starting with Fmoc-Cys(Trt)-Wang resin on a 0.25 mmol scale using 1 mmol amino acid cartridges. All amino acids and palmitic acid were preactivated using HBTU coupling chemistry. The simultaneous removal of peptide from the resin and deprotection of side-chain protecting groups was carried out in TFA containing 5% EDT and 5% $H_2O$ for 2 hours, giving a crude product yield of 250 mg. Purification by preparative HPLC of a 40 mg aliquot of crude material was carried out using a gradient of 90 to 100% B over 50 minutes (A=0.1% TFA/water and B=MeOH) at a flow rate of 9 ml/min. After lyophilisation, 24 mg of pure material was obtained (analytical HPLC, gradient 70–100% B where B=0.1% TFA/acetonitrile, A=0.01% TFA/water: detection—UV 214 nm—product retention time=23 minutes). Further product characterisation was carried out using MALDI mass spectrometry: expected M+H at 1096, found at 1099.

b) Preparation of Gas-filled Microbubbles Comprising DSPS 'doped' with a Thiol-containing Lipid Structure DSPS (4.5 mg) and the lipid structure from (a) above (0.5 mg, 0.4 mmol) were weighed into a clean vial and 0.8 ml of a solution containing 1.4 $\mu$propylene glycol/2.4% glycerol in water was added. The mixture was warmed to 80° C. for 5 minutes (vial shaken during warming) and filtered while still hot through a 40 mm filter. The sample was cooled to room temperature and the head space was flushed with perfluorobutane gas. The vial was shaken in a cap mixer for 45 seconds and then placed on roller table overnight. The resulting microbubbles were washed several times with deionised water and analysed for thiol group incorporation using Ellmans Reagent.

EXAMPLE 48

Preparation of Gas-filled Microbubbles Comprising DSPS Doped with a Thrombus-binding Lipopeptide a) Synthesis of a lipopeptide with affinity for thrombi (Dipalmitoyl-Lys- Asn-Asp-Gly-Asp-Phe-Glu-Glu-Ile-Pro-Glu-Glu-Tyr-Leu-Gln.$NH_2$) ( SEQ ID NO:18)

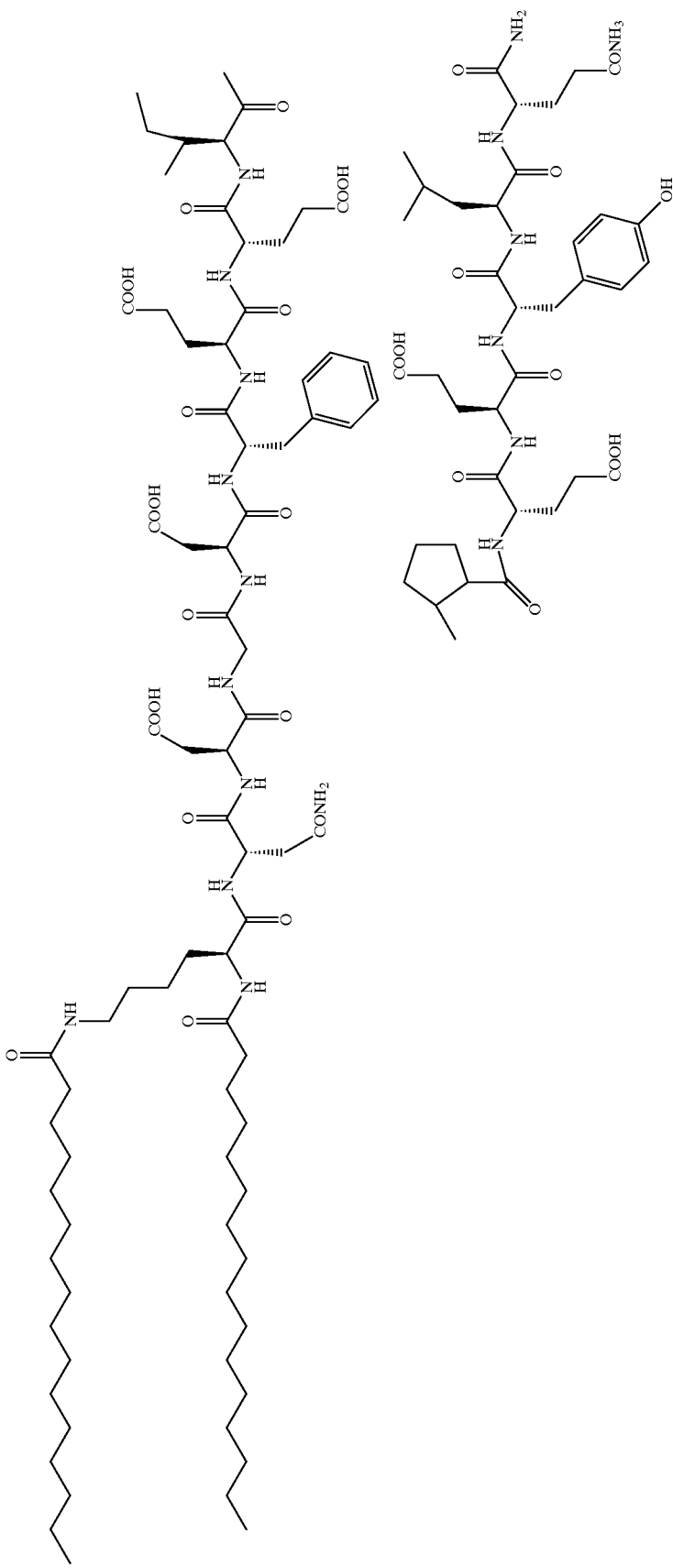

The lipopeptide was synthesised on an ABI 433 A automatic peptide synthesiser starting with Rink amide resin on a 0.1 mmol scale using 1 mmol amino acid cartridges. All amino acids and palmitic acid were preactivated using HBTU before coupling. The simultaneous removal of peptide from the resin and side-chain protecting groups was carried out in TFA containing 5% phenol, 5% EDT, 5% anisole and 5% $H_2O$ for 2 hours, giving a crude product yield of 80 mg. Purification by preparative HPLC of a 20 mg aliquot of the crude material was carried out. After lyophilisation, 6 mg of pure material were obtained. The product was characterised by MALDI mass spectrometry and analytical HPLC.

b) Preparation of Thromi-targeting Ultrasound Microbubbles

DSPS (4.5 mg) and lipopeptide from (a) (1.0 mg) were weighed into a vial and 0.8 ml of a solution of 1.4% propylene glycol/2.4% glycerol was added. The mixture was warmed to 80° C. for 5 minutes and then filtered through a 4 micron filter. After cooling to room temperature the head space was flushed with perfluorobutane gas. The vial was shaken in a cap mixer for 45 seconds and the resulting microbubbles were washed extensively with deionised water. The microbubbles were characterised by microscopy and Coulter counter analysis. MALDI-MS was used to confirm the presence of lipopeptide as described in previous examples.

EXAMPLE 49

Preparation of Transferrin-coated Gas-filled Microbubbles for Targeted Ultrasound Imaging a) Synthesis of a thiol-functionalised lipid molecule (SEQ ID NO:20)

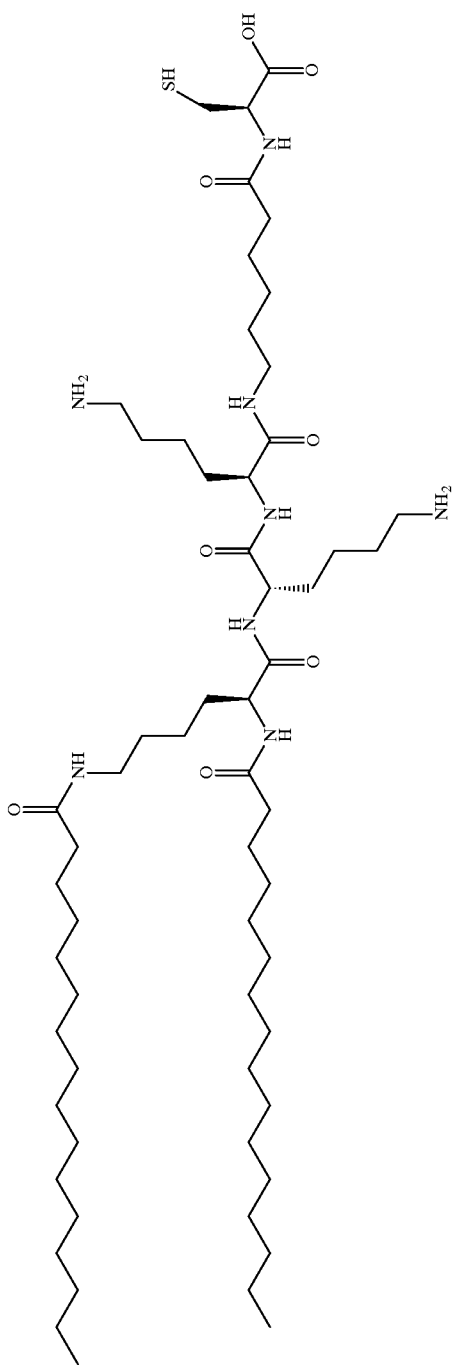

The lipid structure shown above was synthesised on an ABI 433A automatic peptide synthesiser starting with Fmoc-Cys(Trt)-Wang resin on a 0.25 mmol scale using 1 mmol amino acid cartridges. All amino acids and palmitic acid were preactivated using HBTU before coupling. The simultaneous removal of peptide from the resin and deprotection of side-chain protecting groups was carried out in TFA containing 5% EDT and 5% $H_2O$ for 2 hours, giving a crude product yield of 250 mg. Purification by preparative HPLC of a 40 mg aliquot of crude material was carried out using a gradient of 90 to 100% B over 50 minutes (A=0.1% TFA/water and B=MeOH) at a flow rate of 9 ml/min. After lyophilisation, 24 mg of pure material was obtained (analytical HPLC, gradient 70–100% B where B=0.1% TFA/acetonitrile, A=0.01% TFA/water: detection—UV 214 nm—product retention time=23 minutes). Further product characterisation was carried out using MALDI mass spectrometry: expected M+H at 1096, found at 1099.

b) Preparation of Gas-filled Microbubbles Comprising DSPS 'doped' with a Thiol-containing Lipid Structure DSPS (4.5 mg) and lipid structure from (a) above (0.5 mg, 0.4 mmol) were weighed into a clean vial and 0.8 ml of a solution of 1.4% propylene glycol/2.4% glycerol was added. The mixture was warmed to 80° C. for 5 minutes (vial shaken during warming) and filtered while still hot through a 40 mm filter. The sample was cooled to room temperature and the head space was flushed with perfluorobutane gas. The vial was shaken in a cap mixer for 45 seconds and then placed on roller table overnight. The resulting microbubbles were washed several times with deionised water and analysed for thiol group incorporation using Ellmans Reagent.

c) Modification of Transferrin with Fluorescein-NHS and Sulpho-SMPB

To 4 mg of transferrin (Holo, human) in PBS (1 ml) was added 0.5 ml DMSO solution containing 1 mg Sulpho-SMPB and 0.5 mg fluorescein-NHS. The mixture was stirred for 45 minutes at room temperature and then passed through a Sephadex 200 column using PBS as eluent. The protein fraction was collected and stored at 4° C. prior to use.

d) Microbubble Conjugation with Transferrin

To the thiol-containing microbubbles from (b) was added 1 ml of the modified transferrin protein solution from (c). After adjusting the pH of the solution to 9 the conjugation reaction was allowed to proceed for 2 hours at room temperature. Following extensive washing with deionised water the microbubbles were analysed by Coulter counter (97% between 1 and 5 mm) and fluorescence microscopy (highly fluorescent microbubbles).

EXAMPLE 50

Gas-filled Microbubbles Comprising DSPS Incorporating PE-PEG$_{2000}$-Mal Conjugated to Thiolated Trypsin Fluorescein a) Synthesis of Boc-NH-PEG$_{2000}$-DSPE (t-butyl carbamate poly(ethylene glycol)distearoylphosphatidyl-ethanolamine)

DSPE (31 mg) was added to a solution of Boc-NH-PEG$_{200}$-SC (150 mg) in chloroform (2 ml), followed by triethylamine (33 µl). The mixture was stirred at 41° C. for 10 minutes until the starting material had dissolved. The solvent was rotary evaporated and the residue was taken up in acetonitrile (5 ml). The resulting dispersion was cooled to 4° C. and centrifuged, whereafter the solution was filtered and evaporated to dryness. The structure of the resulting product was confirmed by NMR.

b) Synthesis of $H_2N$-PEG$_{2000}$-DSPE (amino-poly(ethylene glycol)-distearoylphosphatidylethanolamine)

Boc-NH-PEG$_{2000}$-DSPE (167 mg) was stirred in 4M hydrochloric acid in dioxane (5 ml) for 2.5 hours at ambient temperature. The solvent was removed by rotary evaporation and the residue was taken up in chloroform (1.5 ml) and washed with water (2×1.5 ml). The organic phase was evaporated in vacuo. TLC analysis (chloroform/methanol/water 13:5:0.8) gave a single ninhydrin positive spot with Rf=0.6; confirmation of the structure was obtained by NMR.

c) Synthesis of Mal-PEG$_{2000}$-DSPE (3-maleimidopropionate poly(ethylene glycol) distearoylphosphatidylethanolamine)

A solution of N-succinimidyl-3-maleimidopropionate (5.6 mg, 0.018 mmol) in tetrahydrofuran (0.2 ml) was added to $H_2N$-PEG-$_{2000}$-DSPE (65 mg, 0.012 mmol) dissolved in tetrahydrofuran (1 ml) and 0.1 M sodium phosphate buffer pH 7.5 (2 ml). The mixture was warmed to 30° C. and the reaction was followed to completion by TLC, whereafter the solvent was removed in vacua. The title material was purified on a flash silica column using 80:20 chloroform-:methanol as eluent. The structure of the pure product was confirmed by NMR and mass spectrometry.

d) Preparation of Gas-filled Microbubbles of DSPS 'doped' with PE-PEG$_{2000}$-Mal DSPS (4.5 mg) and PE-PEG$_{2000}$-Mal from (c) above (0.5 mg) were weighed into a clean vial and 1 ml of a solution of 1.4% propylene glycol/2.4% glycerol was added. The mixture was warmed to 80° C. for 5 minutes and then filtered through a 4.5 mm filter. The sample was cooled to room temperature and the head space was flushed with perfluorobutane gas. The vial was shaken in a cap mixer for 45 seconds and the resulting microbubbles were washed three times with distilled water.

e) Preparation of Fluorescein-labelled Trypsin

To 5 mg of trypsin in PBS (1 ml) was added 0.2 ml DMSO solution containing 1 mg of fluorescein-NHS. The mixture was stirred for 45 minutes at room temperature. A Sephadex 200 column was then charged with the modified protein mixture and product was eluted at a flow rate of 1 ml/min using PBS. The protein fraction (5 ml) was collected and stored at 4° C.

f) Preparation of Thiolated, Fluorescein-labelled Trypsin

To the protein fraction from (e) was added 1 mg of Traut's reagent and the mixture stirred at room temperature for a further 1 hour. 4 ml of the Traut's-modified product was then charged on a Sephadex 200 column and the product was eluted with PBS. The protein fraction containing maximum fluorescent intensity was collected in a total volume of 6 ml.

g) Conjugation of Microbubbles with Thiolated, Fluorescein-labelled Trypsin

Microbubbles from (d) were incubated on a roller table in 1 ml of protein solution from (f) above. The conjugation was allowed to proceed at pH 7.3–7.8 for 10 minutes before centrifugation and removal of the infranatant. The process was repeated a further three times, after which the bubbles were washed four times with water to remove unconjugated protein.

D. Bubbles contained active enzyme as evidenced by the cleavage of an Arg-pNA derivative in PBS.

E. Analysis of the bubbles by Coulter and measurement of echogenicity was carried out.

Figure 2:
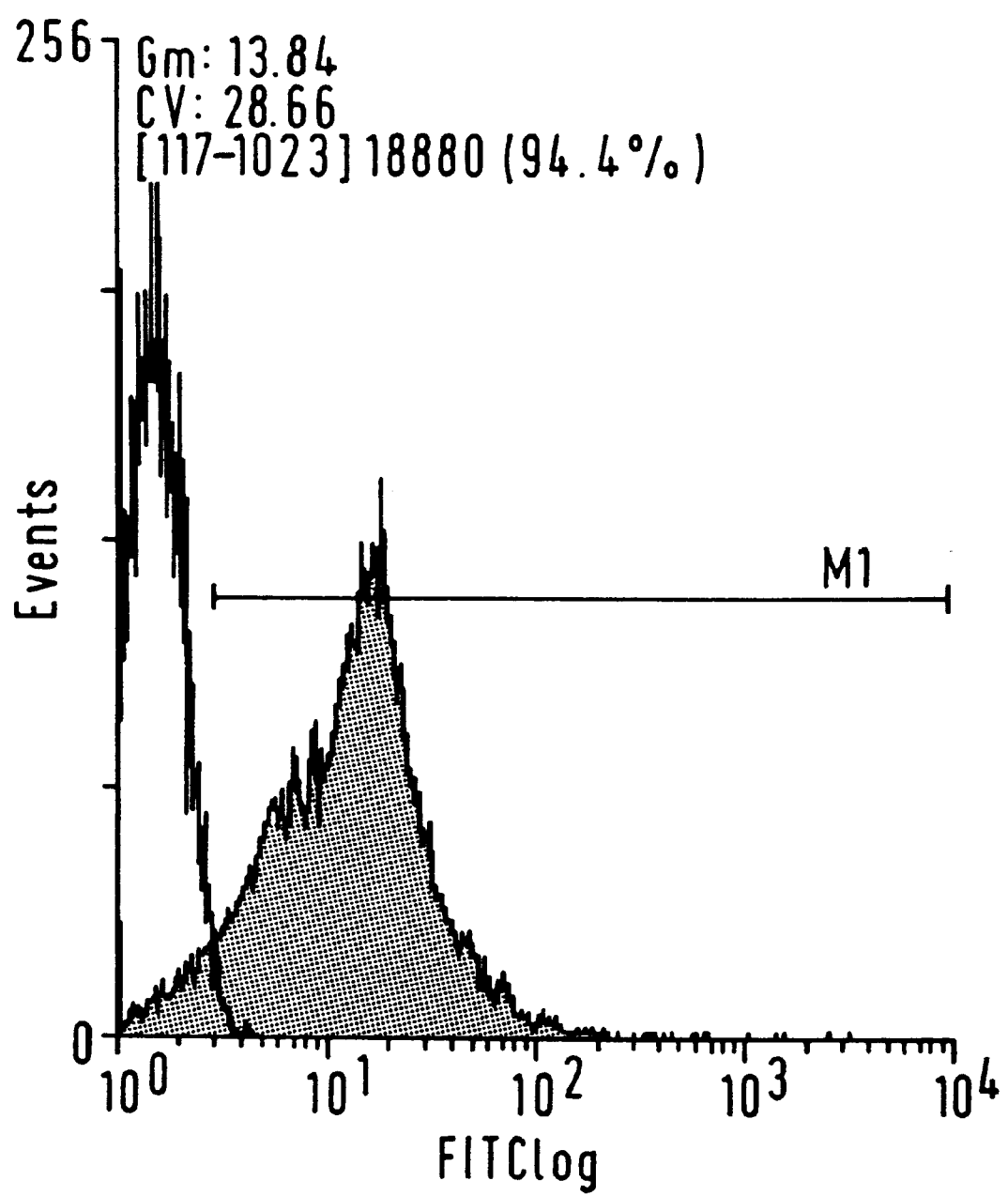
FIG. 2: Flow cytometry data—comparison with negative control bubbles (left curve). 98% of the bubbles were calculated to be fluorescent.

Bubbles were pressure stable (see FIG. 2)

|  | FEK-022-015 |
|---|---|
| Total concentration | 0.83 |
| Diameter 1–3 mm | 40 |

| | FEK-022-015 |
|---|---|
| Diameter 3–5 mm | 28 |
| Diameter 5–7 mm | 13 |
| Freq of max Atten. | 3.3 |
| Atten at 2. Mhz | 4.9 |
| Atten at 3.5 Mhz | 7.8 |
| Atten at 5.0 MHZ | 7.2 |

EXAMPLE 51

Gas-filled Microbubbles Comprising DSPS and a Captopril-containing Molecule for Diagnostic and Therapeutic Applications a) Synthesis of a lipopeptide functionalised with captopril (SEQ ID NO:13)

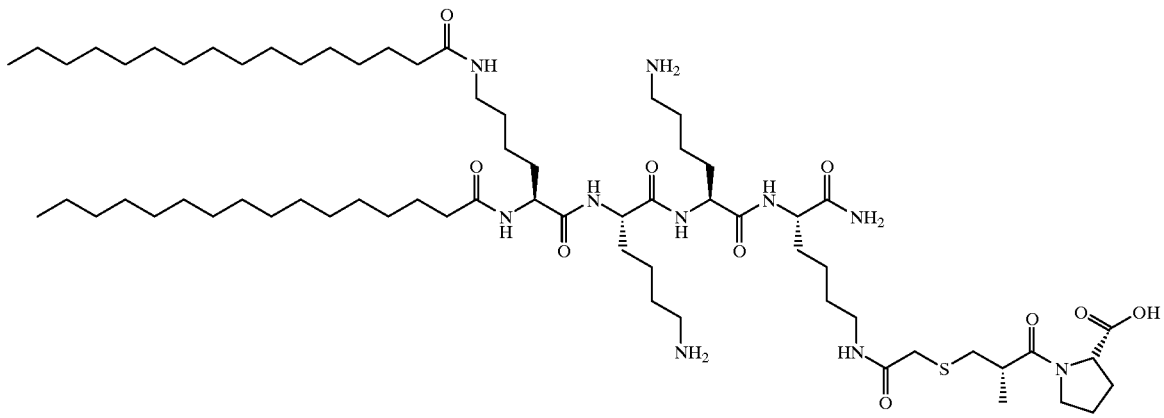

The structure shown above was synthesised by the manual 'bubbler' method starting with Fmoc-protected Rink Amide MBHA resin on a 0.125 mmol scale. Coupling was carried out using standard TBTU/HOBt/DIEA protocol. Bromoacetic acid was coupled through the side-chain of Lys as a symmetrical anhydride using DIC preactivation. Captopril dissolved in DMF was introduced on the solid phase using DBU as base. Simultaneous removal of the peptide from the resin and deprotection of side-chain protecting groups was carried out in TFA containing 5% EDT, 5% water and 5% ethyl methyl sulphide for 2 hours. An aliquot of 10 mg of the crude material was purified by preparative liquid chromatography using a gradient of 70 to 100% B over 60 minutes (A=0.1% TFA/water and B=0.1% TFA/acetonitrile) at a flow rate of 10 ml/min. After lyophilisation, a yield of 2 mg of pure material was obtained (analytical HPLC, gradient 70–100% B over 20 minutes, A=0.1% TFA/water and B=0.1% TFA/acetonitrile, flow rate 1 ml/min, detection UV 214 nm, retention time 26 minutes). Further characterisation was carried out using MALDI mass spectrometry, giving M+H at 1265 as expected.

b) Preparation of Gas-filled Microbubbles Comprising DSPS and a Compound Containing Captopril A solution of 1.4% propylene glycol/2.4% glycerol (1.0 ml) was added to a mixture of DSPS (4.5 mg) and product from (a) (0.5 mg) in a vial. The mixture was sonicated for 5 minutes and then warmed to 80° C. for 5 minutes (vial was shaken during warming). The vial was then cooled and the head space was flushed with perfluorobutane gas. The vial was shaken in a cap mixer for 45 seconds and the resulting microbubbles were extensively washed with deionised water. MALDI mass spectrometry showed no detectable level of compound from (a) in the final wash solution. Incorporation of captopril-containing lipopeptide into the microbubbles was confirmed by MALDI-MS as follows: ca. 50 µl of microbubbles were transferred to a clean vial containing ca. 100 µl of 90% methanol. The mixture was sonicated for 30 seconds and analysed by MALDI mass spectrometry, giving a M+H peak corresponding to lipopeptide from (a).

EXAMPLE 52

Gas-filled Microbubbles Comprising DSPS and a Vector with Affinity for Adrenergic Receptors for Diagnostic and Therapeutic Applications a) Synthesis of a Protected Atenolol Derivative Suitable for Solid Phase Coupling i) Synthesis of methyl 4-[(2,3-epoxy)propoxy]-phenylacetate A mixture of methyl 4-hydroxyphenylacetate (4.98 g, 0.030 mol), epichlorohydrin (23.5 ml, 0.30 mol) and pyridine (121 µl, 1.5 mmol) was stirred at 85° C. for 2 hours. The reaction mixture was cooled and excess epichlorohydrin was distilled off (rotavapor). The residue was taken up in ethyl acetate, washed with brine and dried ($Na_2SO_4$). The solution was filtered and concentrated. The dark residue was chromatographed (silica, hexane/ethyl acetate 7:3) to give 2.25 g (34%) of a colourless oil. $^1H$ (300 MHz) and $^{13}C$ NMR (75 MHz) spectra were in accordance with the structure.

ii) Synthesis of methyl 4-[2-hydroxy-3-[(1-methylethyl)amino]propoxy]phenylacetate A mixture of methyl 4-[(2,3-epoxy)propoxy]phenylacetate (2.00 g, 9.00 mmol), isopropylamine (23 ml, 0.27 mol) and water (1.35 ml, 74.7 mmol) was stirred at room temperature overnight. The reaction mixture was concentrated (rotavapor) and the oily residue was dissolved in chloroform and dried ($Na_2SO_4$). Filtration and concentration gave quantitative yield of a yellow oil that was used in the next step without further purification. The structure was verified by $^1H$ and $^{13}C$ NMR analysis.

iii) Synthesis of 4-[2-hydroxy-3-[(1-methylethyl)amino]propoxy]phenylacetic acid hydrochloride A solution of methyl 4-[2-hydroxy-3-[(1-methylethyl)amino]propoxy]phenylacetate (563 mg, 2.00 mmol) in 6M hydrochloric acid (15 ml) was heated at 100° C. for 4 hours. The reaction mixture was concentrated (rotavapor) and the residue was taken up in water and lyophilised. $^1$H and $^{13}$C NMR spectra were in accordance with the strucure and MALDI mass spectrometry gave a M+H at 268 as expected.

iv) Synthesis of N-Boc-4-[2-hydroxy-3-[(1-methylethyl)amino]propoxy]phenylacetic acid A solution of the 4-[2-hydroxy-3-[(1-methylethyl)amino]propoxy]phenylacetic acid hydrochloride (2.0 mmol) in water (2 ml) was added to a solution of sodium bicarbonate (0.60 g, 7.2 mmol) in water/dioxane (2:1, 15 ml). A solution of di-tert-butyl dicarbonate (0.48 g, 2.2 mmol) in dioxane (5 ml) was added. Progress of the reaction was monitored by TLC analysis (silica, CHCl$_3$/MeOH/AcOH 85:10:5), and portions of di-tert-butyl dicarbonate were added until conversion was complete. The reaction mixture was poured onto water saturated with potassium hydrogen sulphate and organic material was extracted into ethyl acetate. The organic phase was washed with water and brine, dried (Na$_2$SO$_4$) and filtered to give 0.6 g of crude material. The product was purified by chromatography (silica, CHCl$_3$/MeOH/AcOH 85:10:5). The solution was concentrated and the residue was taken up in glacial acetic acid and lyophilised. Yield 415 mg (56%), white solid. The structure was confirmed by $^1$H and $^{13}$C NMR analysis.

b) Synthesis of a lipopeptide functionalised with atenolol (SEQ ID NO:21)

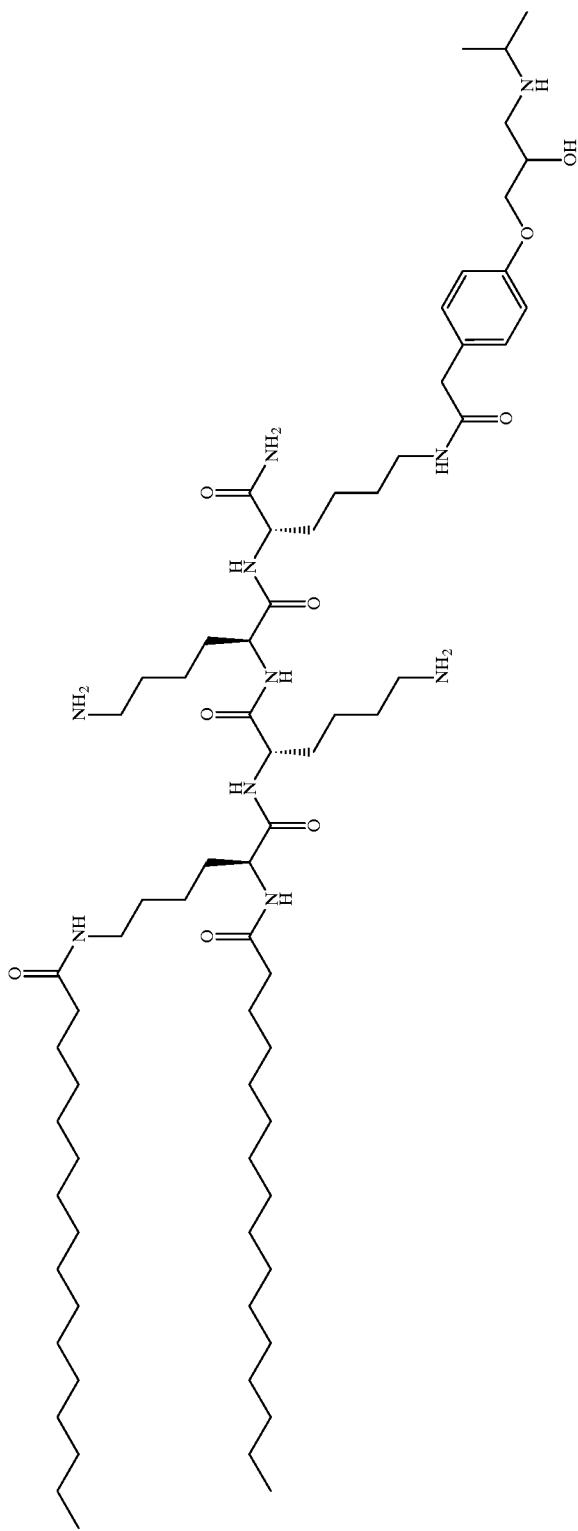

The structure shown above was synthesised by the manual bubbler method starting with Fmoc-protected Rink Amide MBHA resin on a 0.125 mmol scale, using the compound from (a). Coupling was carried out using standard TBTU/HOBt/DIEA protocols. Simultaneous removal of the peptide from the resin and deprotection of side-chain protecting groups was carried out in TFA containing 5% EDT and 5% water for 2 hours. Crude material was precipitated from ether and purified by preparative liquid chromatography using a gradient of 70 to 100% B over 60 minutes (A=0.1% TFA/water and B=0.1% TFA/acetonitrile) at a flow rate of 10 ml/min. After lyophilisation, a yield of 38 mg of pure material was obtained (analytical HPLC, gradient 70–100% B over 20 minutes, A=0.1% TFA/water and B=0.1% TFA/acetonitrile, flow rate 1 ml/minute, detection UV 214 nm, retention time 25 minutes). Further characterisation was carried out using MALDI mass spectrometry (ACH matrix), giving M+H at 1258, expected 1257.

c) Preparation of Gas-filled Microbubbles Comprising DSPS and a Lipopeptide Containing Atenolol A solution of 1.4% propylene glycol/2.4% glycerol (1.0 ml) was added to a mixture of DSPS (4.5 mg) and product from (b) (0.5 mg) in a vial. The mixture was sonicated for 5 minutes, heated at 80° C. for 5 minutes (vial was shaken during warming) and then cooled. The head space was flushed with perfluorobutane gas and the vial was shaken in a cap mixer for 45 seconds, whereafter the contents were extensively washed with deionised water. MALDI mass spectrometry showed no detectable level of compound from (b) in the final wash solution. Incorporation of atenolol-containing lipopeptide into the microbubbles was confirmed by MALDI-MS as follows: ca. 50 µl of microbubbles were transferred to a clean vial containing ca. 100 µl of 90% methanol. The mixture was sonicated for 30 seconds and analysed by MALDI-MS (ACH-matrix), giving a M+H peak at 1259 corresponding to lipopeptide (b).

d) In vitro Analysis

The microbubbles were tested in the in vitro assay as detailed in Example 21. A gradual accumulation of microbubbles binding to the cells was observed.

EXAMPLE 53

Gas-filled Microbubbles Comprising DSPS and a Lipopeptide Consisting of a Heparin Sulphate-binding Peptide (KRKR) (SEQ ID NO:5) and a Fibronectin Peptide (WOPPRARI) (SEQ ID NO:6) for Targeting and a Lipopeptide Containing Atenolol for Therapeutic Application a) Synthesis of a Lipopeptide Consisting of a Heparin Sulphate-binding Peptide (KRKR) (SEQ ID NO:5) and a Fibronectin Peptide (WOPPRARI) (SEQ ID NO:6)

(SEQ ID NO:7)
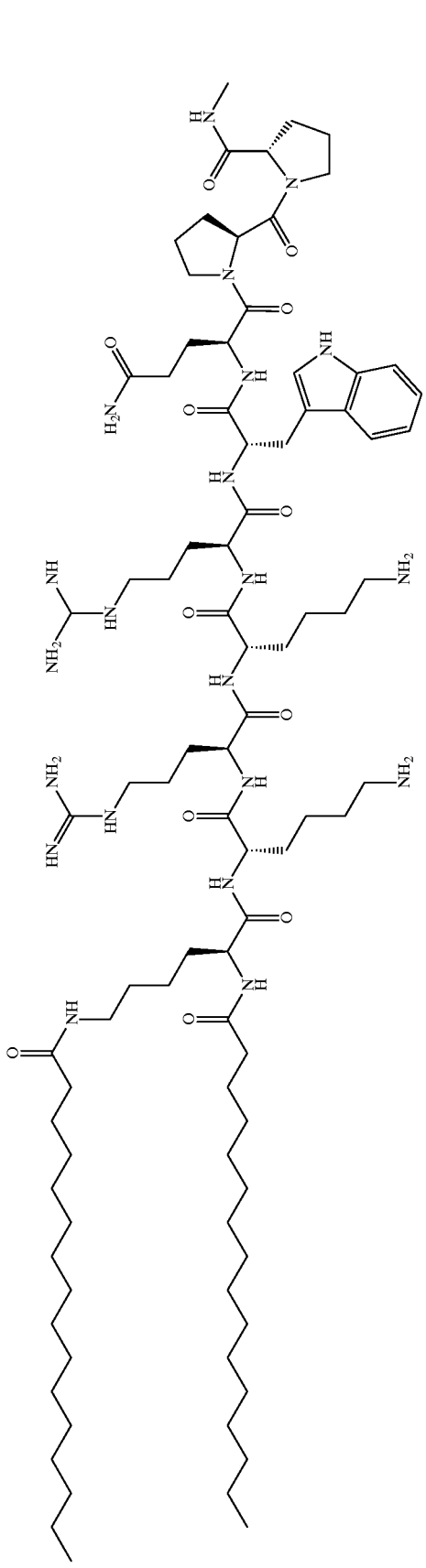
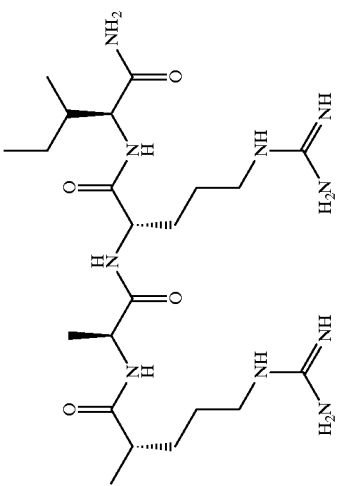

The lipopeptide was synthesised on an ABI 433A automatic peptide synthesiser starting with Fmoc-Ile-Wang resin on a 0.1 mmol scale using 1 mmol amino acid cartridges. All amino acids and palmitic acid were preactivated using HBTU before coupling. The simultaneous removal of peptide from the resin and side-chain protecting groups was carried out in TFA containing 5% phenol, 5% EDT, 5% anisole and 5% H$_2$O for 2 hours, giving a crude product yield of 150 mg. Purification by preparative HPLC of a 40 mg aliquot of crude material was carried out using a gradient of 70 to 100% B over 40 minutes (A=0.1% TFA/water and B=MeOH) at a flow rate of 9 ml/min. After lyophilisation, 16 mg of pure material was obtained (analytical HPLC, gradient 70–100% B where B=MeOH, A=0.01% TFA/water: detection—UV 260 and fluorescence, Ex280, Em350 product retention time=19.44 minutes). Further product characterisation was carried out using MALDI mass spectrometry: expected M+H at 2198, found at 2199.

b) Synthesis of a Protected Atenolol Derivative Suitable for Solid Phase Coupling i) Synthesis of methyl 4-[(2,3-epoxy)propoxy]phenylacetate A mixture of methyl 4-hydroxyphenylacetate (4.98 g, 0.030 mol), epichlorohydrin (23.5 ml, 0.30 mol) and pyridine (121 µl, 1.5 mmol) was stirred at 85° C. for 2 hours. The reaction mixture was cooled, and excess epichlorohydrin was distilled off (rotavapor). The residue was taken up in ethyl acetate, washed with brine and dried (Na$_2$SO$_4$). The solution was filtered and concentrated. The dark residue was chromatographed (silica, hexane/ethyl acetate 7:3) to give 2.25 g (34%) of a colourless oil. $^1$H (300 MHz) and $^{13}$C NMR (75 MHz) spectra were in accordance with the structure.

i) Synthesis of methyl 4-[2-hydroxy-3-[(1-methylethyl)amino]propoxy]phenylacetate A mixture of methyl 4-[(2,3-epoxy)propoxy]phenylacetate (2.00 g, 9.00 mmol), isopropylamine (23 ml, 0.27 mol) and water (1.35 ml, 74.7 mmol) was stirred at room temperature overnight. The reaction mixture was concentrated (rotavapor) and the oily residue was dissolved in chloroform and dried (Na$_2$SO$_4$). Filtration and concentration gave quantitative yield of a yellow oil that was used in the next step without further purification. The structure was verified by $^1$H and $^{13}$C NMR analysis.

iii) Synthesis of 4-[2-hydroxy-3-[(1-methylethyl)amino]propoxy]phenylacetic acid hydrochloride A solution of methyl 4-[2-hydroxy-3-[(1-methylethyl)amino]propoxy]phenylacetate (563 mg, 2.00 mmol) in 6M hydrochloric acid (15 ml) was heated at 100° C. for 4 hours. The reaction mixture was concentrated (rotavapor) and the residue was taken up in water and lyophilised. $^1$H and $^{13}$C NMR spectra were in accordance with the strucure and MALDI mass spectrometry gave a M+H at 268 as expected.

iv) Synthesis of N-Boc-4-[2-hydroxy-3-[(1-methylethyl)amino]propoxy]phenylacetic acid A solution of the 4-[2-hydroxy-3-[(1-methylethyl)amino]propoxy]phenylacetic acid hydrochloride (2.0 mmol) in water (2 ml) was added to a solution of sodium bicarbonate (0.60 g, 7.2 mmol) in water/dioxane (2:1, 15 ml). A solution of di-tert-butyl dicarbonate (0.48 g, 2.2 mmol) in dioxane (5 ml) was added. Progress of the reaction was monitored by TLC analysis (silica, CHCl$_3$/MeOH/AcOH 85:10:5), and portions of di-ter-butyl dicarbonate were added until conversion was complete.

The reaction mixture was poured onto water saturated with potassium hydrogen sulphate and organic material was extracted into ethyl acetate. The organic phase was washed with water and brine, dried (Na$_2$SO$_4$) and filtered to give 0.6 g of crude material. The product was purified by chromatography (silica, CHCl$_3$/MeOH/AcOH 85:10:5). The solution was concentrated and the residue was taken up in glacial acetic acid and lyophilised. Yield 415 mg (56%), white solid. The structure was confirmed by $^1$H and $^{13}$C NMR analysis.

c) Synthesis of a lipopeptide functionalised with atenolol (SEQ ID NO:21)

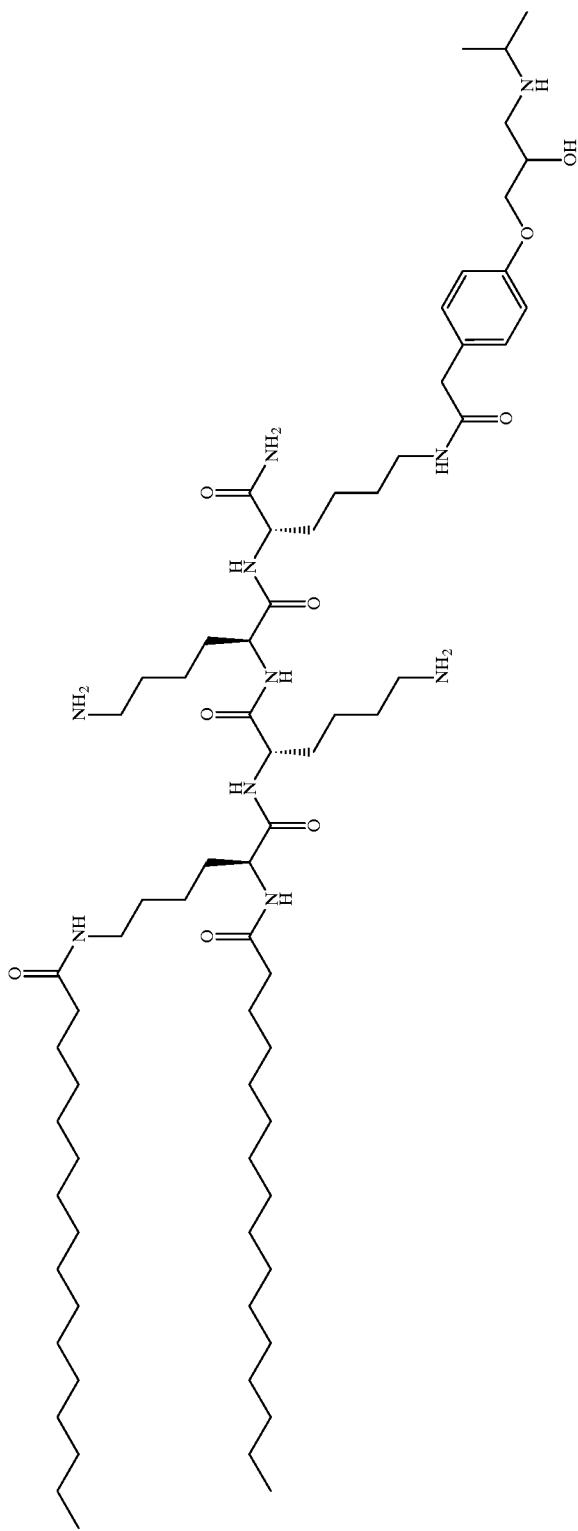

The structure shown above was synthesised by the manual bubbler method starting with Fmoc-protected Rink Amide MBHA resin on a 0.125 mmol scale, using appropriate amino acids, palmitic acid and the compound from (a). Coupling was carried out using standard TBTU/HOBt/DIEA protocols. Simultaneous removal of the peptide from the resin and deprotection of side-chain protecting groups was carried out in TFA containing 5% EDT and 5% water for 2 hours. Crude material was precipitated from ether and purified by preparative liquid chromatography using a gradient of 70 to 100% B over 60 minutes (A=0.1% TFA/water and B=0.1% TFA/acetonitrile) at a flow rate of 10 ml/min. After lyophilisation, a yield of 38 mg of pure material was obtained (analytical HPLC, gradient 70–100% B over 20 minutes, A=0.1% TFA/water and B=0.1% TFA/acetonitrile, flow rate 1 ml/minute, detection UV 214 nm, retention time 25 minutes). Further characterisation was carried out using MALDI mass spectrometry (ACH matrix), giving M+H at 1258, expected 1257.

d) Preparation of Gas-filled Microbubbles Comprising DSPS and a Lipopeptide Consisting of a Heparin Sulphate-binding Peptide (KRKR) (SEQ ID NO:5), a Fibronectin Peptide (WOPPRARI) (SEQ ID NO:6) and a Lipopeptide Containing Atenolol A solution of 1.4% propylene glycol/2.4% glycerol (1.0 ml) was added to a mixture of DSPS (5.0 mg), product from (a) (0.5 mg) and product from (c) (0.5 mg) in a vial. The mixture was sonicated for 5 minutes and then heated at 80° C. for 5 minutes (vial was shaken during warming). The solution was filtered and cooled. The head space was flushed with perfluorobutane gas and the vial was shaken in a cap mixer for 45 seconds, whereafter the contents were extensively washed with deionised water. Incorporation of atenolol-containing lipopeptide into the microbubbles was confirmed by MALDI-MS as follows: ca. 50 µl of microbubbles were transferred to a clean vial containing ca. 100 µl of 90% methanol. The mixture was sonicated for 30 seconds and analysed by MALDI-MS (ACH matrix), giving two M+H peaks at 2202 and 1259, corresponding to lipopeptide (a) and to lipopeptide (c) respectively.

e) In vitro Analysis

The microbubbles were tested in the in vitro assay as detailed in example 21. A gradual accumulation of microbubbles binding to the cells was observed.

EXAMPLE 54

Gas-filled Microbubbles Comprising DSPS and a Lipophilic Derivative of Atenolol with Affinity for Adrenergic Receptors for Diagnostic and Therapeutic Applications a) Synthesis of N-hexadecyl-4-[2-hydroxy-3-[(1-methylethyl)amino]propoxy]phenylacetamide i) Synthesis of methyl 4-[(2,3-epoxy)propoxy]phenylacetate A mixture of methyl 4-hydroxyphenylacetate (4.98 g, 0.030 mol), epichlorohydrin (23.5 ml, 0.30 mol) and pyridine (121 µl, 1.5 mmol) was stirred at 85° C. for 2 hours. The reaction mixture was cooled and excess epichlorohydrin was distilled off (rotavapor). The residue was taken up in ethyl acetate, washed with brine and dried ($Na_2SO_4$). The solution was filtered and concentrated. The dark residue was chromatographed (silica, hexane/ethyl acetate 7:3) to give 2.25 g (34%) of a colourless oil. $^1$H (300 MHz) and $^{13}$C NMR (75 MHz) spectra were in accordance with the structure.

ii) Synthesis of methyl 4-[2-hydroxy-3-[(1-methylethyl)amino]propoxy]phenylacetate A mixture of methyl 4-[(2,3-epoxy)propoxy]phenylacetate (2.00 g, 9.00 mmol), isopropylamine (23 ml, 0.27 mol) and water (1.35 ml, 74.7 mmol) was stirred at room temperature overnight. The reaction mixture was concentrated (rotavapor) and the oily residue was dissolved in chloroform and dried ($Na_2SO_4$). Filtration and concentration gave quantitative yield of a yellow oil that was used in the next step without further purification. The structure was verified by $^1$H and $^{13}$C MR analysis.

ii) Synthesis of 4-[2-hydroxy-3-[(1-methylethyl)amino]propoxy]phenylacetic acid hydrochloride A solution of methyl 4-[2-hydroxy-3-[(1-methylethyl)amino]propoxy]phenylacetate (563 mg, 2.00 mmol) in 6M hydrochloric acid (15 ml) was heated at 100° C. for 4 hours. The reaction mixture was concentrated (rotavapor) and the residue was taken up in water and lyophilised. $^1$H and $^{13}$C NMR spectra were in accordance with the strucure and MALDI mass spectrometry gave a M+H at 268 as expected.

iv) Synthesis of N-Boc-4-[2-hydroxy-3-[(1-methylethyl)amino]propoxy]phenylacetic acid A solution of the 4-[2-hydroxy-3-[(1-methylethyl)amino]propoxy]phenylacetic acid hydrochloride (2.0 mmol) in water (2 ml) was added to a solution of sodium bicarbonate (0.60 g, 7.2 mmol) in water/dioxane (2:1, 15 ml). A solution of di-tert-butyl dicarbonate (0.48 g, 2.2 mmol) in dioxane (5 ml) was added. Progress of the reaction was monitored by TLC analysis (silica, $CHCl_3$/MeOH/AcOH 85:10:5), and portions of di-tert-butyl dicarbonate were added until conversion was complete. The reaction mixture was poured onto water saturated with potassium hydrogen sulphate and organic material was extracted into ethyl acetate. The organic phase was washed with water and brine, dried ($Na_2SO_4$) and filtered to give 0.6 g of crude material. The product was purified by chromatography (silica, $CHCl_3$/MeOH/AcOH 85:10:5). The solution was concentrated and the residue was taken up in glacial acetic acid and lyophilised. Yield 415 mg (56%), white solid. The structure was confirmed by $^1$H and $^{13}$C NMR analysis.

v) Synthesis of N'-Boc, N-hexadecyl-4-[2-hydroxy-3-[(1-methylethyl)amino]propoxy]phenylacetamide A solution of N-Boc-4 [-2-hydroxy-3-[(1-methylethyl)amino]propoxy]phenylacetic acid (92 mg, 0.25 mmol) and hexadecylamine (60 mg, 0.25 mmol) in DMF (5 ml) was cooled to 0° C. HOBt (39 mg, 0.25 mmol) and N-(3-dimethylaminopropyl)-N'-ethylcarbodiimide hydrochloride (water soluble carbodiimide) (48 mg, 0.25 mmol) were added. The reaction mixture was stirred at 0° C. for 1 hour and then at room temperature overnight. The reaction mixture was poured onto water (25 ml) containing sodium carbonate (2.5 g) and sodium chloride (4.0 g). Precipitated material was filtered off, washed with water and taken up in chloroform. The chloroform phase was washed with 5% sodium carbonate and water and dried ($Na_2SO_4$). The solution was filtered and concentrated to give 150 mg of yellow-white crude material. The product was purified by column chromatography (silica, chloroform/methanol 95:5) to give 118 mg (80%) of white material. The structure was verified by $^1$H (500 MHz) and $^{13}$C (125 MHz) NMR. The product was further characterised by MALDI mass spectrometry, giving a M+Na peak at 614 as expected.

vi) Synthesis of N-hexadecyl-4-[2-hydroxy-3-[(1-methylethyl)amino]propoxy]phenylacetamide To a solution of N'-Boc-N-hexadecyl-4-[2-hydroxy-3-[(1-methyl-ethyl)amino]propoxy]phenylacetamide (10 mg) in dichloromethane (9 ml) was added trifluoroacetic acid (1 ml). The reaction mixture was stirred for 2 hours at room temperature. TLC (silica, chloroform/methanol 95:5) showed complete conversion of starting material.

Solvents were evaporated off and the residue was taken up in water/acetonitrile and lyophilised to give a quantitative yield of white solid material. The structure was verified by $^1$H (500 MHz) and $^{13}$C (125 MHz) NMR analysis and further characterised by MALDI mass spectrometry, giving M+H at 492 and M+Na at 514 as expected.

b) Preparation of Gas-filled Microbubbles Comprising DSPS and N-hexadecyl-4-[2-hydroxy-3-[(1-methylethyl)amino]propoxy]phenylacetamide for Diagnostic and Therapeutic Applications A solution of 1.4% propylene glycol/2.4% glycerol (1.0 ml) was added to a mixture of DSPS (4.5 mg) and N-hexadecyl-4-[2-hydroxy-3-[(1-methylethyl)amino]propoxy]phenylacetamide (0.5 mg) in a vial. The mixture was sonicated for 5 minutes and then heated at 80° C. for 5 minutes (vial was shaken during warming). The solution was filtered and cooled. The head space was flushed with perfluorobutane gas and the vial was shaken in a cap mixer for 45 seconds, whereafter the contents were extensively washed with deionised water. Incorporation of compound from (a) into the microbubbles was confirmed by MALDI-MS as follows; ca. 50 µl of microbubbles were transferred to a clean vial containing ca. 100 µl of 90% methanol. The mixture was sonicated for 30 seconds and analysed by MALDI-MS, giving a M+H peak at 492 corresponding to N-hexadecyl-4-[2-hydroxy-3-[(1-methylethyl)amino]propoxy]phenylacetamide.

EXAMPLE 55

Gas-filled microbubbles Encapsulated with DSPS and a Compound Containing Folic Acid for Diagnostic Applications a) Synthesis of a Lipopeptide Containing Folic Acid (SEQ ID NO: 22)

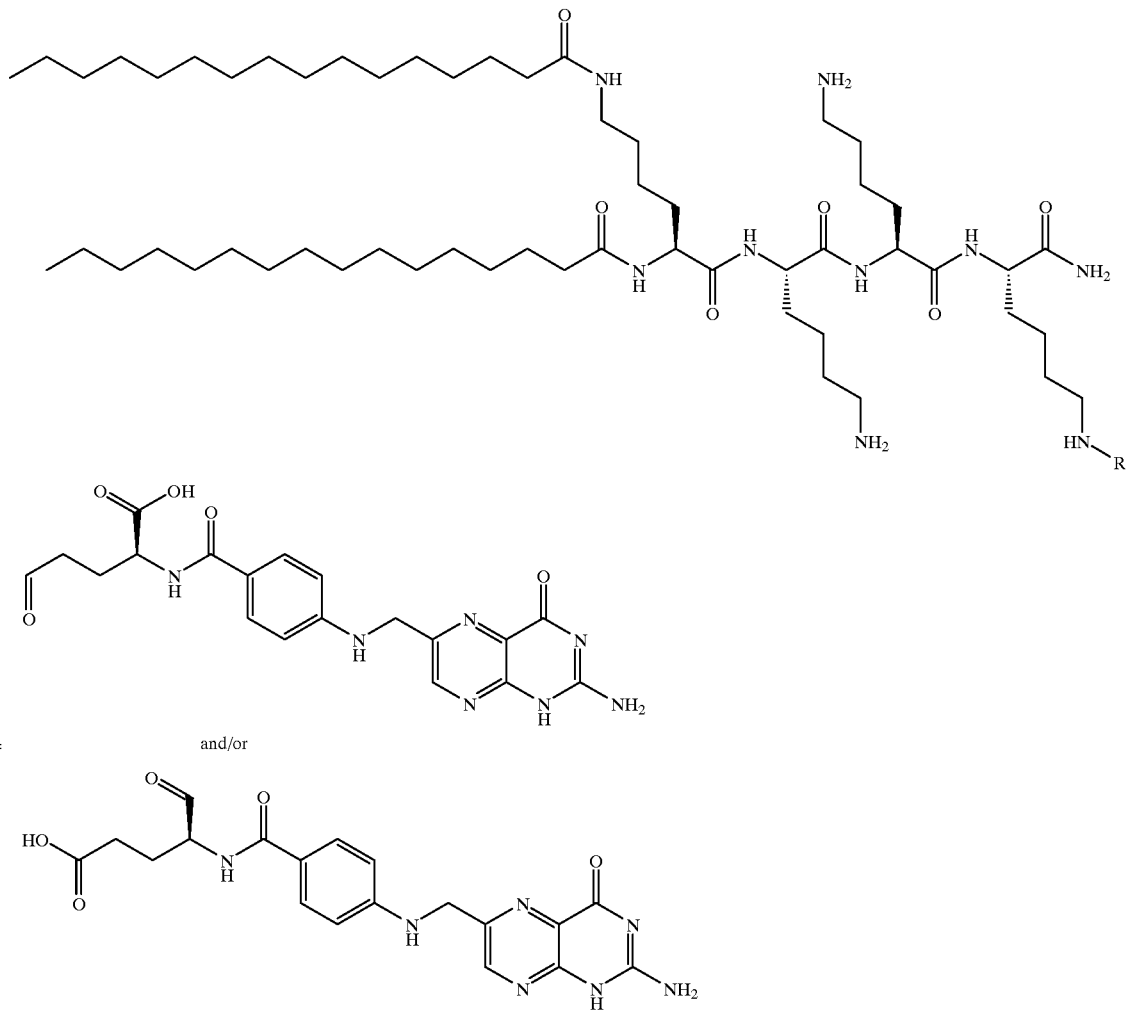

The structure shown above was synthesised by the manual bubbler method starting with Fmoc-protected Rink Amide MBHA resin on a 0.125 mmol scale, using appropriate amino acids, palmitic acid and folic acid. Coupling was carried out using standard TBTU/HOBt/DIEA protocols. Simultaneous removal of the peptide from the resin and deprotection of side-chain protecting groups was carried out in TFA containing 5% EDT and 5% water for 2 hours. Crude material was precipitated from ether and analysed by MALDI mass spectrometry, giving a M+H peak corresponding to the structure at 1435, expected 1430. The material was further characterised by analytical HPLC, gradient 70–100% B over 20 minutes, A=0.1% TFA/water and B=0.1% TFA/acetonitrile, flow rate 1.0 ml/minute, giving a product peak with retention time 27 minutes detected at UV 368 nm.

b) Preparation of Gas-filled Microbubbles Comprising DSPS and a Lipopeptide Containing Folic Acid A solution of 1.4% propylene glycol/2.4% glycerol (1.0 ml) was added to a mixture of DSPS (4.5 mg) and product from (a) (0.5 mg) in a vial. Dilute ammonia (to pH 8) and DMSO (40 µl) were added and the mixture was sonicated for 5 minutes and then heated at 80° C. for 5 minutes (vial was shaken during warming). The solution was filtered and cooled. The head space was flushed with perfluorobutane gas and the vial was shaken in a cap mixer for 45 seconds, whereafter the contents were extensively washed with deionised water. Incorporation of structure from (a) into the bubbles was confirmed by MALDI-MS as follows: ca. 50 µl of microbubbles were transferred to a clean vial containing ca. 100 µl of 90% methanol. The mixture was sonicated for 30 seconds and analysed by MALDI-MS (ACH matrix), giving a M+H peak at 1238 corresponding to structure from (a).

c) In vitro Analysis

The microbubbles were tested in the in vitro assay as detailed in Example 21. A gradual accumulation of microbubbles binding to the cells was observed.

EXAMPLE 56

Gas-filled Microbubbles Comprising DSPS and a Cholesteryl Ester of Chlorambucil for Diagnostic and Therapeutic Applications a) Synthesis of Cholesteryl 4-[4-[bis(2-chloroethyl)amino] phenyl]butanoate DIC (170 µl, 1.10 mmol) was added to a solution of chlorambucil (669 mg, 2.20 mmol) in dry dichloromethane (15 ml). The mixture was stirred at room temperature for 0.5 hour and added to a solution of cholesterol (387 mg, 1.00 mmol) and DMAP (122 mg, 1.00 mmol) in dichloromethane (10 ml). The reaction mixture was stirred overnight and then poured onto 5% sodium bicarbonate. The phases were separated and the organic phase was washed with brine and dried ($MgSO_4$). The solution was filtered and concentrated and the product was purified by column chromatography (silica, chloroform) to give 560 mg (83%) of colouless oil. The product was characterised by MALDI mass spectrometry, giving M+H at 674 as expected. Further characterisation was carried out using $^1H$ (500 MHz) and $^{13}C$ (125 MHz) NMR analysis, giving spectra in accordance with the structure.

b) Preparation of Gas-filled Microbubbles Comprising DSPS and a Cholesteryl Ester of Chlorambucil for Diagnostic and/or Therapeutic Applications A solution of 1.4% propylene glycol/2.4% glycerol (1.0 ml) was added to a mixture of DSPS (4.5 mg) and product from (a) (0.5 mg) in a vial. The mixture was sonicated for 5 minutes and then heated at 80° C. for 5 minutes (vial was shaken during warming) and cooled. The head space was flushed with perfluorobutane gas and the vial was shaken in a cap mixer for 45 seconds, whereafter the contents were extensively washed with deionised water. MALDI mass spectrometry showed no detectable level of compound from (a) in the final wash solution. Incorporation of chlorambucil cholesteryl ester into the bubbles was confirmed by MALDI-MS as follows: ca. 50 µl of microbubbles were transferred to a clean vial containing ca. 100 µl of 90% methanol. The mixture was sonicated for 30 seconds and analysed by MALDI-MS, giving a M+H peak at 668 corresponding to structure from (a).

EXAMPLE 57

Gas-filled Microbubbles Comprising DSPS and a Lipopeptide Containing Atenolol and a Cholesterol Derivative of Chlorambucil for Diagnostic and Therapeutic Applications a) Synthesis of a Protected Atenolol Derivative Suitable for Solid Phase Coupling i) Synthesis of methyl 4-[(2,3-epoxy)propoxy] phenylacetate A mixture of methyl 4-hydroxyphenylacetate (4.98 g, 0.030 mol), epichlorohydrin (23.5 ml, 0.30 mol) and pyridine (121 µl, 1.5 mmol) was stirred at 85° C. for 2 hours. The reaction mixture was cooled and excess epichlorohydrin was distilled off (rotavapor). The residue was taken up in ethyl acetate, washed with brine and dried ($Na_2SO_4$). The solution was filtered and concentrated. The dark residue was chromatographed (silica, hexane/ethyl acetate 7:3) to give 2.25 g (34%) of a colourless oil. $^1H$ (300 MHz) and $^{13}C$ NMR (75 MHz) spectra were in accordance with the structure.

ii) Synthesis of methyl 4-[2-hydroxy-3-[(1-methylethyl) amino]propoxy]phenylacetate A mixture of methyl 4-[(2,3-epoxy)propoxy] phenylacetate (2.00 g, 9.00 mmol), isopropylamine (23 ml, 0.27 mol) and water (1.35 ml, 74.7 mmol) was stirred at room temperature overnight. The reaction mixture was concentrated (rotavapor) and the oily residue was dissolved in chloroform and dried ($Na_2SO_4$). Filtration and concentration gave quantitative yield of a yellow oil that was used in the next step without further purification. The structure was verified by $^1H$ and $^{13}C$ NMR analysis.

iii) Synthesis of 4-[2-hydroxy-3-[(1-methylethyl)amino] propoxy]phenylacetic acid hydrochloride A solution of methyl 4-[2-hydroxy-3-[(1-methylethyl) amino]propoxy]phenylacetate (563 mg, 2.00 mmol) in 6M hydrochloric acid (15 ml) was heated at 100° C. for 4 hours. The reaction mixture was concentrated (rotavapor) and the residue was taken up in water and lyophilised. $^1H$ and $^{13}C$ NMR spectra were in accordance with the structure and MALDI mass spectrometry gave a M+H at 268 as expected.

iv) Synthesis of N-Boc-4-[2-hydroxy-3-[(1-methylethyl) amino]propoxy]phenylacetic acid A solution of the 4-[2-hydroxy-3-[(1-methylethyl)amino] propoxy]phenylacetic acid hydrochloride (2.0 mmol) in water (2 ml) was added to a solution of sodium bicarbonate (0.60 g, 7.2 mmol) in water/dioxane (2:1, 15 ml). A solution of di-tert-butyl dicarbonate (0.48 g, 2.2 mmol) in dioxane (5 ml) was added. Progress of the reaction was monitored by TLC analysis (silica, $CHCl_3$/MeOH/AcOH 85:10:5), and portions of di-tert-butyl dicarbonate were added until conversion was complete. The reaction mixture was poured onto water saturated with potassium hydrogen sulphate and organic material was extracted into ethyl acetate. The organic phase was washed with water and brine, dried ($Na_2SO_4$) and filtered to give 0.6 g of crude material. The product was purified by chromatography (silica, $CHCl_3$/ MeOH/AcOH 85:10:5). The solution was concentrated and the residue was taken up in glacial acetic acid and lyophilised. Yield 415 mg (56%), white solid. The structure was confirmed by $^1H$ and $^{13}C$ NMR analysis.

b) Synthesis of a lipopeptide functionalised with atenolol (SEQ ID NO:21)

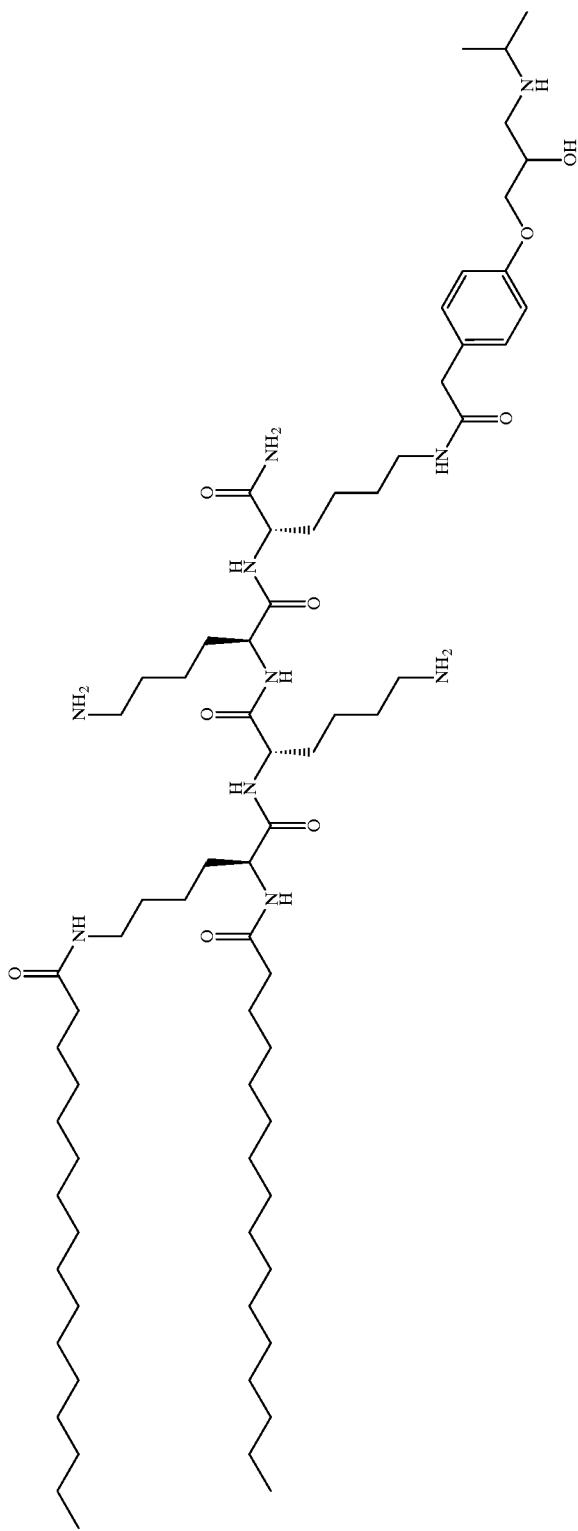

151

The structure shown above was synthesised by the manual bubbler method starting with Fmoc-protected Rink Amide MBHA resin on a 0.125 mmol scale, using appropriate amino acids, palmitic acid and the compound from (a). Coupling was carried out using standard TBTU/HOBt/DIEA protocols. Simultaneous removal of the peptide from the resin and deprotection of side-chain protecting groups was carried out in TFA containing 5% EDT and 5% water for 2 hours. Crude material was precipitated from ether and purified by preparative liquid chromatography using a gradient of 70 to 100% B over 60 minutes (A=0.1% TFA/water and B=0.1% TFA/acetonitrile) at a flow rate of 10 ml/min. After lyophilisation, a yield of 38 mg of pure material was obtained (analytical HPLC, gradient 70–100% B over 20 minutes, A=0.1% TFA/water and B=0.1% TFA/acetonitrile, flow rate 1 ml/minute, detection UV 214 nm, retention time 25 minutes). Further characterisation was carried out using MALDI mass spectrometry (ACH matrix), giving M+H at 1258, expected 1257.

c) Synthesis of Cholesteryl 4-[4-[bis(2-chloroethyl)amino] phenyl]butanoate

DIC (170 μl, 1.10 mmol) was added to a solution of chlorambucil (669 mg, 2.20 mmol) in dry dichloromethane (15 ml). The mixture was stirred at room temperature for 0.5 hour and added to a solution of cholesterol (387 mg, 1.00 mmol) and DMAP (122 mg, 1.00 mmol) in dichloromethane (10 ml). The reaction mixture was stirred overnight and then poured onto 5% sodium bicarbonate. The phases were separated and the organic phase was washed with brine and dried ($MgSO_4$). The solution was filtered and concentrated and the product was purified by column chromatography (silica, chloroform) to give 560 mg (83%) of colouless oil. The product was characterised by MALDI mass spectrometry, giving M+H at 674 as expected. Further characterisation was carried out using $^1H$ (500 MHz) and $^{13}C$ (125 MHz) NMR analysis, giving spectra in accordance with the structure.

d) Preparation of Gas-filled Microbubbles Comprising DSPS and a Lipopeptide Containing Atenolol and a Cholesteryl Ester of Chloambucil A solution of 1.4% propylene glycol/2.4 μglycerol (1.0 ml) was added to a mixture of DSPS (5.0 mg), product from (b) (0.5 mg) and product from (c) (0.5 mg) in a vial. The mixture was sonicated for 5 minutes and then warmed to 80° C. for 5 minutes (vial was shaken during warming). The solution was filtered and cooled. The head space was flushed with perfluorobutane gas and the vial was shaken in a cap mixer for 45 seconds, whereafter the contents were extensively washed with deionised water. Incorporation of compounds (b) and (c) into the microbubbles was confirmed by MALDI-MS as follows: ca. 50 μl of microbubbles were transferred to a clean vial containing ca. 100 μl of 90% methanol. The mixture was sonicated for 30 seconds and analysed by MALDI-MS (ACH-matrix), giving a M+H peak corresponding to lipopeptide (b) and cholesteryl ester (c).

e) In vitro Analysis

The microbubbles were tested in the in vitro assay as detailed in Example 21. A gradual accumulation of microbubbles binding to the cells was observed.

152

EXAMPLE 58

Gas-fiiled Microbubbles Comprising DSPS and a Lipopeptide Containing Atenolol for Cell Targeting and a Lipophilic Thiol Ester of Captopril for Therapeutic Use a) Synthesis of a Protected Atenolol Derivative Suitable for Solid Phase Coupling i) Synthesis of methyl 4-[(2,3-epoxy)propoxy] phenylacetate A mixture of methyl 4-hydroxyphenylacetate (4.98 g, 0.030 mol), epichlorohydrin (23.5 ml, 0.30 mol) and pyridine (121 μl, 1.5 mmol) was stirred at 85° C. for 2 hours. The reaction mixture was cooled and excess epichlorohydrin was distilled off (rotavapor). The residue was taken up in ethyl acetate, washed with brine and dried ($Na_2SO_4$). The solution was filtered and concentrated. The dark residue was chromatographed (silica, hexane/ethyl acetate 7:3) to give 2.25 g (34 μ) of a colourless oil. $^1H$ (300 MHz) and $^{13}C$ NMR (75 MHz) spectra were in accordance with the structure.

ii) Synthesis of methyl 4-[2-hydroxy-3-[(1-methylethyl) amino]propoxy]phenylacetate A mixture of methyl 4-[(2,3-epoxy)propoxy] phenylacetate (2.00 g, 9.00 mmol), isopropylamine (23 ml, 0.27 mol) and water (1.35 ml, 74.7 mmol) was stirred at room temperature overnight. The reaction mixture was concentrated (rotavapor) and the oily residue was dissolved in chloroform and dried ($Na_2SO_4$). Filtration and concentration gave quantitative yield of a yellow oil that was used in the next step without further purification. The structure was verified by $^1H$ and $^{13}C$ NMR analysis.

iii) Synthesis of 4-[2-hydroxy-3-[(1-methylethyl)amino] propoxy]phenylacetic acid hydrochloride A solution of methyl 4-[2-hydroxy-3-[(1-methylethyl) amino]propoxy]phenylacetate (563 mg, 2.00 mmol) in 6M hydrochloric acid (15 ml) was heated at 100° C. for 4 hours. The reaction mixture was concentrated (rotavapor) and the residue was taken up in water and lyophilised. $^1H$ and $^{13}C$ NMR spectra were in accordance with the strucure and MALDI mass spectrometry gave a M+H at 268 as expected.

iv) Synthesis of N-Boc-4-[2-hydroxy-3-[(1-methylethyl) amino]propoxy]phenylacetic acid A solution of the 4-[2-hydroxy-3-[(1-methylethyl)amino] propoxy]phenylacetic acid hydrochloride (2.0 mmol) in water (2 ml) was added to a solution of sodium bicarbonate (0.60 g, 7.2 mmol) in water/dioxane (2:1, 15 ml). A solution of di-tert-butyl dicarbonate (0.48 g, 2.2 mmol) in dioxane (5 ml) was added. Progress of the reaction was monitored by TLC analysis (silica, $CHCl_3$/MeOH/AcOH 85:10:5), and portions of di-tert-butyl dicarbonate were added until conversion was complete. The reaction mixture was poured onto water saturated with potassium hydrogen sulphate and organic material was extracted into ethyl acetate. The organic phase was washed with water and brine, dried ($Na_2SO_4$) and filtered to give 0.6 g of crude material. The product was purified by chromatography (silica, $CHCl_3$/MeOH/AcOH 85:10:5). The solution was concentrated and the residue was taken up in glacial acetic acid and lyophilised. Yield 415 mg (56%), white solid. The structure was confirmed by $^1H$ and $^{13}C$ NMR analysis.

b) Synthesis of a lipopeptide functionalised with atenolol (SEQ ID NO:21)

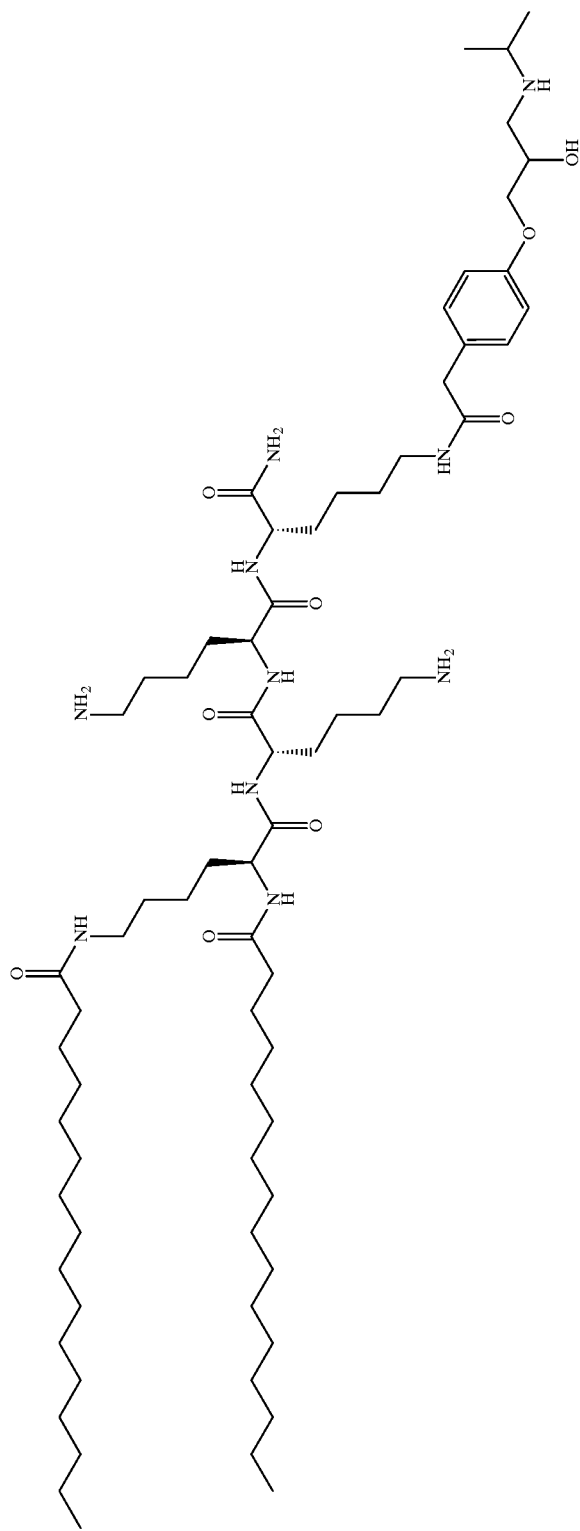

The structure shown above was synthesised by the manual bubbler method starting with Fmoc-protected Rink Amide MBHA resin on a 0.125 mmol scale, using appropriate amino acids, palmitic acid and the compound from (a). Coupling was carried out using standard TBTU/HOBt/DIEA protocols. Simultaneous removal of the peptide from the resin and deprotection of side-chain protecting groups was carried out in TFA containing 5% EDT and 5% water for 2 hours. Crude material was precipitated from ether and purified by preparative liquid chromatography using a gradient of 70 to 100% B over 60 minutes (A=0.1% TFA/water and B=0.1% TFA/acetonitrile) at a flow rate of 10 ml/min. After lyophilisation, a yield of 38 mg of pure material was obtained (analytical HPLC, gradient 70–100% B over 20 minutes, A=0.1% TFA/water and B=0.1% TFA/acetonitrile, flow rate 1 ml/minute, detection UV 214 nm, retention time 25 minutes). Further characterisation was carried out using MALDI mass spectrometry (ACH matrix), giving M+H at 1258, expected 1257.

c) Synthesis of Cholanic Acid Thiol Ester of Captopril

A mixture of 5-β-cholanic acid (361 mg, 1.00 mmol) and DIC (77 μl, 0.50 mmol) in dichloromethane (5 ml) was stirred for 10 minutes and then added to a solution of captopril (130 mg, 0.600 mmol) and DBU (180 μl, 1.20 mmol) in dichloromethane (10 ml). The reaction mixture was stirred overnight and then poured onto dilute hydrochloric acid. Chloroform (30 ml) was added. The phases were separated and the organic phase was washed with water and brine and dried ($MgSO_4$). After filtration and concentration, the crude material was chromatographed (silica, chloroform/methanol/acetic acid 95:4:1). The product was lyophilised from a acetonitrile/water/ethanol mixture. Yield 137 mg (49%) of off-white solid. The structure was verified by $^1H$ (500 MHz) and $^{13}C$ (125 MHz) NMR spectroscopy. Further characterisation was carried out using MALDI mass spectrometry, giving a M+Na peak in positive mode at m/z 584.

d) Preparation of Gas-filled Microbubbles Comprising DSPS and a Lipopeptide Containing Atenolol for Cell Targeting and a Lipophilic Thiol Ester of Captopril for Therapeutic Use A solution of 1.4% propylene glycol/2.4% glycerol (1.0 ml) was added to a mixture of DSPS (5.0 mg) and products from (b) (0.5 mg) and (c) (0.5 mg) in a vial. The mixture was sonicated for 5 minutes and then heated at 80° C. for 5 minutes (vial was shaken during warming) and cooled. Head space was flushed with perfluorobutane gas and the vial was shaken in a cap mixer for 45 seconds followed by extensive washing with deionised water. MALDI mass spectrometry showed no detectable level of compound from (b) or (c) in the final wash solution. Incorporation of compounds from (b) and (c) into the microbubbles was confirmed by MALDI-MS as follows: ca. 50 μl of microbubbles were transferred to a clean vial containing ca. 100 μl of 90% methanol. The mixture was sonicated for 30 seconds and analysed by MALDI-MS (ACH-matrix), giving peaks according to structures from (b) and (c) respectively.

e) In vitro Analysis

The microbubbles were tested in the in vitro assay as detailed in Example 21. A gradual accumulation of microbubbles binding to the cells was observed.

EXAMPLE 59

Gas-filled Microbubbles Comprising Phosphatidylserine and biotinamide-PEG-β-Alacholesterol and a Cholesteryl Ester of Chlorambucil for Diagnostic and Therapeutic Applications a) Synthesis of Cholesteryl N-Boc-β-alaninate DIC (510 μl) was added to a solution of Boc-β-Ala-OH (1.25 g, 6.60 mmol) in dichloromethane (15 ml) under an inert atmosphere. The reaction mixture was stirred for 30 minutes and then transferred to a flask containing a solution of cholesterol (1.16 g, 3.00 mmol) and DMAP (367 mg, 3.00 mmol) in dichloromethane (15 ml). The reaction mixture was stirred for 2 hours and then poured onto an aqeous solution of potassium hydrogen sulphate. After phase separation the aqueous phase was extracted with chloroform. The combined organic phases were washed with aqueous potassium hydrogen sulphate and water and dried ($MgS_4$). After filtration and evaporation the crude product was chromatographed (silica, chloroform/methanol 99:1) to give 1.63 g (97%) of white solid. The structure was confirmed by $^1H$ NMR (500 MHz).

b) Synthesis of Cholesteryl β-alaninate Hydrochloride

A solution of compound from (a) (279 mg, 0.500 mmol) in 1M hydrochloric acid in 1,4-dioxane (5 ml) was stirred at room temperature for 4 hours. The reaction mixture was concentrated to give a quantitative yield of cholesteryl β-alaninate hydrochloride. The structure was confirmed by $^1H$ NMR (500 MHz) analysis and by MALDI mass spectrometry, giving a M+Na peak at 482, expected 481.

c) Biotin-$PEG_{3400}$-β-Ala-Cholesterol

To a solution of cholesteryl β-alaninate hydrochloride (15 mg, 0.03 mmol) in chloroform/wet methanol (2.6:1, 3 ml) was added triethylamine (42 μl, 0.30 mmol). The mixture was stirred for 10 minutes at room temperature and a solution of biotin-$PEG_{3400}$-NHS (100 mg, 0.03 mmol) in 1,4-dioxane (1 ml) was added dropwise. After stirring at room temperature for 3 hours the mixture was evaporated to dryness and the residue was purified by flash chromatography to give white crystals, yield 102 mg (89%). The structure was verified by MALDI-MS and by NMR analysis.

d) Synthesis of Cholesteryl 4-[4-[bis(2-chloroethyl)amino]phenyl]butanoate

DIC (170 μl, 1.10 mmol) was added to a solution of chlorambucil (669 mg, 2.20 mmol) in dry dichloromethane (15 ml). The mixture was stirred at room temperature for 0.5 hour and added to a solution of cholesterol (387 mg, 1.00 mmol) and DMAP (122 mg, 1.00 mmol) in dichloromethane (10 ml). The reaction mixture was stirred overnight and then poured onto 5% sodium bicarbonate. The phases were separated and the organic phase was washed with brine and dried ($MgSO_4$). The solution was filtered and concentrated and the product was purified by column chromatography (silica, chloroform) to give 560 mg (83%) yield of colouless oil. The product was characterised by MALDI mass spectrometry, giving M+H at 674 as expected. Further characterisation was carried out using $^1H$ (500 MHz) and $^{13}C$ (125 MHz) NMR analysis, giving spectra in accordance with the structure.

e) Preparation of Gas-filled Microbubbles

A solution of 1.4% propylene glycol/2.4% glycerol (1.0 ml) was added to a mixture of DSPS (5 mg) and products from (c) (0.5 mg) and (d) (0.5 mg) in a vial. The mixture was sonicated for 5 minutes and then heated at 80° C. for 5 minutes (vial was shaken during warming) and cooled. The head space was flushed with perfluorobutane gas and the vial was shaken in a cap mixer for 45 seconds, whereafter the contents were extensively washed with deionised water.

MALDI mass spectrometry showed no detectable level of compound from (c) or (d) in the final wash solution. Incorporation of compounds from (c) and (d) into the microbubbles was confirmed by MALDI-MS as follows: ca. 50 μl of microbubbles were transferred to a clean vial containing ca. 100 μl of 90% methanol. The mixture was sonicated for 30 seconds and analysed by MALDI-MS (ACH-matrix), giving M+H peaks corresponding to compounds from (c) and (d).

EXAMPLE 60

Gas-filled Microbubbles Comprising DSPS and a Lipopeptide Containing a Derivative of Bestatin for Diagnostic and Therapeutic Applications a) Synthesis of a lipopeptide containing a derivative of bestatin (SEQ ID NO:23)

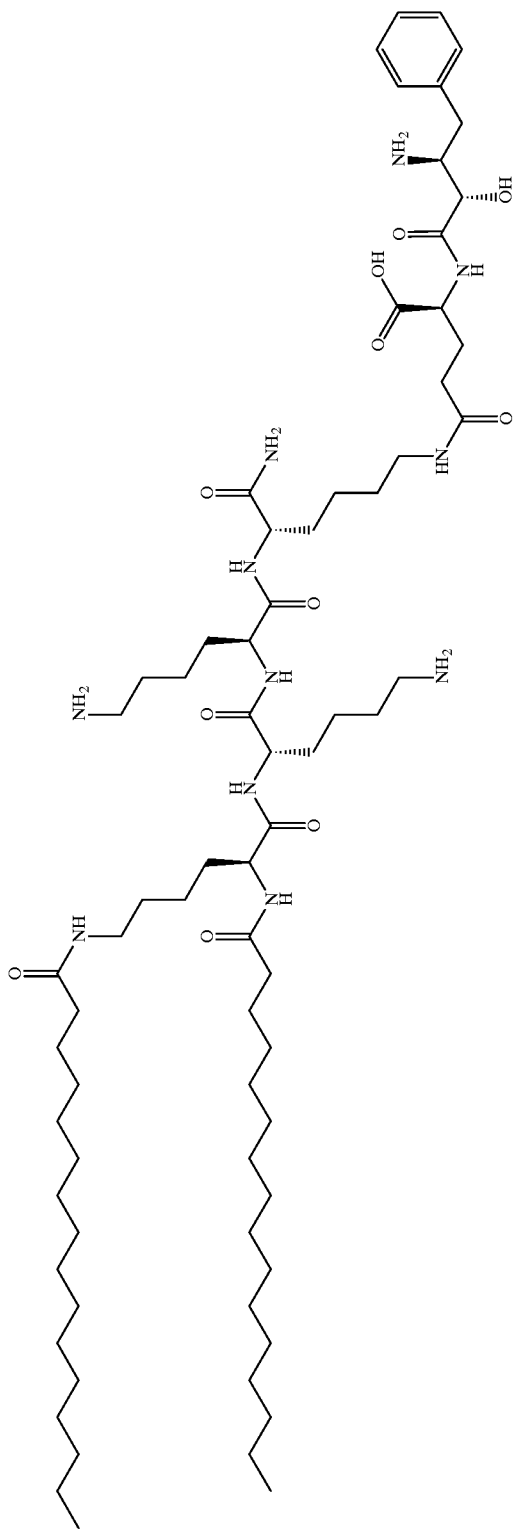

The structure shown above was synthesised by the manual bubbler method starting with Fmoc-protected Rink Amide MBHA resin on a 0.125 mmol scale, using appropriate amino acids and palmitic acid. Coupling was carried out using standard TBTU/HOBt/DIEA protocols. Simultaneous removal of the peptide from the resin and deprotection of side-chain protecting groups was carried out in TFA containing 5% EDT and 5% water for 2 hours. Crude material was precipitated from ether and purified by preparative liquid chromatography using a gradient of 70 to 100% B over 60 minutes (A=0.1% TFA/water and B=0.1% TFA/acetonitrile) at a flow rate of 10 ml/min. After lyophilisation, a yield of 12 mg of pure material was obtained (analytical HPLC, gradient 70–100% B over 20 minutes, A=0.1% TFA/water and B=0.1% TFA/acetonitrile, flow rate 1 ml/minute, detection UV 214 nm, retention time 25 minutes). Further characterisation was carried out using MALDI mass spectrometry (ACH matrix), giving M+H at 1315, expected 1314.

b) Preparation of Gas-filled Microbubbles Comprising DSPS and a Lipopeptide Containing a Derivative of Bestatin for Diagnostic and Therapeutic Applications A solution of 1.4% propylene glycol/2.4% glycerol (1.0 ml) was added to a mixture of DSPS (4.5 mg) and product from (a) (0.5 mg) in a vial. The mixture was sonicated for 5 minutes and then heated at 80° C. for 5 minutes (vial was shaken during warming) and cooled. The head space was flushed with perfluorobutane gas and the vial was shaken in a cap mixer for 45 seconds and the contents were extensively washed with deionised water. MALDI mass spectrometry showed no detectable level of compound from (b) in the final wash solution. Incorporation of atenolol-containing lipopeptide into the microbubbles was confirmed by MALDI-MS as follows: ca. 50 $\mu$l of microbubbles were transferred to a clean vial containing ca. 100 $\mu$l of 90% methanol. The mixture was sonicated for 30 seconds and analysed by MALDI-MS (ACH-matrix), giving a M+H peak at 1320, expected at 1314, corresponding to lipopeptide from (a).

c) In vitro Analysis

The microbubbles were tested in the in vitro assay as detailed in Example 21. A gradual accumulation of microbubbles binding to the cells was observed.

EXAMPLE 61

Gas-filled Microbubbles Comprising DSPS and a Lipopeptide Containing Chlorambucil for Diagnostic and Therapeutic Applications a) Synthesis of a lipopeptide containing chlorambucil (SEQ ID NO:24)

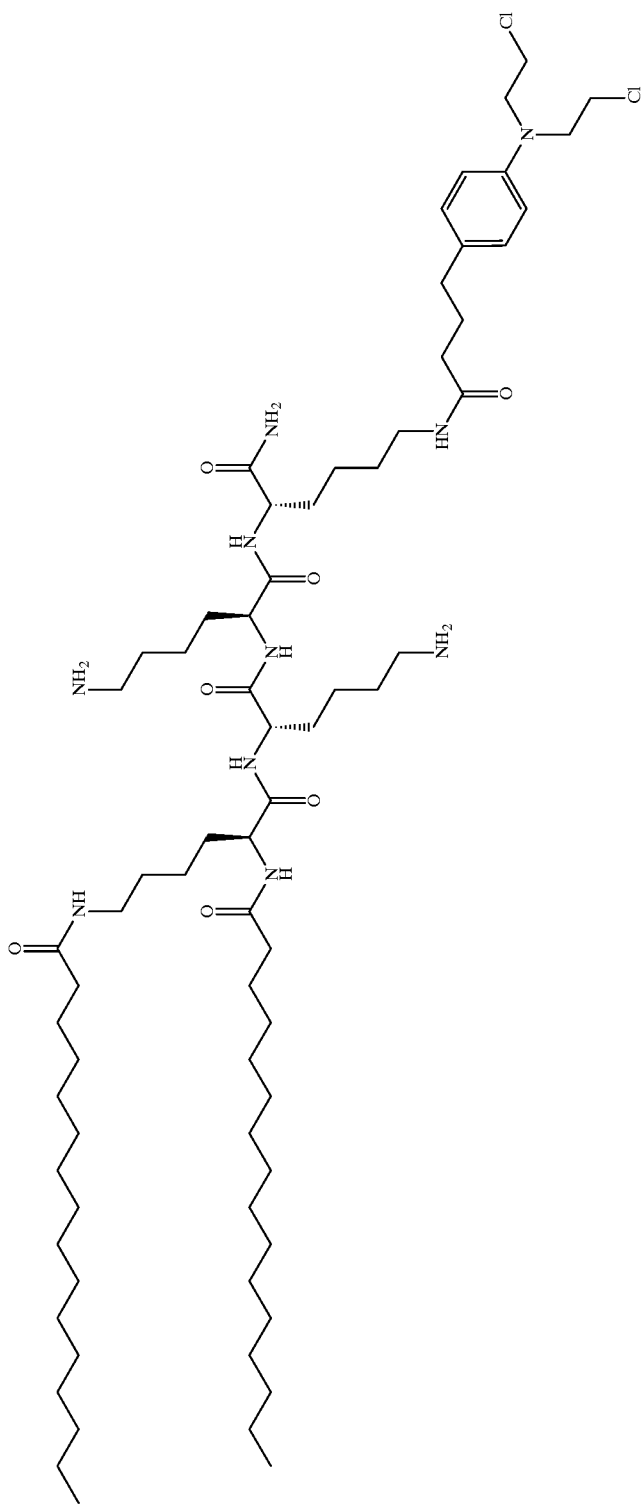

The structure shown above was synthesised by the manual bubbler method starting with Fmoc-protected Rink Amide MBHA resin on a 0.125 mmol scale, using appropriate amino acids and palmitic acid. Coupling was carried out using standard TBTU/HOBt/DIEA protocol. Chlorambucil was coupled through the side-chain of Lys as a symmetrical anhydride using DIC preactivation.

Simultaneous removal of the peptide from the resin and deprotection of side-chain protecting groups was carried out in TFA containing 5% EDT, 5% water and 5% ethyl methyl sulphide for 2 hours. An aliqout of 10 mg of the crude material was purified by preparative liquid chromatography using a gradient of 70 to 100% B over 60 minutes (A=0.1% TFA/water and B=0.1% TFA/acetonitrile) at a flow rate of 10 ml/min. After lyophilisation, a yield of 30 mg of pure material was obtained (analytical HPLC, gradient 70–100% B over 20 minutes, A=0.1% TFA/water and B=0.1% TFA/acetonitrile, flow rate 1 ml/minute, detection UV 214 nm retention time 26.5 minutes). Further characterisation was carried out using MALDI mass spectrometry, giving M+H at 1295, expected 1294.

b) Preparation of Gas-filled Microbubbles Comprising DSPS and a Lipopeptide Containing Chlorambucil for Diagnostic and Therapeutic Applications A solution of 1.4% propylene glycol/2.4% glycerol (1.0 ml) was added to a mixture of DSPS (4.5 mg) and product from (a) (0.5 mg) in a vial. The mixture was sonicated for 5 minutes and then heated at 80° C. for 5 minutes (vial was shaken during warming) and cooled. The head space was flushed with perfluorobutane gas and the vial was shaken in a cap mixer for 45 seconds, whereafter the contents were extensively washed with deionised water. MALDI mass spectrometry showed no detectable level of compound from (a) in the final wash solution. Incorporation of chlorambucil-containing lipopeptide into-the bubbles was confirmed by MALDI-MS as follows: ca. 50 μl of microbubbles were transferred to a clean vial containing ca. 100 μl of 90% methanol. The mixture was sonicated for 30 seconds and analysed by MALDI-MS (ACH-matrix), giving a M+H peak at 1300, expected at 1294 and a M+Na peak at 1324, expected 1317.

c) In vitro Analysis

The microbubbles were tested in the in vitro assay as detailed in Example 21. A gradual accumulation of microbubbles binding to the cells was observed.

EXAMPLE 62

Gas-filled Microbubbles Comprising DSPS, a Lipopeptide Containing Atenolol and a Lipophilic Derivative of Captopril for Diagnostic and Therapeutic Applications a) Synthesis of a Protected Atenolol Derivative Suitable for Solid Phase Coupling i) Synthesis of methyl 4-[(2,3-epoxy)propoxy]phenylacetate A mixture of methyl 4-hydroxyphenylacetate (4.98 g, 0.030 mol), epichlorohydrin (23.5 ml, 0.30 mol) and pyridine (121 μl, 1.5 mmol) was stirred at 85° C. for 2 hours. The reaction mixture was cooled, and excess epichlorohydrin was distilled off (rotavapor). The residue was taken up in ethyl acetate, washed with brine and dried ($Na_2SO_4$). The solution was filtered and concentrated. The dark residue was chromatographed (silica, hexane/ethyl acetate 7:3) to give 2.25 g (34%) of a colourless oil. $^1$H (300 MHz) and $^{13}$C NMR (75 MHz) spectra were in accordance with the structure.

ii) Synthesis of methyl 4-[2-hydroxy-3-[(1-methylethyl)amino]propoxy]phenylacetate A mixture of methyl 4-[(2,3-epoxy)propoxy]phenylacetate (2.00 g, 9.00 mmol), isopropylamine (23 ml, 0.27 mol) and water (1.35 ml, 74.7 mmol) was stirred at room temperature overnight. The reaction mixture was concentrated (rotavapor) and the oily residue was dissolved in chloroform and dried ($Na_2SO_4$). Filtration and concentration gave quantitative yield of a yellow oil that was used in the next step without further purification. The structure was verified by $^1$H and $^{13}$C NMR analysis.

iii) Synthesis of 4-[2-hydroxy-3-[(1-methylethyl)amino]propoxy]phenylacetic acid hydrochloride A solution of methyl 4-[2-hydroxy-3-[(1-methylethyl)amino]propoxy]phenylacetate (563 mg, 2.00 mmol) in 6M hydrochloric acid (15 ml) was heated at 100° C. for 4 hours. The reaction mixture was concentrated (rotavapor) and the residue was taken up in water and lyophilised. $^1$H and $^{13}$C NMR spectra were in accordance with the strucure and MALDI mass spectrometry gave a M+H at 268 as expected.

iv) Synthesis of N-Boc-4-[2-hydroxy-3-[(1-methylethyl)amino]propoxy]phenylacetic acid A solution of the 4-[2-hydroxy-3-[(1-methylethyl)amino]propoxy]phenylacetic acid hydrochloride (2.0 mmol) in water (2 ml) was added to a solution of sodium bicarbonate (0.60 g, 7.2 mmol) in water/dioxane (2:1, 15 ml). A solution of di-tert-butyl dicarbonate (0.48 g, 2.2 mmol) in dioxane (5 ml) was added. Progress of the reaction was monitored by TLC analysis (silica, $CHCl_3$/MeOH/AcOH 85:10:5), and portions of di-tert-butyl dicarbonate were added until conversion was complete. The reaction mixture was poured onto water saturated with potassium hydrogen sulphate and organic material was extracted into ethyl acetate. The organic phase was washed with water and brine, dried ($Na_2SO_4$) and filtered to give 0.6 g of crude material. The product was purified by chromatography (silica, $CHCl_3$/MeOH/AcOH 85:10:5). The solution was concentrated and the residue was taken up in glacial acetic acid and lyophilised. Yield 415 mg (56% ), white solid. The structure was confirmed by $^1$H and $^{13}$C NMR analysis.

b) Synthesis of a lipopeptide functionalised with atenolol (SEQ ID NO:21)

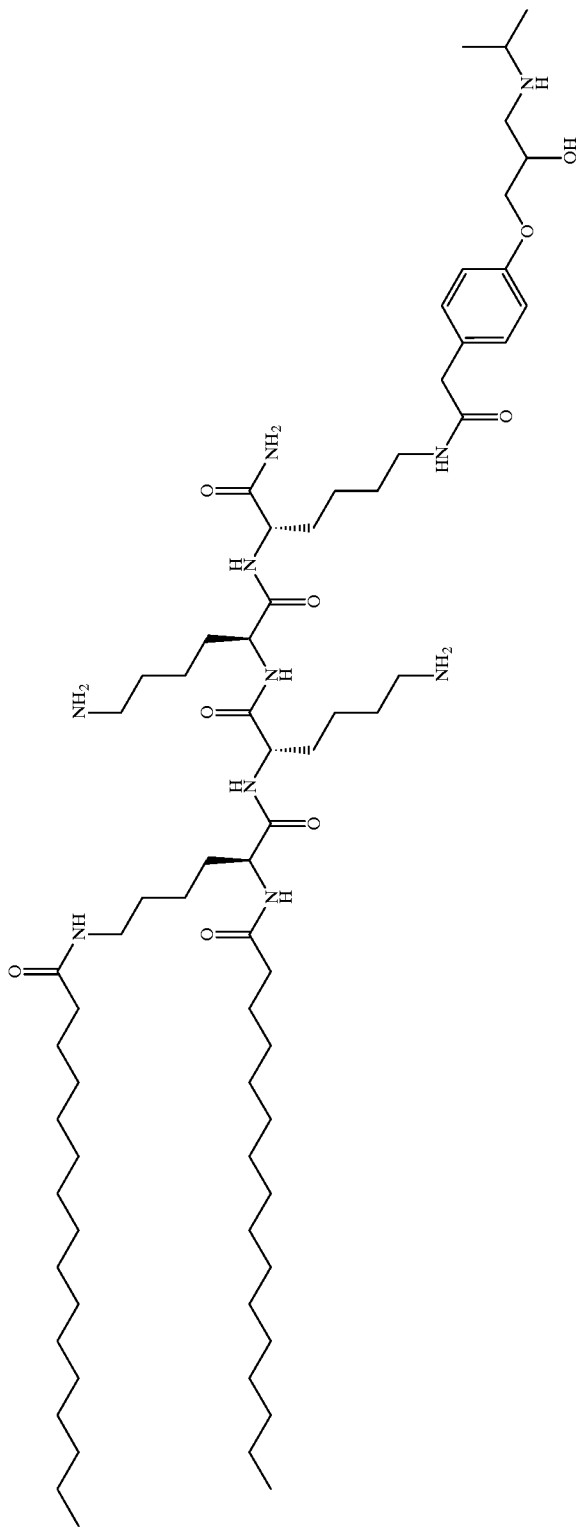

The structure shown above was synthesised by the manual bubbler method starting with Fmoc-protected Rink Amide MBHA resin on a 0.125 mmol scale, using appropriate amino acids, palmitic acid and the compound from (a). Coupling was carried out using standard TBTU/HOBt/DIEA protocols. Simultaneous removal of the peptide from the resin and deprotection of side-chain protecting groups was carried out in TFA containing 5% EDT and 5% water for 2 hours. Crude material was precipitated from ether and purified by preparative liquid chromatography using a gradient of 70 to 100% B over 60 minutes (A=0.1% TFA/water and B=0.1% TFA/acetonitrile) at a flow rate of 10 ml/min. After lyophilisation, a yield of 38 mg of pure material was obtained (analytical HPLC, gradient 70–100% B over 20 minutes, A=0.1% TFA/water and B=0.1% TFA/acetonitrile, flow rate 1 ml/minute, detection UV 214 nm, retention time 25 minutes). Further characterisation was carried out using MALDI mass spectrometry (ACH matrix), giving M+H at 1258, expected 1257.

c) Synthesis of N-[(S)-3-hexadecylthio-2-methylpropionyl] proline

DIEA (188 4l, 1.10 mmol) was added to a solution of 1-iodohexadecane (176 mg, 0.500 mmol), captopril (120 mg, 0.550 mmol) and DBU (165 pl, 1.10 mmol) in tetrahydrofuran (5 ml). The mixture was heated at 70° C. for 2 hours and then concentrated. The residue was poured onto water saturated with potassium hydrogen sulphate and organic material was extracted into chloroform. The organic phase was washed with water and dried (MgSO$_4$). The product was purified by chromatography (silica, CHCl$_3$/MeOH/AcOH 85:10:5) and lyophilised to give 105 mg (48%) of white solid material. The structure was verified by $^1$H (500 Mhz) and $^{13}$C (125 Mhz) NMR analysis and further characterised by MALDI mass spectrometry, giving M–H in negative mode at m/z 440 as expected.

d) Preparation of Gas-filled Microbubbles Comprising DSPS, a Lipopeptide Containing Atenolol and a Lipophilic Derivative of Captopril for Diagnostic and Therapeutic Applications A solution of 1.4% propylene glycol/2.4% glycerol (1.0 ml) was added to a mixture of DSPS (4.5 mg) and products from (b) (0.5 mg) and (c) in a vial. The mixture was sonicated for 5 minutes and then heated at 80° C. for 5 minutes (vial was shaken during warming) and cooled. The head space was flushed with perfluorobutane gas and the vial was shaken in a cap mixer for 45 seconds, whereafter the contents were extensively washed with deionised water. MALDI mass spectrometry showed no detectable level of compound from (b) or (c) in the final wash solution. Incorporation of compounds (b) and (c) into the microbubbles was confirmed by MALDI-MS as follows: ca. 50 µl of microbubbles were transferred to a clean vial containing ca. 100 µl of 90% methanol. The mixture was sonicated for 30 seconds and analysed by MALDI-MS (ACH-matrix), giving M+H peaks corresponding to structures (b) and (c) respectively.

e) In vitro Analysis

The microbubbles were tested in the in vitro assay as detailed in Example 21. A gradual accumulation of microbubbles binding to the cells was observed.

EXAMPLE 63

Gas-filled Microbubbles Comprising DSPS and a Cholesterol Derivative of Atenolol for Diagnostic and Therapeutic Applications a) Synthesis of Methyl 4-[(2,3-epoxy)propoxy] phenylacetate A mixture of methyl 4-hydroxyphenylacetate (4.98 g, 0.030 mol), epichlorohydrin (23.5 ml, 0.30 mol) and pyridine (121 µl, 1.5 mmol) was stirred at 85° C. for 2 hours. The reaction mixture was cooled, and excess epichlorohydrin was distilled off (rotavapor). The residue was taken up in ethyl acetate, washed with brine and dried (Na$_2$SO$_4$). The solution was filtered and concentrated. The dark residue was chromatographed (silica, hexane/ethyl acetate 7:3) to give 2.25 g (34%) of a colourless oil. $^1$H (300 MHz) and $^{13}$C NMR (75 MHz) spectra were in accordance with the structure.

b) Synthesis of Methyl 4-[2-hydroxy-3-[(1-methylethyl) amino]propoxy]phenylacetate A mixture of methyl 4-[(2,3-epoxy)propoxy] phenylacetate (2.00 g, 9.00 mmol), isopropylamine (23 ml, 0.27 mol) and water (1.35 ml, 74.7 mmol) was stirred at room temperature overnight. The reaction mixture was concentrated (rotavapor) and the oily residue was dissolved in chloroform and dried (Na$_2$SO$_4$). Filtration and concentration gave quantitative yield of a yellow oil that was used in the next step without further purification. The structure was verified by $^1$H and $^{13}$C NMR analysis.

c) Synthesis of 4-[2-hydroxy-3-[(1-methylethyl)amino] propoxy]phenylacetic acid hydrochloride A solution of methyl 4-[2-hydroxy-3-[(1-methylethyl) amino]propoxy]phenylacetate (563 mg, 2.00 mmol) in 6M hydrochloric acid (15 ml) was heated at 100° C. for 4 hours. The reaction mixture was concentrated (rotavapor) and the residue was taken up in water and lyophilised. $^1$H and $^{13}$C NMR spectra were in accordance with the strucure and MALDI mass spectrometry gave a M+H at 268 as expected.

d) Synthesis of N-Boc-4-[2-hydroxy-3-[(1-methylethyl) amino]propoxy]phenylacetic acid A solution of the 4-[2-hydroxy-3-[(1-methylethyl)amino] propoxy]phenylacetic acid hydrochloride (2.0 mmol) in water (2 ml) was added to a solution of sodium bicarbonate (0.60 g, 7.2 mmol) in water/dioxane (2:1, 15 ml). A solution of di-tert-butyl dicarbonate (0.48 g, 2.2 mmol) in dioxane (5 ml) was added. Progress of the reaction was monitored by TLC analysis (silica, CHCl3/MeOH/AcOH 85:10:5), and portions of di-tert-butyl dicarbonate were added until conversion was complete. The reaction mixture was poured onto water saturated with potassium hydrogen sulphate and organic material was extracted into ethyl acetate. The organic phase was washed with water and brine, dried (Na$_2$SO$_4$) and filtered to give 0.6 g of crude material. The product was purified by chromatography (silica, CHCl$_3$/MeOH/AcOH 85:10:5). The solution was concentrated and the residue was taken up in glacial acetic acid and lyophilised. Yield 415 mg (56%), white solid. The structure was confirmed by $^1$H and $^{13}$C NMR analysis.

e) Synthesis of Cholesteryl N-Boc-β-alaninate

DIC (510 µl) was added to a solution of Boc-β-Ala-OH (1.25 g, 6.60 mmol) in dichloromethane (15 ml) under an inert atmosphere. The reaction mixture was stirred for 30 minutes and then transferred to a flask containing a solution of cholesterol (1.16 g, 3.00 mmol) and DMAP (367 mg, 3.00 mmol) in dichloromethane (15 ml). The reaction mixture was stirred for 2 hours and then poured onto an aqeous solution of potassium hydrogen sulphate.

After phase separation the aqueous phase was extracted with chloroform. The combined organic phases were washed with aqueous potassium hydrogen sulphate and water and dried (MgSO$_4$). After filtration and evaporation the crude product was chromatographed (silica, chloroform/methanol 99:1) to give 1.63 g (97%) of white solid. The structure was confirmed by $^1$H NMR (500 MHz).

f) Synthesis of Cholesteryl β-alaninate Hydrochloride

A solution of compound from (a) (279 mg, 0.500 mmol) in 1M hydrochloric acid in 1,4-dioxane (5 ml) was stirred at room temperature for 4 hours. The reaction mixture was concentrated to give a quantitative yield of cholesteryl β-alaninate hydrochloride. The structure was confirmed by 1H NMR (500 MHz) analysis and by MALDI mass spectrometry, giving a M+Na peak at 482, expected 481.

g) Synthesis of Cholesteryl N-Boc-4-[2-hydroxy-3-[1-methylethyl)amino]propoxy]phenylacetyl-β-alaninate.

To a solution of N-Boc-4-[2-hydroxy-3-[(1-methylethyl)amino]propoxy]phenylacetic acid (55 mg, 0.15 mmol) and cholesteryl β-alaninate hydrochloride (74 mg, 0.15 mmol) in DMF (5 ml) was added DIEA (26 ml, 0.15 mmol). HOBt (23 mg, 0.15 mmol) and water-soluble carbodiimide (WSC) (29 mg, 0.15 mmol) were added. The reaction mixture was stirred at room temperature overnight and then poured onto water (25 ml) containing sodium carbonate (2.5 g) and sodium chloride (4.0 g). Precipitated material was extracted into chloroform. The organic phase was washed with water and dried (MgSO$_4$). After filtration and concentration, crude material (132 mg) was purified by column chromatography (silica, chloroform/methanol/acetic acid, 95:4:1). Pooled fractions were concentrated, taken up in glacial acetic acid and lyophilised. Yield 83 mg (69%), yellow-white solid. Structure was confirmed by $^1$H NMR analysis.

h) Synthesis of Cholesteryl 4-[2-hydroxy-3-[(1-methylethyl)amino]propoxy]phenylacetyl-β-alaninate Trifluoroacetate To a solution of N-Boc-4-[2-hydroxy-3-[(1-methylethyl)amino]propoxy]phenylacetyl-β-alaninate (40 mg, 0.05 mmol) in dry dichloromethane (4 ml) was added trifluoroacetic acid (2 ml). The reaction mixture was stirred for 2 hours and then concentrated. The product was lyophilised from a acetonitrile/water mixture to give a quantitative yield of white-yellow material. The product was characterised by MALDI mass spectrometry giving M+H at 708 as expected.

i) Preparation of Gas-filled Microbubbles Comprising DSPS and a Cholesterol Derivative of Atenolol for Diagnostic and Therapeutic Applications A solution of 1.4% propylene glycol/2.4% glycerol (1.0 ml) was added to a mixture of DSPS (4.5 mg) and product from (h) (0.5 mg) in a vial. The mixture was sonicated for 5 minutes and then heated at 80° C. for 5 minutes (vial was shaken during warming) and cooled. The head space was flushed with perfluorobutane gas and the vial was shaken in a cap mixer for 45 seconds, whereafter the contents were extensively washed with deionised water. MALDI mass spectrometry showed no detectable level of compound from (b) in the final wash solution. Incorporation of compound from (h) into the microbubbles was confirmed by MALDI mass spectrometry.

j) In vitro Analysis

The microbubbles were tested in the in vitro assay as detailed in Example 21. A gradual accumulation of bubbles binding to the cells was observed.

EXAMPLE 64

Preparation of Multiple-sepecific Transferrin/avidin-coated Gas-filled Microbubbles for Targeted Ultrasound Imaging This example is directed to the preparation of microbubbles containing vectors for targeted ultrasound/therapy.

a) Synthesis of a thiol-functionalised lipid molecule: Dipalmitoyl-Lys-Lys-Lys-Aca-Cys.OH (SEQ ID NO:20)

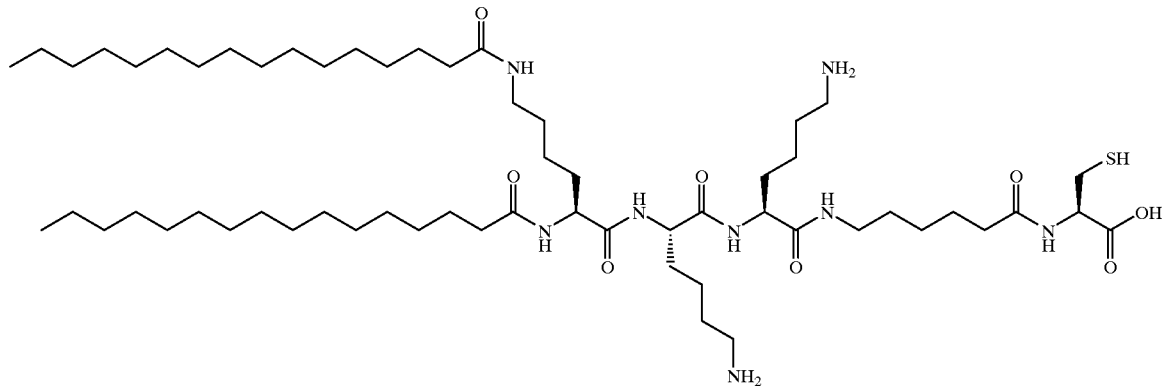

The lipid structure shown above was synthesised on an ABI 433A automatic peptide synthesiser starting with Fmoc-Cys(Trt)-Wang resin on a 0.25 mmol scale using 1 mmol amino acid cartridges. All amino acids and palmitic acid were preactivated using HBTU coupling chemistry. The simultaneous removal of peptide from the resin and deprotection of side-chain protecting groups was carried out in TFA containing 5% EDT and 5% H$_2$O for 2 hours, giving a crude product yield of 250 mg. Purification by preparative HPLC of a 40 mg aliquot of crude material was carried out using a gradient of 90 to 100% B over 50 minutes (A 0.1% TFA/water and B=MeOH) at a flow rate of 9 ml/min. After lyophilisation, 24 mg of pure material was obtained (analytical HPLC, gradient 70–100% B where B 0.1% TFA/acetonitrile, A 0.01% TFA/water: detection—UV 214 nm—product retention time=23 minutes). Further product characterisation was carried out using MALDI mass spectrometry: expected M+H at 1096, found at 1099.

b) Preparation of gas-containing Microbubbles Comprising DSPS 'doped' with a Thiol-containing Lipid Structure DSPS (4.5 mg) and the lipid structure from (a) above (0.5 mg) were weighed into a clean vial and 0.8 ml of a solution containing 1.4% propylene glycol/2.4% glycerol in water was added. The mixture was warmed to 80° C. for 5 minutes (vial shaken during warming) and filtered while still hot through a 40 micron filter. The sample was cooled to room temperature and the head space was flushed with perfluorobutane gas. The vial was shaken in a cap mixer for 45 seconds and then placed on aroller table overnight. The resulting microbubbles were washed several times with deionised water and analysed for thiol group incorporation using Ellmans Reagent.

c) Modification of Transferrin and Avidin with Fluorescein-NHS and Sulpho-SMPB

To a mixture of 2 mg of transferrin (Holo, human) and 2 mg of avidin in PBS (1 ml) was added 0.5 ml of a DMSO solution containing 1 mg Sulpho-SMPB and 0.5 mg flucrescein-NHS. The mixture was stirred for 45 minutes at room temperature then passed through a Sephadex 200 column using PBS as eluent. The protein fraction was collected and stored at 4° C. prior to use.

d) Microbubble Conjugation with Modified Transferrin/aidin

To the thiol-containing microbubbles from (b) was added 1 ml of the modified transferrin/avidin protein solution from (c). After adjusting the pH of the solution to 9, the conjugation reaction was allowed to proceed for 2 hours at room temperature. Following extensive washing with deionised water the microbubbles were analysed by Coulter counter (81% between 1 and 7 micron) and fluorescence microscopy (highly fluorescent microbubbles were observed).

EXAMPLE 65

Gene Transfer by Gas-filled Microbubbles

This example is directed at the preparation of targeted microbubbles for gene transfer.

a) Preparation of Gas-filled Microbubbles Comprising DSPS and Lipopeptide Coated with Poly-L-lysine DSPS (4.5 mg) and lipopeptide from Example 41 (0.5 mg) were weighed in two 2 ml vials. To each vial, 0.8 ml propylene glycol/glycerol (4%) in water was added. Each solution was heated at 80° C. for 5 minutes, shaken and then cooled to ambient temperature, whereafter the headspaces were flushed with perfluorobutane. The vials were shaken on a cap-mixer at 4450 oscillations/minute for 45 seconds and put on a roller table for 5 minutes. The content of the vials were mixed and the resulting sample was washed by centrifugation at 2000 rpm for 5 minutes. The infranatant was removed and the same volume of distilled water was added. The washing procedure was repeated once. Poly-L-lysine HBr (20.6 mg) was dissolved in 2 ml water, then an aliquot (0.4 ml) was made up to 2 ml with water. To 1.2 ml of the diluted poly-L-lysine solution was added 0.12 ml of the DSPS-lipopeptide microbubble suspension. Following incubation, excess polylysine was removed by extensive washing with water.

b) Transfection of Cells

Endothelial cells (ECV 304) were cultured in 6 well plates to a uniform subconfluent layer. A transfection mixture consisting of 5 µg DNA (an Enhanced Green Fluorescent Protein vector from CLONTECH) and 50 µl of microbubble suspension from (a) in RPMI medium at a final volume of 250 µl was prepared. The mixture was left standing for 15 minutes at room temperature then 1 ml of complete RPMI medium was added. The medium was removed from the cell culture dish and the DNA-microbubble mixture was added to the cells. The cells were incubated in a cell culture incubator (37° C.).

c) Ultrasonic Treatment

After 15 minutes incubation, selected wells were exposed to continious wave ultrasound of 1 MHz, 0.5 W/cm$^2$, for 30 seconds.

d) Incubation and Examination

The cells were further incubated in the cell culture incubator (37° C.) for approximately 4.5 hours. The medium containing DNA-microbubbles was then removed by aspiration, and 2 ml complete RPMI medium was added. The cells were incubated for 40–70 hours before examination. Most of the medium was then removed and the cells were examined by fluorescence microscopy. The results were compared to the results from control experiments where DNA or DNA-polylysine were added to the cells.

EXAMPLE 66

Flotation of Endothelial Cells by Microbubbles with Vectors that Specifically Bind to the Endothelial Cells This experiment was carried out to show that the present invention can be used for separation of cells to which the microbubbles are targeted. The human endothelial cell line ECV 304, derived from a normal umbilical cord (ATCC CRL-1998) was cultured in Nunc culture flasks (chutney 153732) in RPMI 1640 medium to which L-glutamine (200 mM), penicillin/streptomycin (10,000 U/ml and 10,00 µg/ml) and 10% fetal calf serum were added. The cells were subcultured following trypsination with a split ratio of 1:5 to 1:7 when reaching confluence. 2 million cells from trypsinated confluent cultures were added to each set of five centrifuge tubes. Then control microbubbles or microbubbles binding to endothelial cells, made as described in Example 21 and in Example 38, were added at 2, 4, 6 ,8 or 10 million bubbles per tube. The cells at the bottom of the tubes after centrifugation at 400 g for 5 minutes were counted with a Coulter counter. It was found the 4 or more microbubbles binding to a cell brought the cells to the top of the fluid in the centrifugation tube. All cells were floated by the microbbbles from Example 38 whereas about 50% were floated with the microbubbles from Example 21.

EXAMPLE 67

Gas-filled Microbubbles of Distearoyl-phosphatidylserine Comprising a Lipopeptide Containing a Vector with Affinity for Endothelin Receptors for Targeted Ultrasound Imaging a) Synthesis of 4'-[(3,4-dimethyl-5-isoxazolyl)sulfamoyl] succinanilic acid To a solution of sulfisoxazole (267 mg, 1.00 mmol) in DMF (10 ml) was added succinic anhydride (1.00 g, 10.0 mmol) and 4-dimethylaminopyridine (122 mg, 1.00 mmol). The reaction mixture was stirred at 80° C. for 2 hours and then concentrated. The residue was taken up in 5% aqueous sodium bicarbonate solution and extracted with ethyl acetate. The aqueous solution was acidified with dilute hydrochloric acid and organic material was extracted into ethyl acetate. The organic phase was washed with dilute hydrochloric acid, water and brine, treated with active charcoal and dried (MgSO$_4$). The solution was filtered and concentrated to give 280 mg (76%) of white solid. The structure was verified by $^1$H (300 MHz) and $^{13}$C (75 MHz) NMR spectroscopy. Further characterisation was carried out using MALDI mass spectrometry (ACH matrix), giving a M+Na peak at m/z 390 and a M+K peak at m/z 406 as expected.

b) Synthesis of a lipopeptide functionalised with sulfisoxazole (SEQ ID NO:25)

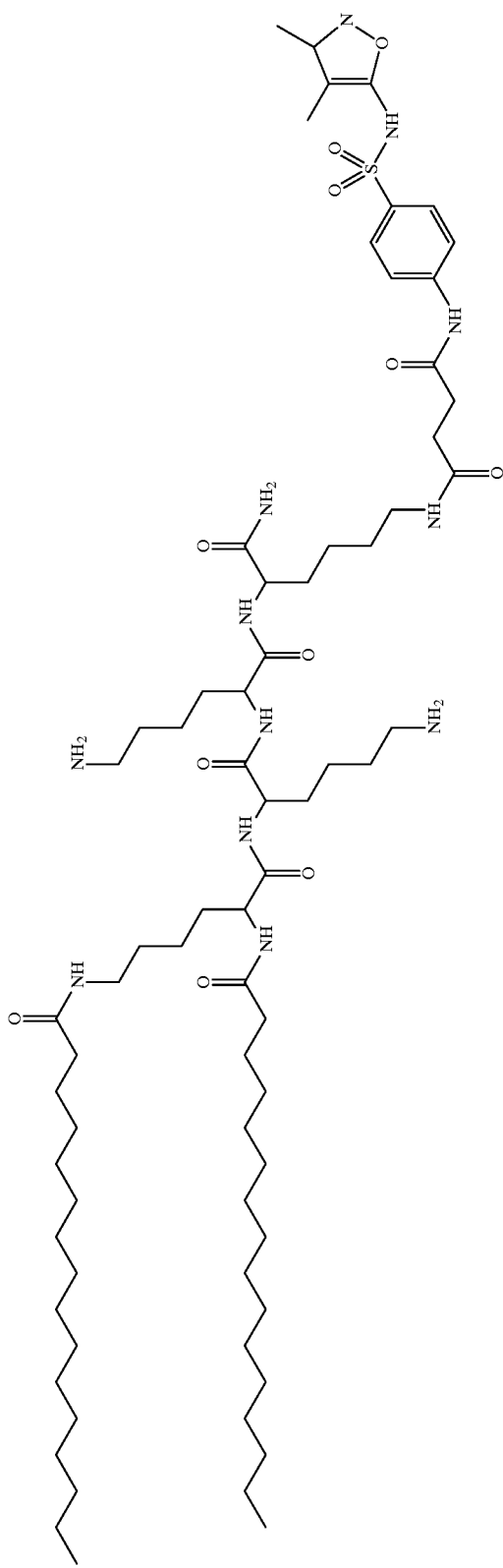

The structure shown above was synthesised on a manual nitrogen bubbler apparatus starting with Fmoc-protected Rink Amide BMHA resin on a 0.125 mmol scale, using appropriate amino acids , palmitic acid and the compound from (a). Coupling was carried out using standard TBTU/ HOBt/DIEA protocols. Simultaneous removal of the peptide from the resin and deprotection of side-chain protecting groups was carried out in TFA containing 5% EDT and 5% water for 2 hours. Crude material was precipitated from ether. The product was analysed by analytical HPLC, gradient 70–100% B over 20 minutes, A=0.1% TFA/water and B=0.1% TFA/acetonitrile, flow rate 1 ml/minute, detection UV 214 nm, retention time 27 minutes). Further characterisation was carried out using MALDI mass spectrometry, giving a M+H at m/z 1359, expected 1356.

c) Preparation of Gas-filled Microbubbles Comprising the Compound from (b)

A solution of 1.4% propylene glycol/2.4% glycerol (1.0 ml) was added to a mixture of DSPS (4.5 mg) and product from (b) (0.5 mg) in a vial. The mixture was sonicated for 5 minutes and then heated at 80° C. for 5 minutes (vial was shaken during warming) and cooled. The head space was flushed with perfluorobutane gas and the vial was shaken in a cap mixer for 45 seconds followed by extensive washing with deionised water. MALDI mass spectrometry showed no detectable level of compound from (b) in the final wash solution. Incorporation of isoxazole-containing lipopeptide into the microbubbles was confirmed by MALDI-MS as follows: ca. 50 µl of microbubbles were transferred to a clean vial containing ca. 100 µl of 90% methanol. The mixture was sonicated for 30 seconds and analysed by MALDI-MS (ACH-matrix), giving a m+H peak at m/z 1359 corresponding to lipopeptide (b).

What is claimed is:

1. A combined formulation comprising:
   i) a first administrable composition comprising a targetable ultrasound diagnostic agent comprising a suspension in an aqueous carrier liquid of a reporter comprising gas filled microbubbles stabilised by monolayers of film forming surfactant, said microbubbles further comprising at least one vector which binds a target; and
   ii) a second administrable composition comprising a substance which displaces or releases said microbubbles from its target.

2. A combined formulation as claimed in claim 1 wherein the gas is air, nitrogen, oxygen, carbon dioxide, hydrogen, an inert gas, a sulphur fluoride, selenium hexafluoride, a low molecular weight hydrocarbon, a ketone, an ester, a halogenated low molecular weight hydrocarbon or a mixture of any of the foregoing.

3. A combined formulation as claimed in claim 2 wherein the gas is a perfluorinated ketone, a perfluorinated ether or a perfluorocarbon.

4. A combined formulation as claimed in claim 2 wherein the gas is sulphur hexafluoride or a perfluoropropane, a perfluorobutane or a perfluoropentane.

5. A combined formulation as claimed in claim 1 wherein the film-forming surfactant material is a non-polymeric and non-polymerisable wall-forming surfactant material, a polymer surfactant material or a phospholipid.

6. A combined formulation as claimed in claim 5 wherein at least 75% of the film-forming surfactant material comprises phospholipid molecules individually bearing net overall charge.

7. A combined formulation as claimed in claim 6 wherein at least 75% of the film-forming surfactant material comprises one or more phospholipids selected from the group consisting of phosphatidylserines, phosphatidylglycerols, phosphatidylinositols, phosphatidic acids and cardiolipins.

8. A combined formulation as claimed in claim 7 wherein at least 80% of said phospholipids are phosphatidylserines.

9. A combined formulation as claimed in claim 1 wherein the film-forming surfactant material comprises a lipopeptide.

10. A combined formulation as claimed in claim 1 wherein the vector is selected from the group consisting of antibodies; cell adhesion molecules; cell adhesion molecule receptors; cytokines; growth factors; peptide hormones; non-peptide agonists/antagonists and non-bioactive binders of receptors for cell adhesion molecules, cytokines, growth factors and peptide hormones; oligonucleotides; DNA-binding drugs; protease substrates/inhibitors; and small bioactive molecules.

11. A combined formulation as claimed in claim 1 wherein the vector or vectors have affinity for targets at a level such that the agent interacts with but does not fixedly bind to said targets.

12. A combined formulation as claimed in claim 11 wherein the vector or vectors are selected from the group consisting of ligands for cell adhesion proteins and cell adhesion proteins which have corresponding ligands on endothelial cell surfaces.

13. A combined formulation as claimed in claim 1 wherein the vector or vectors are sited such that they are not readily exposed to the target.

14. A combined formulation as claimed in claim 1 wherein the vector is covalently coupled or linked to the reporter.

15. A combined formulation as claimed in claim 1 wherein the vector is coupled or linked to the reporter through electrostatic charge interactions.

16. A combined formulation as claimed in claim 1 wherein the vector is coupled or linked to the reporter by means of avidin-biotin and/or streptavidin-biotin interactions.

17. A method to determine a perfusion rate in a targeted area which method comprises administering the combined formulation of claim 1 to a targeted area and measuring the rate at which the agent of the first composition is displaced or released from the targeted area after the administration of the second composition using ultrasound imaging.

* * * * *

SEQUENCE LISTING

```
<160> NUMBER OF SEQ ID NOS:   31

<210> SEQ ID NO 1
<211> LENGTH: 4
<212> TYPE: PRT
<213> ORGANISM: Artificial Sequence
<220> FEATURE:
<223> OTHER INFORMATION: Description of Artificial
      Sequence:RGDC-Mal-PEG3400-DSPE

<400> SEQUENCE: 1

Arg Gly Asp Cys
  1

<210> SEQ ID NO 2
<211> LENGTH: 25
<212> TYPE: PRT
<213> ORGANISM: Artificial Sequence
<220> FEATURE:
<223> OTHER INFORMATION: Description of Artificial Sequence:Peptide
      comprising phosphatidylserine-binding and
      heparin-binding sections

<400> SEQUENCE: 2

Phe Asn Phe Arg Leu Lys Ala Gly Gln Lys Ile Arg Phe Gly Ala Ala
  1               5                  10                  15

Ala Trp Glu Pro Pro Arg Ala Arg Ile
             20                  25

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence:
      Heparin-binding peptide

<400> SEQUENCE: 3

Trp Glu Pro Pro Arg Ala Arg Ile
  1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence:
```

```
          Linker sequence
<221> NAME/KEY: MOD_RES
<222> LOCATION: (1)
<223> OTHER INFORMATION: MTX-phenylalanine

<400> SEQUENCE: 4

Phe Lys Leu Arg Leu Cys
 1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence:Heparin
      sulphate binding peptide

<400> SEQUENCE: 5

Lys Arg Lys Arg
 1

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence:
      Fibronectin peptide

<400> SEQUENCE: 6

Trp Gln Pro Pro Arg Ala Arg Ile
 1               5

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence:
      Lipopeptide consisting of a heparin sulphate binding peptide
      and a fibronectin peptide
<221> NAME/KEY: MOD_RES
<222> LOCATION: (1)
<223> OTHER INFORMATION: Dipalmitoyl-lysine

<400> SEQUENCE: 7

Lys Lys Arg Lys Arg Trp Gln Pro Pro Arg Ala Arg Ile
 1               5                  10

<210> SEQ ID NO 8
<211> LENGTH: 24
<212> TYPE: PRT
<213> ORGANISM: Artificial Sequence
<220> FEATURE:
<223> OTHER INFORMATION: Description of Artificial Sequence:
      Fibronectin peptide sequence

<400> SEQUENCE: 8

Phe Asn Phe Arg Leu Lys Ala Gly Gln Lys Ile Arg Phe Gly Gly Gly
 1               5                  10                  15

Gly Trp Gln Pro Pro Arg Ala Ile
            20

<210> SEQ ID NO 9
<211> LENGTH: 6
<212> TYPE: PRT
<213> ORGANISM: Artificial Sequence
<220> FEATURE:
```

```
<223> OTHER INFORMATION: Description of Artificial Sequence:
      Biotinylated endothelin-1 peptide
<221> NAME/KEY: MOD_RES
<222> LOCATION: (1)
<223> OTHER INFORMATION: Biotin-D-Trp

<400> SEQUENCE: 9

Trp Leu Asp Ile Ile Trp
 1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence:
      Biotinylated fibrin-anti-polymerant peptide
<221> NAME/KEY: MOD_RES
<222> LOCATION: (1)
<223> OTHER INFORMATION: Biotinylated-Gly
<221> NAME/KEY: MOD_RES
<222> LOCATION: (10)
<223> OTHER INFORMATION: AMIDATION

<400> SEQUENCE: 10

Gly Pro Arg Pro Pro Glu Arg His Gln Ser
 1               5                   10

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence:
      Lipopeptide containing RGD sequence and fluorescein reporter
      group
<221> NAME/KEY: MOD_RES
<222> LOCATION: (1)
<223> OTHER INFORMATION: Dipalmitoyl-Lys
<221> NAME/KEY: MOD_RES
<222> LOCATION: (4)
<223> OTHER INFORMATION: Acetyl-RGD-K-fluorescein side chain

<400> SEQUENCE: 11

Lys Lys Lys Lys Gly
 1               5

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence:
      Endothelial cell binding lipopeptide
<221> NAME/KEY: MOD_RES
<222> LOCATION: (1)
<223> OTHER INFORMATION: 2-n-hexadecylstearyl-Lys
<221> NAME/KEY: MOD_RES
<222> LOCATION: (18)
<223> OTHER INFORMATION: AMIDATION

<400> SEQUENCE: 12

Lys Leu Ala Leu Lys Leu Ala Leu Lys Ala Leu Lys Ala Ala Leu Lys
 1               5                   10                  15

Leu Ala

<210> SEQ ID NO 13
<211> LENGTH: 4
<212> TYPE: PRT
<213> ORGANISM: Artificial Sequence
```

```
<220> FEATURE:
<223> OTHER INFORMATION: Description of Artificial Sequence:
      Lipopeptide functionalised with captopril
<221> NAME/KEY: MOD_RES
<222> LOCATION: (1)
<223> OTHER INFORMATION: Dipalmitoyl-Lys
<221> NAME/KEY: MOD_RES
<222> LOCATION: (4)
<223> OTHER INFORMATION: Amide linked via side chain to captopril
<221> NAME/KEY: MOD_RES
<222> LOCATION: (4)
<223> OTHER INFORMATION: AMIDATION

<400> SEQUENCE: 13

Lys Lys Lys Lys
  1

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence:
      Lipopeptide with an affinity for endothelial cells
<221> NAME/KEY: MOD_RES
<222> LOCATION: (1)
<223> OTHER INFORMATION: Dipalmitoyl-Lys
<221> NAME/KEY: MOD_RES
<222> LOCATION: (4)
<223> OTHER INFORMATION: Acp
<221> NAME/KEY: MOD_RES
<222> LOCATION: (13)
<223> OTHER INFORMATION: AMIDATION

<400> SEQUENCE: 14

Lys Lys Lys Xaa Ile Arg Arg Val Ala Arg Pro Pro Leu
  1               5                  10

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence:
      Lipopeptide comprising an interleukin-1 receptor binding
      peptide
<221> NAME/KEY: MOD_RES
<222> LOCATION: (1)
<223> OTHER INFORMATION: Dipalmitoyl-Lys

<400> SEQUENCE: 15

Lys Gly Asp Trp Asp Gln Phe Gly Leu Trp Arg Gly Ala Ala
  1               5                  10

<210> SEQ ID NO 16
<211> LENGTH: 12
<212> TYPE: PRT
<213> ORGANISM: Artificial Sequence
<220> FEATURE:
<221> NAME/KEY: MOD_RES
<222> LOCATION: (1)
<223> OTHER INFORMATION: Dabsyl-Tyr
<221> NAME/KEY: MOD_RES
<222> LOCATION: (10)
<223> OTHER INFORMATION: RGDS chain linked via NH2 group of lysine
<223> OTHER INFORMATION: Description of Artificial Sequence:Branched
      core peptide comprising a dabsylated atherosclerotic
      plaque-binding sequence and RGDS

<400> SEQUENCE: 16

Tyr Arg Ala Leu Val Asp Thr Leu Lys Lys Gly Cys
  1               5                  10
```

```
<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence:Synthetic
      oligonucleotide
<221> NAME/KEY: misc_feature
<222> LOCATION: (1)
<223> OTHER INFORMATION: Biotinylated

<400> SEQUENCE: 17
gaaaggtagt ggggtcgtgt gccgg                                              25

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence:
      Lipopeptide with affinity for thrombi
<221> NAME/KEY: MOD_RES
<222> LOCATION: (1)
<223> OTHER INFORMATION: Dipalmitoyl-Lys
<221> NAME/KEY: MOD_RES
<222> LOCATION: (15)
<223> OTHER INFORMATION: AMIDATION

<400> SEQUENCE: 18

Lys Asn Asp Gly Asp Phe Glu Glu Ile Pro Glu Glu Tyr Leu Gln
 1               5                  10                  15

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence:
      Lipopeptide
<221> NAME/KEY: MOD_RES
<222> LOCATION: (1)
<223> OTHER INFORMATION: Dipalmitoyl-Lys
<221> NAME/KEY: MOD_RES
<222> LOCATION: (5)
<223> OTHER INFORMATION: Biotinylated-Lys

<400> SEQUENCE: 19

Lys Trp Lys Lys Lys Gly
 1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial
      Sequence:Thiol-functionalised lipid molecule
<221> NAME/KEY: MOD_RES
<222> LOCATION: (1)
<223> OTHER INFORMATION: Dipalmitoyl-Lys
<221> NAME/KEY: MOD_RES
<222> LOCATION: (4)
<223> OTHER INFORMATION: Acp

<400> SEQUENCE: 20

Lys Lys Lys Xaa Cys
 1               5

<210> SEQ ID NO 21
```

```
<211> LENGTH: 4
<212> TYPE: PRT
<213> ORGANISM: Artificial Sequence
<220> FEATURE:
<223> OTHER INFORMATION: Description of Artificial Sequence:
      Lipopeptide functionalised with atenolol
<221> NAME/KEY: MOD_RES
<222> LOCATION: (1)
<223> OTHER INFORMATION: Dipalmitoyl-Lys
<221> NAME/KEY: MOD_RES
<222> LOCATION: (4)
<223> OTHER INFORMATION: Lysine with side chain linked via amide bond
      to atenolol
<221> NAME/KEY: MOD_RES
<222> LOCATION: (4)
<223> OTHER INFORMATION: AMIDATION

<400> SEQUENCE: 21

Lys Lys Lys Lys
 1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence:
      Lipopeptide containing folic acid
<221> NAME/KEY: MOD_RES
<222> LOCATION: (1)
<223> OTHER INFORMATION: Dipalmitoyl-Lys
<221> NAME/KEY: MOD_RES
<222> LOCATION: (4)
<223> OTHER INFORMATION: AMIDATION
<221> NAME/KEY: MOD_RES
<222> LOCATION: (4)
<223> OTHER INFORMATION: Lysine with side chain linked via amide bond
      to folic acid

<400> SEQUENCE: 22

Lys Lys Lys Lys
 1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence:
      Lipopeptide containing a derivative of bestatin
<221> NAME/KEY: MOD_RES
<222> LOCATION: (1)
<223> OTHER INFORMATION: Dipalmitoyl-Lys
<221> NAME/KEY: MOD_RES
<222> LOCATION: (4)
<223> OTHER INFORMATION: AMIDATION
<221> NAME/KEY: MOD_RES
<222> LOCATION: (4)
<223> OTHER INFORMATION: Lysine with side chain linked via amide bond
      to derivative of bestatin

<400> SEQUENCE: 23

Lys Lys Lys Lys
 1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence:
      Lipopeptide containing chlorambucil
<221> NAME/KEY: MOD_RES
```

```
<222> LOCATION: (1)
<223> OTHER INFORMATION: Dipalmitoyl-Lys
<221> NAME/KEY: MOD_RES
<222> LOCATION: (4)
<223> OTHER INFORMATION: AMIDATION
<221> NAME/KEY: MOD_RES
<222> LOCATION: (4)
<223> OTHER INFORMATION: Lysine with side chain linked via amide bond
      to chlorambucil

<400> SEQUENCE: 24

Lys Lys Lys Lys
  1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence:
      Lipopeptide functionalised with sulfisoxazole
<221> NAME/KEY: MOD_RES
<222> LOCATION: (1)
<223> OTHER INFORMATION: Dipalmitoyl-Lys
<221> NAME/KEY: MOD_RES
<222> LOCATION: (4)
<223> OTHER INFORMATION: AMIDATION
<221> NAME/KEY: MOD_RES
<222> LOCATION: (4)
<223> OTHER INFORMATION: Lysine with side chain linked via amide bond
      to sulfisoxazole

<400> SEQUENCE: 25

Lys Lys Lys Lys
  1

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence:
      Atherosclerotic plaque-binding peptide

<400> SEQUENCE: 26

Tyr Arg Ala Leu Val Asp Thr Leu Lys
  1               5

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence:
      Atherosclerotic plaque-binding peptide

<400> SEQUENCE: 27

Tyr Ala Lys Phe Arg Glu Thr Leu Glu Asp Thr Arg Asp Arg Met Tyr
  1               5                  10                  15

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence:
      Atherosclerotic plaque-binding peptide

<400> SEQUENCE: 28

Arg Ala Leu Val Asp Thr Glu Phe Lys Val Lys Gln Glu Ala Gly Ala
```

```
                1               5              10              15
Lys

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence:Thrombus
      binding peptide

<400> SEQUENCE: 29

Asn Asp Gly Asp Phe Glu Glu Ile Pro Glu Glu Tyr Leu Gln
  1               5                  10

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence:Thrombus
      binding peptide

<400> SEQUENCE: 30

Gly Pro Arg Gly
  1

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence:Platelet
      binding peptide

<400> SEQUENCE: 31

Pro Leu Tyr Lys Lys Ile Ile Lys Lys Leu Leu Glu Ser
  1               5                  10
```